United States Patent
Lin et al.

(10) Patent No.: US 11,826,426 B2
(45) Date of Patent: Nov. 28, 2023

(54) NANOSCALE METAL-ORGANIC LAYERS AND METAL-ORGANIC NANOPLATES FOR X-RAY INDUCED PHOTODYNAMIC THERAPY, RADIOTHERAPY, RADIODYNAMIC THERAPY, CHEMOTHERAPY, IMMUNOTHERAPY, AND ANY COMBINATION THEREOF

(71) Applicant: The University of Chicago, Chicago, IL (US)

(72) Inventors: Wenbin Lin, Chicago, IL (US); Kaiyuan Ni, Chicago, IL (US); Guangxu Lan, Chicago, IL (US)

(73) Assignee: The University of Chicago, Chicago, IL (US)

( * ) Notice: Subject to any disclaimer, the term of this patent is extended or adjusted under 35 U.S.C. 154(b) by 280 days.

(21) Appl. No.: 16/634,486

(22) PCT Filed: Aug. 2, 2018

(86) PCT No.: PCT/US2018/045005
§ 371 (c)(1),
(2) Date: Jan. 27, 2020

(87) PCT Pub. No.: WO2019/028250
PCT Pub. Date: Feb. 7, 2019

(65) Prior Publication Data
US 2020/0254095 A1    Aug. 13, 2020

Related U.S. Application Data

(60) Provisional application No. 62/623,826, filed on Jan. 30, 2018, provisional application No. 62/540,275, filed on Aug. 2, 2017.

(51) Int. Cl.
*A61K 41/00* (2020.01)
*A61P 35/00* (2006.01)
*A61K 33/243* (2019.01)
*A61K 45/06* (2006.01)
*A61K 47/34* (2017.01)
*A61N 5/10* (2006.01)

(52) U.S. Cl.
CPC ........ *A61K 41/0071* (2013.01); *A61K 33/243* (2019.01); *A61K 41/0057* (2013.01); *A61K 45/06* (2013.01); *A61K 47/34* (2013.01); *A61N 5/10* (2013.01); *A61P 35/00* (2018.01)

(58) Field of Classification Search
CPC .............. A61K 41/0071; A61K 33/243; A61K 41/0057; A61K 45/06; A61K 47/34; A61K 31/282; A61N 5/10; A61N 5/062; A61N 2005/1098; A61P 35/00; C07D 213/26; C07D 213/55; C07D 487/22
See application file for complete search history.

(56) References Cited

U.S. PATENT DOCUMENTS

| | | | |
|---|---|---|---|
| 4,405,771 A | 9/1983 | Jagur | |
| 5,147,806 A | 9/1992 | Kamin et al. | |
| 5,213,788 A | 5/1993 | Ranney | |
| 5,591,730 A | 1/1997 | Stoller et al. | |
| 5,641,623 A | 6/1997 | Martin | |
| 5,648,508 A | 7/1997 | Yaghi | |
| 5,827,925 A | 10/1998 | Tremont et al. | |
| 5,858,784 A | 1/1999 | Debs et al. | |
| 5,871,710 A | 2/1999 | Bogdanov et al. | |
| 6,013,638 A | 1/2000 | Crystal et al. | |
| 6,022,737 A | 2/2000 | Niven et al. | |
| 6,136,295 A | 10/2000 | Edwards et al. | |
| 6,180,082 B1 | 1/2001 | Woltering et al. | |
| 6,384,019 B1 | 5/2002 | Myhren et al. | |
| 6,565,873 B1 | 5/2003 | Shefer et al. | |
| 6,818,227 B1 | 11/2004 | Uster et al. | |
| 6,878,838 B2 | 4/2005 | Lin et al. | |
| 6,984,400 B2 | 1/2006 | Golomb et al. | |
| 7,060,290 B1 | 6/2006 | Morimoto et al. | |

(Continued)

FOREIGN PATENT DOCUMENTS

| | | |
|---|---|---|
| CA | 2896797 A1 | 7/2014 |
| CN | 1673258 | 9/2005 |

(Continued)

OTHER PUBLICATIONS

Cao Metal-Organic Layers Angew Chem. Int. Ed., 55, p. 4962, March (Year: 2016).*

(Continued)

*Primary Examiner* — Matthew P Coughlin
*Assistant Examiner* — Thurman Wheeler
(74) *Attorney, Agent, or Firm* — Jenkins, Taylor & Hunt, P.A.

(57) ABSTRACT

Metal-organic layers (MOLs) and metal-organic nanoplates (MOPs) comprising photosensitizers are described. The MOLs and MOPs can also include moieties capable of absorbing X-rays or other ionizing irradiation energy and/or scintillation. Optionally, the photo sensitizer or a derivative thereof can form a bridging ligand of the MOL or MOP. Also described are methods of using MOLs and MOPs in photodynamic therapy, X-ray induced photodynamic therapy (X-PDT), radiotherapy (RT), radiodynamic therapy, or in radiotherapy-radiodynamic therapy (RT-RDT), either with or without the co-administration of another therapeutic agent, such as a chemotherapeutic agent or an immunomodulator.

25 Claims, 29 Drawing Sheets

(56) References Cited

U.S. PATENT DOCUMENTS

| | | |
|---|---|---|
| 7,196,210 B2 | 3/2007 | Yaghi et al. |
| 7,263,170 B2 | 8/2007 | Pellegrino |
| 7,271,156 B2 | 9/2007 | Krieg et al. |
| 7,354,912 B2 | 4/2008 | Lichtenberger |
| 7,430,282 B2 | 9/2008 | Mori et al. |
| 7,704,972 B2 | 4/2010 | Couvreur et al. |
| 7,803,785 B2 | 9/2010 | Gallop et al. |
| 7,985,868 B1 | 7/2011 | Bauer |
| 8,158,153 B2 | 4/2012 | Liversidge et al. |
| 8,623,837 B2 | 1/2014 | Fewell |
| 8,653,292 B2 | 2/2014 | Hafizovic et al. |
| 8,668,764 B2 | 3/2014 | Brown et al. |
| 8,691,748 B2 | 4/2014 | Yaghi et al. |
| 8,722,018 B2 | 5/2014 | Port et al. |
| 9,072,774 B2 | 7/2015 | Zheng et al. |
| 9,162,079 B2 | 10/2015 | Levy et al. |
| 9,302,003 B2 | 4/2016 | Sanche et al. |
| 9,693,957 B2 | 7/2017 | Lin et al. |
| 10,118,169 B2 | 11/2018 | Lin et al. |
| 10,206,871 B2 | 2/2019 | Lin et al. |
| 10,350,275 B2 | 7/2019 | Aguilar-Cordova |
| 10,517,822 B2 | 12/2019 | Lin et al. |
| 10,596,116 B2 | 3/2020 | Lin et al. |
| 10,647,733 B2 | 5/2020 | Lin et al. |
| 10,780,045 B2 | 9/2020 | Lin et al. |
| 10,806,694 B2 | 10/2020 | Lin et al. |
| 10,953,393 B2 | 3/2021 | Lin et al. |
| 11,246,877 B2 | 2/2022 | Lin et al. |
| 11,389,422 B2 | 7/2022 | Lin et al. |
| 2001/0018187 A1 | 8/2001 | Sun et al. |
| 2002/0064520 A1 | 5/2002 | Rozenberg et al. |
| 2002/0115747 A1 | 8/2002 | Feldheim et al. |
| 2002/0127224 A1 | 9/2002 | Chen |
| 2002/0187184 A1 | 12/2002 | Golomb et al. |
| 2005/0112131 A1 | 5/2005 | Pogue et al. |
| 2005/0147963 A1 | 7/2005 | Su et al. |
| 2005/0227929 A1 | 10/2005 | Masferrer |
| 2006/0204754 A1 | 9/2006 | Kang |
| 2006/0210639 A1 | 9/2006 | Liversidge et al. |
| 2006/0228554 A1 | 10/2006 | Tan et al. |
| 2006/0233883 A1 | 10/2006 | Ishihara et al. |
| 2007/0076851 A1 | 4/2007 | Pellegrino |
| 2007/0088161 A1 | 4/2007 | Stockel et al. |
| 2007/0218049 A1 | 9/2007 | Chen et al. |
| 2007/0259966 A1 | 11/2007 | Cagnoni et al. |
| 2008/0063714 A1 | 3/2008 | Sahouani et al. |
| 2008/0095699 A1 | 4/2008 | Zheng et al. |
| 2008/0124281 A1 | 5/2008 | Gao et al. |
| 2008/0280851 A1 | 11/2008 | Myhren et al. |
| 2008/0286352 A1 | 11/2008 | Kumar et al. |
| 2008/0292714 A1 | 11/2008 | Garlich et al. |
| 2009/0317335 A1 | 12/2009 | Lin et al. |
| 2010/0189222 A1 | 7/2010 | Eaton et al. |
| 2010/0211137 A1 | 8/2010 | Kim et al. |
| 2010/0286022 A1 | 11/2010 | Yaghi et al. |
| 2011/0053862 A1 | 3/2011 | Xie et al. |
| 2011/0135571 A1 | 6/2011 | Lin et al. |
| 2011/0238001 A1 | 9/2011 | Chen et al. |
| 2011/0281815 A1 | 11/2011 | Ahrabi et al. |
| 2012/0093918 A1 | 4/2012 | Sanche et al. |
| 2012/0130146 A1 | 5/2012 | Picard et al. |
| 2012/0142641 A1 | 6/2012 | Venkatraman |
| 2012/0226217 A1 | 9/2012 | Klaveness et al. |
| 2012/0253191 A1 | 10/2012 | Zheng et al. |
| 2012/0301537 A1 | 11/2012 | Ishida et al. |
| 2013/0171228 A1 | 7/2013 | Morris |
| 2013/0209755 A1 | 8/2013 | Hustad et al. |
| 2014/0066625 A1 | 3/2014 | Mautino et al. |
| 2014/0107333 A1 | 4/2014 | Ma et al. |
| 2014/0127763 A1 | 5/2014 | Zheng et al. |
| 2014/0220143 A1 | 8/2014 | Dhar et al. |
| 2014/0234210 A1 | 8/2014 | Lin et al. |
| 2014/0235568 A1 | 8/2014 | Song et al. |
| 2014/0335015 A1 | 11/2014 | Pottier et al. |
| 2015/0086541 A1 | 3/2015 | Aguilar-Cordova |
| 2016/0346204 A1 | 12/2016 | Lin et al. |
| 2016/0354468 A1 | 12/2016 | Scherz et al. |
| 2017/0173572 A1 | 6/2017 | Lin et al. |
| 2017/0182486 A1 | 6/2017 | Lin et al. |
| 2017/0231903 A1 | 8/2017 | Lin et al. |
| 2017/0333347 A1 | 11/2017 | Lin et al. |
| 2018/0153796 A1 | 6/2018 | Lin et al. |
| 2018/0214563 A1 | 8/2018 | Li et al. |
| 2018/0361370 A1 | 12/2018 | Lin et al. |
| 2019/0209460 A1 | 7/2019 | Lin et al. |
| 2019/0269706 A1 | 9/2019 | Lin et al. |
| 2019/0314324 A1 | 10/2019 | Lin et al. |
| 2020/0085742 A1 | 3/2020 | Lin et al. |
| 2020/0222321 A1 | 7/2020 | Lin et al. |
| 2020/0261403 A1 | 8/2020 | Lin et al. |
| 2020/0324276 A1 | 10/2020 | Lin et al. |
| 2021/0053042 A1 | 2/2021 | Lin et al. |
| 2023/0293698 A1 | 9/2023 | Lin et al. |

FOREIGN PATENT DOCUMENTS

| | | | |
|---|---|---|---|
| CN | 1874789 A | 12/2006 | |
| CN | 101511353 A | 8/2009 | |
| CN | 102256622 A | 11/2011 | |
| CN | 102448497 | 5/2012 | |
| CN | 102573914 A | 7/2012 | |
| CN | 102648004 | 8/2012 | |
| CN | 105457038 A | 4/2016 | |
| CN | 105873569 A | 8/2016 | |
| CN | 109310702 A | 2/2019 | |
| CN | 107001031 B | 11/2019 | |
| CN | 110731961 A | 1/2020 | |
| CN | 105873569 B | 7/2020 | |
| CN | 111194232 B | 1/2023 | |
| EP | 2 729 180 | 5/2014 | |
| EP | 2729180 B1 | 1/2019 | |
| EP | 3439666 A1 | 2/2019 | |
| EP | 3494974 A1 | 6/2019 | |
| EP | 3206987 B1 | 7/2020 | |
| FR | 2910009 A1 | 6/2008 | |
| JP | 2007-516221 A | 6/2007 | |
| JP | 2010-523595 A | 7/2010 | |
| JP | 2013507399 A | 3/2013 | |
| JP | 2015-527301 A | 9/2015 | |
| JP | 6590802 B2 | 9/2019 | |
| JP | 6731404 B2 | 7/2020 | |
| JP | 7090034 | 6/2022 | |
| WO | WO 2004/028508 A1 | 4/2004 | |
| WO | WO2004/101575 A2 | 11/2004 | |
| WO | WO 2006/087722 A1 | 8/2006 | |
| WO | WO2006/102117 | 9/2006 | |
| WO | WO2007/090295 | 8/2007 | |
| WO | WO2007/108618 | 9/2007 | |
| WO | WO2007/124131 | 11/2007 | |
| WO | WO 2008/10263 | 1/2008 | |
| WO | WO 2008/016172 A1 | 2/2008 | |
| WO | WO 2008/102632 A1 | 8/2008 | |
| WO | WO 2008/124639 A2 | 10/2008 | |
| WO | WO 2009/014532 A1 | 1/2009 | |
| WO | WO2009/139939 | 11/2009 | |
| WO | WO 2010/065751 A2 | 6/2010 | |
| WO | WO 2010/096464 A1 | 8/2010 | |
| WO | WO 2011/044671 A1 | 4/2011 | |
| WO | WO 2011/049743 A1 | 4/2011 | |
| WO | WO 2012/042024 | 4/2012 | |
| WO | WO 2012/161196 A1 | 11/2012 | |
| WO | WO 2013/009701 A2 | 1/2013 | |
| WO | WO 2013/009701 A9 | 1/2013 | |
| WO | WO 2013/068965 | 5/2013 | |
| WO | WO 2013/188763 A1 | 12/2013 | |
| WO | WO 2015/069926 A1 | 5/2015 | |
| WO | WO 2015/149068 A1 | 10/2015 | |
| WO | WO 2015/149072 A1 | 10/2015 | |
| WO | WO-2016061256 A1 * | 4/2016 | ........... A61K 31/282 |
| WO | WO 2017/066328 A1 | 4/2017 | |

(56) References Cited

FOREIGN PATENT DOCUMENTS

| WO | WO 2017/201528 A1 | 11/2017 |
|---|---|---|
| WO | WO 2021/237209 A1 | 11/2021 |

OTHER PUBLICATIONS

Advisory Action corresponding to U.S. Appl. No. 16/302,185 dated Nov. 10, 2020.
Advisory Action corresponding to U.S. Appl. No. 15/034,799 dated Jun. 5, 2018.
Advisory Action corresponding to U.S. Appl. No. 15/613,847 dated Aug. 13, 2019.
Allison et al., "Oncologic photodynamic therapy photosensitizers: A clinical review," Photodiagnosis and Photodynamic Therapy, vol. 7, No. 2, pp. 61-75 (Jun. 2010).
Ash et al., "New drugs and future developments in photodynamic therapy," Eur. J. Cancer, vol. 29A, No. 12, pp. 1781-1783 (1993).
Bechet et al., "Nanoparticles as vehicles for delivery of photodynamic therapy agents," Trends in biotechnology, vol. 26, No. 11, pp. 612-621 (2008).
Biel, "Photodynamic Therapy of Head and Neck Cancers," Photodynamic Therapy, Methods in Molecular Biology, Springer+Business Media, LLC, vol. 635 (25 pages), pp. 281-296 (2010).
Bonvalot et al. First-In-Human Study Testing a New Radioenhancer Using Nanoparticles (NBTXR3) Activated by Radiation Therapy In Patients With Locally Advanced Soft Tissue Sarcomas. Clinical Cancer Research, vol. 23, No. 4, 1297, pp. 908-917 (2016).
Bowden et al., "Hydrothermal syntheses and crystal structures of three zinc succinates: $Zn(C4H4O4)-\alpha$, $Zn(C4H4O4)-\beta$ and $K2Zn(C4H4O4)2$," Dalton Transactions. pp. 936-939 (2003).
Brannon-Peppas et al., "Nanoparticle and targeted systems for cancer therapy," Advanced Drug Delivery Reviews. vol. 56 pp. 1649-1659 (2004).
Bretscher. "Asymmetrical Lipid Bilayer Structure for Biological Membranes," Nature New Biology, vol. 236, pp. 11-12 (Year: 1972).
Bulin et al, "X-ray-Induced Singlet Oxygen Activation with Nanoscintillator-Coupled Porphyrins," J. Phys. Chem. C, 117, pp. 21583-21589 (2013).
Cai et al. "Telodendrimer nanocarrier for co-delivery of paclitaxel and cisplatin: A synergistic combination nanotherapy for ovarian cancer treatment," Biomaterials 37, 2015, pp. 456-468, available online Oct. 31, 2014.
Cai et al., "Metal-Organic Framework-Based Nanomedicine Platforms for Drug Delivery and Molecular Imaging," Small Journal, vol. 11, No. 37, pp. 4806-4822 (2015).
Cancellation of Oral Proceedings corresponding to European Application No. 15851357.2 dated Feb. 28, 2022.
Carter et al., "Porphyrin-phospholipid liposomes permeabilized by near-infrared light," Nature communications, vol. 5, No. 3546 (25 pages), pp. 1-11 (Apr. 3, 2014).
Catala et al., "Cyanide-Bridged CrIII-NiII Superparamagnetic Nanoparticles," Advanced Materials. vol. 15, No. 10 pp. 826-829 (2003).
Cavka et al., "A New Zirconium Inorganic Building Brick Forming Metal Organic Frameworks with Exceptional Stability," J. Am. Chem. Soc., vol. 130, No. 42, pp. 13850-13851 (2008).
Celli et al., "Imaging and photodynamic therapy: mechanisms, monitoring, and optimization." Chem. Rev., vol. 110(5), pp. 2795-2838 (2010).
Chatterjee et al., "Nanoparticles in photodynamic therapy: an emerging paradigm." Advanced Drug Delivery Reviews, vol. 60(15), pp. 1627-1637 (2008).
Che et al., "Generation of Binuclear (d8.d8) Platinum and Rhodium Complexes by Pulse Radiolysis", American Chemical Society, vol. 106, No. 18, pp. 5143-5145 (1984).
Chebbi et al., "In vitro assessment of liposomal neridronate on MDA-MB-231 human breast cancer cells," International Journal of Pharmaceutics 383 pp. 116-122 (2010).
Chen et al. "Dihydroartemisinin induces apoptosis and sensitizes human ovarian cancer cells to carboplatin therapy," Journal of Cellular and Molecular Medicine, vol. 13, No. 7, 2009, pp. 1358-1370. (Year: 2009).
Chen et al., "Biomimetic Catalysis of a Porous Iron-Based Metal-Metalloporphyrin Framework," Inorganic Chemistry, vol. 51, No. 23, pp. 12600-12602 (2012).
Chen et al., "Co-delivery of Doxorubicin and Bcl-2 siRNA by Mesoporous Silica nanoparticiles Enhances the Efficacy of Chemotherapy in Multidrug-Resistant Cancer Cells**," vol. 5, No. 23, pp 2673-2677 (2009).
Chen et al., "Immuno gold nanocages with tailored optical properties for targeted photothermal destruction of cancer cells," Nano Lett., vol. 7, No. 5, pp. 1318-1322 (11 pages) (Apr. 2007).
Chen et al., "Nanoscintillator-mediated X-ray inducible photodynamic therapy for in vivo cancer treatment," Nano letters, vol. 15, pp. 2249-2256 (2015).
Chen et al., "Synthesis, characterization and osteoconductivity properties of bone fillers based on alendronate-loaded poly(e-caprolactone)/hydroxyapatite microspheres," J Mater Sci. vol. 22 pp. 547-555 (2011).
Chen et al., "Using nanoparticles to enable simultaneous radiation and photodynamic therapies for cancer treatment," Journal of nanoscience and nanotechnology, vol. 6, pp. 1159-1166 (2006).
Cheng et al., "Highly efficient drug delivery with gold nanoparticle vectors for in vivo photodynamic therapy of cancer." J. Am. Chem. Soc., vol. 130(32), pp. 10643-10647 (2008).
Cheng et al., "Near Infrared Light-Triggered Drug Generation and Release From Gold Nanoparticle Carriers for Photodynamic Therapy," Small, vol. 10, No. 9, pp. 1799-1804 (13 pages) (Feb. 2014).
Cho et al., "Targeted delivery of siRNA-generating DNA nanocassettes using multifunctional nanoparticles," vol. 9, No. 11, p. 1964-1973 (2013).
Cobley et al., "Gold nanostructures: a class of multifunctional materials for biomedical applications," Chem. Soc. Rev., vol. 40, pp. 44-56 (2011).
Coleman, et al., "Latest research and clinical treatment of advanced-stage epithelial ovarian cancer," Nat Rev Clin Oncol , vol. 10, pp. 211-224 (2013).
Communication corresponding to European Application No. 15851357.2-1110 dated Nov. 11, 2022.
Communication corresponding to European Application No. 15851357.2-1110 dated Nov. 15, 2022.
Communication corresponding to European Application No. 15851357.2-1110 dated Dec. 1, 2022.
Communication of Extended European Search Report corresponding to Application No. 15851357.2 dated Feb. 28, 2018.
Communication of the Extended European Search Report corresponding to European Application No. 14860910.0 dated Jun. 27, 2017.
Communication regarding Oral proceedings corresponding to European Application No. 15851357.2-1110 dated Aug. 23, 2022.
Communication regarding Oral proceedings corresponding to European Application No. 15851357.2 dated Dec. 14, 2022.
Corrected Notice of Allowability corresponding to U.S. Appl. No. 16/302,185 dated Dec. 14, 2021.
Craig, B. D.; Anderson, D. B., eds. (1995) Handbook of Corrosion Data, Materials Park, Ohio: ASM International, pp. 76 and 77.
Cunha et al., "Rationalization of the entrapping of the bioactive molecules into a series of functionalized porous zirconium terephthalate MOFs," J. Mater, Chem., vol. 1, pp. 1101-1108 (2013).
Cutler et al., "Spherical Nucleic Acids," Journal of the American Chemical Society, 134, p. 1 376-1391 (2012).
Dai et al. Electron Crystallography Reveals Atomic Structures of Metal-Organic Nanoplates with M12 (µ3-O) 8 (µ3-OH) 8 (µ2-OH) 6 (M=Zr, Hf) Secondary Building Units. Inorganic Chemistry 56, 8128-8134 (2017).
DeKrafft et al, "Zr- and Hf-based nanoscale metal-organic frameworks as contrast agents for computed tomography," J Mater Chem; 22(35), pp. 18139-18144 (2012).
DeKrafft et al., "Iodinated Nanoscale Coordination Polymers as Potential Contrast Agents for Computed Tomography**," Angewandte Chemie, vol. 48, pp. 9901-9904 (2009).

(56) References Cited

OTHER PUBLICATIONS

Della Rocca et al., "Nanoscale Metal-Organic Frameworks for Biomedical Imaging and Drug Delivery," Acc. Chem. Res., vol. 44, No. 10, pp. 957-968 (2011).
Demel et al., "Lanthanide-Porphyrin Hybrids: from Layered Structures to Metal-Organic Frameworks with Photophysical Properties," Inorg. Chem., 52; pp. 2779-2786 (2013).
Deng et al., "Irradiation and anti-PD-L1 treatment synergistically promote antitumor immunity in mice," The Journal of clinical investigation, 124, 687 (2014).
Dinca et al., "Hydrogen Storage in Microporous Metal-Organic Frameworks with Exposed Metal Sites," Angew Chem Int Edit 47, p. 6766-6779 (2008).
Djurovich et al., "Cyclometalated iridium and platinum complexes as singlet oxygen photosensitizers: quantum yields, quenching rates, and correlation with electronic structures." Dalton Transactions, 34, pp. 3763-3770 (2007).
Dolmans et al., "Photodynamic therapy for cancer." Nature Reviews Cancer, vol. 3, pp. 380-387 (May 2003).
Dougherty, "Photodynamic Therapy," Photochem. and Photobiol., vol. 58, No. 6, pp. 895-900 (Dec. 1993).
Driggers (ed), Encyclopedia of Optical Engineering, vol. 1, pp. 324-325 (2003).
Duan et al. "Immunostimulatory nanomedicines synergize with checkpoint blockade immunotherapy to eradicate colorectal tumors," nature communications, 10:1899, pp. 1-15 (2019).
Dunn et al., "Cancer immunoediting: from immunosurveillance to tumor escape," Nature Immunology vol. 3, pp. 991-998 (2002). [Abstract—pp. 1-14].
Elsaie (ed), Photodynamic Therapy New Research, Chapter 2: Nanostructured Third Generation Photosensitizers for Anticancer Photodynamic Therapy, 2013 (abstract only).
Ercole et al. "Cholesterol Modified Self-Assemblies and Their Application to Nanomedicine," Biomacromolecules, vol. 16, pp. 1886-1914 (2015).
Ethirajan et al., "The role of porphyrin chemistry in tumor imaging and photodynamic therapy." Chem Soc Rev, vol. 40(1), pp. 340-362 (2011).
European Search Report corresponding to European application No. 17800330 dated Nov. 12, 2019.
Extended European Search Report corresponding to Application No. 12810577.2 dated Feb. 4, 2015.
Extended European Search Report corresponding to European Application No. 19151591.5 dated May 13, 2019.
Extended European Search Report Corresponding to European Application No. 18840272.1 dated Jun. 17, 2021.
Fang et al., "The EPR effect: Unique features of tumor blood vessels for drug delivery, factors involved, and limitations and augmentation of the effect," Adv. Drug Deliv. Rev., vol. 63, No. 3, pp. 136-151 (Mar. 2011).
Feng et al., "Metal-Organic Frameworks Based on Previously Unknown Zr8/Hf8 Cubic Clusters," Inorganic Chemistry, vol. 52, No. 21, pp. 12661-12667 (2013).
Feng et al., "Zirconium-Metalloporphyrin PCN-222: Mesoporous Metal-Organic Frameworks with Ultrahigh Stability as Biomimetic Catalysts**," Angew. Chem. Int. Ed., vol. 51, No. 41, pp. 10307-10310 (2012).
Feng et al., "Zirconium-Metalloporphyrin PCN-222: Mesoporous Metal-Organic Frameworks with Ultrahigh Stability as Biomimetic Catalysts**," Angew. Chem., vol. 124, pp. 10453-10456 (2012).
Fire et al., "Potent and specific genetic interference by double-stranded RNA in Caenorhabditis elegans," Nature, vol. 391, p. 806-811 (Feb. 1998).
Foged, "siRNA Delivery with Lipid-based Systems:Promises and Pitfalls," Curr Top Med Chem, vol. 12, p. 97-107 (2012).
Freitas et al., "Biological basis for analysis of lasers' action in infectious processes. Biofilm, Interaction of light with matter,pathophysiological aspects," in Microbial pathogens and strategies for combating them: science, technology and education (A. Méndez-Vilas, Ed.), pp. 306-310 (2013).
Gao et al., "Metal-metalloporphyrin frameworks: a resurging class of functional materials," Chemical Society Reviews, vol. 43, pp. 5841-5866 (2014).
Garcia-Fresnadillo et al., "Singlet-Oxygen (1Δg) Production by Ruthenium (II) complexes containing polyazaheterocyclic ligands in methanol and in water." Helvetica Chimica Acta, vol. 79(4), pp. 1222-1238 (1996).
Giger et al. "Gene delivery with bisphosphonate-stabilized calciun1 phosphate nanoparticles," Journal of Controlled Release. vol. 150 pp. 87-93 (2011).
Giraudo et al. "An amino-bisphosphonate targets MMP-9-expressing macrophages and angiogenesis to impair cervical carcinogenesis," The Journal of Clinical Investigation. vol. 114, No. 5 pp. 623-633 (2004).
Giustini et al., "Microstructure and Dynamics of the Water-in-Oil CTAB/n-Pentanol/n-Hexane/Water Microemulsion: A Spectroscopic and Conductivity Study," Journal of Physical Chemistry, vol. 100, No. 8, pp. 3190-3198 (1996).
Graf et al., "A General Method for the Controlled Embedding of Nanoparticles in Silica Colloids," Langmuir, vol. 22, No. 13, pp. 5604-5610 (2006).
Graf et al., "A General Method To Coat Colloidal Particles with Silica," Langmuir, vol. 19, No. 17 pp. 6693-6700 (2003).
Graham et al., "The classic Wells-Dawson polyoxometalate, K6 [α-P2W18O62]· 14H2O. Answering an 88 year-old question: what is its preferred, optimum synthesis?" Inorganic Chemistry, vol. 47(9), pp. 3679-3686 (2008).
Granados-Oliveros, "Visible light production of superoxide anion with MCarboxyphenylporphyrins (M=H, Fe, Co, Ni, Cu, and Zn) free and anchored on TiO2: EPR characterization," Journal of Molecular Catalysis A: Chemical, vol. 339, 1-2, pp. 79-85 (2011).
Hafeman et al. "Evaluation of liposomal clodronate for treatment of malignant histiocytosis in dogs," Cancer Immunol. Immunother. vol. 59 pp. 441-452 (2010).
Hajri et al., "In vitro and in vivo efficacy of photofrin and pheophorbide a, a bacteriochlorin, in photodynamic therapy of colonic cancer cells," Photochem Photobiol, vol. 75, No. 2, pp. 140-148 (2002).
Hamblin et al., "Photodynamic therapy: a new antimicrobial approach to infectious disease?" Photoch Photobio Sci, vol. 3(5), pp. 436-450 (2004).
Hauptvogel et al., "Flexible and Hydrophobic Zn-Based Metal-Organic Framework," Inorg. Chem., vol. 50, pp. 8367-8374 (2011).
He et al. "Self-assembled Nanoscale Coordination Polymers Carrying siRNAs and Cisplatin for Effective Treatment of Resistant Ovarian Cancer," Author Manuscript, available in PMC 2016, pp. 1-25, published in final edited form as Biomaterials, vol. 36, pp. 124-133 (2015).
He et al., "Core-shell nanoscale coordination polymers combine chemotherapy and photodynamic therapy to potentiate checkpoint blockade cancer immunotherapy." Nature Communications, vol. 7 (2016).
He et al., Nanoscale Coordination Polymers Codeliver Chemotherapeutics and siRNAs to Eradicate Tumors of Cisplatin-Resistant Ovarian Cancer, JACS, vol. 138, pp. 6010-6019 (2016).
He et al., "Nanoscale Metal-Organic Frameworks for Real-Time Intracellular pH Sensing in Live Cells," J. Am. Chem. Soc., vol. 136, No. 35, pp. 12253-12256 (2014).
He et al., "Nanoscale Metal-Organic Frameworks for the Co-Delivery of Cisplatin and Pooled siRNAs to Enhance Therapeutic Efficacy in Drug-Resistant Ovarian Cancer Cells," J. Am. Chem. Soc., vol. 136, No. 14, pp. 5181-5184 (2014).
He et al., "Self-assembled core-shell nanoparticles for combined chemotherapy and photodynamic therapy of resistant head and neck cancers." ACS Nano, vol. 9(1), pp. 991-1003 (2015).
Henderson et al., "Interaction of Photodynamic Therapy and Hyperthermia: Tumor Response and Cell Survival Studies after Treatment of Mice in Vivo," Cancer research, vol. 45, pp. 6071-6077 (1985).
Horcajada et al., "Porous metal-organic-framework nanoscale carriers as a potential platform for drug delivery and imaging," Nat Mater., vol. 9, pp. 172-178 (2010).

(56) References Cited

OTHER PUBLICATIONS

Horikawa et al., "A Programmable Signaling Molecular Recognition Nanocavity Prepared by Molecular Imprinting and Post-Imprinting Modifications." Angew. Chem., vol. 128, pp. 13217-13221 (2016).
Huxford-Phillips et al., "Lipid-coated nanoscale coordination polymers for targeted cisplatin delivery," RSC Advances, vol. 3, No. 34, pp. 14438-14443 (Jan. 2013).
Huynh et al., "In situ conversion of porphyrin microbubbles to nanoparticles for multimodality imaging." Nat Nanotechnol, vol. 10(4), pp. 325-332 (2015).
Idris et al., "In vivo photodynamic therapy using upconversion nanoparticles as remote-controlled nanotransducers." Nat. Med., vol. 18(10), pp. 1580-1585 (2012).
Intention to Grant corresponding to European Application No. 15851357.2 dated Jan. 30, 2020.
International Preliminary Report on Patentability Corresponding to International application No. PCT/US 2018/045005 dated Feb. 13, 2020.
International Search Report and the Written Opinion of the International Searching Authority Corresponding to International application No. PCT/US 2018/045005 dated Oct. 3, 2018.
Interview Summary corresponding to U.S. Appl. No. 15/034,799 dated Jul. 5, 2018.
Interview Summary corresponding to U.S. Appl. No. 16/800,855 dated Oct. 27, 2021.
Jerjes et al., "Photodynamic therapy vs. photochemical internalization: the surgical margin," Head & Neck Oncology, vol. 3(1):53, pp. 1-2 (2011).
Ji et al., "Size Control of Gold Nanocrystals in Citrate Reduction: The Third Role of Citrate," J. Am. Chem. Soc., vol. 129, pp. 13939-13948 (2007).
Jin et al. "Energy Transfer from Quantum Dots to Metal-Organic Frameworks for Enhanced Light Harvesting" and Supporting Information, Journal of the American Chemical Society, vol. 135, pp. 955-958, S1-S13 (2013).
Jin et al., "Targeting-Triggered Porphysome Nanostructure Disruption for Activatable Photodynamic Therapy," Advanced Healthcare Materials, vol. 3, No. 8, pp. 1240-1249 (2014).
Kalayda et al., "Synthesis, Structure, and Biological Activity of New Azine-Bridged Dnuclear Platinum(II) Complexes," Eur. J. Inorg. Chem., pp. 4347-4355 (2003).
Kanofsky, "Measurement of singlet-oxygen In Vivo: Progress and Pitfalls," Photochem Photobiol., vol. 87, No. 1, pp. 14-17 (2011).
Kaščáková et al.,"X-ray-induced radiophotodynamic therapy (RPDT) using lanthanide micelles: Beyond depth limitations," Nano Research, vol. 8, No. 7, pp. 2373-2379 (2015).
Kelland, "The resurgence of platinum-based cancer chemotherapy,". Nature Reviews Cancer , 7, 573-584 (2007).
Kitabwalla et al., "RNA interference—a new weapon against HIV and beyond," The New England Journal of Medicine, vol. 347, No. 17, pp. 1364-1367 (Oct. 24, 2002).
Kroemer et al., "Immunogenic Cell Death in Cancer Therapy," Annu. Rev. Immunol., vol. 31, pp. 51-72 (Mar. 2013).
Kudinov et al., "On the Possibility of Combining Radiotherapy and Photodynamic Therapy." CLEO: Science and Innovations. Optical Society of America, pp. 1-2 (2014).
Kumar et al., "In vivo biodistribution and clearance studies using multimodal organically modified silica nanoparticles.," ACS nano, vol. 4, No.2, pp. 699-708 (19 pages) (Feb. 23, 2010).
Lal et al., "Nanoshell-enabled photothermal cancer therapy: impending clinical impact," Acc. Chem. Res., vol. 41, No. 12, pp. 1842-1851. (Dec. 2008).
Lan et al., "Nanoscale metal-organic frameworks for phototherapy of cancer," Coordination Chemistry Reviews, vol. 379, No. 15, pp. 65-81 (2019).
Lan et al., "Nanoscale Metal-Organic Layers for Deeply Penetrating X-ray-Induced Photodynamic Therapy," and Supporting Information, Angew. Chem., vol. 129, No. 40, 34 pages (2017).
Landesman-Milo et al. (2015) "Nanomedicine as an emerging platform for metastatic lung cancer therapy," Cancer Metastasis Reviews, vol. 34, pp. 291-301, published online May 7, 2015.
Lee et al., "Disulfide-Based Multifunctional Conjugates for Targeted Theranostic Drug Delivery," Accounts of Chemical Research, vol. 48, pp. 2935-2946 (2015).
Lee et al., "Light-Harvesting Metal-Organic Frameworks (MOFs): Efficient Strut-to-Strut Energy Transfer in Bodipy and Porphyrin-Based MOFs," Journal of the American Chemical Society, vol. 133, pp. 15858-15861 (2011).
Lee et al., "Metal-organic framework materials as catalysts," Chem Soc Rev, 38, 1450-1459 (2009).
Lee et al., "Porphyrins & Phthalocyanines web themed issue," Chemical Communications, vol. 48, pp. 5512-5514 (2012).
Leigh, "Comprehensive Coordination Chemistry II From Biology to Nanotechnology," Journal of Organometallic Chemistry. vol. 689, No. 16, pp. 2733-2742 (2004).
Letter regarding decision to grant a Japanese Patent corresponding to Japanese Patent Application No. 2014-520238 dated Oct. 31, 2016.
Levine, D., et al. "Olsalazine-Based Metal-Organic Frameworks as Biocompatible Platforms for H2 Adsorption and Drug Delivery." Journal of the American Chemical Society 138, 10143-10150 (2016).
Li et al., "Design and synthesis of an exceptionally stable and highly porous metal-organic framework" Nature 402, p. 276-279 (1999).
Liu et al., "Coercing bisphosphonates to kill cancer cells with nanoscale coordination polymerst," Chem. Commun. vol. 48 pp. 2668-2670 (2012).
Liu et al., "Phosphorescent Nanoscale Coordination Polymers as Contrast Agents for Optical Imaging**," Angewandte Chemie International Edition, vol. 50, pp. 3696-3700 (2011).
Liu et al., "Self-assembled nanoscale coordination polymers with trigger release properties for effective anticancer therapy," Author manuscript, Nature Communications, pp. 1-25 (2014).
Liu et al., "Self-assembled nanoscale coordination polymers with trigger release properties for effective anticancer therapy," Nature Communications, vol. 5, 4182, pp. 1-11 (2014).
Loo et al., "Immunotargeted Nanoshells for Integrated Cancer Imaging and Therapy," Nano letters, vol. 5, No. 4, pp. 709-711 (2005).
Lovell et al., "Porphysome nanovesicles generated by porphyrin bilayers for use as multimodal biophotonic contrast agents," Nat. Mater., vol. 10(4), pp. 324-332 (2011).
Lowery et al., "Cost-effectiveness of early palliative care intervention in recurrent platinum-resistant ovarian cancer," Gynecol Oncol 2013, 130, p. 426-430 (2013).
Lowry et al., "Single-Layer Electroluminescent Devices and Photoinduced Hydrogen Production from an Ionic Iridium(III) Complex." Chem. Mater. vol. 17, pp. 5712-5719 (2005).
Lu et al., "A Chlorin-Based Nanoscale Metal-Organic Framework for Photodynamic Therapy of Colon Cancers," J. Am. Chem. Soc., vol. 137, No. 24 (11 pages), pp. 7600-7603 (2015).
Lu et al., "Chlorin-based Nanoscale Metal-Organic Framework Systemically Rejects Colorectal Cancers via Synergistic Photodynamic Therapy and Checkpoint Blockade Immunotherapy." Journal of the American Chemical Society, 138, pp. 12502-12510 (2016).
Lu et al., "Low Dose X-ray Radiotherapy-Radiodynamic Therapy via Nanoscale Metal-organic Frameworks Enhances Checkpoint Blockade Immunotherapy" Nature Biomedical Engineering (Mar. 28, 2018) DOI: 10.1038/541551-018-0203-4.
Lu et al.. "Nanoscale Metal-Organic Framework for Highly Effective Photodynamic Therapy of Resistant Head and Neck Cancer," J. Am. Chem. Soc., vol. 136(48), pp. 16712-16715 (Nov. 19, 2014).
Mack et al., "The effects of terbium on the cellular accumulation of cisplatin in MDA-MB-231 human breast tumor cells," Cancer Chemotherapy and Pharmacology. vol. 39, pp. 217-222 (1997).
Maeda et al., "Mechanism of tumor-targeted delivery of macromolecular drugs, including the EPR effect in solid tumor and clinical overview of the prototype polymeric drug SMANCS," J. Controlled Release, vol. 74, pp. 47-61 (2001).
Maggiorella et al., "Nanoscale radiotherapy with hafnium oxide nanoparticles," Future oncology 8, 1167-1181 (2012).

(56) References Cited

OTHER PUBLICATIONS

Manna et al., "Metal-Organic Framework Nodes Support Single-Site Magnesium—Alkyl Catalysts for Hydroboration and Hydroamination Reactions," Journal of the American Chemical Society, vol. 138, pp. 7488-7491 (2016).
Marchesini et al., "Ex vivo optical properties of human colon tissue." Lasers Surg. Med., vol. 15(4), pp. 351-357 (1994).
Matsumura et al., "A New Concept for Macromolecular Therapeutics in Cancer Chemotherapy: Mechanism of Tumoritropic Accumulation of Proteins and the Antitumor Agent Smancs," Cancer Research, vol. 46, pp. 6387-6392 (1986).
Matsuo et al., "TOPK inhibitor induces complete tumor regression in xenograft models of human cancer through inhibition of cytokinesis," Science Translational Medicine, Oct. 22, 2014, vol. 6, 259ra145, pp. 1-9.
Mellman et al., "Cancer immunotherapy comes of age," Nature, vol. 480, pp. 480-489 (2011).
Meng, H.; Liong, M.; Xia, T.; Li, Z.; Ji, Z.; Zink, J. I.; Nel, A. E. ACS nano 4, p. 4539-4550 (2010).
Merkel et al., "Radiationless decay of singlet molecular oxygen in solution. Experimental and theoretical study of electronic-to-vibrational energy transfer," J. Am. Chem. Soc., vol. 94, No. 21, pp. 7244-7253 (1972).
Min, Y., et al. Antigen-capturing nanoparticles improve the abscopal effect and cancer immunotherapy. Nature nanotechnology 12, 877 (2017).
Moan et al., "The photodegradation of porphyrins in cells can be used to estimate the lifetime of singlet oxygen," Photochem Photobiol., vol. 53, No. 4, pp. 549-553 (1991).
Morris et al., "Nucleic Acid-Metal Organic Framework (MOF) Nanoparticle Conjugates," J. Am. Chem. Soc., vol. 136, No. 20, pp. 7261-7264 (2014).
Morris et al., "Synthesis, Structure, and Metalation of Two New Highly Porous Zirconium Metal-Organic Frameworks," Inorg. Chem., 51, pp. 6443-6445 (2012).
Mukhopadhyay et al., "Conjugated Platinum (IV)—Peptide Complexes for Targeting Angiogenic Tumor Vasculature," Bioconjugate Chemistry, vol. 19, No. 1, pp. 39-49 (2008).
Mura et al., "Lipid prodrug nanocarriers in cancer therapy," Journal of Controlled Release, vol. 208, pp. 25-41 (2015).
Navath et al., "Dendrimer-drug conjugates for tailored intracellular drug release based on glutathione levels." Bioconjugate Chemistry, vol. 19(12), pp. 2446-2455 (2008).
Neufeld et al. (2020) High-Z metal-organic frameworks for X-ray radiation-based cancer theranostics, Accepted Manuscript, 11 pages [Published in final edited form as: Chem. Eur. J., vol. 27, Iss. 10, pp. 3229-3237].
Ng et al., "Molecular interactions in organic nanoparticles for phototheranostic applications." Chem. Rev., vol. 115(19), pp. 11012-11042 (2015).
Ni et al., "Nanoscale metal-organic frameworks enhance radiotherapy to potentiate checkpoint blockade immunotherapy." Nat. Commun., vol. 9(1), Article No. 2351 (2018).
Notice of Allowance corresponding to U.S. Appl. No. 16/302,185 dated Sep. 30, 2021.
Corrected Notice of Allowability corresponding to U.S. Appl. No. 16/302,185 dated Oct. 8, 2021.
Notice of allowance and Fee(s) Due, Examiner-Initiated Interview Summary, and Notice of Allowability Corresponding to U.S. Appl. No. 14/131,575 dated Feb. 27, 2017.
Notice of Allowance and Interview Summary corresponding to U.S. Appl. No. 15/034,799 dated Jun. 14, 2019.
Notice of Allowance and Interview Summary corresponding to U.S. Appl. No. 15/884,036 dated Jun. 24, 2020.
Notice of Allowance corresponding to Chinese Patent Application No. 201480072258.0 dated Apr. 20, 2020.
Notice of Allowance corresponding to Chinese Patent Application No. 201880064003.8 dated Nov. 2, 2022.
Notice of Allowance corresponding to Chinese Patent Application Serial No. 201580068173X dated Aug. 12, 2019.
Notice of Allowance corresponding to U.S. Appl. No. 15/613,847 dated Nov. 6, 2019.
Notice of Allowance corresponding to U.S. Appl. No. 15/518,665 dated Sep. 26, 2018.
Notice of Allowance corresponding to U.S. Appl. No. 15/884,036 dated Apr. 10, 2019.
Notice of Allowance corresponding to U.S. Appl. No. 16/235,752 dated May 6, 2020.
Notice of Opposition corresponding to European Patent Application No. 15851357.2-1110 dated Apr. 7, 2021.
Notices of Opposition corresponding to European Patent Application No. 15851357.2-1110 dated Apr. 20, 2021.
Notification Concerning Transmittal of International Preliminary Report on Patentability (Chapter I of the Patent CooperationTreaty) corresponding to International Patent Application No. PCT/US2012/045954 dated Jan. 23, 2014.
Notification Concerning Transmittal of International Preliminary Report on Patentability (Chapter I of the Patent CooperationTreaty) corresponding to International Patent Application No. PCT/US2014/064388 dated May 19, 2016.
Notification Concerning Transmittal of International Preliminary Report on Patentability and the Written Opinion of the International Searching Authority corresponding to International Application No. PCT/US2015/055574 dated Apr. 27, 2017.
Notification Concerning Transmittal of International Preliminary Report on Patentability (Chapter I of the Patent Cooperation Treaty) corresponding to International Patent Application No. PCT/US2009/034867 dated Sep. 2, 2010.
Notification Concerning Transmittal of International Preliminary Report on Patentability for International Application No. PCT/US2017/033822, dated Nov. 29, 2018.
Notification of the First Office Action Corresponding to Chinese Application No. 201880064003.8 dated Jul. 21, 2021.
Notification of Transmittal of the International Search Authority and the Written Opinion of the International Searching Authority, or the Declaration corresponding to PCT/US2015/055574 dated Feb. 18, 2016.
Notification of Transmittal of the International Search Report and the Written Opinion of the International Searching Authority, or the Declaration corresponding to International Application No. PCT/US2012/045954 dated Jan. 28, 2013.
Notification of Transmittal of the International Search Report and the Written Opinion of the International Searching Authority, or the Declaration corresponding to International Application No. PCT/US14/64388 dated Feb. 9, 2015.
Notification of Transmittal of the International Search Report and the Written Opinion of the International Searching Authority, or the Declaration corresponding to International Application No. PCT/US2009/034867 dated Feb. 3, 2010.
Notification of Transmittal of the International Search Report and the Written Opinion of the International Searching Authority, or the Declaration for International Application No. PCT/US1733822, dated Aug. 29, 2017.
Nyman: "Polyoxometalates and Other Metal-Oxo Clusters in Nature," In: Encyclopedia of Geochemistry, Springer International Publishing, pp. 1-5 (2016).
Office Action (Restriction Requirement) corresponding to U.S. Appl. No. 14/131,575 dated Nov. 20, 2015.
Office Action (Restriction Requirement) corresponding to U.S. Appl. No. 15/613,847 dated Jun. 18, 2018.
Office Action (Restriction Requirement) corresponding to U.S. Appl. No. 15/518,665 dated Dec. 12, 2017.
Office Action (Restriction Requirement) corresponding to U.S. Appl. No. 15/884,036 dated Nov. 6, 2018.
Office Action (Restriction Requirement) corresponding to U.S. Appl. No. 16/235,752 dated Jul. 10, 2019.
Office Action (Restriction Requirement) corresponding to U.S. Appl. No. 16/302,185 dated Jan. 13, 2020.
Office Action (Restriction Requirement) corresponding to U.S. Appl. No. 16/800,855 dated May 7, 2021.
Office Action and Search Report corresponding to Chinese Patent Application Serial No. 2019110019242 dated Jun. 8, 2022.

(56) References Cited

OTHER PUBLICATIONS

Office Action corresponding to Chinese Patent Application No. 2019110019242 dated Jan. 20, 2023.
Office Action corresponding to Chinese Patent Application No. 2014800722580 dated Jun, 27, 2018.
Office Action corresponding to Chinese Patent Application No. 2014800722580 dated Mar. 20, 2019.
Office Action corresponding to Chinese Patent Application No. 2014800722580 dated Nov. 11, 2019.
Office Action corresponding to Chinese Patent Application No. 201780031000X dated Jun. 10, 2020.
Office Action corresponding to Chinese Patent Application No. 201780031000X dated Dec. 3, 2021.
Office Action corresponding to Chinese Patent Application No. 201780031000X dated Apr. 2, 2021.
Office Action corresponding to Chinese Patent Application No. 201780031000X dated Jun. 28, 2022 (translatlon).
Office Action corresponding to Chinese Patent Application No. 2018800640038 dated Mar. 9, 2022.
Office Action corresponding to Chinese Patent Application Serial No. 201580068173X date Oct. 31, 2018.
Office Action corresponding to Chinese Patent Application Serial No. 201580068173X dated Apr. 10, 2019.
Office Action corresponding to European Application No. 17800330. 7-1112 dated Sep. 9, 2021.
Office Action corresponding to European Application Serial No. 15851357.2 dated Jun. 7, 2019.
Office Action corresponding to European Application Serial No. 19151591.5 dated Oct. 27, 2021.
Office Action corresponding to European Patent Application Serial No. 12810577.2 dated Jan. 5, 2017.
Office Action corresponding to European Patent Application Serial No. 14860910.0 dated Jan. 29, 2019.
Office Action corresponding to European Patent Application Serial No. 14860910.0-1109 dated Jan. 27, 2021.
Office Action corresponding to Japanese Application No. 2017-520324 dated Jul. 9, 2019.
Office Action corresponding to Japanese Patent Application No. 2017520324 dated Feb. 12, 2020.
Office Action corresponding to Japanese Patent Application No. 2014-520238 dated Mar. 14, 2016.
Office Action corresponding to Japanese Patent Application No. 2016-528894 dated Jul. 17, 2018.
Office Action corresponding to Japanese Patent Application No. 2016-528894 dated Feb. 4, 2019.
Office Action corresponding to Japanese Patent Application No. 2019-167976 dated Jul. 27, 2020.
Office Action corresponding to Japanese Patent Application No. 2018-561060 dated Apr. 5, 2021.
Office Action corresponding to Japanese Patent Application No. 2018-561060 dated Nov. 8, 2021.
Office Action corresponding to Japanese Patent Application No. 2020-505792 dated Sep. 12, 2022.
Office Action corresponding to U.S. Appl. No. 14/131,575 dated Aug. 12, 2016.
Office Action corresponding to U.S. Appl. No. 14/131,575 dated Dec. 16, 2016.
Office Action corresponding to U.S. Appl. No. 15/034,799 dated Sep. 21, 2017.
Office Action corresponding to U.S. Appl. No. 15/034,799 dated Mar. 22, 2018.
Office Action corresponding to U.S. Appl. No. 15/034,799 dated Sep. 21, 2018.
Office Action corresponding to U.S. Appl. No. 15/613,847 dated Dec. 10, 2018.
Office Action corresponding to U.S. Appl. No. 15/034,799 dated Mar. 20, 2019.
Office Action corresponding to U.S. Appl. No. 15/613,847 dated Jun. 5, 2019.
Office Action corresponding to U.S. Appl. No. 15/518,665 dated May 16, 2018.
Office Action corresponding to U.S. Appl. No. 15/884,036 dated Jan. 30, 2019.
Office Action corresponding to U.S. Appl. No. No. 16/235,752 dated Oct. 24, 2019.
Office Action corresponding to U.S. Appl. No. 15/884,036 dated Nov. 21, 2019.
Office Action corresponding to U.S. Appl. No. 16/235,752 dated Feb. 20, 2020.
Office Action corresponding to U.S. Appl. No. 16/302,185 dated Apr. 17, 2020.
Office Action correspoonding to U.S. Appl. No. 16/302,185 dated Jul. 28, 2020.
Office Action corresponding to U.S. Appl. No. 16/302,185 dated Jan. 8, 2021.
Office Action corresponding to U.S. Appl. No. 16/800,855 dated Jan. 5, 2022.
Office Action corresponding to U.S. Appl. No. 16/800,855 dated Jul. 28, 2022.
Office Action corresponding to U.S. Appl. No. 16/577,818 dated Aug. 5, 2021.
Office Action corresponding to U.S. Appl. No. 16/577,818 dated Apr. 14, 2022.
Office Communication corresponding to U.S. Appl. No. 16/302,185 dated Jun. 4, 2021.
Official Action (Restriction Requirement) corresponding to U.S. Appl. No. 12/918,748 dated Oct. 18, 2012.
Official Action corresponding to U.S. Appl. No. 12/918,748 dated Mar. 28, 2013.
Pass, "Photodynamic Therapy in Oncology: Mechanisms and Clinical Use," Journal of the National Cancer Institute, vol. 85, No. 6, pp. 443-456 (1993).
Pinna et al., "Non-Aqueous Synthesis of High-Purity Metal Oxide Nanopowders Using an Ether Elimination Process," Advanced Materials, vol. 16 (23-24), pp. 2196-2200 (2004).
Polley et al. "Atomistic Simulations of a Multicomponent Asymmetric Lipid Bilayer," The Journal of Physical Chemistry B, vol. 116, pp. 13403-13410 (Year: 2012).
Putaj et al. "Polyoxometalates containing late transition and noble metal atoms," Coordination Chemistry Reviews, vol. 255, Iss. 15-16, pp. 1642-1685 (2011).
Ramírez et al. "Glucuronidation of OTS167 in Humans Is Catalyzed by UDP-Glucuronosyltransferases UGT1A1, UGT1A3, UGT1A8, and UGT1A10," Drug Metabolism and Disposition, vol. 43, pp. 928-935 (2015).
Raouane et al. "Lipid Conjugated Oligonucleotides: A Useful Strategy for Delivery," Bioconjugate Chemistry, vol. 23, pp. 1021-1104 (2012).
Ravel et al., "Athena, Artemis, Hephaestus: data analysis for X-ray absorption spectroscopy using IFEFFIT." J. Synchrotron Rad., vol. 12(4), pp. 537-541 (2005).
Rehr et al., "Theoretical approaches to x-ray absorption fine structure." Rev. Mod. Phys., vol. 72(3), pp. 621-654 (2000).
Request to Change Date of Oral Proceedings corresponding to European Application No. 15851357.2 dated Feb. 22, 2022.
Retif et al. "Nanoparticles for radiation therapy enhancement: the key parameters," Theranostics, vol. 5, pp. 1030-1045 (2015).
Rieter et al., "Nanoscale Coordination Polymers for Platinum-Based Anticancer Drug Delivery," Journal of the American Chemical Society. vol. 130, No. 35, pp. 11584-11585 (2008).
Rieter et al., "Nanoscale Metal-Organic Frameworks as Potential Multimodal Contrast Enhancing Agents," J Am Chem Soc., vol. 128, No. 28, pp. 9024-9025 (2006).
Roberts, et al., "Identification of genes associated with platinum drug sensitivity and resistance in human ovarian cancer cells," Brit J Cancer, vol. 92, pp. 1149-1158 (2005).
Rodgers et al., "Lifetime of 02(IΔ) in Liquid Water As Determined by Time-Resolved Infrared Lummescence Measurements," J. Am. Chem. Soc., vol. 104, pp. 5541-5543 (1982).
Rosi, et al., "Rod Packings and Metal-Organic Frameworks Constructed from Rod-Shaped Sedcondary Building Units," J Am Chem Soc, vol. 127, pp. 1504-1518 (2005).

(56) References Cited

OTHER PUBLICATIONS

Roy et al., "Ceramic-based nanoparticles entrapping water-insoluble photosensitizing anticancer drugs: a novel drug-carrier system for photodynamic therapy." Journal of the American Chemical Society, vol. 125(26), pp. 7860-7965 (2003).
Salzano et al. (2014) "Polymeric micelles containing reversibly w phospholipid-modified anti-survivin siRNA: A promising strategy to overcome drug resistance in cancer," Cancer Letters, vol. 343, pp. 224-231.
Salzano et al. "Self-assembly nanoparticles for the delivery of bisphosphonates into tumors," International Journal of Pharmaceutics, vol. 403, No. 1-2, pp. 292-297 (2011).
Samia et al., "Semiconductor Quantum Dots for Photodynamic Therapy," J. Am. Chem. Soc., vol. 125, No. 51, pp. 15736-15737 (2003).
Scandola et al., "Photophysical properties of metal-mediated assemblies of porphyrins," Coord. Chem. Rev., vol. 250, pp. 1471-1496 (2006).
Schaate et al., "Modulated synthesis of Zr-Based metal-organic frameworks: from nano to single crystals," Chem-Eur J, 17, p. 6643-6651 (2011).
Schöder, "Head and Neck Cancer," Nuclear Oncology; Pathophysiology and Clinical Applications, Sprinter Science+Businessd Media New York, pp. 269-295 (2013).
Senge et al., "Temoporfin (Foscan®, 5,10,15,20-Tetra(m-Hydroxyphenyl)chlorin)—A Second-Generation Photosensitizer," Photochem. Photobiol., vol. 87, No. 6, pp. 1240-1296 (Sep. 2011).
Shahzad et al., "Novel strategies for reversing platinum resistance," Drug Resist Updates 12, p. 148-152 (2009).
Sheats, "History of Organometallic Polymers," Journal of Macromolecular Science: Part A—Chemistry, vol. 15, No. 6, pp. 1173-1199 (1981).
Sheng et al. (2011) "The intracellular plasmid DNA localization of cationic reducible cholesterol-disulfide lipids," Biomaterials, vol. 32, pp. 3507-3519.
Shi et al., "In-vitro osteogenesis of synovium stem cells induced by controlled release of bisphosphate additives from microspherical meso porous silica composite," Biomaterials. vol. 30, No. 23-24, pp. 3996-4005 (2009).
Shmeeda et al. "Delivery of zoledronic acid encapsulated in folate-targeted liposome results in potent in vitro cytotoxic activity on tumor cells," Journal of Controlled Release 146 pp. 76-83 (2010).
Smith et al., "Second window for in vivo imaging," Author Manuscript, 3 pages, published in final edited form as: Nat Nano, vol. 4(11), pp. 710-711 (2009).
Snyder et al., "Subcellular, Time-Resolved Studies of Singlet Oxygen in Single Cells," J. Am. Chem. Soc., vol. 127, pp. 14558-14559 (2005).
Spokoyny et al., "Infinite coordination polymer nano- and microparticle structures," Chem. Soc. Rev., vol. 38, pp. 1218-1227 (2009).
St-Denis et al., "Diffusivity of oxygen in water," Can J Chem Eng., vol. 49, No.6, pp. 885 (Dec. 1971).
Stevens et al. (2004) "A Folate Receptor-Targeted Lipid Nanoparticle Formulation for a Lipophilic Paclitaxel Prodrug," Pharmaceutical Research, vol. 21, No. 12, pp. 2153-2157.
Su et al., "Supramolecular Crafting of Self-Assembling Camptothecin Prodrugs with Enhanced Efficacy against Primary Cancer Cells," Theranostics, vol. 6, Iss. 7, pp. 1065-1074 (2016).
Summons for Oral Proceedings corresponding to European Application No. 15851357.2 dated Feb. 15, 2022.
Summons for Oral Proceedings corresponding to European Application No. 15851357.2 dated Mar. 1, 2022.
Summons for Oral Proceedings corresponding to European Application No. 15851357.2-1110 dated Oct. 27, 2022.
Sun et al., "Nanosized Camptothecin Conjugates for Single and Combined Drug delivery," European Journal of Biomedical Research, vol. 2, No. 1 pp. 8-15 (2016).
Takizawa et al., "Photooxidation of 1,5-dihydroxynaphthalene with iridium complexes as singlet oxygen sensitizers." Photochemical & Photobiological Sciences vol. 10(6), pp. 895-903 (2011).
Taylor-Pashow et al., "Post-synthetic modification of iron-carboxylate nanoscale metal-organic frameworks for imaging and drug delivery," Author Manuscript, J Am Chem Soc., pp. 1-10 (2009).
Taylor-Pashow et al., "Postsynthetic Modifications of Iron-Carboxylate Nanoscale Metal-Organic Frameworks for Imaging and Drug Delivery," J Am Chem Soc., vol. 131, No. 40, pp. 14261-14263 (2009).
Tranchemontagne et al., "Secondary building units, nets and bonding in the chemistry of metal-organic frameworks," Chem. Soc. Rev., vol. 38, pp. 1257-1283 (2009).
Uemura et al., "Prussian Blue Nanoparticles Protected by Poly(vinylpyrrolidone)," Journal of the American Chemical Society, vol. 125, No. 26, pp. 7814-7815 (2003).
Vaucher et al., "Molecule-Based Magnetic Nanoparticles: Synthesis of Cobalt Hexacyanoferrate, Cobalt Pentacyanonitrosylferrate, and Chromium Hexacyanochromate Coordination Polymers in Water-in-Oil Microemulsions," Nano Letters. vol. 2, No. 3, pp. 225-229 (2002).
Vaucher et al., "Synthesis of Prussian Blue Nanoparticles and Nanocrystal Superlattices in Reverse Microemulsions," Angew. Chem. Int. Ed. vol. 39, No. 10, pp. 1793-1796 (2000).
Vaughan, et al., "Rethinking ovarian cancer: recommendations for improving outcomes," Nat Rev Cancer, 11, 719-725, pp. 1-19 (2011).
Vesper et al., "Photodynamic therapy (PDT): An evolving therapeutic technique in head and neck cancer treatment," Head & Neck Cancer: Current Perspectives, Advances, and Challenges, Springer Netherlands, vol. 9789400758278, pp. 649-676 (2013).
Wang et al. "Disulfide Bond Bridge Insertion Turns Hydrophobic Anticancer Prodrugs into Self-Assembled Nanomedicines." Nano Letters, vol. 14, pp. 5577-5583, published Sep. 4, 2014. (Year: 2014).
Wang et al. "Metal-Organic Frameworks as A Tunable Platform for Designing Functional Molecular Materials," Author Manuscript, 32 pages, published in final edited form as: J. Am. Chem. Soc., vol. 135, No. 36, pp. 13222-13234 (2013).
Wang et al., "Comparison Study of Gold Nanohexapods, Nanorods, and Nanocages for Photothermal Cancer Treatment," ACS Nano, vol. 7, No. 3, pp. 2068-2077 (Feb. 2013).
Wang et al., "Elucidating Molecular Iridium Water Oxidation Catalysts Using Metal-Organic Frameworks: A Comprehensive Structural, Catalytic, Spectroscopic, and Kinetic Study," Journal of the American Chemical Society, vol. 134, pp. 19895-19908 (2012).
Wang et al., "Nanoparticle delivery of cancer drugs," Annual Review of Medicine, vol. 63, pp. 185-198 (2012).
Wang et al., "Near-infrared light induced in vivo photodynamic therapy of cancer based on upconversion nanoparticles." Biomaterials, vol. 32(36), pp. 6145-6154 (2011).
Wang et al., "One-Step Synthesis of β meso-Unsubstituted Dipyrromethane," Synlett, pp. 1267-1268 (1995).
Wang et al., "Postsynthetic modification of metal-organic frameworks," Chem Soc Rev 38, p. 1315-1329 (2009).
Wang et al., "Pt Nanoparticles@Photoactive Metal-Organic Frameworks: Efficient Hydrogen Evolution via Synergistic Photoexcitation and Electron Injection," Journal of the American Chemical Society, vol. 134(17), pp. 7211-7214 (2012).
Wang et al., "Synergistic Assembly of Heavy Metal Clusters and Luminescent Organic Bridging Ligands in Metal-Organic Frameworks for Highly Efficient X-ray Scintillation," Journal of the American Chemical Society, vol. 136(17), pp. 6171-6174 (2014).
Wang et al., "Synergistic Assembly of Heavy Metal Clusters and Luminescent Organic Bridging Ligands in Metal-Organic Frameworks for Highly Efficient X-ray Scintillation," [Supporting information for Journal of the American Chemical Society, vol. 136, pp. 6171-6174 (2014)] 13 pages.
White et al., "Photooxidation of Diglycine in Confined Media. Application of the Microreactor Model for Spin-Correlated Radical Pairs in Reverse Micelles and Water-in-Oil Microemulsions," Langmuir, vol. 21, No. 7, pp. 2721-2727 (2005).
Wong et al., "Fluorescence Probing of Inverted Micelles. The State of Solublized Water Clusters in Alkane/Diisooctyl Sulfosuccinate

(56) References Cited

OTHER PUBLICATIONS (Aerosol OT) Solution," Journal of the American Chemical Society, vol. 98, No. 9, pp. 2391-2397 (1976).

Xiong et al., "Traceable multifunctional micellar nanocarriers for cancer-targeted co-delivery of MDR-1 siRNA and doxorubicin," ACS nano, vol. 5, No. 6, p. 5202-5213 (2011).

Xu et al., "Nanoscale Metal-Organic Frameworks for Ratiometric Oxygen Sensing in Live Cells," Journal of the American Chemical Society, 138(7), pp. 2158-2161 (2016).

Xu et al., "Reverse micellar synthesis of CdS nanoparticles and self-assembly into a superlattice," Materials Letters, vol. 58, pp. 2623-2626 (2004).

Yamada et al., "Synthesis and Isolation of Cobalt Hexacyanoferrate/Chromate Metal Coordination Nanopolymers Stabilized by Alkylamino Ligand with Metal Elemental Control," Journal of the Amerlcan Chemical Society, vol. 126, pp. 9482-9483 (2004).

Yellepeddi et al., "Comparative evaluation of small-molecule chemosensitizers in reversal of cisplatin resistance in ovarian cancer cell," Anticancer Res 32, p. 3651-3658 (2012).

Yoon et al. "Efficient photosensitization by a chlorin-polyoxometalate supramolecular complex," Inorganic Chemistry, vol. 53, No. 1, pp. 3-5 (2014).

Yu et al., "Immobilization of polymer-stabilized metal colloids by a modified coordination capture: preparation of supported metal colloids with singular catalytic properties," Journal of Molecular Catalysis A: Chemical, vol. 142, pp. 201-211 (1999).

Zhang et al., "Antibody-linked spherical nucleic acids for cellular targeting," Journal of the American Chemical Society, 134, 16488-16491, pp. 1-11 (2012).

Zhang et al., "Biomimicry in metal-organic material," Coordination Chemistry Reviews, vol. 293-294, pp. 327-356 (2015).

Zhang et al., "Metal-Organic Frameworks Stabilize Solution-Inaccessible Cobalt Catalysts for Highly Efficient Broad-Scope Organic Transformations." J. Am. Chem. Soc., vol. 138, pp. 3241-3249 (2016).

Zhang et al., "Photosensitizing metal-organic framework enabling visible-light-driven proton reduction by a Wells-Dawson-type polyoxometalate." Journal of the American Chemical Society, vol. 137(9), pp. 3197-3200 (2015).

Zhang et al., "Three-Dimensional Lanthanoid-Containing Coordination Frameworks: Structure, Magnetic and Fluorescent Properties," European Journal of Inorganic Chemistry, pp. 766-772 (2005).

Zhao et al., "Synthesis and biochemical applications of a solid cyclic nitrone spin trap: a relatively superior trap for detective superoxide anions and glutathiyl radicals." Free Radical Biol. Med., vol. 31(5), pp. 599-606 (2001).

Zhu et al., "Merging Photoredox and Organometallic Catalysts in a Metal-Organic Framework Significantly Boosts Photocatalytic Activities." Angew. Chem., vol. 57(43), pp. 14090-14094 (2018).

Zou, et al., "Enhanced apoptosis of ovarian cancer cells via nanocarrier-mediated codelivery of siRNA and doxorubicin," Int J Nanomed, 7, pp. 3823-3835 (2012).

Allavena, P.; et al.,a "The Yin-Yang of tumorassociatedmacrophages in neoplastic progression and immune surveillance," ImmunolRev. 2008, 222 (1), pp.155-161.

An, J., (2009) "Cation-triggered drug release from a porous zinc-adeninate metal-organic framework," J Am. Chem. Soc, 131 (24), pp. 8376-8377.

Brahmer, J.R., et al., "Safety and activity of anti-PD-LI antibody in patients with advanced cancer,". New England Journal of Medicine 2012, 366, pp. 2455-2465.

Brody, J.D., et al.,(2010) "In situ vaccination with a TLR9 agonist induces systemic lymphoma regression: a phase I/II study," Journal of clinical oncology, 28, pp. 4324.

Castano, AP.,et al., (2006) "Photodynamic therapy and anti-tumour immunity," Nature Reviews Cancer 6, 535.

Chao, M. P.; et al (2010) "Calreticulin is the dominant pro-phagocytic signal on multiple human cancers and is counterbalanced by CD47," Sci. Transl. Med, 2(63), pp. 63ra94-63ra94.

Chao, Y., et al.,(2018) "Combined local immunostimulatory radio-isotope therapy and systemic immune checkpoint blockade imparts potent antitumour responses," Nature Biomedical Engineering, 2, 611.

Chen, Q.; et al., (2019) "Bioresponsive Protein Complex of aPDI and aCD47 Antibodies for Enhanced Immunotherapy," Nano Lett., 19 (8), pp. 4879-4889.

Chen, Q.; et al., (2019) "In situ sprayed bioresponsive immunotherapeutic gel for post-surgical cancer treatment," Nat. Nanotechnol., 14 (1), pp. 89-97.

Deng, L., et al.,(2014) "STING-dependent cytosolic DNA sensing promotes radiation-induced type I interferon-dependent antitumor immunity in immunogenic tumors," Immunity, 41, pp. 843-852.

Du, B.,et al., (2018) "Transport and interactions of nanoparticles in the Kidneys," Nature Reviews Materials.

Emming, S.,et al., (2019) "Tiered DNA sensors for escalating responses,". Science 365, 1375-1376.

Feng, M.; et al., (2019) "Phagocytosis checkpoints as new targets for cancer immunotherapy,". Nat. Rev. Cancer, 19 (10), pp 568-586.

Figdor, C.G., et al., "Dendritic cell immunotherapy: mapping the way," Nature medicine 2004, 10,475.

Gilliet, M., (2008) "Plasmacytoid dendritic cells: sensing nucleic acids in viral infection and autoimmune diseases," Nature Reviews Immunology, 8, pp. 5 594.

Goldman, B.;et al., (2009) "The cancer vaccine roller coaster.," Nature biotechnology, 27, pp. 129-138, 624.

Gong, T., et al., (2019) "DAMP-sensing receptors in sterile inflammation and inflammatory diseases," Nature Revrews Immunology, pp. 95-112.

Hu, Z., et al., (2018) "Towards personalized, tumour-specific, therapeutic vaccines for cancer,". Nature Reviews Immunology, 18, pp. 168-182.

International Preliminary Report correcsponding to International application No. PCT/US2021/033886 dated Dec. 1, 2022.

International Search Report and Written Opinion corresponding to International application No. PCT/US 2021/033886 dated Sep. 28, 2021.

Jaiswal, S.; et al.,(2009) "CD47 is upregulated on circulating hematopoietic stem cells and leukemia cells to avoid phagocytosis,". Cell, 138 (2), 15 pp. 271-285.

Ji P. (2019) "Strongly Lewis Acidic Metal-Oranic Frameworks for Continuous Flow Catalysis," Jour. Amer. Chem. Soc. vol. 141; pp. 14878-14888.

Jiang, W., et al., Designing nanomedicine for immuno-oncology. Nature Biomedical Engineering 2017, 1, 0029.

Karnath, et al., (2018)., "A Review on Imiquimod Therapy and Discussion on Optimal Management of Basal Cell Carcinomas," Clin. Drug Investig., 38 (10), 883-899.

Kawai, T., S. et al.,(2010) "The role of pattern-recognition receptors m innate immunity: update or Toll-like receptors," Nature immunology, 11, pp. 373-384.

Kepp, O., et al., (2019) "Oncolysis without virusesinducing systemic anticancer immune responses with local therapies,". Nature Reviews Clinical Oncology,pp. 1-16.

Klinman, D.M., (2004) "Immunotherapeutic uses of CpG oligodeoxynucleotides," Nature Reviews Immunology, 4, 249.

Kojima, Y.; et al., (2016) "CD47-blocking antibodies restore phagocytosis and prevent atherosclerosis,". Nature, 536 (7614), 86-90.

Kuai, R., et al., (2017) "Designer vaccine nanodiscs for personalized cancer immunotherapy," Nature materlals, 16, 18 Pages.

Lan, G., et al.,(2019) "Nanoscale Metal-Organic Framework Hierarchically Combines High-Z Components for Multifarious Radio-Enhancement". J Am. Chem. Soc., 141, pp. 6859-6863.

Liu, H., et al.,(2014) Structure-based programmmg of lymph-node targeting in molecular vaccines. Nature, 507, 519.

Liu, X.; et al., (2015) "CD47 blockade triggers T cell-mediated destruction of immunogenic tumors.," Nat. Med., 21 (10), 1209.

Lou, et al., (2019) "Advancing cancer immunotherapies with nanotechnology," Adv. Ther., 2 (4), 1800128.

Louttit, C.; et al., (2019) "Bioinspired nucleic acid structures for immune modulation," Biomater, 119287.

(56) References Cited

OTHER PUBLICATIONS

Luo, M., et al., "A STING-activating nanovaccine for cancer immunotherapy," Nature nanotechnology 2017, 12,648.
Ma, L., et al., Enhanced CAR-T cell activity against solid tumors by vaccine boosting through the chimeric receptor. Science 2019, 365, 162-168.
Mahoney, K.M., et al., (2015) "Combination cancer immunotherapy and new immunomodulatory targets," Nature reviews Drug discovery, 14, pp. 561-584.
Nam, J.; Son, S.; Park, K. S.; Zou, W.; Shea, L. D.; Moon, J. J., Cancer nanomedicine for combination cancer immunotherapy. Nat. Rev. Mater. 2019, 4 (6), 398-414.
Ni, K., et al., Nanoscale metal-organic frameworks enhance radiotherapy to potentiate checkpoint blockade immunotherapy. Nature communications 2018, 9, 2351.
Ni, K., et al., Nanoscale metal-organic frameworks for mitochondria-targeted radiotherapy radiodynamic therapy. Nature communications 2018, 9, 4321.
Ni K., Nanoscale metal-organic frameworks for x-ray activated in situ cancer vaccination, Science Advances 2020, 6:eabb5223 (13 Pages).
Ni, K.; Lan, G.; Chan, C.; Duan, X.; Guo, N.; Veroneau, S. S.; Weichselbaum, R. R.; Lin, W., Ultrathin Metal-Organic-Layer Mediated Radiotherapy-Radiodynamic Therapy. Matter 2019, 1 (5), 1331-1353.
O'Neill, L. A; Golenbock, D.; Bowie, AG., The history of Toll-like receptorsredefining innate immunity. Nat. Rev. Immunol. 2013, 13 (6), 453-460.
Purcell, AW., McCluskey, J., Rossjohn, J., More than one reason to rethink the use of peptides in vaccine design. Nature reviews Drug discovery 2007, 6, 404.
Quan Y., Metal-Organic Layers for Synergistic Lewis Acid and Photoredox Catalysis, Journ. Amer. Chem. Soc. 2020, vol. 142; pp. 1746-1751.
Radovic-Moreno, AF., et al., Immunomodulatory spherical nucleic acids. Proceedings of the National Academy of Sciences, U.S.A 2015, 112, 3892-3897.
Rodell, C. B.; et al., (2018) "TLR7/8-agonist-loaded nanoparticles promote the polarization of tumour-associated macrophages to enhance cancer immunotherapy," Nat. Biomed. Eng., 2 (8), 578.
Rosi, N.L., et al., Oligonucleotide-modified gold nanoparticles for intracellular gene regulation. Science 2006, 312, 1027-1030.
Sahin, U., Tureci, 0., Personalized vaccines for cancer immunotherapy. Science 2018, 359, 1355-1360.
Scheetz, L., et al., Engineering patient-specific cancer immunotherapies. Nature biomedical engineering 2019, 3, 768-782.
Shae, D., et al., Endosomolytic polymersomes increase the activity of cyclic dinucleotide STING agonists to enhance cancer immunotherapy. Nature nanotechnology 2019, 14,269.
Song, W.,et al.,(2017) "Nanomaterials for cancer immunotherapy," Biomaterials, 148, 16-30.
Wang, S., et al., General and direct method for preparing oligonucleotidefunctionalized metal-organic framework Nanoparticles. Journal of the American Chemical Society 2017, 139, 9827-9830.
Weiner, G.J., et al., (1997) "Immunostimulatory oligodeoxynucleotides containing the CpG motif are effective as immune adjuvants in tumor antigen immunization," Proceedings of the National Academy of Sciences, 94, 10833-10837.
Wu, M (2017) "Metal-organic framework (MOF)-based drug/cargo delivery and cancer therapy," Adv. Mater., 29 (23), 1606134.
Xiong, Z.; et al., (2011) "Topical Imiquimod has Therapeutic and Immunomodulatory Effects Against Intracranial Tumors,". J Immunother, 34 (3).
Zhang, Y.-N., et al., Nanoparticle size influences antigen retention and presentation in lymph node follicles for humoral immunity. Nano letters 2019, 19, 7226-7235.
Notice of Publication corresponding to European Application No. 21808625.4-1109 dated Feb. 1, 2023.
Lutz, M.B., Schuler, G., Immature, semi-mature and fully mature dendritic cells: which signals induce tolerance or immunity? Trends in immunology 2002, 23, 445-449.
Tanyi, J.L., et al., Personalized cancer vaccine effectively mobilizes antitumor T cell immunity in ovarian cancer. Science translational medicine 2018, 10, eaa0593 I.
Wang, H., Mooney D.J., Biomaterial-assisted targeted modulation of immune cells in cancer treatment. Nature Materials 2018, 17, 761-772.
Weichselbaum, R.R., et al., (2017) "Radiotherapy and immunotherapy: a beneficial liaison," Nature reviews Clinical oncology, 14,365.
Wilson, D.S., et al.,(2019) "Antigens reversibly conjugated to a polymeric glyco-adjuvant induce protective humoral and cellular immunity," Nature materials, 18,175.
Interlocutory decision in Opposition proceedings (Art. 101(3)(a) and 106(2) EPC) corresponding to European Application No. 15851357.2-1110 dated Apr. 3, 2023.
Office Action corresponding to U.S. Appl. No. 16/800,855 dated Apr. 12, 2023.
Office Action corresponding to Japanese Patent Application No. 2020-505792 dated Mar. 13, 2023.
Corrected Notice of Allowability corresponding to U.S. Appl. No. 16/800,855 dated Sep. 8, 2023.
Notice of Allowance corresponding to U.S. Appl. No. 16/800,855 dated Aug. 30, 2023.
Notice of Allowance corresponding to Japanese Patent Application No. 2020-505792 dated Sep. 12, 2023.
Notice of Decision to Grant corresponding to European Application No. 19151591.5-1109 dated Sep. 21, 2023.
Notice of Intention to Grant corresponding to European Application No. 14860910.0-1109 dated Sep. 19, 2023.
Intention to Grant corresponding to European Application No. 19151591.5-1109 dated May 16, 2023.
Notice of Publication corresponding to European Patent Application No. 21808625.4-1109 dated Feb. 1, 2023.
Office Action corresponding to European Patent Application No. 14860910.0-1109 dated Mar. 22, 2023.
Office Action corresponding to Japanese Patent Application No. 2022-032275 dated May 23, 2023.

* cited by examiner

NANOSCALE METAL-ORGANIC LAYERS AND METAL-ORGANIC NANOPLATES FOR X-RAY INDUCED PHOTODYNAMIC THERAPY, RADIOTHERAPY, RADIODYNAMIC THERAPY, CHEMOTHERAPY, IMMUNOTHERAPY, AND ANY COMBINATION THEREOF

RELATED APPLICATIONS

The presently disclosed subject matter claims the benefit of U.S. Provisional Patent Application Ser. No. 62/540,275, filed Aug. 2, 2017; and U.S. Provisional Patent Application Ser. No. 62/623,826, filed Jan. 30, 2018, the disclosures of each of which are incorporated herein by reference in their entireties.

GOVERNMENT INTEREST

This invention was made with government support under Grant No. U01-CA198989 awarded by the National Institutes of Health. The government has certain rights in the invention.

TECHNICAL FIELD

The present disclosure relates to metal-organic layers (MOLs) and metal-organic nanoplates (MOPs) and their applications as functional two-dimensional materials in X-ray induced photodynamic therapy (X-PDT), radiotherapy (RT), radiotherapy (RT), radiotherapy-radiodynamic therapy (RT-RDT), chemotherapy, immunotherapy, or any combination thereof. The MOLs and MOPs can comprise secondary building units (SBU) that comprise heavy metal atoms, such as Hf, and bridging ligands that comprise or that can be bonded to photosensitizers (PS).

Abbreviations

° C.=degrees Celsius
Å=angstrom
%=percentage
μg=microgram
μl=microliter
μmol=micromole
μmol=micromolar
AFM=atomic-force microscopy
bpy=2,2'-bipyridine
BPY=4',6'-dibenzoato-[2,2-bipyridine]-4-carboxylate
CLSM=confocal laser scanning microscopy
cm=centimeter
DBBC=5,15-di(p-benzoato)bacteriochlorin
DBC=5,15-di(p-benzoato)chlorin
DBP=5,15-di(p-benzoato)porphyrin
DMF=dimethylformamide
DMSO=dimethylsulfoxide
eV=electronvolts
g=gram
Gy=gray
h=hour
Hf=hafnium
$H_3BPY$=4',6'-dibenzoato-[2,2'-dipyridine]-4-carboxylic acid
$IC_{50}$=fifty percent inhibitory concentration
ICP-MS=inductively coupled plasma-mass spectrometry
Ir=iridium
keV=kiloelectronvolt
kg=kilogram
kVp=peak kilovoltage
Ln=lanthanide
mA=milliampere
mg=milligram
min=minute
mL=milliliter
mm=millimeter
mM=millimolar
mmol=millimole
MOF=metal-organic framework
MOL=metal-organic layer
MOP=metal-organic nanoplates
MRI=magnetic resonance imaging
m-THPC=tetra(m-hydroxyphenyl)chlorin
mW=milliwatt
ng=nanogram
NIR=near infrared
nm=nanometer
nMOF=nanoscale metal-organic frameworks
NMR=nuclear magnetic resonance
OD=optical density
PBS=phosphate buffered saline
PDT=photodynamic therapy
PEG=polyethylene glycol
ppy=2-phenyl-pyridine
PS=photosensitizer
Pt=platinum
PVP=polyvinylpyrrolidone
PXRD=powder x-ray diffraction
QPDC=5,5'-di(4-carboxyl-phenyl)-2,2'-bipyridine
RDT=radiodynamic therapy
$REF_{10}$=radiation enhancement factors at 10% cell survival
RES=reticuloendothelial system
RNO=4-nitroso-N,N-dimethylanaline
RT=radiotherapy
Ru=ruthenium
SBU=secondary building units
s=seconds
SOSG=singlet oxygen sensor green
TEM=transmission electron microscopy
TFA=trifluoroacetic acid
TBC=5,10,15,20-tetra(p-benzoato)chlorin
TBP=5,10,15,20-tetra(p-benzoato)-porphyrin
UV=ultraviolet
XAS=X-ray absorption spectroscopy
X-PDT=X-ray induced photodynamic therapy
Z=atomic number
Zn=zinc
Zr=zirconium

BACKGROUND

Photodynamic therapy (PDT) can be an effective anticancer treatment option. PDT involves the administration of a tumor-localizing photosensitizer (PS) followed by light activation to generate highly cytotoxic reactive oxygen species (ROS), particularly singlet oxygen ($^1O_2$), which trigger cell apoptosis and necrosis. By localizing both the PS and the light exposure to tumor regions, PDT can selectively kill tumor cells while preserving local tissues. PDT has been used to treat patients with many different types of cancer, including head and neck tumors, breast cancer, gynecological tumors, brain tumors, colorectal cancer, mesothelioma, and pancreatic cancer. For example, the use of PDT for treating cancers in the head and neck is particularly advantageous over traditional treatment modalities, e.g., surgery and irradiation, as PDT causes less destruction of surrounding tissues and reduces aesthetic and functional impairments. Porphyrin molecules such as PHOTOFRIN®, VERTEPORFIN®, FOSCAN®, PHOTOCHLOR®, and TALAPORFIN® are among the most commonly used PSs for PDT. However, although they have efficient photochemistry for ROS generation, their suboptimal tumor accumulation after systemic administration can limit the efficacy of PDT in the clinic.

Radiotherapy ("RT") has served as a powerful local anticancer therapy for over a century, yet the efficacy of RT has been limited by its toxic effects on normal tissue, as well as the tendency of tumor cells to develop radioresistance, resulting in local failures. Enhanced X-ray energy absorption by high-Z atoms has motivated the design of a number of high-Z element-containing radioenhancers, such as gold nanoparticles, hafnium oxide nanoparticles, and a series of iodine-containing compounds.

However, there remains an ongoing need for additional compositions and methods to provide RT and/or PDT with increased efficiency and specificity. There is also a need for compositions and methods for providing RT and/or PDT in combination with other treatment modalities, such as chemotherapy, immunotherapy, and combinations thereof.

SUMMARY

In some embodiments, the presently disclosed subject matter provides a metal-organic layer (MOL) or metal-organic nanoplate (MOP), wherein the MOL or MOP comprises periodic repeats of metal-based secondary building units (SBUs) and organic bridging ligands, wherein one or more of the SBUs comprise a metal ion capable of absorbing x-rays, and wherein each SBU is bonded to at least one other SBU via coordinative bonding to the same bridging ligand, and wherein the MOL or MOP comprises a photosensitizer.

In some embodiments, the metal ion capable of absorbing x-rays is an ion of an element selected from the group comprising Hf, a lanthanide metal, Ba, Ta, W, Re, Os, Ir, Pt, Au, Pb, and Bi, optionally wherein the metal ion is a Hf ion. In some embodiments, one or more of the SBUs comprise a Hf oxo cluster, optionally a $Hf_{12}$ oxo cluster or a $Hf_6$ oxo cluster.

In some embodiments, each of the organic bridging ligands is a dicarboxylate or a tricarboxylate. In some embodiments, at least one of the organic bridging ligands comprises a nitrogen donor moiety, optionally wherein the nitrogen donor moiety is selected from the group comprising a bipyridine, a phenyl-pyridine, a phenanthroline, and a terpyridine. In some embodiments, at least one of the organic bridging ligands comprises a ligand selected from the group comprising 4',6'-dibenzoato-[2,2'-bipyridine]-4-carboxylate (BPY) and 4,4'-(2,2'-bipyridine]-5,5'-diyl) dibenzoate (QPDC).

In some embodiments, at least one of the organic bridging ligands comprises the photosensitizer or a derivative of the photosensitizer, optionally wherein at least one of the bridging ligands comprises a moiety selected from the group comprising a porphyrin, a chlorin, a chlorophyll, a phthalocyanine, a ruthenium (Ru) coordination complex, and an iridium (Ir) coordination complex. In some embodiments, at least one bridging ligand comprises a Ru coordination complex or an Ir coordination complex, wherein said Ru or Ir coordination complex comprises: (a) a di- or tricarboxylate ligand further comprising a nitrogen-donor group; (b) a Ru or Ir ion complexed to the nitrogen-donor group in the di- or tricarboxylate ligand, and (c) one or more additional ligands complexed to the Ru or Ir ion, optionally wherein each of the one or more additional ligands is independently selected from the group comprising substituted or unsubstituted 2,2'-bipyridine (bpy) and substituted or unsubstituted 2-phenyl-pyridine (ppy), wherein substituted bpy and substituted ppy comprise bpy or ppy substituted with one or more aryl group substituents, optionally wherein the one or more aryl group substituents are selected from halo and halo-substituted alkyl, further optionally wherein the one or more aryl group substituents are selected from fluoro and trifluoromethyl.

In some embodiments, the Ru or Ir coordination complex comprises a complex comprising a carboxylate of one of the formulas:

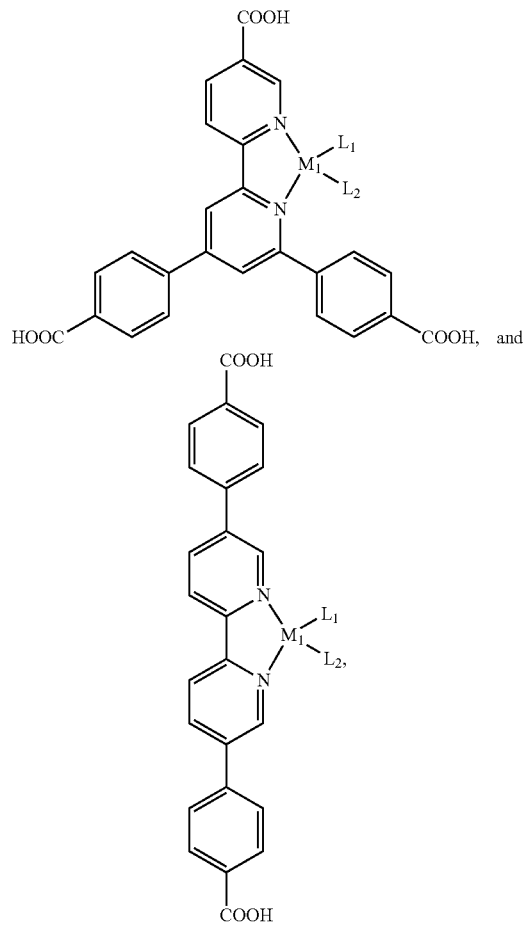

wherein: $M_1$ is Ru or Ir; and $L_1$ and $L_2$ are each have a structure of the formula:

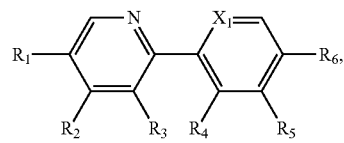

wherein $X_1$ is CH or N; and each of $R_1$, $R_2$, $R_3$, $R_4$, $R_5$, and $R_6$ is independently selected from the group comprising H, halo, alkyl, and substituted alkyl, optionally wherein the substituted alkyl is perhaloalkyl. In some embodiments, $X_1$ is N. In some embodiments, $X_1$ is CH. In some embodiments, $R_2$, $R_3$, and $R_5$ are each H. In some embodiments, $R_1$ is perfluoromethyl and/or $R_4$ and $R_6$ are each fluoro.

In some embodiments, at least one of the organic bridging ligands is 5, 15-di(p-benzoato)porphyrin (DBP), optionally wherein nitrogen atoms of the DBP are complexed to a metal ion, optionally wherein the metal ion is a platinum (Pt) ion.

In some embodiments, the MOL or MOP has a thickness of less than about 12 nanometers (nm). In some embodiments, the MOL or MOP is a MOL having a thickness ranging from about 1.2 nm to about 3 nm, optionally ranging from about 1.2 nm to about 1.7 nm.

In some embodiments, the MOL or MOP comprises $Hf_{12}$ oxo cluster SBUs and at least one organic bridging ligand selected from the group comprising bis(2,2'-bipyridine)(5,5'-di(4-carboxyl-phenyl)-2,2'-bipyridine)-ruthenium(II) chloride (QDPC-Ru); bis(4-phenyl-2-pyridine)(5,5'-di(4-carboxyl-phenyl)-2,2'-bipyridine)iridium(III) chloride (QDPC-Ir); 5,15-di(p-benzoato)porphyrin (DBP); platinum-complexed 5, 15-di(p-benzoato)porphyrin (DBP-Pt); and bis[2-(2',4'-difluorophenyl)-5-(trifluoromethyl)pyridine]5,5'-di(4-carboxyl-phenyl)-2,2'-bipyridine iridium (QDPC-Ir—F). In some embodiments, the MOL or MOP comprises $Hf_6$ oxo cluster SBUs and at least one organic bridging ligand selected from the group comprising bis(2,2-bipyridine)-4',6'-dibenzoato-[2,2'-dipyridine]-4-carboxylate ruthenium (II) chloride (BPY-Ru); bis(4-phenyl-2-pyridine)-4',6'-dibenzoato-[2,2'-dipyridine]-4-carboxylate iridium (III) chloride (BPY-Ir); and bis[2-(2',4'-difluorophenyl)-5-(trifluoromethyl)pyridine]-4',6'-dibenzoato-[2,2'-bipyridine]-4-carboxylate iridium bridging ligands (BPY-Ir—F).

In some embodiments, the MOL or MOP further comprises a poly(ethylene glycol) (PEG) moiety, optionally wherein the PEG moiety is attached to the MOL or MOP via a disulfide group-containing linker moiety coordinated to metal ions in the SBUs. In some embodiments, the MOL or MOP further comprises oxaliplatin or a prodrug thereof coordinated to a MOL or MOP metal ion or encapsulated in said MOL or MOP. In some embodiments, the MOL or MOP further comprises a polyoxometalate (POM) encapsulated in the MOL or MOP. In some embodiments, the MOL or MOP further comprises an immunotherapy agent, optionally wherein the immunotherapy agent is selected from the group comprising an agonist of DNA or RNA sensors, a TLR3 agonist, a TLR7 agonist, a TLR9 agonist, a stimulator of interferon genes (STING) agonist, and an indoleamine 2,3-dioxygenate (IDO) inhibitor (IDOi), further optionally wherein the immunotherapy agent is a CpG ODN or STING agonist that is electrostatically bonded to a positively charged moiety in the MOL or MOP.

In some embodiments, the presently disclosed subject matter provides a composition comprising a nanoscale metal-organic framework (nMOF) comprising $Hf_{12}$ oxo cluster SBUs and bis(4-phenyl-2-pyridine)(5,5'-di(4-carboxyl-phenyl)-2,2'-bipyridine)iridium(III) chloride ($Hf_{12}$-QPDC-Ir nMOF). In some embodiments, the composition further comprises a polyoxometalate (POM) encapsulated within the nMOF. In some embodiments, the composition further comprises a poly(ethylene glycol) (PEG) attached to said nMOF via a disulfide group-containing linker moiety coordinated to Hf ions in the nMOF. In some embodiments, the composition further comprises an immunotherapy agent, optionally wherein the immunotherapy agent is selected from the group consisting of an agonist of DNA or RNA sensors, a TLR3 agonist, a TLR7 agonist, a TLR9 agonist, a stimulator of interferon genes (STING) agonist, and an indoleamine 2,3-dioxygenate (IDO) inhibitor (IDOi), further optionally wherein the immunotherapy agent is a CpG ODN or STING agonist that is electrostatically bonded to a positively charged moiety in the nMOF.

In some embodiments, the presently disclosed subject matter provides a composition comprising a nanoscale metal-organic framework (nMOF) comprising $Hf_{12}$ oxo cluster SBUs and 5, 15-di(p-benzoato)porphyrin bridging ligands complexed to platinum ($Hf_{12}$-DBP-Pt nMOF). In some embodiments, the composition further comprises oxaliplatin encapsulated within the nMOF.

In some embodiments, the presently disclosed subject matter provides a pharmaceutical composition comprising a MOL or MOP comprising periodic repeats of metal-based secondary building units (SBUs) and organic bridging ligands, wherein one or more of the SBUs comprise a metal ion capable of absorbing x-rays, wherein each SBU is bonded to at least one other SBU via coordinative bonding to the same bridging ligand, and wherein the MOL or MOP comprises a photosensitizer; a composition comprising a $Hf_{12}$-QPDC-Ir nMOF; or a composition comprising a $Hf_{12}$-DBP-Pt nMOF; and a pharmaceutically acceptable carrier.

In some embodiments, the presently disclosed subject matter provides a method for treating a disease in a subject in need thereof, the method comprising: administering to the subject a MOL or MOP comprising periodic repeats of metal-based secondary building units (SBUs) and organic bridging ligands, wherein one or more of the SBUs comprise a metal ion capable of absorbing x-rays, wherein each SBU is bonded to at least one other SBU via coordinative bonding to the same bridging ligand, and wherein the MOL or MOP comprises a photosensitizer; a composition comprising a $Hf_{12}$-QPDC-Ir nMOF; a composition comprising a $Hf_{12}$-DBP-Pt nMOF; or a pharmaceutical composition thereof; and exposing at least a portion of the subject to ionizing irradiation energy, optionally X-rays. In some embodiments, the subject is a mammal, optionally a human.

In some embodiments, the disease is selected from the group comprising a head tumor, a neck tumor, breast cancer, a gynecological tumor, a brain tumor, colorectal cancer, lung cancer, mesothelioma, a soft tissue sarcoma, skin cancer, connective tissue cancer, adipose cancer, stomach cancer, anogenital cancer, kidney cancer, bladder cancer, colon cancer, prostate cancer, central nervous system cancer, retinal cancer, blood cancer, a neuroblastoma, multiple myeloma, lymphoid cancer, and pancreatic cancer, optionally wherein the disease is colon cancer or pancreatic cancer. In some embodiments, the disease is a metastatic cancer.

In some embodiments, the method further comprises administering to the subject an additional therapeutic agent or treatment, such as an immunotherapy agent and/or a cancer treatment selected from the group comprising surgery, chemotherapy, toxin therapy, cryotherapy and gene therapy. In some embodiments, the method further comprises administering an immunotherapy agent, optionally wherein the immunotherapy agent is an immune checkpoint inhibitor.

Accordingly, it is an object of the presently disclosed subject matter to provide MOLs and MOPs and nanoscale metal-organic frameworks comprising photosensitizers and X-ray absorbing moieties, as well as methods of using such compositions in treating disease, such as cancer.

An object of the presently disclosed subject matter having been stated hereinabove, and which is achieved in whole or in part by the presently disclosed subject matter, other objects will become evident as the description proceeds

DETAILED DESCRIPTION

Figure 1A:
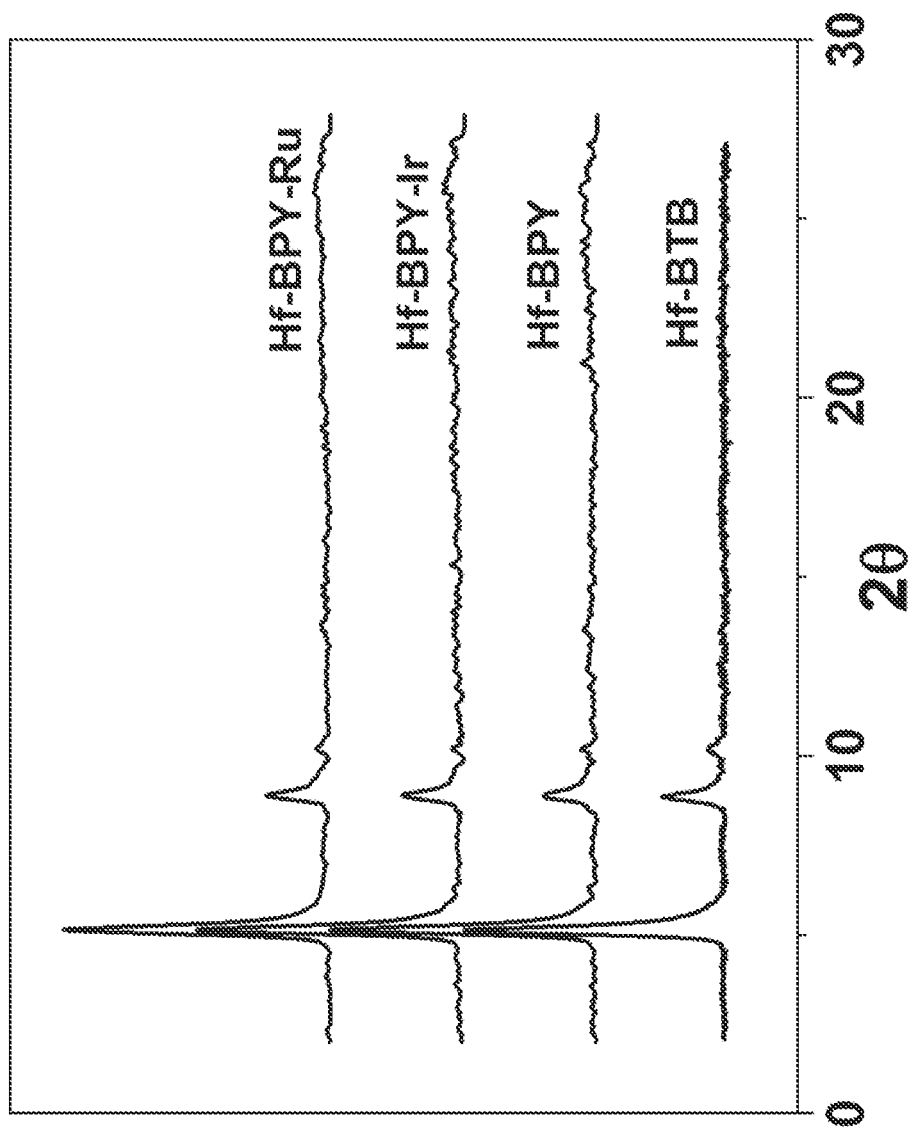
FIG. 1A is a graph showing the powder x-ray diffraction (PXRD) patterns of metal-organic layers (MOLs) including a MOL comprising a hafnium (Hf)-containing secondary building units (SBUs) and 4',6'-dibenzoato-[2,2-bipyridine]-4-carboxylate (BPY) bridging ligands (Hf-BPY, second from bottom); a MOL comprising Hf-containing SBUs and bridging ligands comprising a coordination complex comprising a BPY ligand, a ruthenium (Ru) ion and two bipyridine (bpy) ligands (Hf-BPY-Ru, top); and a MOL comprising Hf-containing SBUs and bridging ligands comprising a coordination complex comprising a BPY ligand, an iridium (Ir) ion, and two phenyl-pyridine (ppy) ligands (Hf-BPY-Ir, second from top). For comparison, the PXRD pattern of a MOL comprising Hf-containing SBUs and benzene-tribenzoate (BTB) bridging ligands is also shown at the bottom.

In some embodiments, the presently disclosed subject matter relates to metal-organic layers (MOLs) and metal-organic nanoplates (MOPs) and their applications as functional two-dimensional materials for photodynamic therapy (PDT), X-ray induced PDT (X-PDT), radiotherapy (RT), radiotherapy-radiodynamic therapy (RT-RDT), chemotherapy, immunotherapy, and any combination thereof. The MOLs and MOPs can comprise secondary building units (SBUs) that comprise heavy metal atoms, such as Hf, and bridging ligands that comprise or that can be bonded to photosensitizers (PS), such as Ir(bpy(ppy)$_2$]$^+$- or Ru(bpy)$_3^{2+}$-complexed tricarboxylate and dicarboxylate ligands. The heavy metal in the SBU can absorb X-rays and transfer energy to the photosensitizer to induce PDT by generating reactive oxygen species (ROS). In some embodiments, the SBU can absorb X-rays and generate ROS to provide RT-RDT. The ability of X-rays to penetrate deeply into tissue and efficient ROS diffusion through ultrathin two-dimensional (2-D) MOLs (~1.2 nm) and MOPs provide highly effective X-PDT and RT-RDT to afford good anticancer efficacy in vitro and in vivo. Accordingly, the presently disclosed subject matter provides, in some embodiments, MOLs and MOPs as a class of functional 2D materials for use in biomedical applications.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. Although any methods, devices, and materials similar or equivalent to those described herein can be used in the practice or testing of the presently disclosed subject matter, representative methods, devices, and materials are now described. All publications, patent applications, patents, and other references mentioned herein are incorporated by reference in their entirety. Throughout the specification and claims, a given chemical formula or name shall encompass all optical and stereoisomers, as well as racemic mixtures where such isomers and mixtures exist.

I. Definitions

While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, for example, reference to "a metal ion" includes a plurality of such metal ions, and so forth.

Unless otherwise indicated, all numbers expressing quantities of size, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value or to an amount of size (i.e., diameter), weight, concentration or percentage is meant to encompass variations of in one example ±20% or ±10%, in another example ±5%, in another example ±1%, and in still another example ±0.1% from the specified amount, as such variations are appropriate to perform the disclosed methods.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including," "containing," or "characterized by" is inclusive or open-ended and does not exclude additional, unrecited elements or method steps. "Comprising" is a term of art used in claim language which means that the named elements are present, but other elements can be added and still form a construct or method within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein the term "alkyl" can refer to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. In some embodiments, there can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R" wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Heteroaryl" as used herein refers to an aryl group that contains one or more non-carbon atoms (e.g., O, N, S, Se, etc) in the backbone of a ring structure. Nitrogen-containing heteroaryl moieties include, but are not limited to, pyridine, imidazole, benzimidazole, pyrazole, pyrazine, triazine, pyrimidine, and the like.

"Aralkyl" refers to an -alkyl-aryl group, optionally wherein the alkyl and/or aryl moiety is substituted.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH═CH—CH═CH—; —CH═CH—$CH_2$—; —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons.

The term "arylene" refers to a bivalent aromatic group, e.g., a bivalent phenyl or napthyl group. The arylene group can optionally be substituted with one or more aryl group substituents and/or include one or more heteroatoms.

The term "amino" refers to the group —$N(R)_2$ wherein each R is independently H, alkyl, substituted alkyl, aryl, substituted aryl, aralkyl, or substituted aralkyl. The terms "aminoalkyl" and "alkylamino" can refer to the group —$N(R)_2$ wherein each R is H, alkyl or substituted alkyl, and wherein at least one R is alkyl or substituted alkyl. "Arylamine" and "aminoaryl" refer to the group —$N(R)_2$ wherein each R is H, aryl, or substituted aryl, and wherein at least one R is aryl or substituted aryl, e.g., aniline (i.e., —$NHC_6H_5$).

The term "thioalkyl" can refer to the group —SR, wherein R is selected from H, alkyl, substituted alkyl, aralkyl, substituted aralkyl, aryl, and substituted aryl. Similarly, the terms "thioaralkyl" and "thioaryl" refer to —SR groups wherein R is aralkyl and aryl, respectively.

The terms "halo", "halide", or "halogen" as used herein refer to fluoro, chloro, bromo, and iodo groups.

The terms "hydroxyl" and "hydroxy" refer to the —OH group.

The terms "mercapto" or "thiol" refer to the —SH group.

The terms "carboxylate" and "carboxylic acid" can refer to the groups —C(═O)O⁻ and —C(═O)OH, respectively. The term "carboxyl" can also refer to the —C(═O)OH group. In some embodiments, "carboxylate" or "carboxyl" can refer to either the —C(═O)O⁻ or —C(═O)OH group. In some embodiments, when the term "carboxylate" is used in reference to an anion of a SBU, the term "carboxylate" can be used to refer to the anion $HCO_2^-$ and, thus, can be synonymous with the term "formate".

The term "phosphonate" refers to the —P(═O)$(OR)_2$ group, wherein each R can be independently H, alkyl, aralkyl, aryl, or a negative charge (i.e., wherein effectively there is no R group present to bond to the oxygen atom, resulting in the presence of an unshared pair of electrons on the oxygen atom). Thus, stated another way, each R can be present or absent, and when present is selected from H, alkyl, aralkyl, or aryl.

The term "phosphate" refers to the —OP(═O)$(OR')_2$ group, where R' is H or a negative charge.

The terms "bonding" or "bonded" and variations thereof can refer to either covalent or non-covalent bonding. In some cases, the term "bonding" refers to bonding via a coordinate bond.

The term "conjugation" can refer to a bonding process, as well, such as the formation of a covalent linkage or a coordinate bond.

As used herein, the term "metal-organic framework" or "MOF" refers to a solid two- or three-dimensional network comprising both metal and organic components, wherein the organic components include at least one, and typically more than one carbon atom. In some embodiments, the material is crystalline. In some embodiments, the material is amorphous. In some embodiments, the material is porous. In some embodiments, the metal-organic matrix material is a coordination polymer, which comprises repeating units of coordination complexes comprising a metal-based secondary building unit (SBU), such as a metal ion or metal complex, and a bridging polydentate (e.g., bidentate or tridentate) organic ligand. In some embodiments, the material contains more than one type of SBU or metal ion. In some embodiments, the material can contain more than one type of organic bridging ligand.

The term "nanoscale metal-organic framework" can refer to a nanoscale particle comprising an MOF.

The terms "nanoscale particle," "nanomaterial," and "nanoparticle" refer to a structure having at least one region with a dimension (e.g., length, width, diameter, etc.) of less than about 1,000 nm. In some embodiments, the dimension is smaller (e.g., less than about 500 nm, less than about 250 nm, less than about 200 nm, less than about 150 nm, less than about 125 nm, less than about 100 nm, less than about 80 nm, less than about 70 nm, less than about 60 nm, less than about 50 nm, less than about 40 nm, or even less than about 30 nm). In some embodiments, the dimension is between about 30 nm and about 250 nm (e.g., about 30, 40, 50, 60, 70, 80, 90, 100, 110, 120, 130, 140, 150, 160, 170, 180, 190, 200, 210, 220, 230, 240, or 250 nm).

In some embodiments, the nanoparticle is approximately spherical. When the nanoparticle is approximately spherical, the characteristic dimension can correspond to the diameter of the sphere. In addition to spherical shapes, the nanomaterial can be disc-shaped, plate-shaped (e.g., hexagonally plate-like), oblong, polyhedral, rod-shaped, cubic, or irregularly-shaped.

As used herein, the terms "nanoplate", "metal-organic nanoplates", and "MOP" refer to a MOF with a plate- or disc-like shape, i.e., wherein the MOF is substantially longer and wider than it is thick. In some embodiments, the MOP is at least 2, 3, 4, 5, 6, 7, 8, 9, 10, 25, or 50 times longer and/or wider than it is thick. In some embodiments, the MOP is less than about 100 nm, 50 nm, or about 30 nm thick. In some embodiments, the MOP is between about 3 nm and about 30 nm thick (e.g., about 5, 10, 15, 20, 25, or 30 nm thick). In some embodiments, the MOP is between about 3 nm and about 12 nm thick (e.g., 3, 4, 5, 6, 7, 8, 9, 10, 11, or 12 nm thick). In some embodiments, the MOP is about two, three, four, five, six, seven, eight, nine or ten layers thick. In some embodiments, the MOP is between about two and about five layers thick, wherein each layer is about the thickness of a SBU. In some embodiments, the MOP is crystalline. In some embodiments, the MOP is amorphous. In some embodiments, the MOP is porous. In some embodiments, a strongly coordinating modulator, such as a monocarboxylic acid like acetic acid (AcOH), formic acid, benzoic acid, or trifluoroacetic acid (TFA), is used to control the nanoplate morphology of the MOP and to introduce defects (missing bridging ligands) to enhance the diffusion of ROS through MOP channels.

As used herein, the term "metal-organic layer" (or "MOL") refers to a solid, mainly two-dimensional network comprising both metal and organic components, wherein the organic components include at least one, and typically more than one carbon atom. In some embodiments, the MOL is crystalline. In some embodiments, the MOL is amorphous. In some embodiments, the MOL is porous.

In some embodiments, the MOL is a coordination polymer, which comprises repeating units of coordination complexes comprising a metal-based secondary building unit (SBU), such as a metal ion or metal complex, and a bridging polydentate (e.g., bidentate or tridentate) organic ligand. In some embodiments, the bridging ligand is essentially planar. In some embodiments, a majority of bridging ligands bind to at least three SBUs. In some embodiments, the material contains more than one type of SBU or metal ion. In some embodiments, the material can contain more than one type of bridging ligand.

In some embodiments, the MOL can be essentially a monolayer of a coordination complex network between the SBUs and the bridging ligands where the monolayer extends in the x- and y-planes but has a thickness of only about one SBU.

In some embodiments, the MOL can be a monolayer of a substantially planar coordination complex network between the SBUs and the bridging ligands wherein substantially all of the bridging ligands are in the same plane. In some embodiments, more than 80%, 85%, 90%, or 95% of the bridging ligands are substantially in the same plane. In some embodiments, more than 95%, 96%, 97%, 98%, 99%, or about 100% of the bridging ligands are in the same plane. Thus, while the MOL can extend in the x- and y-planes for a distance that can comprise the length and/or diameter of multiple SBUs and bridging ligands, in some embodiments, the MOL can have a thickness of only about one SBU. In some embodiments, the thickness of the MOL is about 3 nm or less (e.g., about 3, 2, or about 1 nm or less) and the width, length, and/or diameter of the MOL is at least about 5 times, 10 times, 20 times, 30 times, 40 times, 50 times, 60 times, 70 times, 80 times, 90 times, or about 100 times or more the thickness of the MOL. In some embodiments, the MOL has a sheet-like shape. In some embodiments, the MOL has a plate-like or disc-like shape. In some embodiments, a strongly coordinating modulator, such as a monocarboxylic acid like acetic acid (AcOH), formic acid, benzoic acid, or trifluoroacetic acid (TFA), is used to control the nanoplate morphology of the MOL and to introduce defects (missing bridging ligands) to enhance the diffusion of ROS through MOL channels.

In contrast to an MOL and/or MOP, the terms "metal-organic framework", "nanoscale metal-organic framework", "MOF" and/or "nMOF" as used herein typically refer to a solid metal-organic matrix material particle wherein each of the length, width, thickness, and/or diameter of the MOF is greater than about 30 or 31 nm (or greater than about 50 nm or greater than about 100 nm) and/or wherein none of the width, length, and/or diameter of the MOF is 5 or more times greater than the thickness of the MOF.

A "coordination complex" is a compound in which there is a coordinate bond between a metal ion and an electron pair donor, ligand or chelating group. Thus, ligands or chelating groups are generally electron pair donors, molecules or molecular ions having unshared electron pairs available for donation to a metal ion.

The term "coordinate bond" refers to an interaction between an electron pair donor and a coordination site on a metal ion resulting in an attractive force between the electron pair donor and the metal ion. The use of this term is not intended to be limiting, in so much as certain coordinate bonds also can be classified as having more or less covalent character (if not entirely covalent character) depending on the characteristics of the metal ion and the electron pair donor.

As used herein, the term "ligand" refers generally to a species, such as a molecule or ion, which interacts, e.g., binds, in some way with another species. More particularly, as used herein, a "ligand" can refer to a molecule or ion that binds a metal ion in solution to form a "coordination complex." See Martell, A. E., and Hancock, R. D., *Metal Complexes in Aqueous Solutions*, Plenum: New York (1996), which is incorporated herein by reference in its entirety. The terms "ligand" and "chelating group" can be used interchangeably. The term "bridging ligand" can refer to a group that bonds to more than one metal ion or complex, thus providing a "bridge" between the metal ions or complexes. Organic bridging ligands can have two or more groups with unshared electron pairs separated by, for example, an alkylene or arylene group. Groups with unshared electron pairs, include, but are not limited to, —$CO_2H$, —$NO_2$, amino, hydroxyl, thio, thioalkyl, —$B(OH)_2$, —$SO_3H$, $PO_3H$, phosphonate, and heteroatoms (e.g., nitrogen, oxygen, or sulfur) in heterocycles.

The term "coordination site" when used herein with regard to a ligand, e.g., a bridging ligand, refers to a unshared electron pair, a negative charge, or atoms or functional groups cable of forming an unshared electron pair or negative charge (e.g., via deprotonation under at a particular pH).

The term "hydrophilic polymer" as used herein generally refers to hydrophilic organic polymers, such as but not limited to, polyvinylpyrrolidone (PVP), polyvinylmethylether, polymethyloxazoline, polyethyloxazoline, polyhydroxy-propyloxazoline, polyhydroxypropylmethacrylamide, polymethyacrylamide, polydimethylacrylamide, polyhydroxylpropylmethacrylate, polyhydroxy-ethylacrylate, hydroxymethylcellulose, hydroxyethylcellulose, polyethylene-imine (PEI), polyethyleneglycol (i.e., PEG) or another hydrophilic poly(alkyleneoxide), polyglycerine, and polyaspartamide. The term "hydrophilic" refers to the ability of a molecule or chemical species to interact with water. Thus, hydrophilic polymers are typically polar or have groups that can hydrogen bond to water.

The term "photosensitizer" (PS) refers to a chemical compound or moiety that can be excited by light of a particular wavelength, typically visible or near-infrared (NIR) light, and produce a reactive oxygen species (ROS). For example, in its excited state, the photosensitizer can undergo intersystem crossing and transfer energy to oxygen ($O_2$) (e.g., in tissues being treated by PDT) to produce ROSs, such as singlet oxygen ($^1O_2$). Any known type of a photosensitizer can be used in accordance with the presently disclosed subject matter.

In some embodiments, the photosensitizer is a porphyrin, a chlorophyll, a dye, or a derivative or analog thereof, such as a porphyrin, chlorophyll or dye comprising one or more additional aryl or alkyl group substituents, having one or more carbon-carbon double bonds replaced by a carbon-carbon single bond, and/or comprising a substituent (e.g., a substituted alkylene group) that can covalently substituted with a bond to an organic bridging ligand). In some embodiments, porphyrins, chlorins, bacteriochlorins, or porphycenes can be used. In some embodiments, the photosensitizer can have one or more functional groups, such as carboxylic acid, amine, or isothiocyanate, e.g., for using in attaching the photosensitizer to another molecule or moiety, such as an organic bridging ligand or a SBU, and/or for providing an additional site or sites to enhance coordination or to coordinate an additional metal or metals. In some embodiments, the photosensitizer is a porphyrin or a derivative or analog thereof. Exemplary porphyrins include, but are not limited to, hematoporphyrin, protoporphyrin and tetraphenylporphyrin (TPP). Exemplary porphyrin derivatives include, but are not limited to, pyropheophorbides, bacteriochlorophylls, chlorophylla, benzoporphyrin derivatives, tetrahydroxyphenyl chlorins, purpurins, benzochlorins, naphthochlorins, verdins, rhodins, oxochlorins, azachlorins, bacteriochlorins, tolyporphyrins and benzobacteriochlorins. Porphyrin analogs include, but are not limited to, expanded porphyrin family members (such as texaphyrins, sapphyrins and hexaphyrins), porphyrin isomers (such as porphycenes, inverted porphyrins, phthalocyanines, and naphthalocyanines), and TPP substituted with one or more functional groups.

In some embodiments, the PS is a metal coordination complex comprising a metal (e.g., Ru or Ir) and one or more nitrogen donor ligands, e.g., one or more nitrogen-containing aromatic groups. In some embodiments, the one or more nitrogen donor ligands are selected from the group including, but not limited to, a bipyridine (bpy), a phenanthroline, a terpyridine, or a phenyl-pyridine (ppy), each of which can optionally be substituted with one or more aryl group substituents (e.g., on a carbon atom of the aromatic group).

The term "cancer" as used herein refers to diseases caused by uncontrolled cell division and/or the ability of cells to metastasize, or to establish new growth in additional sites. The terms "malignant", "malignancy", "neoplasm", "tumor," "cancer" and variations thereof refer to cancerous cells or groups of cancerous cells.

Particular types of cancer include, but are not limited to, skin cancers (e.g., melanoma), connective tissue cancers (e.g., sarcomas), adipose cancers, breast cancers, head and neck cancers, lung cancers (e.g., mesothelioma), stomach cancers, pancreatic cancers, ovarian cancers, cervical cancers, uterine cancers, anogenital cancers (e.g., testicular cancer), kidney cancers, bladder cancers, colorectal cancers (i.e., colon cancers or rectal cancers), prostate cancers, central nervous system (CNS) cancers, retinal cancer, blood, neuroblastomas, multiple myeloma, and lymphoid cancers (e.g., Hodgkin's and non-Hodgkin's lymphomas).

The term "metastatic cancer" refers to cancer that has spread from its initial site (i.e., the primary site) in a patient's body.

The terms "anticancer drug", "chemotherapeutic", and "anticancer prodrug" refer to drugs (i.e., chemical compounds) or prodrugs known to, or suspected of being able to treat a cancer (i.e., to kill cancer cells, prohibit proliferation of cancer cells, or treat a symptom related to cancer). In some embodiments, the term "chemotherapeutic" as used herein refers to a non-PS molecule that is used to treat cancer and/or that has cytotoxic ability. Such more traditional or conventional chemotherapeutic agents can be described by mechanism of action or by chemical compound class, and can include, but are not limited to, alkylating agents (e.g., melphalan), anthracyclines (e.g., doxorubicin), cytoskeletal disruptors (e.g., paclitaxel), epothilones, histone deacetylase inhibitors (e.g., vorinostat), inhibitors of topoisomerase I or II (e.g., irinotecan or etoposide), kinase inhibitors (e.g., bortezomib), nucleotide analogs or precursors thereof (e.g., methotrexate), peptide antibiotics (e.g., bleomycin), platinum based agents (e.g., cisplatin or oxaliplatin), retinoids (e.g., tretinoin), and vinka alkaloids (e.g., vinblastine).

II. General Considerations

Photodynamic therapy (PDT) is a phototherapy that combines three non-toxic components—a photosensitizer (PS), a light source, and tissue oxygen—to cause toxicity to malignant and other diseased cells. The most widely accepted mechanism of PDT involves energy transfer from the light-excited PS to oxygen molecules in the tissue to generate reactive oxygen species (ROS), particularly singlet oxygen ($^1O_2$), which induces cellular toxicity. PDT can lead to localized destruction of diseased tissues via selective uptake of the PS and/or local exposure to light, providing a minimally invasive cancer therapy.

Selective delivery of chemotherapeutics to tumors is preferred for successful chemotherapy. Similarly, localization of PSs in tumors is preferred for effective PDT. However, many PSs are hydrophobic in nature, which not only leads to insufficient tumor localization, but also causes PS aggregation to diminish the PDT efficacy. Significant synthetic modifications are thus preferred for rendering these PSs more effective PDT agents in vivo.

An alternative approach is to use nanocarriers to selectively deliver therapeutic or PDT agents to tumors via the enhanced permeation and retention effect (EPR) and sometimes, via active tumor targeting with small molecule or biologic ligands that bind to overexpressed receptors in cancers. Nanoscale metal-organic frameworks (nMOFs), constructed from metal ion/ion clusters and organic bridging ligands can be used as a nanocarrier platform for therapeutic and imaging agents. Compared to other nanocarriers, nMOFs combine many beneficial features into a single delivery platform, including tunable chemical compositions and crystalline structures; high porosity; and bio-degradability. As described further hereinbelow, in some embodiments, the use of two-dimensional nanocarriers, i.e., MOLs and MOPs, constructed from metal ion clusters and organic bridging ligands can provide improved therapeutics, e.g., for PDT, X-PDT, and RT-RDT, as compared to thicker nMOFs.

II.A. Porphyrin-Based Nanocarriers for Photodynamic Therapy

According some embodiments of the presently disclosed subject matter, Hf-porphyrin MOLs and MOPs can be prepared and used for PDT. Without wishing to be bound to any one theory, it is believed that incorporation of a porphyrin-derived bridging ligand into a MOL or MOP can give several advantages over other nanoparticle PDT agents. First, the PS molecules or moieties can be well-isolated in the MOL or MOP framework to avoid aggregation and self-quenching of the excited states. Second, coordination of porphyrin ligands to heavy metal (e.g., Hf) centers can promote intersystem crossing to enhance ROS generation efficiency. Third, the thin and porous MOL or MOP structure can provide a pathway for facile diffusion of ROS (such as singlet oxygen ($^1O_2$)) out of the MOL or MOP to exert cytotoxic effects on cancer cells. Further, high PS loading can be achieved with MOLs and MOPs to provide effective PDT of difficult-to-treat cancers.

Accordingly, in some embodiments, the presently disclosed subject matter provides a MOL or MOP comprising SBUs linked together via porphyrin-based bridging ligands, e.g., porphyrins, derivatives of porphyrins, and/or metal complexes thereof.

II.B. Chlorin-Based Nanocarriers for Photodynamic Therapy of Colon Cancers

Hematoporphyrin derivatives were developed as the first generation PSs, leading to the clinical application of the first PDT agent PHOTOFRIN®. However, the photophysical properties of porphyrins are not preferred for certain applications, with the absorption peaks typically near the high energy edge of the tissue-penetrating window (600-900 nm) and small extinction coefficient (ε) values. Reduction of porphyrins to chlorins has been shown to shift the absorption to a longer wavelength with a concomitant increase in ε. For instance, reduction of 5,10,15,20-m-tetra(hydroxyphenyl) porphyrin to its chlorin derivative red-shifts the last Q-band from 644 to 650 nm along with a dramatic enhancement in ε from 3400 $M^{-1} \cdot cm^{-1}$ to 29600 $M^{-1} \cdot cm^{-1}$.

Accordingly, in some embodiments, the presently disclosed subject matter provides MOLs or MOPs comprising SBUs linked together via chlorin-based bridging ligands or ligands based on other reduced forms of porphyrins, such as bacteriochlorin.

II.C. MOLs and/or MOPs for Highly Efficient X-Ray Induced Photodynamic Therapy

Radiotherapy is one of the most common and efficient cancer treatment modalities. In cancer radiotherapy, tumors are irradiated with high-energy radiation (for example, X-rays) to destroy malignant cells in a treated volume. MOLs and MOPs enable the treatment of deep cancer by the combination of radiotherapy and PDT. According to some embodiments of the presently disclosed subject matter, MOLs or MOPs having SBUs with high Z metal ions (e.g., Zr or Hf) can serve as effective X-ray antenna by absorbing X-ray photons and converting them to fast electrons through the photoelectric effect. The generated electrons then excite multiple PSs in the MOL or MOP through inelastic scattering, leading to efficient generation of hydroxy radicals and $^1O_2$. Additional embodiments can comprise MOLs or MOPs with SBUs comprising lanthanide metals (such as La, Ce, Pr, Nd, Pm, Sm, Eu, Gd, Tb, Dy, Ho, Er, Tm, Yb, and Lu), Ba, Ta, W, Re, Os, Ir, Pt, Au, Pb, and Bi, or any metal ion that strongly absorbs x-ray radiation.

In some embodiments, MOLs or MOPs constructed from heavy metals such as Hf and Bi as metal connecting points and porphyrin-derivatives, chlorin-derivatives, or metal-containing dyes, including $Ru(bpy)_3^{2+}$ and $Ir(ppy)_2(bpy)^+$ (bpy is 2,2'-bipyridine and ppy is 2-phenylpyridine), as bridging ligands are provided according to the presently disclosed subject matter. The application of such MOPs and MOLs in X-ray induced PDT/RT is demonstrated further hereinbelow in the Examples. These MOLs and MOPs are able to excite the photosensitizers with X-ray energy for subsequent singlet oxygen generation, thus serving as efficient therapeutic agents for X-ray induced PDT. The advantages of this class of nanocarriers can include: 1) the combination of two effective treatments (radiation therapy and PDT); 2) a modality capable and efficient for deep cancer treatment; 3) a lowered risk of radiation damage to healthy tissue; and 4) a simple, relatively inexpensive and efficient treatment.

In certain embodiments, the presently disclosed MOLs and MOPs can comprise or further comprise a polyoxometalate (POM), such as a tungsten, molybdenum, or niobate polyoxometalate, a metallic nanoparticle, such as a gold, palladium, or platinum nanoparticle, or a metal oxide nanoparticle, such as a hafnium oxide or niobium oxide nanoparticle, located in the MOL and/or MOP cavities or channels (e.g., physically sequestered/encapsulated in cavities or channels in a MOL and/or MOP).

II.D. MOLs and/or MOPs for Radiotherapy and Radiotherapy-Radiodynamic Therapy

In some embodiments, MOLs and/or MOPs constructed from Hf metal clusters (or other high Z element metals) and ligands with negligible photosensitization properties can be provided. The ability of Hf metal clusters to absorb ionizing irradiation energy, such as X-rays, γ-rays, β-irradiation, neutron beam irradiation, electron beam irradiation, or proton irradiation, coupled with rapid diffusion of ROS (particularly hydroxyl radical (OH)) out of the MOL or MOP channels can provide highly effective radiotherapy. In some embodiments, the Hf metal cluster can absorb ionizing irradiation energy (e.g., X-ray photons) leading to RT via the production of ROS (e.g., ·OH radicals) and RDT by exciting the photosensitizers within the NMOFs to generate ROS (e.g., singlet oxygen ($^1O_2$)).

In some embodiments, the presently disclosed subject matter provides a radioenhancer based on a MOL or MOP comprising an X-ray absorbing metal ion by taking advantage of the ability of the MOL or MOP to enhance RT and RDT. Facile diffusion of generated ROS through open channels along the smallest dimension of the MOL or MOP is in part responsible for their high RT-RDT.

II.E. Combined PDT and Immunotherapy

PDT can selectively kill tumor cells while preserving adjacent normal tissue. PDT does not incur cross-resistance with radiotherapy or chemotherapy, and therefore, is useful in the treatment of cancer patients who have not responded significantly to traditional radiotherapy and/or chemotherapy. PDT can provoke a strong acute inflammatory reaction observed as localized edema at the targeted site. The inflammation elicited by PDT is a tumor antigen nonspecific process orchestrated by the innate immune system. PDT is particularly effective in rapidly generating an abundance of alarm/danger signals, such as damage-associated molecular patterns (DAMPs), at the treated site that can be detected by the innate immunity alert elements. PDT-mediated enhancement of antitumor immunity is believed due to the stimulation of dendritic cells by dead and dying tumor cells and can be accompanied by the recruitment and activation of CD8+ cytotoxic T cells (CTLs) followed by the formation of immune memory cells and resistance to subsequent tumor growth.

According to some embodiments of the presently disclosed subject matter, DBP-MOLs and other MOLs and MOPs of the presently disclosed subject matter can be used to effect combined PDT and immunotherapy. A number of inorganic, organic, and hybrid materials are known to strongly absorb near-infrared light to generate single oxygen. The therapeutic use of such PDT materials can be combined with immune checkpoint inhibitor therapy.

Exemplary photosensitizers for such combination therapy include, but are not limited to: upconversion nanoparticles, such as $NaYF_4$ (for example, doped at a ratio of Y:Yb: Er=78%:20%:2%), combined with chlorin e6 or MC540; photosensitizers-embedded in silica-based nanoparticles, such as 2-devinyl-2-(1-hexyloxyethyl) pyropheophorbide (HPPH) loaded silica nanoparticles; polymer micelle loaded photosensitizers, such as Zn(II)phthalocyanine loaded in $DSPE-PEG_{5k}$ polymer micelles; liposome based photosensitizer delivery systems, such as 5,10,15,20-tetrakis(m-hydroxyphenyl)chlorin encapsulated in a liposome and 5-aminolevulinic acid (ALA) encapsulated liposome; human serum albumin based photosensitizer delivery systems, such as HSA-pheophorbide a conjugate particles; dendrimer based photosensitizer delivery systems, such as PEG-attached poly(propyleneimine) or poly(amido amine) loaded with rose bengal and PpIX; porphyrin-, chlorin- or bacteriochlorin-conjugated phospholipid based bilayer delivery systems, such as porphyrin-lipid conjugates (pyrolipid) self-assembly nanovesicles (Porphysome) and NCP@Pyrolipid. In some embodiments, these photosensitizers form nanocomposites with the presently disclosed MOLs and MOPs. In some embodiments, these photosensitizers (or the photosensitizers from the exemplary photosensitizer delivery systems) can be part of the presently disclosed MOLs and MOPs. For example, in some embodiments, these photosensitizers or their derivatives can be bridging ligands or attached to bridging ligands of the presently disclosed MOLs and MOPs.

II.F. Combined X-PDT or RT-RDT and Immunotherapy

According to some embodiments of the presently disclosed subject matter, X-ray-induced (or other ionizing irradiation energy-induced) PDT or RT-RDT can be combined with inhibitor-based immunotherapy to cause systemic rejection of established tumors using adaptive immune response, e.g., cytotoxic T cells. When combined with immunotherapeutic agents, not only the effective eradication of primary tumor, but also suppression/eradication of distant metastatic tumor can be accomplished using MOL and/or MOP-based X-PDT or RT-RDT effects. In some embodiments, the antitumor efficacy can be enhanced by adding chemotherapeutics that are known to cause immunogenic cell death.

A number of inorganic materials are known to strongly absorb X-rays (or other ionizing irradiation energy) and convert the absorbed energy to visible and near-infrared light. The emitted near-infrared light from these scintillating nanomaterials can then be absorbed by the nearby photosensitizers to enable X-ray (or other ionizing irradiation energy) induced PDT effects. In some embodiments, the absorbed energy can lead to the production of ROS and/or the excitation of nearby photosensitizers, leading to the production of ROS. Other types of materials can also achieve X-ray induced PDT or RT-RDT. When this X-ray induced PDT or RT-RDT is combined with immune checkpoint inhibitors, excellent radioimmunotherapy can be obtained. Examples of X-ray scintillating nanomaterials include, but are not limited to: $LnO_3$:Ln' nanoparticles, $LnO_2S$ Ln' nanoparticles or $LnX_3$:Ln' nanoparticles, where Ln=Y, La, Ce, Pr, Nd, Sm, Eu, Gd, Tb, Dy, Ho, Er, Tm, Yb, Lu, Ln'=Ce, Pr, Eu, Tb, etc. and X=F, Cl, Br, and I; X-ray scintillator MOFs. MOLs and MOPs, such as $M_6(\mu_3\text{—}O)_4$ $(\mu_3\text{-OH})_4L_6$, where M=Hf, Zr, or Ce; and L=9,10-anthracenylbisbenzoic acid and other formulations of MOFs, MOPs, and MOLs containing heavy metal secondary building units; lanthanide based MOFs, MOPs, and MOLs, the SBU include but not limited to: $Ln_4(\mu_4\text{-OH}_2)(CO_2)_8(SO_4)_4$, [Ln $(OH_2)(CO_2)_3]_n$ (infinite 1-D chain), $[Ln(OH_2)(CO_2)_4]_n$ (infinite 1-D chain), $[Ln(CO_2)_3\text{-}Ln(OH_2)_2(CO_2)_3]_n$ (infinite 1-D chain), where Ln=La, Ce, Pr, Nd, Sm, Eu, Gd, Tb, Dy, Ho, Er, Tm, Yb, Lu and/or their mixture combination; the bridging ligands include but not limited to [1,4-benzoic dicarboxylate], [2,5-dimethoxy-1,4-benzenedicarboxylate], [1,3,5-benzoic tricarboxylate], [1,3,5-benzenetrisbenzoate], [5-(pyridin-4-yl)isophthalic acid], [4,4',4"-S-triazine-2,4,6-triyl tribenzoate], [biphenyl-3,4',5-tricarboxylate], [4,4'-[(2,5-Dimethoxy-1,4-phenylene)di-2,1-ethenediyl]bis-benzoic acid], etc.; quantum dots, such as ZnS:M quantum dots (M=Cu, Co, Mn, Eu, etc.) or carbon dots; gold nanoparticles, or platinum or other third-row metal particles; and other X-ray scintillators, such as $SrAl_2O_4$:$Eu^{2+}$; $NaYF_4$: $Tb^{3+}$, $Er^{3+}$.

Examples of photosensitizers conjugated to X-ray scintillating nanoparticles, MOLs and/or MOPs for use in X-ray induced PDT or RT-RDT include, but are not limited to: photosensitizers coordinatively bonded to a nanoparticle, MOL, or MOP surface, where the coordination methods include but are not limited to carboxylate or phosphate coordination (such as via the coordination of a carboxylate or phosphate group on the PS to open metal sites (e.g., $Ln^{3+}$, $Zn^{2+}$, etc.) on nanoparticles, MOLs or MOPs); thiol coordination to nanoparticles, MOLs or MOPs, (via PSs containing thiols conjugating to nanoparticles, MOLs or MOPs through the coordination of thiol groups to open metal sites); polymer conjugation and surface coating, for example, via covalently conjugating PSs to oligomers or polymers with functional groups (e.g., cyclodextrin, polyethylene glycol (PEG), poly (maleic acid) derivatives, etc.) and conjugating the scintillator nanoparticles, MOLs or MOPs through coordination of additional functional groups (e.g., carboxylates, thiols, hydroxyls, amines, etc.) to the metals on the nanoparticle, MOL or MOP surface; covalent bonding to a MOF, MOL or MOP ligand, for example via amide conjugation, ester conjugation, thiourea conjugation, "click chemistry", disulfide bond conjugation, etc.; surface modification of porous materials, and entrapment, mesoporous silica coating and entrapment.

II.G. Refinement of X-Ray Set-Ups for X-Ray Induced Photodynamic Therapy.

In some embodiments of the presently disclosed subject matter, the X-ray (or other ionizing irradiation energy) source can be refined to enhance the X-PDT or RT-RDT effects to enable more efficient cancer cell killing. In some embodiments, the X-ray irradiator can include a panoramic irradiator comprising at least one X-ray source inside a shielded enclosure, the one or more sources each operable to emit X-ray flux across an area equal to the proximate facing surface area of the tumor. See U.S. Patent Application Publication No. 2010/0189222 and WO 2011/049743, each of which is incorporated by reference herein in its entirety. An X-ray generator based on a tungsten target emission is suited for this application. The output energy typically ranges from 100 to 500 kV. In certain embodiments, at least one removable attenuator or filter of selected materials, which contains at least one metal with atomic number >20, is involved in this application. Each attenuator could be a flat board or a board with gradient thickness. See U.S. Pat. No. 7,430,282 incorporated by reference herein in its entirety. The attenuator could be also modulated with periodically spaced grids/holes. The output X-ray energy can be adjusted after filtration by the attenuator to maximize the energy absorption of radiosensitizers/radioscintillators in this application. An X-ray bandpass filter with an x-ray refractive lens for refracting x-rays can also be used. See WO2008/102632, incorporated by reference herein in its entirety.

III. Compositions

III.A. Metal-Organic Layers (MOLs) and Metal-Organic Nanoplates (MOPs) for Therapeutic Applications By combining three intrinsically nontoxic components—a photosensitizer (PS), light, and tissue oxygen—to generate cytotoxic reactive oxygen species (ROS), particularly singlet oxygen ($^1O_2$), photodynamic therapy (PDT) provides a highly effective phototherapy against cancer. See Celli et al., 2010; Dolmans et al., 2003; Ethirajan et al., 2011; Hamblin and Hasan, 2004; and Pass, 1993. Because ROS indiscriminately kill both diseased and normal cells, it is desirable to selectively localize PSs in tumors in order to enhance PDT efficiency and minimize collateral damage to normal tissues. See Bechet et al., 2008; Ng and Zheng, 2015; Huynh et al., 2015; Carter et al., 2014; Lovell et al., 2011; Idris et al., 2012; He et al., 2015; He et al., 2016; Cheng et al., 2008; Chatterjee et al., 2008; Roy et al., 2003; and Wang et al., 2011. The stable framework and crystalline structure of nMOFs allows for high PS loading and prevents PS self-quenching whereas the porosity of the nMOFs facilitates ROS diffusion. See Lu et al., 2016; Lu et al., 2015; and Lu et al., 2014. However, because the lifetime of ROS is short, it is not typically feasible for all the species generated to diffuse out of the 3-D structure of nMOFs to exert cytotoxicity on cellular organelles, thus limiting the overall efficacy of PDT in vivo.

The 2-D structure of MOLs and MOPs can allow ROS to diffuse more freely, thus presenting an improved platform for nanoscale PSs for efficient PDT. Accordingly, the presently disclosed subject matter is based, in one aspect, on reducing the dimensionality of the nMOFs to provide 2-D MOLs and/or MOPs and exciting the MOLs and/or MOPs with more tissue-penetrating X-rays to improve in vivo PDT efficacy. In some embodiments, reducing the dimensionality can comprise preparing the MOL or MOP by contacting MOL or MOP starting materials (e.g., a metal compound comprising a high Z metal element and an organic bridging ligand) in the presence of a strongly coordinating modulator, such as a monocarboxylic acid like acetic acid (AcOH), benzoic acid, formic acid, or trifluoroacetic acid (TFA) or in the presence of higher concentrations these monocarboxylic acids and/or higher water contents (than used in the preparation of a nMOF). The inclusion of the monocarboxylic acid (or of a higher amount of monocarboxylic acid than used during the preparation of a nMOF) can serve to cap the MOL or MOP SBUs, thereby controlling morphology and introducing defects (missing bridging ligands) to enhance the diffusion of ROS through MOL or MOP channels. Thus, the presently disclosed subject matter provides, in some embodiments, a MOL and/or an MOP that comprises an x-ray (or other ionizing radiation) absorbing component and a PS. In some embodiments, the presently disclosed subject matter provides a MOL and/or an MOP that comprises an x-ray (or other ionizing radiation) absorbing component and an organic scintillator (e.g., an anthracene-containing moiety).

In some embodiments, the presently disclosed subject matter provides a MOL or MOP, wherein the MOL comprises periodic repeats of metal-based secondary building units (SBUs) and organic bridging ligands, wherein each SBU is bonded to at least one other SBU via coordinative bonding to the same organic bridging ligand, and wherein the MOL or MOP comprises a photosensitizer. In some embodiments, one or more of the SBUs contain ions of a high Z-metal that can absorb ionizing irradiation energy, such as X-ray, γ-ray, β-irradiation, or proton irradiation. In some embodiments, one or more of the SBUs are metal-oxo clusters with a structure that strongly absorbs ionizing irradiation energy. In some embodiments, one or more of the organic bridging ligands also contain a high Z-metal ion (e.g., an ion of an element where Z (i.e., the atomic number or proton number) is greater than about 40) that can absorb ionizing irradiation energy. In some embodiments, the bridging ligands can generate reactive oxygen species (ROS) such as singlet oxygen ($^1O_2$), superoxide ($\cdot O_2^-$), hydrogen peroxide ($H_2O_2$), and hydroxyl radicals ($\cdot OH$), upon ionizing irradiation.

In some embodiments, the metal ion capable of absorbing x-rays is an ion of an element selected from the group comprising Hf, the lanthanide metals (such as La, Ce, Pr, Nd, Pm, Sm, Eu, Gd, Tb, Dy, Ho, Er, Tm, Yb, and Lu), Ba, Ta, W, Re, Os, Ir, Pt, Au, Pb, and Bi. In some embodiments, the one or more SBUs comprise combinations of metals (either in the same SBU or in different SBUs). In some embodiments, the metal ion is a Hf ion. In some embodiments, the SBUs are metal oxo clusters comprising one or more of Hf, a lanthanide metal, Ba, Ta, W, Re, Os, Ir, Pt, Au, Pb and Bi. In some embodiments, the metal ion is Zr. In some embodiments, the SBUs are Zr oxo clusters. In some embodiments, the oxo clusters comprise anions selected from oxide ($O^{2-}$), hydroxide ($OH^-$), $S^{2-}$, $SH^-$, and formate ($HCO_2^-$). In some embodiments, the oxo clusters are capped with anions derived from a strongly coordinating modulator, such as a monocarboxylic acid. Thus, in some embodiments, the oxo clusters are capped with an anion selected from the group including, but not limited to, acetate, formate, benzoate, and trifluoroacetate.

In some embodiments, one or more of the SBUs comprise a Hf oxo cluster. For example, one or more of the SBUs can be selected from the group including, but not limited to an $Hf_6$ oxo cluster (e.g., $Hf_6O_4(OH)_4(HCO_2)_{12}$), a $Hf_{12}$ oxo cluster (e.g., $Hf_{12}O_8(OH)_{14}(HCO_2)_{18}$), an $Hf_{18}$ oxo cluster (e.g., $Hf_{18}O_{12}(OH)_{24}(HCO_2)_{24}$) and an $Hf_{24}$ oxo cluster (e.g., $Hf_{24}O_{16}(OH)_{34}(HCO_2)_{30}$). In some embodiments, one or more of the SBUs comprise a $Hf_6$ oxo cluster (e.g., $[Hf_6O_4(OH)_4(HCO_2)_6]$) or an $Hf_{12}$ oxo cluster. In some embodiments, one or more of the SBUs comprise a $Hf_6$ oxo cluster. In some embodiments, one or more of the SBUs comprise a $Hf_{12}$ oxo cluster.

As noted above, each SBU is bonded to at least one other SBU via coordinative bonding to the same bridging ligand. Stated another way, each SBU is bonded via a coordinative bond to at least one bridging ligand, which is also coordinatively bonded to at least one other SBU.

Any suitable bridging ligand or ligands can be used. In some embodiments, each bridging ligand is an organic compound comprising multiple coordination sites, wherein the multiple coordination sites are essentially co-planar or are capable of forming coordinative bonds that are coplanar. The coordination sites can each comprise a group capable of forming a coordinate bond with a metal cation or a group capable of forming such a group. Thus, each coordination site can comprise an unshared electron pair, a negative charge, or an atom or functional group capable of forming an unshared electron pair or negative charge. Typical coordination sites include, but are not limited to, functional groups such as carboxylate and derivatives there (e.g., esters, amides, anhydrides), nitrogen-containing groups (e.g., amines, nitrogen-containing aromatic and non-aromatic heterocycles), alcohols, phenols and other hydroxyl-substituted aromatic groups; ethers, acetylacetonate (i.e., $-C(=O)CH_2C(=O)CH_3$), phosphonates, phosphates, thiols, and the like.

In some embodiments, each bridging ligand comprises between 2 and 10 coordination sites (i.e., 2, 3, 4, 5, 6, 7, 8, 9, or 10 coordination sites). In some embodiments, each bridging ligand is capable of binding to two or three SBUs. In some embodiments, each of the organic bridging ligands is a dicarboxylate or a tricarboxylate.

The coordination sites of the organic bridging ligand can be bonded to the same polyvalent (e.g., divalent or trivalent) linking group, such as an arylene group. In some embodiments, the MOL or MOP comprises one or more organic bridging ligand comprising a di- or tricarboxylate of a di- or tricarboxylic acid selected from the group comprising, but not limited to, the group:
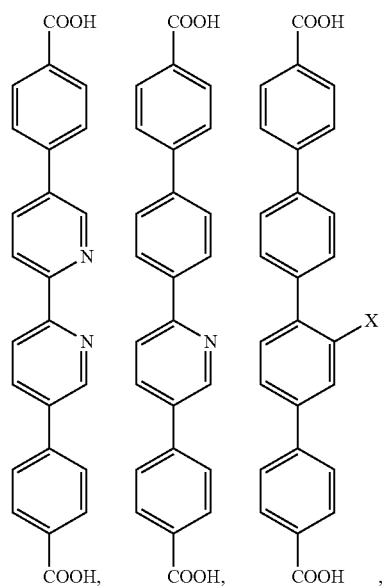
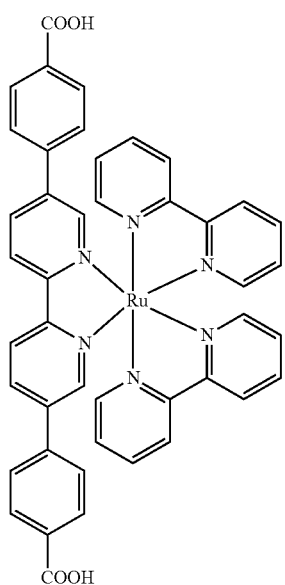
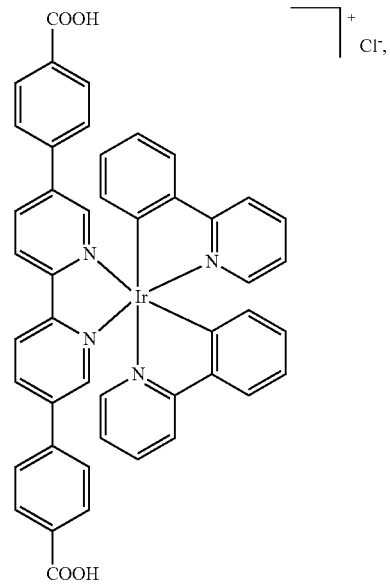
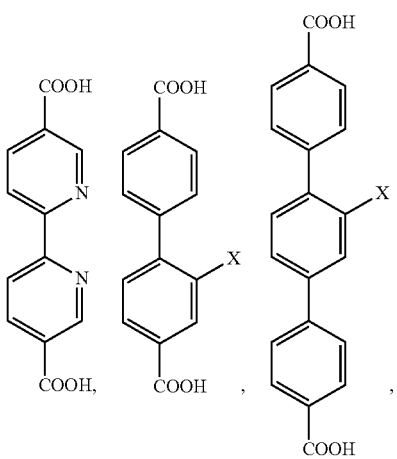
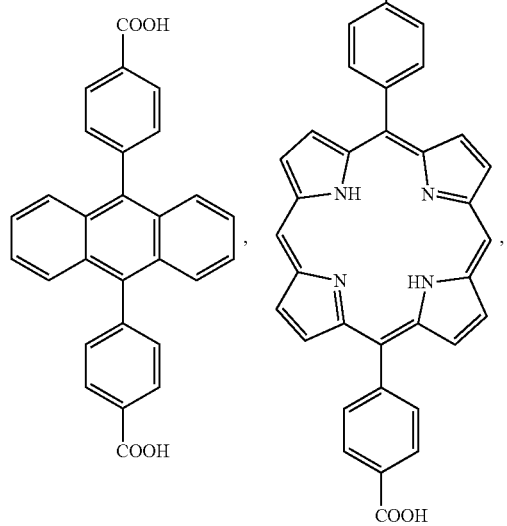

-continued

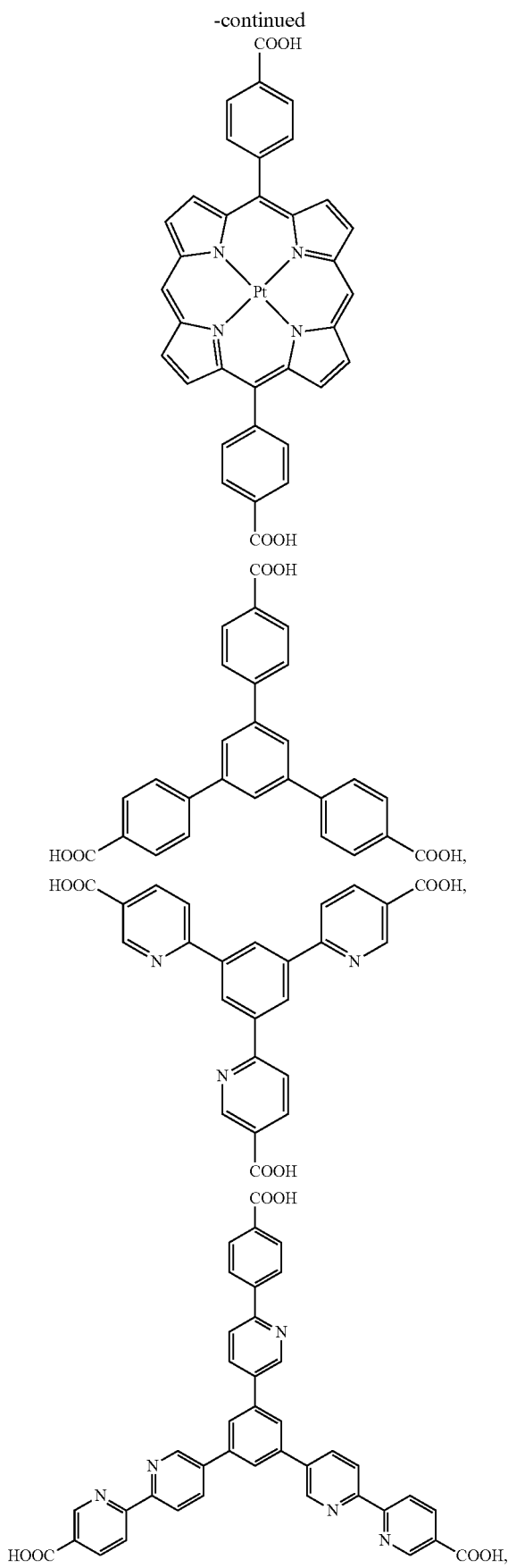

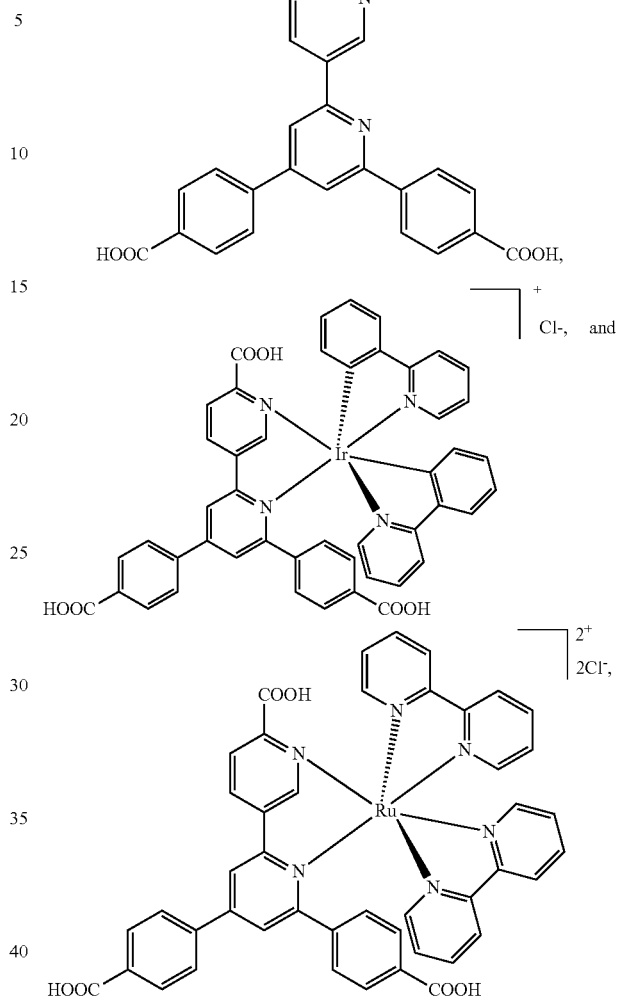

where X, if present, is selected from H, halo (e.g., Cl, Br, or I), OH, SH, $NH_2$, nitro ($NO_2$), alkyl, substituted alkyl (e.g., hydroxy-substituted alkyl, thiol-substituted alkyl, or amino-substituted alkyl) and the like. In some embodiments, X comprises a covalently attached photosensitizer such as, but not limited to, a dye, a porphyrin, a chlorin, a bacteriochlorin, a porphycene, or a chlorophyll, or a derivative or analog thereof. For example, X can be a porphyrin covalently attached to the bridging ligand via an alkylene linker moiety and an amide, ester, thiourea, disulfide, or ether bond.

In some embodiments, the linking group of the organic bridging ligand comprises a nitrogen donor moiety. In some embodiments, the organic bridging ligand can comprise a nitrogen donor moiety selected from the group comprising, but not limited to, a bipyridine, a phenyl-pyridine, a phenanthroline, and a terpyridine, which can optionally be substituted with one or more aryl group substituent at one or more of the carbon atoms of the nitrogen donor moiety. In some embodiments, at least one of the organic bridging ligands comprises a ligand selected from the group consisting of 4',6'-dibenzoato-[2,2'-bipyridine]-4-carboxylate (BPY), 4'-(4-carboxyphenyl)-[2,2':6',2''-terpyridine]-5,5''-dicarboxylate (TPY), and 4,4'-(2,2'-bipyridine]-5,5'-diyl)

dibenzoate (QPDC). In some embodiments, at least one of the organic bridging ligands comprises QPDC or BPY.

In some embodiments, at least one of the bridging ligands comprises the photosensitizer or a derivative of the photosensitizer. In some embodiments, the photosensitizer or its derivative can be a coordination complex, wherein one of the ligands of the coordination complex is a di- or tricarboxylate (or comprises two or three other groups that can coordinate to a metal ion, such as thiol, hydroxy, amino or phosphate). Thus, in some embodiments, the photosensitizer is bound to the MOL or MOP through a coordinate bonds (i.e., to metals in the SBUs).

In some embodiments, the photosensitizer or its derivative is attached to a bridging ligand via a covalent bond. The photosensitizer can be covalently bonded to the organic bridging ligands of the MOL or MOP e.g., through amide conjugation, ester conjugation, thiourea conjugation, click chemistry, or disulfide bond conjugation. In some embodiments, the covalent bonding further includes a linker group between the MOL or MOP and the PS. Such linker groups include, but are not limited to moieties such as cyclodextrin, polyethylene glycol, poly(maleic acid), or a $C_2$-$C_{15}$ linear or branched alkyl chain.

In some embodiments, at least one of the bridging ligands comprises a porphyrin, a chlorin, a chlorophyll, a phthalocyanine, a ruthenium coordination complex (e.g., a ruthenium-bipyridine complex), or an iridium coordination complex (e.g., an iridium-bipyridine complex). In some embodiments, at least one bridging ligand comprises a ruthenium or iridium coordination complex comprising 4,4'-dibenzoato-[2,2'-bipyridine]-4-carboxylate (QDPC). In some embodiments, the ruthenium or iridium coordination complex further comprises one or more 2,2'-bipyridine (bpy), 2-phenyl-pyridine (ppy), substituted bpy, or substituted ppy, i.e., as additional ligands of the Ir or Ru ion.

For example, in some embodiments, at least one bridging ligand comprises a Ru coordination complex or an Ir coordination complex, wherein said Ru or Ir coordination complex comprises: (a) a di- or tricarboxylate ligand further comprising a nitrogen-donor group; (b) a Ru or Ir ion complexed to the nitrogen-donor group in the di- or tricarboxylate ligand, and (c) one or more additional ligands complexed to the Ru or Ir ion. In some embodiments, each of the one or more additional ligands is independently selected from the group comprising substituted or unsubstituted bpy and substituted or unsubstituted ppy (i.e., wherein substituted bpy and substituted ppy comprise bpy or ppy substituted with one or more aryl group substituents). In some embodiments, the bpy and/or the ppy are substituted with one or more aryl group substituent selected from the group comprising, but not limited to, halo (i.e., I, Br, Cl, or F) and halo-substituted alkyl (i.e., an alkyl group substituted with one or more halo group). In some embodiments, the alkyl group of halo-substituted alkyl group is a $C_1$-$C_6$ alkyl group (e.g., methyl, ethyl, propyl, butyl, pentyl, or hexyl), which can be a straight chain group or a branched alkyl group. In some embodiments, the halo-substituted alkyl group is a halo-substituted methyl group. In some embodiments, the halo-substituted alkyl is a perhaloalkyl group (i.e., wherein all of the hydrogen atoms of the alkyl group are replaced by halo). In some embodiments, one or more aryl group substituents are selected from fluoro and trifluoromethyl.

In some embodiments, the di- or tricarboxylate ligand of the Ru or Ir coordination complex is BPY or QDPC. Thus, in some embodiments, the Ru or Ir coordination complex comprises a complex comprising a carboxylate of one of the formulas:

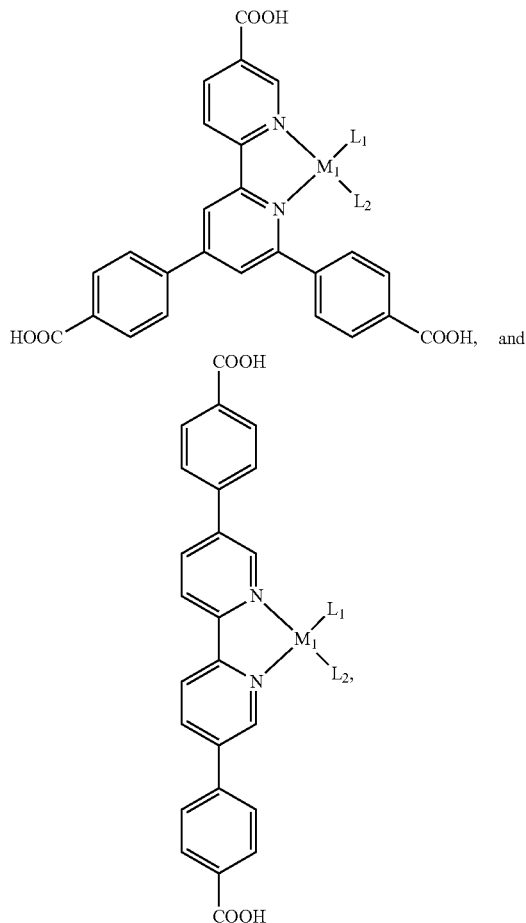

wherein $M_1$ is Ru or Ir; and $L_1$ and $L_2$ each have a structure of the formula:

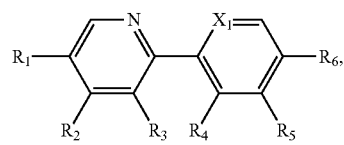

wherein $X_1$ is CH or N; and each of $R_1$, $R_2$, $R_3$, $R_4$, $R_5$, and $R_6$ is independently selected from the group consisting of H, halo, alkyl, and substituted alkyl, optionally wherein the substituted alkyl is perhaloalkyl. $L_1$ and $L_2$ can be the same or different. In some embodiments, $L_1$ and $L_2$ are the same.

In some embodiments, $X_1$ is N (i.e., $L_1$ and/or $L_2$ are bpy ligands). In some embodiments, $X_1$ is CH (i.e., $L_1$ and/or $L_2$ is a ppy ligand).

In some embodiments, at least $R_2$, $R_3$, and $R_5$ are H. In some embodiments, each of $R_1$-$R_6$ are H. In some embodiments, $R_1$ is perfluoromethyl. In some embodiments, $R_4$ and/or $R_6$ are F. In some embodiments, $R_4$ and $R_6$ are each F. In some embodiments, $R_1$ is perfluormethyl and $R_4$ and $R_6$ are each F.

In some embodiments, the least one of the organic bridging ligands is a porphyrin, chlorin, bacteriochlorin or a derivate or analog thereof (e.g., an expanded porphyrin), optionally complexed to a metal ion, such as, but not limited to, Pt. In some embodiments, at least one bridging ligand is selected from the group comprising, but not limited to, 5, 15-di(p-benzoato)porphyrin (DBP) or a derivative and/or a metal complex thereof; 5,15-di(p-benzoato)chlorin (DBC) or a derivative and/or metal complex thereof; and 5, 15-di (p-benzoato)bacteriochlorin (DBBC) or a derivative and/or a metal complex thereof. In some embodiments, at least one of the organic bridging ligands is DBP. In some embodiments, the nitrogen atoms of the DBP are complexed to a metal ion. In some embodiments, the metal ion is selected from the group including, but not limited to, a platinum (Pt) ion, an iridium (Ir) ion, a tungsten (W) ion, or a gold (Au) ion In some embodiments, the MOL or MOP has a thickness of less than about 30 nm, less than about 25 nm, less than about 20 nm, less than about 15 nm, less than about 12 nm, or less than about 10 nm. For example, in some embodiments, the MOL or MOP is a MOP having a thickness of between about 3 nm and about 30 nm (i.e., about 3, 4, 5, 6, 7, 8, 9, 10, 11, 12, 13, 14, 15, 16, 17, 18, 19, 20, 21, 22, 23, 24, 25, 26, 27, 28, 29, or about 30 nm). In some embodiments, the MOP has a thickness of between about 3 nm and about 12 nm. In some embodiments, the MOP has a thickness of two, three, four or five SBUs.

In some embodiments, the MOL or MOP has a thickness of less than about 12 nm or less than about 10 nm. In some embodiments, the MOL or MOP is a MOL. In some embodiments, the MOL has a thickness of about 3 nm or less. In some embodiments, the MOL has a thickness of between about 1 nm and about 3 nm (i.e., about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or about 3.0 nm). In some embodiments, the MOL has a thickness between about 1.2 nm to about 1.7 nm. In some embodiments, the MOL has a thickness of about one SBU.

In some embodiments, the MOL or MOP comprises $Hf_{12}$ oxo cluster SBUs and at least one organic bridging ligand selected from the group comprising bis(2,2'-bipyridine)(5, 5'-di(4-carboxyl-phenyl)-2,2'-bipyridine) ruthenium(II) chloride (QDPC-Ru); bis(4-phenyl-2-pyridine)(5,5'-di(4-carboxyl-phenyl)-2,2'-bipyridine)iridium(III) chloride (QDPC-Ir); 5,15-di(p-benzoato)porphyrin (DBP); platinum-complexed 5, 15-di(p-benzoato)porphyrin (DBP-Pt); and bis[2-(2',4'-diflurophenyl)-5-(trifluoromethyl)pyridine](5, 5'-di(4-carboxyl-phenyl)-2,2'-bipyridine iridium (QDPC-Ir—F). Thus, in some embodiments, the MOL or MOP is selected from the group comprising, but not limited to, $Hf_{12}$-QDPC-Ru, $Hf_{12}$-QDPC-Ir, $Hf_{12}$-DBP, $Hf_{12}$-DBP-Pt, and $Hf_{12}$-QDPC-Ir—F. In some embodiments, the $Hf_{12}$-QDPC-Ru, $Hf_{12}$-QDPC-Ir, $Hf_{12}$-DBP, $Hf_{12}$-DBP-Pt, or $Hf_{12}$-QDPC-Ir—F is a MOL.

In some embodiments, the MOL or MOP comprises $Hf_6$ oxo cluster SBUs and at least one organic bridging ligand selected from the group comprising bis(2,2-bipyridine)-4', 6'-dibenzoato-[2,2'-dipyridine]-4-carboxylate ruthenium (II) chloride (BPY-Ru); bis(4-phenyl-2-pyridine)-4',6'-dibenzoato-[2,2'-dipyridine]-4-carboxylate iridium (III) chloride (BPY-Ir); and bis[2-(2',4'-diflurophenyl)-5-(trifluoromethyl) pyridine]-4',6'-dibenzoato-[2,2'-bipyridine]-4-carboxylate iridium bridging ligands (BPY-Ir—F). Thus, in some embodiments, the MOL or MOP is $Hf_6$-BPY-Ru, $Hf_6$-BPY-Ir, or $Hf_6$-BPY-Ir. In some embodiments, the $Hf_6$-BPY-Ru, $Hf_6$-BPY-Ir, or $Hf_6$-BPY-Ir is a MOL.

In some embodiments, the MOL or MOP can be covalently or electrostatically bonded to a hydrophilic polymer, such as, but not limited to, a polyethylene glycol (PEG) moiety or polyvinylpyrolidine (PVP) moiety, e.g., in order to prolong the circulation half-life of the MOL or MOP and/or to render the MOL or MOP less antigenic. In some embodiments, the hydrophilic polymer can have a weight average molecular weight or a number average molecular weight of between about 1,000 and about 6,000. In some embodiments, the MOL or MOP further comprises a PEG moiety. In some embodiments, the PEG moiety is covalently bonded to the MOL or MOP. For instance, in some embodiments, the PEG moiety can be attached to the MOL or MOP via a disulfide group-containing linker moiety coordinated to metal ions in the SBUs. In some embodiments, the disulfide group-containing linker moiety has a formula —S—S-alkylene-$X_2$, wherein $X_2$ is C(=O)O— or another functional group that coordinates to metal, e.g., phosphate, phosphonate, ester, acetylacetonate, etc. In some embodiments, the disulfide group-containing linker moiety has a formula —S—S—$(CH_2)_x$—C(=O)O—, wherein x is an integer between 1 and 12 (i.e., 1, 2, 3, 4, 5, 6, 7, 8, 9, 10, 11, or 12). In some embodiments, x is 2.

In some embodiments, the MOL or MOP (or a composition comprising the MOL or MOP) further comprises an additional therapeutic agent, such as an immunotherapy agent or a chemotherapeutic agent (or another small molecule therapeutic agent). In some embodiments, the therapeutic agent is a chemotherapeutic agent, such as, but not limited to, a platinum-containing agent (e.g., cisplatin, oxaliplatin, or another chemotherapeutic platinum coordination complex or prodrug thereof) doxorubicin, daunorubicin, docetaxel, mitoxanthrone, paclitaxel, digitoxin, digoxin, and septacidin. In some embodiments, the chemotherapeutic agent is covalently or electrostatically bonded to the MOL or MOP. In some embodiments, the chemotherapeutic agent is physically sequestered (e.g., encapsulated) in pores or channels in the MOL or MOP. In some embodiments, the chemotherapeutic agent is a platinum-containing agent, such as cisplatin or oxaliplatin, encapsulated or coordinatively bound to the MOL or MOP. In some embodiments, the chemotherapeutic agent is oxaliplatin or a prodrug thereof.

In some embodiments, the MOL or MOP (or a composition comprising the MOL or MOP) further comprises an immunotherapy agent. In some embodiments, the immunotherapy agent can be non-covalently bound to or physically encapsulated in the MOL or MOP. In some embodiments, the immunotherapeutic agent is selected from the group including, but not limited to, an agonist of DNA or RNA sensors, such as a RIG-1 agonist, a TLR3 agonist (e.g., polyinosinic:polycytidylic acid), a TLR7 agonist (such as imiquimod), a TLR9 agonist (e.g., CpG oligodeoxynucleotides (ODN)), a stimulator of interferon genes (STING) agonist (e.g., STINGVAX or ADU-S100), or a indoleamine 2,3-dioxygenate (IDO) inhibitor (IDOi). In some embodiments, the IDOi is selected from the group including, but not limited to indoximod (i.e., 1-methyl-D-tryptophan), BMS-986205, epacadostat (i.e., ICBN24360), and 1-methyl-L-tryptophan. In some embodiments, negatively charged immunotherapy agents, such as nucleotide-based immunotherapy agents (e.g., a TLR9 agonist like CpG ODN or a STING agonist like STINGVAX and ADU-S100), can be incorporated into a MOL or MOP via electrostatic interactions with positively charged moieties, such as metal ions, e.g., the metal ions in an Ir or Ru coordination complex.

In some embodiments, the presently disclosed MOL or MOP can further comprise an additional X-ray absorbing agent, such as a polyoxometalate (POM) (e.g., a tungsten, molybdenum, or niobate polyoxometalate), a metallic nanoparticle, such as a gold, palladium, or platinum nanoparticle, or a metal oxide nanoparticle, such as a hafnium oxide or niobium oxide nanoparticle. In some embodiments, the POM, metallic nanoparticle or metal oxide nanoparticle is physically sequestered (e.g., encapsulated) within pores or cavities in the MOL or MOP. In some embodiments, the POM, metallic nanoparticle or metal oxide nanoparticle is electrostatically bonded to metal ions of the MOL or MOP SBUs. In some embodiments, the presently disclosed MOP or MOP further comprises a POM, e.g., encapsulated in the MOL or MOP. In some embodiments, the POM is a tungsten polyoxometalate.

III.B. $Hf_{12}$ Oxocluster Nanoscale Metal-Organic Frameworks

In some embodiments, the presently disclosed subject matter provides a nanoscale metal-organic framework (nMOF) (i.e., a MOF having a thickness or diameter greater than about 30 nm, such as between about 31 nm and about 250 nm or between about 31 nm and about 120 nm) comprising $Hf_{12}$ oxo cluster SBUs and organic bridging ligands, wherein the nMOF comprises a PS. In some embodiments, one or more of the bridging ligands comprises a bridging ligand selected from the group comprising QPDC, an Ir or Ru complex comprising QPDC, DBP, and DBP-Pt.

For example, in some embodiments, at least one bridging ligand comprises a Ru coordination complex or an Ir coordination complex, wherein said Ru or Ir coordination complex comprises: (a) QPDC; (b) a Ru or Ir ion complexed to the QPDC, and (c) one or more additional ligands complexed to the Ru or Ir ion. In some embodiments, each of the one or more additional ligands is independently selected from the group comprising substituted or unsubstituted bpy and substituted or unsubstituted ppy (i.e., wherein substituted bpy and substituted ppy comprise bpy or ppy substituted with one or more aryl group substituents). In some embodiments, bpy and/or ppy are substituted with one or more aryl group substituent selected from the group comprising halo (i.e., I, Br, Cl, or F) and halo-substituted alkyl (i.e., an alkyl group substituted with one or more halo group). In some embodiments, the alkyl group of halo-substituted alkyl group is a $C_1$-$C_6$ alkyl group (e.g., methyl, ethyl, propyl, butyl, pentyl, or hexyl), which can be a straight chain group or a branched alkyl group. In some embodiments, the halo-substituted alkyl group is a halo-substituted methyl group. In some embodiments, the halo-substituted alkyl is a perhaloalkyl group (i.e., wherein all of the hydrogen atoms of the alkyl group are replaced by halo). In some embodiments, one or more aryl group substituents are selected from fluoro and trifluoromethyl.

In some embodiments, one or more bridging ligand comprises QPDC-Ir (i.e., an Ir ion complexed to QPDC and two ppy ligands) or DBP-Pt. In some embodiments, the nMOF is $Hf_{12}$-QPDC-Ir. In some embodiments, the nMOF is $Hf_{12}$-DBP-Pt.

In some embodiments, the nMOF further comprises a POM (e.g., a tungsten polyoxometallate). In some embodiments, the POM is encapsulated in the nMOF.

In some embodiments, the nMOF further comprises a hydrophilic polymer, such as, but not limited to, a polyethylene glycol (PEG) moiety or polyvinylpyrolidine (PVP) moiety. The hydrophilic polymer can prolong the circulation half-life of the nMOF and/or make the nMOF less antigenic. In some embodiments, the nMOF further comprises a PEG moiety. In some embodiments, the PEG moiety is covalently bonded to the nMOF. For instance, in some embodiments, the PEG moiety can be attached to the nMOF via a disulfide group-containing linker moiety coordinated to metal ions in the SBUs. In some embodiments, the disulfide group-containing linker has a formula —S—S-alkylene-$X_2$, wherein $X_2$ is C(=O)O— or another functional group that coordinates to metal, e.g., phosphate, phosphonate, ester, acetylacetonate, etc. In some embodiments, the disulfide group-containing linker has a formula —S—S—$(CH_2)_x$—C(=O) O—, wherein x is an integer between 1 and 12 (i.e., 1, 2, 3, 4, 5, 6, 7, 8, 9, 10, 11, or 12). In some embodiments, x is 2.

In some embodiments, the nMOF (or the composition comprising the nMOF) further comprises an additional therapeutic agent, such as an immunotherapy agent or a chemotherapeutic agent. In some embodiments, the therapeutic agent is a chemotherapeutic agent, such as, but not limited to, oxaliplatin, doxorubicin, daunorubicin, docetaxel, mitoxanthrone, paclitaxel, digitoxin, digoxin, and septacidin. In some embodiments, the chemotherapeutic agent is covalently or electrostatically bonded to the nMOF. In some embodiments, the chemotherapeutic agent is physically sequestered (e.g., encapsulated) in pores or channels in the nMOF. In some embodiments, the chemotherapeutic agent is a platinum-containing agent, such as cisplatin or oxaliplatin or a prodrug thereof, encapsulated or coordinatively bound to the nMOF. In some embodiments, the chemotherapeutic agent is oxaliplatin or a prodrug thereof.

In some embodiments, the nMOF further comprises an immunotherapy agent, e.g., non-covalently bound or physically encapsulated in the nMOF. In some embodiments, the immunotherapeutic agent is selected from the group including, but not limited to, an agonist of DNA or RNA sensors, such as a RIG-1 agonist, a TLR3 agonist (e.g., polyinosinic:polycytidylic acid), a TLR7 agonist (such as imiquimod), a TLR9 agonist (e.g., CpG oligodeoxynucleotides (ODN)), a stimulator of interferon genes (STING) agonist (e.g., STINGVAX or ADU-S100), or a indoleamine 2,3-dioxygenate (IDO) inhibitor (IDOi). In some embodiments, the IDOi is selected from the group including, but not limited to indoximod (i.e., 1-methyl-D-tryptophan), BMS-986205, epacadostat (i.e., ICBN24360), and 1-methyl-L-tryptophan. In some embodiments, negatively charged immunotherapy agents, such as nucleotide-based immunotherapy agents (e.g., a TLR9 agonist like CpG ODN or a STING agonist like STINGVAX and ADU-S100), can be incorporated into a nMOF via electrostatic interactions with positively charged moieties, such as metal ions, e.g., the metal ions in a Ir or Ru coordination complex.

In some embodiments, the nMOF is $Hf_{12}$-QPDC-Ir further comprising a POM or another inorganic scintillator encapsulated within the nMOF. In some embodiments, the nMOF is $Hf_{12}$-QPDC-Ir further comprising PEG attached to the nMOF via a disulfide group-containing linker coordinated to Hf ions in the nMOF. In some embodiments, the nMOF is $Hf_{12}$-QPDC-Ir further comprising a POM and a PEG moiety. In some embodiments, the nMOF is $Hf_{12}$-DBP-Pt further comprising oxaliplatin encapsulated within the nMOF.

III.C. Pharmaceutical Compositions/Formulations

In some embodiments, the presently disclosed subject matter provides a pharmaceutical composition or formulation comprising a MOL, MOP, or nMOF as described herein and a pharmaceutically acceptable carrier, e.g., a pharmaceutically acceptable carrier that is pharmaceutically acceptable in humans. In some embodiments, the composition can also include other components, such as, but not limited to anti-oxidants, buffers, bacteriostatics, bactericidal antibiotics, suspending agents, thickening agents, and solutes that render the composition isotonic with the bodily fluids of a subject to whom the composition is to be administered. In some embodiments, the pharmaceutical composition or formulation further includes an additional therapeutic agent, such as a conventional chemotherapeutic agent or an immunotherapy agent. For example, in some embodiments, the pharmaceutical composition or formulation further includes an antibody immunotherapy agent (e.g., an antibody immune checkpoint inhibitor, such as, but not limited to, a PD-1/PD-L1 antibody, a CTLA-4 antibody, an OX40 antibody, a TIM3 antibody, a LAG3 antibody, an anti-CD47 antibody).

The compositions of the presently disclosed subject matter comprise, in some embodiments, a composition that includes a pharmaceutically acceptable carrier. Any suitable pharmaceutical formulation can be used to prepare the compositions for administration to a subject. In some embodiments, the composition and/or carriers can be pharmaceutically acceptable in humans.

For example, suitable formulations can include aqueous and non-aqueous sterile injection solutions that can contain anti-oxidants, buffers, bacteriostatics, bactericidal antibiotics, and solutes that render the formulation isotonic with the bodily fluids of the subject; and aqueous and non-aqueous sterile suspensions that can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are sodium dodecyl sulfate (SDS), in one example in the range of 0.1 to 10 mg/ml, in another example about 2.0 mg/ml; and/or mannitol or another sugar, for example in the range of 10 to 100 mg/ml, in another example about 30 mg/ml; and/or phosphate-buffered saline (PBS).

It should be understood that in addition to the ingredients particularly mentioned above, the formulations of this presently disclosed subject matter can include other agents conventional in the art having regard to the type of formulation in question. For example, sterile pyrogen-free aqueous and non-aqueous solutions can be used.

IV. Methods of Using MOLs, MOPs, and $Hf_{12}$ Oxocluster nMOFs for Photodynamic Therapy and X-Ray Induced Photodynamic Therapy, Radiotherapy, Radiodynamic Therapy, and/or Radiotherapy-Radiodynamic Therapy In some embodiments, the presently disclosed subject matter provides methods of using the presently disclosed MOLs, MOPs, and nMOFs in photodynamic therapy (PDT), X-ray induced photodynamic therapy (X-PDT), radiotherapy (RT), radiodynamic therapy (RDT) and/or radiotherapy-radiodynamic therapy (RT-RDT), either with or without the co-administration of one or more immunotherapeutic agent and/or one or more chemotherapeutic agent. For instance, in some embodiments, the presently disclosed subject matter provides MOLs or MOPs comprising PSs for use in treating a disease, e.g., cancer or a pathogenic infection, via PDT, X-PDT, RT, and/or RT-RDT.

Thus, in some embodiments, the presently disclosed subject matter provides a method for treating a disease in a subject in need of treatment of the disease, wherein the method comprises: administering to the patient an MOL or MOP (or one of the presently disclosed nMOFs); and illuminating the patient with visible or near infrared (NIR) light. In some embodiments, at least one or more bridging ligand is or comprises the PS or a derivative thereof.

The subject can be illuminated, for example, on a portion of the anatomy affected the disease or near a site affected by the disease. In some embodiments, the subject is illuminated on a portion of the anatomy selected from, but not limited to, the skin or the gastrointestinal tract. In some embodiments, the subject's blood is illuminated.

In some embodiments, the disease is cancer. For example, the disease can be selected from the group comprising a head tumor, a neck tumor, breast cancer, a gynecological tumor, a brain tumor, colorectal cancer, lung cancer, mesothelioma, a soft tissue sarcoma, and pancreatic cancer. In some embodiments, the method can further comprise administering to the patient an additional cancer treatment (e.g., surgery, a conventional chemotherapeutic agent, immunotherapy, etc.).

In some embodiments, the presently disclosed subject matter provides a method for treating a disease (e.g., cancer or an infection) using X-ray induced PDT and/or RT, wherein the absorption of ionizing irradiation (e.g., X-rays) by a moiety present in a MOL or MOP (or $Hf_{12}$ oxocluster nMOF of the presently disclosed subject matter) can provide the light required for PDT and/or the energy required for ROS generation. Such methods can be suitable, for example, when the site of disease is not near the surface of the subject's anatomy or is otherwise not able to be illuminated sufficiently by visible or NIR light. The method can involve administering to a subject in need of treatment a MOL or MOP (or nMOF) of the presently disclosed subject matter and irradiating at least a portion of the patient with ionizing radiation. In some embodiments, the ionizing radiation is x-rays (e.g., in one to fifty fractions). In some embodiments, the SBUs of the MOL or MOP (or nMOF) contains metal cations capable of absorbing x-rays and the organic bridging ligand comprises a di- or tricarboxylate further comprising a nitrogen-containing group, such as a bipyridine moiety, or a porphyrin, optionally complexed to a metal ion, such as Ru, Ir, Pt, W, or Au.

In some embodiments, the disease is cancer. In some embodiments, the cancer is selected from a head tumor, a neck tumor, breast cancer, a gynecological tumor, a brain tumor, colorectal cancer, lung cancer, mesothelioma, a soft tissue sarcoma, skin cancer, connective tissue cancer, adipose cancer, stomach cancer, anogenital cancer, kidney cancer, bladder cancer, colon cancer, prostate cancer, central nervous system cancer, retinal cancer, blood cancer, a neuroblastoma, multiple myeloma, lymphoid cancer, and pancreatic cancer, In some embodiments, the disease is selected from colorectal cancer, colon cancer, and pancreatic cancer. In some embodiments, the disease is a metastatic cancer. In some embodiments, the method can further comprise administering to the patient an additional cancer treatment, such as, surgery, chemotherapy, toxin therapy, cryotherapy, immunotherapy, and gene therapy.

According to some embodiments of the presently disclosed subject matter, the use of an immunotherapy agent can enhance the PDT, RT, or X-ray induced PDT treatment. Thus, in some embodiments, the presently disclosed methods can further comprise administering to the subject an immunotherapy agent, either simultaneously with a MOL, MOP or nMOF and/or the irradiating, or prior to or after administering the MOL, MOP or nMOF and/or the irradiating.

The immunotherapy agent for use according to the presently disclosed subject matter can be any suitable immunotherapy agent known in the art. Immunotherapeutic agents suitable for use in the presently disclosed subject matter include, but are not limited to: PD-1, PD-L1, CTLA-4, IDO and CCR7 inhibitors, that is, a composition that inhibits or modifies the function, transcription, transcription stability, translation, modification, localization, or secretion of a polynucleotide or polypeptide encoding the target or a target associated ligand, such as anti-target antibody, a small molecule antagonist of the target, a peptide that blocks the target, a blocking fusion protein of the target, or small-interfering ribonucleic acid (siRNA)/shRNA/microRNA/pDNA suppressing the target. Antibodies that can be used according to the presently disclosed subject matter include, but are not limited to: anti-CD52 (Alemtuzumab), anti-CD20 (Ofatumumab), anti-CD20 (Rituximab), anti-CD47 antibodies, anti-GD2 antibodies, etc. Conjugated monoclonal antibodies for use according to the presently disclosed subject matter include but are not limited to: radiolabeled antibodies (e.g., Ibritumomab tiuxetan (Zevalin), etc.), chemolabeled antibodies (antibody-drug conjugates (ADCs)), (e.g., Brentuximab vedotin (Adcetris), Ado-trastuzumab emtansine (Kadcyla), denileukin diftitox (Ontak) etc.). Cytokines for use according to the presently disclosed subject matter include, but are not limited to: interferons (i.e., IFN-α, INF-γ), interleukins (i.e. IL-2, IL-12), TNF-α, etc. Other immunotherapeutic agents for use according to the presently disclosed subject matter include, but are not limited to, polysaccharide-K, neoantigens, etc.

In some embodiments, the immunotherapy agent can be selected from the group comprising an anti-CD52 antibody, an anti-CD20 antibody, an anti-CD20 antibody, anti-CD47 antibody an anti-GD2 antibody, a radiolabeled antibody, an antibody-drug conjugate, a cytokine, polysaccharide K and a neoantigen. Suitable cytokine immunotherapy agents can be, for example, an interferon (IFN), an interleukin (IL), or tumor necrosis factor alpha (TNF-α). In some embodiments, the cytokine immunotherapy agent is selected from IFN-α, INF-γ, IL-2, IL-12 and TNF-α. In some embodiments, the immunotherapy agent can be selected from an agonist of DNA or RNA sensors, such as a RIG-I agonist (e.g., a compound described in U.S. Pat. No. 7,271,156, incorporated herein by reference in its entirety), a TLR3 agonist (e.g., polyinosinic:polycytidylic acid), a TLR7 agonist (e.g., imiquimod), a TLR9 agonist (e.g., CpG ODN), and a STING agonist (e.g., STINGVAX or ADU-S100). In some embodiments, the immunotherapy agent is selected from the group comprising a PD-1 inhibitor (e.g., pembrolizumab or nivolumab), a PD-L1 inhibitor (e.g., atezolizumab, avelumab, or durvalumab), a CTLA-4 inhibitor (e.g., ipilimumab), an IDO inhibitor (e.g., indoximod, BMS-986205, or epacadostat), and a CCR7 inhibitor.

In some embodiments, the methods described above can further comprise administering to the patient an immunotherapy agent, such as, but not limited to a PD-1/PD-L1 antibody, an IDO inhibitor, CTLA-4 antibody, an OX40 antibody, a TIM3 antibody, a LAG3 antibody, an siRNA targeting PD-1/PD-L1, an siRNA targeting IDO and an siRNA targeting CCR7, as well as any other immunotherapy agent as recited elsewhere herein or that is known in the art.

In some embodiments, the presently disclosed subject matter provides a method of treating a disease (e.g., cancer) that combines X-ray induced PDT and immunotherapy. Accordingly, in some embodiments, the presently disclosed subject matter provides a method comprising: administering to a patient a MOL or MOP comprising a photosensitizer and an SBU that contains a metal ion that absorbs X-rays (e.g., Hf); irradiating at least a portion of the patient with X-rays (e.g., in one to fifty fractions); and administering to the patient an immunotherapy agent.

In some embodiments, the cancer is selected from a head tumor, a neck tumor, breast cancer, a gynecological tumor, a brain tumor, colorectal cancer, lung cancer, mesothelioma, a soft tissue sarcoma, skin cancer, connective tissue cancer, adipose cancer, lung cancer, stomach cancer, anogenital cancer, kidney cancer, bladder cancer, colon cancer, colorectal cancer, prostate cancer, central nervous system cancer, retinal cancer, blood cancer, neuroblastoma, multiple myeloma, lymphoid cancer and pancreatic cancer. In some embodiments, the disease is metastatic cancer.

In some embodiments, any of the above-described methods can further comprise administering to the patient an additional cancer treatment. The additional cancer treatment can be selected on the basis of the cancer being treated and/or on other factors, such as the patient's treatment history, overall health, etc., in accordance with the best judgement of the treating physician. The additional cancer treatment can be selected from the group including, but not limited to, surgery, radiotherapy, chemotherapy, toxin therapy, immunotherapy, cryotherapy and gene therapy. In some embodiments, the additional cancer treatment can comprise administering to the patient a conventional chemotherapeutic, such as, but not limited to, a platinum-containing agent (e.g., cisplatin or oxaliplatin or a prodrug thereof), doxorubicin, daunorubicin, docetaxel, mitoxanthrone, paclitaxel, digitoxin, digoxin, and septacidin or another conventional chemotherapeutic known in the art. The additional chemotherapeutic agent can be present in the MOL, MOP, or nMOF (e.g., encapsulated or coordinatively or covalently bonded to the MOL, MOP, or nMOF). Alternatively, the additional chemotherapeutic agent can be present in the same pharmaceutical composition or formulation as the MOL, MOP, or nMOF or in a separate pharmaceutical composition or formulation, administered prior to, simultaneously with, or after administration of the pharmaceutical composition or formulation comprising the MOL, MOP or nMOF and/or the irradiation.

In some embodiments, the additional cancer treatment can involve administering to the patient a drug formulation selected from the group comprising a polymeric micelle formulation, a liposomal formulation, a dendrimer formulation, a polymer-based nanoparticle formulation, a silica-based nanoparticle formulation, a nanoscale coordination polymer formulation, a nanoscale metal-organic framework formulation, and an inorganic nanoparticle (gold, iron oxide nanoparticles, etc.) formulation. In some embodiments, the drug formulation can be a formulation including a conventional chemotherapeutic.

The subject can be exposed to the ionizing irradiation energy in any suitable manner and/or using any suitable equipment, such as that currently being used for delivering X-rays in a medical or veterinary setting. In some embodiments, the X-ray source and/or output can be refined to enhance disease treatment. For instance, the X-rays can be generated using a peak voltage, current and/or, optionally, a filter chosen to minimize DNA damage in the patient due to X-ray irradiation and maximize X-ray absorption by the scintillator.

In some embodiments, the subjects are irradiated with a linear accelerator (LINAC), using conventional techniques, Intensity-Modulated Radiation Therapy (IMRT), Image Guided Radiation Therapy (IGRT), or Stereotactic Body Radio Therapy (SBRT), a $^{60}$Co radiation source, an implanted radioactive seed such as the ones used in brachytherapy, an orthovoltage or supervoltage X-ray irradiator, a high energy electron beam generated from LINAC, or a proton source. In some embodiments, the irradiating can comprise generating X-rays using a tungsten or another metal target, Cobalt-60 sources (cobalt unit), linear accelerators (linacs), Ir-192 sources, and Cesium-137 sources. In some embodiments, the irradiating comprises passing the X-rays (e.g., the X-rays generated using a tungsten target) or other ionizing radiation through a filter prior to irradiation the subject. In some embodiments, the filter can comprise an element with an atomic number of at least 20. In some embodiments, the filter comprises copper (Cu). In some embodiments, the filter can have a thickness that is less than about 5 millimeters (mm). In some embodiments, the filter can have a thickness of less than about 4 mm (e.g., less than about 3 mm, less than out 1 mm, less than about 0.5 mm, less than about 0.4 mm, less than about 0.3 mm, less than about 0.2 mm, or less than about 0.1 mm).

The X-rays can be generated using a peak voltage, current and/or, optionally, a filter chosen to minimize DNA damage in the patient due to X-ray irradiation and maximize X-ray absorption by the scintillator. In some embodiments, the X-rays are generated using a peak voltage that is less than about 230 kVp. In some embodiments, the peak voltage is less than about 225 kVp, less than about 200 kVp, less than about 180 kVp, less than about 160 kVp, less than about 140 kVp, less than about 120 kVp, less than about 100 kVp, or less than about 80 kVp. In some embodiments, the X-rays are generated using a peak voltage that is about 120 kVp.

In some embodiments, X-rays are generated by placing radioactive sources inside the subject on a temporary or permanent basis. In some embodiments, a MOL, MOP or nMOF of the presently disclosed subject matter is injected along with the implantation of a radioactive source.

V. Subjects

The methods and compositions disclosed herein can be used on a sample either in vitro (for example, on isolated cells or tissues) or in vivo in a subject (i.e. living organism, such as a patient). In some embodiments, the subject or patient is a human subject, although it is to be understood that the principles of the presently disclosed subject matter indicate that the presently disclosed subject matter is effective with respect to all vertebrate species, including mammals, which are intended to be included in the terms "subject" and "patient". Moreover, a mammal is understood to include any mammalian species for which employing the compositions and methods disclosed herein is desirable, particularly agricultural and domestic mammalian species.

As such, the methods of the presently disclosed subject matter are particularly useful in warm-blooded vertebrates. Thus, the presently disclosed subject matter concerns mammals and birds. More particularly provided are methods and compositions for mammals such as humans, as well as those mammals of importance due to being endangered (such as Siberian tigers), of economic importance (animals raised on farms for consumption by humans), and/or of social importance (animals kept as pets or in zoos) to humans, for instance, carnivores other than humans (such as cats and dogs), swine (pigs, hogs, and wild boars), rodents (such as rats, mice, hamsters, guinea pigs, etc.), ruminants (such as cattle, oxen, sheep, giraffes, deer, goats, bison, and camels), and horses. Also provided is the treatment of birds, including the treatment of those kinds of birds that are endangered, kept in zoos or as pets (e.g., parrots), as well as fowl, and more particularly domesticated fowl, for example, poultry, such as turkeys, chickens, ducks, geese, guinea fowl, and the like, as they are also of economic importance to humans. Thus, also provided is the treatment of livestock including, but not limited to domesticated swine (pigs and hogs), ruminants, horses, poultry, and the like.

VI. Administration

Suitable methods for administration of a composition of the presently disclosed subject matter include, but are not limited to intravenous and intratumoral injection, oral administration, subcutaneous administration, intraperitoneal injection, intracranial injection, and rectal administration. Alternatively, a composition can be deposited at a site in need of treatment in any other manner, for example by spraying a composition within the pulmonary pathways. The particular mode of administering a composition of the presently disclosed subject matter depends on various factors, including the distribution and abundance of cells to be treated and mechanisms for metabolism or removal of the composition from its site of administration. For example, relatively superficial tumors can be injected intratumorally. By contrast, internal tumors can be treated following intravenous injection.

In some embodiments, the method of administration encompasses features for regionalized delivery or accumulation at the site to be treated. In some embodiments, a composition is delivered intratumorally. In some embodiments, selective delivery of a composition to a target is accomplished by intravenous injection of the composition followed by photodynamic treatment (light irradiation) of the target.

For delivery of compositions to pulmonary pathways, compositions of the presently disclosed subject matter can be formulated as an aerosol or coarse spray. Methods for preparation and administration of aerosol or spray formulations can be found, for example, in U.S. Pat. Nos. 5,858,784; 6,013,638; 6,022,737; and 6,136,295.

VII. Doses

An effective dose of a composition of the presently disclosed subject matter is administered to a subject. An "effective amount" is an amount of the composition sufficient to produce detectable treatment. Actual dosage levels of constituents of the compositions of the presently disclosed subject matter can be varied so as to administer an amount of the composition that is effective to achieve the desired effect for a particular subject and/or target. The selected dosage level can depend upon the activity (e.g., RT, PDT, or X-PDT activity or MOL and/or MOP loading) of the composition and the route of administration.

After review of the disclosure herein of the presently disclosed subject matter, one of ordinary skill in the art can tailor the dosages to an individual subject, taking into account the particular formulation, method of administration to be used with the composition, and nature of the target to be treated. Such adjustments or variations, as well as evaluation of when and how to make such adjustments or variations, are well known to those of ordinary skill in the art.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Hf-DBY-Ir and Hf-DBY-Ru MOLs

1.1 Materials and Animals

All starting materials were purchased from Sigma-Aldrich (St. Louis, Missouri, United States of America) and Fisher (Thermo Fisher Scientific, Waltham, Massachusetts, United States of America), unless otherwise noted, and used without further purification.

Two types of murine colon adenocarcinoma cells, CT26 and MC38, were used for the biological studies. Cells were purchased from the American Type Culture Collection (Rockville, Maryland, United States of America). CT26 cells were cultured in Roswell Park Memorial Institute (RPMI) 1640 medium (GE Healthcare, Chicago, Illinois, United States of America) supplemented with 10% FBS (Hyclone Laboratories, Inc., Logan, Utah, United States of America). MC38 cells were cultured in Dulbecco's Modified Eagle's Medium (DMEM) medium (GE Healthcare, Chicago, Illinois, United States of America) supplemented with 10% FBS.

BALB/c mice and C57BL/6 mice (5-8 weeks) were obtained from Envigo RMS, Inc. (Indianapolis, Indiana, United States of America).

1.2. Synthesis of 4',6'-dibenzoato-[2,2'-bipyridine]-4-carboxylic acid ($H_3BPY$), [($H_3BPY$)Ir(ppy)$_2$]Cl ($H_3BPY$-Ir, ppy=2-phenylpyridine), and [($H_3BPY$)Ru(bpy)$_2$]Cl$_2$ ($H_3BPY$-Ru, bpy=2,2'-bipyridine)

1-(5-methylpyridin-2-yl)ethanone: The synthesis of 1-(5-methylpyridin-2-yl)ethanone was modified from a reported protocol. See Cao et al., 2016. 2-bromo-5-methylpyridine (20 g, 116 mmol) was dissolved in 220 mL of dry $Et_2O$ and cooled to −78° C. n-BuLi (47 mL, 2.5 M in hexanes) was added dropwise over 1 hour. The mixture was stirred at −78° C. for 90 min before dimethylacetamide (12 mL) was added dropwise and stirred for another 3 hours. Sat. $NH_4Cl$ (aq.) was added to quench the reaction. The aqueous layer was washed with $Et_2O$ twice and all the organic parts were combined, dried over anhydrous $Mg_2SO_4$, and filtered. After evaporation of the solvent, the residue was subjected to flash column chromatography on silica gel (10:90 EtOAc/$CH_2Cl_2$ as eluent), affording 1-(5-methylpyridin-2-yl)ethanone (9.4 g, 68.6 mmol, 59% yield) as a colorless oil. $^1$H NMR (500 MHz, CDCl$_3$): δ 8.50 (s, 1H), 7.95 (d, 1H, J=8.0 Hz), 6.21 (m, 1H), 2.70 (s, 3H), 2.42 (s, 3H).

Scheme 1. Synthesis of 4-(5-methylpyridin-2-yl)formylvinyl benzoic acid.

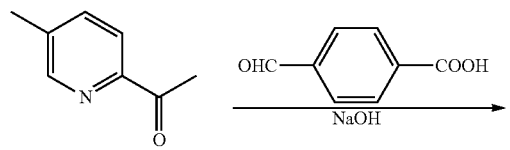

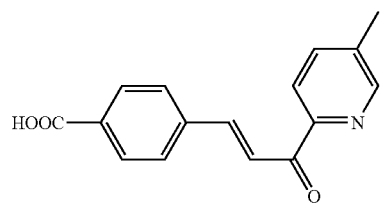

4-(5-methylpyridin-2-yl)formylvinyl benzoic acid: As shown in Scheme 1, above, 1-(5-methylpyridin-2-yl)ethanone (10.65 g, 71 mmol) was dissolved in EtOH (35 mL) and then added dropwise to a mixed solution of 4-carboxybenzaldehyde (9.38 g, 69.6 mmol) and NaOH (3.76 g, 94 mmol) in EtOH/$H_2O$ (1:1 v/v, 105 mL). The reaction mixture was stirred at room temperature overnight. The precipitate was separated via filtration and dissolved in MeOH/$H_2O$ (1:1 v/v). 1M HCl was added to adjust the pH to 3 to afford white precipitate, which was collected via filtration and washed with MeOH/$H_2O$. This procedure produced 4-(5-methylpyridin-2-yl)-formylvinyl benzoic acid in 22% yield (4.09 g, 15.3 mmol). $^1$H NMR (500 MHz, DMSO-d$_6$): δ 13.15 (br, 1H), 8.65 (s, 1H), 8.35 (d, 1H, J=16.0 Hz), 7.8-8.1 (m, 7H), 2.43 (s, 3H).

Scheme 2. Synthesis of 1-(2-oxo-2-(p-tolyl)ethyl)pyridin-1-ium.

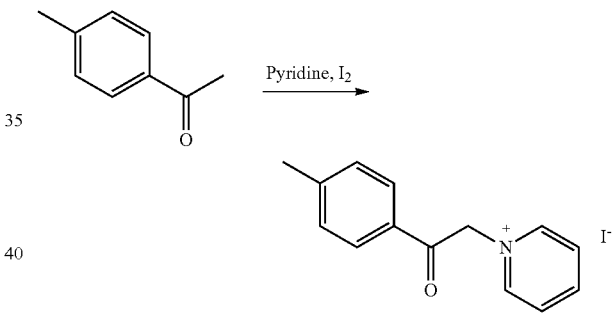

1-(2-oxo-2-(p-tolyl)ethyl)pyridin-1-ium: As shown in Scheme 2, above, 4'-methylacetonphenone (1.336 mL, 10 mmol), pyridine (10 mL), and $I_2$ (2.54 g, 10 mmol) were stirred and heated at 120° C. overnight. After cooling to 0° C., brown crystals precipitated. The crystals were filtered and washed with cold pyridine, CHCl$_3$, and Et$_2$O, then dried in vacuo to afford 1-(2-oxo-2-(p-tolyl)ethyl)pyridin-1-ium (2.50 g, 7.4 mmol, 74% yield). $^1$H NMR (500 MHz, DMSO-d$_6$) δ 8.99 (d, 2H, J=6.5 Hz), 9.74 (t, 1H, J=8.0 Hz), 8.28 (t, 2H, J=7.0 Hz), 7.98 (d, 2H, J=7.0 Hz), 7.49 (d, 2H, J=8.0 Hz), 6.43 (s, 2H), 2.46 (s, 3 Hz).

Scheme 3. Synthesis of 4-[2-(4-methylphenyl)-6-(5-methylpyridin-2-yl)-pyridin-4-yl]benzoic acid.

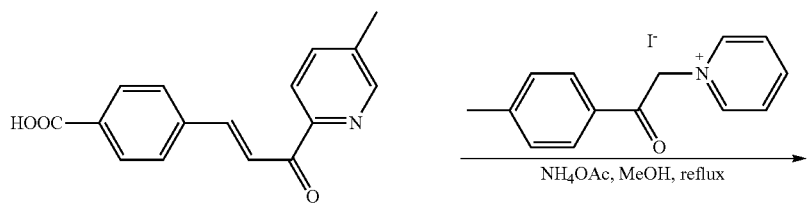

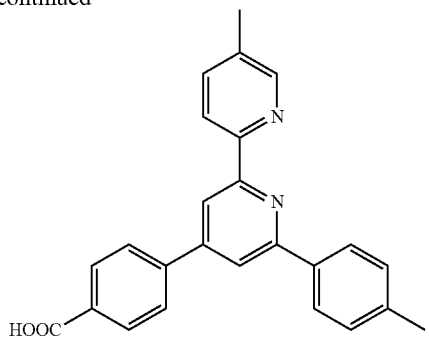

4-[2-(4-methylphenyl)-6-(5-methylpyridin-2-yl)pyridin-4-yl]benzoic acid: As shown in Scheme 3, above, 4-(5-methylpyridin-2-yl)formylvinyl benzoic acid (4.00 g, 15.0 mmol) and 1-[2-(4-methylphenyl)-2-oxoethyl]-pyridinium iodide (5.60 g, 16.5 mmol) were dissolved in 90 mL MeOH, followed by the addition of $NH_4OAc$ (11.5 g, 106 mmol). The reaction mixture was stirred under reflux for 6 h. After cooling to 0° C., the precipitate was filtered and washed with cold MeOH and $Et_2O$ to obtain 4-[2-(4-methylphenyl)-6-(5-methylpyridin-2-yl)pyridin-4-yl]benzoic acid (3.4 g, 8.94 mmol, 60% yield) as a white solid. $^1$H NMR (500 MHz, DMSO-$d_6$): δ 8.60-8.58 (2H), 8.53 (d, 1H, J=8.0 Hz), 8.33-8.25 (m, 3H), 8.14-8.08 (m, 4H), 7.84 (d, 1H, J=7.0 Hz), 7.38 (d, 2H, J=8.0 Hz), 2.40 (s, 6H).

mixture was heated at 90° C. overnight. More $KMnO_4$ (5 g×5, 46.8 mmol) was added to the reaction mixture to ensure complete oxidation. After refluxing for 5 days, the reaction mixture was cooled to room temperature, and EtOH was added to react with residual $KMnO_4$. The mixture was filtered, and the filtrate was put into a rotovap to remove most of the solvent. 1M HCl was added to the concentrated filtrate to adjust the pH to 3. White precipitates were collected via filtration, washed with copious amounts of water, and dried in vacuo to afford 4',6'-dibenzoato-[2,2'-bipyridine]-4-carboxylic acid (3.54 g, 8.05 mmol, 90% yield). $^1$H NMR (500 MHz, DMSO-$d_6$): δ 12.23 (br, 3H), 9.24 (s, 1H), 8.79-8.76 (m, 2H), 8.53-8.49 (m, 4H), 8.18-8.11 (m, 6H).

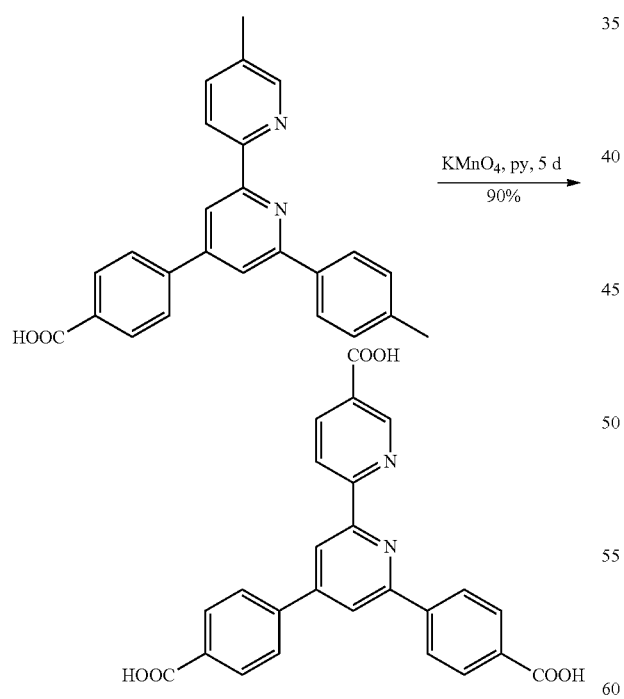

Scheme 4. Synthesis of $H_3$BPY.

4',6'-dibenzoato-[2,2'-bipyridine]-4-carboxylic acid ($H_3$BPY): As shown in Scheme 4, above, 4-[2-(4-methylphenyl)-6-(5-methylpyridin-2-yl)pyridin-4-yl]benzoic acid (3.4 g, 8.94 mmol) was dissolved in pyridine/$H_2O$ (3:1 v/v, 240 mL), followed by the addition of potassium permanganate ($KMnO_4$, 5.00 g, 31.6 mmol). The reaction

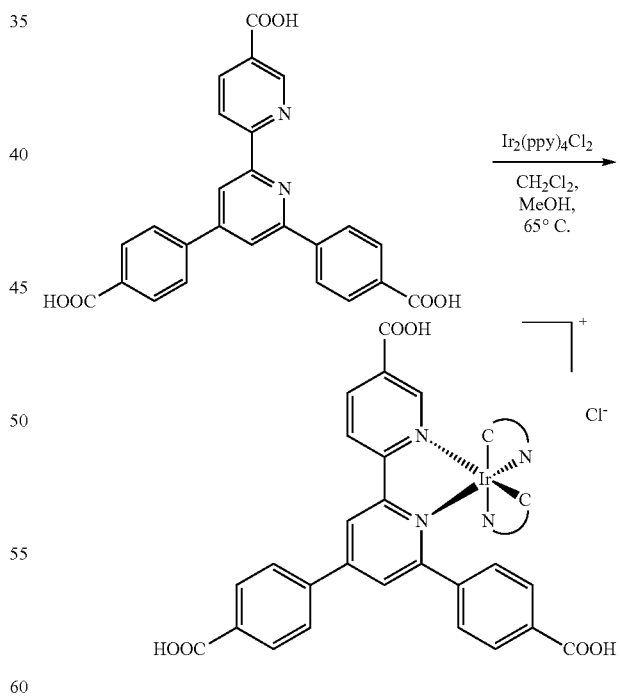

Scheme 5. Synthesis of [($H_3$BPY)—Ir(ppy)$_2$]Cl

As shown in Scheme 5, above, $H_3$BPY (202 mg, 0.459 mmol) in $CH_2Cl_2$ (15 mL) was added to a stirred suspension of [Ir(ppy)$_2$Cl]$_2$ (246 mg, 0.230 mmol) in MeOH (25 mL). The reaction mixture was stirred overnight at 68° C. After cooling to room temperature, the solvent was removed by a rotovap. The residue was dissolved in MeOH and subjected to filtration. The filtrate was collected and concentrated.

After adding a large amount of Et$_2$O, orange precipitate formed and was collected by filtration, then washed with Et$_2$O/MeOH and Et$_2$O, to afford [(H$_3$BPY)Ir(ppy)$_2$]Cl (H$_3$BPY-Ir) as an orange solid (328 mg, 0.335 mmol, 73% yield). $^1$H NMR (500 MHz, DMSO-d$_6$): δ 12.85 (br, 3H), 9.35 (d, 2H), 8.63 (d, 2H, J=8.0 Hz), 8.35 (d, 2H, J=8.5 Hz), 8.25 (s, 1H), 8.15-8.11 (m, 5H), 8.05-8.01 (m, 2H), 7.94-7.86 (m, 3H), 7.72 (s, 1H, J=7.5 Hz), 7.35-7.23 (m, 4H), 7.17 (t, 1H), 6.91 (t, 1H), 6.80 (t, 1H), 6.44 (t, 1H), 6.25 (t, 1H), 5.82 (d, 1H), 5.41 (d, 1H). ESI-MS: m/z=941.4 ([M−Cl]$^+$).

Scheme 6. Synthesis of [(H$_3$BPY)Ru(bpy)$_2$]Cl$_2$

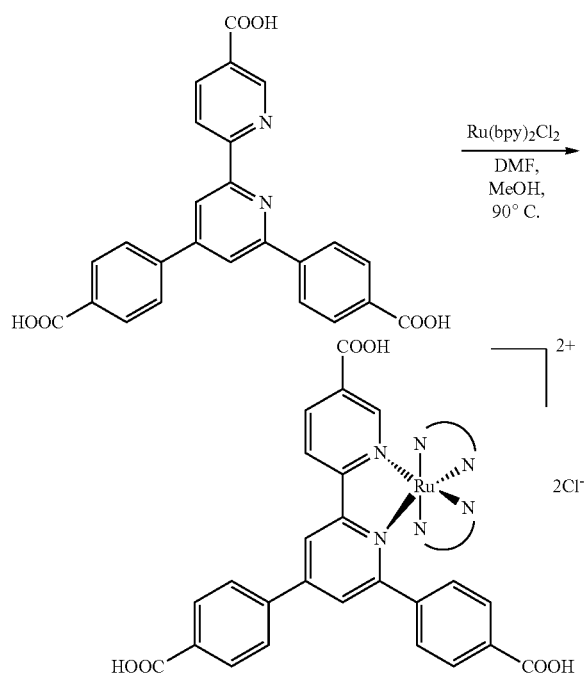

As shown in Scheme 6, above, H$_3$BPY (22 mg, 0.050 mmol) in DMF (15 mL) was added to a stirred suspension of Ru(bpy)$_2$Cl$_2$ (28.8 mg, 0.058 mmol) in MeOH (15 mL). The reaction mixture was stirred overnight at 90° C. After cooling to room temperature, the solvent was removed by a rotovap. The residue was dissolved in MeOH and subjected to filtration. The filtrate was collected and concentrated. After adding a large amount of Et$_2$O, brown precipitate formed and was collected by filtration, then washed with Et$_2$O/MeOH and Et$_2$O, to afford [(H$_3$BPY)Ru(bpy)$_2$]Cl$_2$ (H$_3$BPY-Ru) as brown solid (22.6 mg, 0.025 mmol, 49% yield). $^1$H NMR (500 MHz, DMSO-d$_6$): δ 9.29 (s, 1H), 9.20 (d, 1H), 8.75 (t, 2H), 8.69 (d, 1H), 8.38 (d, 1H), 8.33-8.30 (m, 4H), 8.25 (t, 1H), 8.18 (t, 1H), 8.11 (d, 2H), 8.10-8.07 (m, 1H), 7.89 (s, 2H), 7.83 (d, 1H), 7.65-7.53 (m, 5H), 7.42-7.40 (m, 2H), 7.21 (s, 1H), 6.95 (d, 1H), 6.84 (t, 1H), 6.32 (s, 1H). ESI-MS: m/z=427.2 ([M−2Cl]$^{2+}$).

1.3. Synthesis and Characterization of Hf- and Zr-Based Metal-Organic Layers Preparation of Hf-BPY or Zr-BPY MOL: To a 20 mL glass vial was added 2.5 mL of HfCl$_4$ solution [5.60 mg/mL in N,N-dimethylformamide (DMF)] or 2.5 mL of ZrCl$_4$ solution (4.07 mg/mL in DMF), 2.5 mL of the H$_3$BPY solution (5 mg/mL in DMF), 0.5 mL of formic acid, and 0.75 mL of water. The reaction mixture was kept in a 120° C. oven for 24 hours. The white precipitate was collected by centrifugation and washed with DMF and ethanol.

Preparation of Hf-BPY-Ir or Zr-BPY-Ir MOL: To a 2.5 mL methanol suspension of Hf-BPY MOL (15 mg) or Zr-BPY MOL (11 mg) was added 2.5 mL [Ir(ppy)$_2$Cl]$_2$ solution (6 mg/mL in DMF). The reaction mixture was kept in a 70° C. oven for 3 days. The orange precipitate was collected by centrifugation and washed with DMF and ethanol.

Preparation of Hf-BPY-Ru MOL or Zr-BPY-Ru MOL: To a 2.5 mL methanol suspension of Hf-BPY MOL (15 mg) or Zr-BPY MOL (11 mg) was added 2.5 mL Ru(bpy)$_2$Cl$_2$ solution (5.4 mg/mL in DMF). The reaction mixture was kept in a 70° C. oven for 3 days. The brown precipitate was collected by centrifugation and washed with DMF and ethanol.

1.4. X-Ray Absorption Spectroscopy

Data collection: X-ray absorption data were collected at Beam line 10-BM-A, B at the Advanced Photon Source (APS) at Argonne National Laboratory (Lemont, Illinois, United States of America). Spectra were collected at the ruthenium K-edge (22117 eV) or iridium L$_3$-edge (11215 eV) in transmission mode. The X-ray beam was monochromatized by a Si(111) monochromater and detuned by 50% to reduce the contribution of higher-order harmonics below the level of noise. A metallic ruthenium or platinum foil standard was used as a reference for energy calibration and was measured simultaneously with experimental samples. For ruthenium samples, the incident beam intensity (I$_0$), transmitted beam intensity (I$_t$), and reference (I$_r$) were measured by 20 cm ionization chambers with gas compositions of 44% N$_2$ and 56% Ar, 5% N$_2$ and 95% Ar, and 100% N$_2$, respectively. For iridium samples, the incident beam intensity (I$_0$), transmitted beam intensity (I$_t$), and reference (I$_r$) were measured by 20 cm ionization chambers with gas compositions of 96% N$_2$ and 4% Ar, 18% N$_2$ and 82% Ar, and 100% N$_2$, respectively. Data were collected over six regions: −250 to −30 eV (10 eV step size, dwell time of 0.25 s), −30 to −12 eV (5 eV step size, dwell time of 0.5 s), −12 to 30 eV (1.1 eV step size for ruthenium samples or 0.6 eV step size of iridium samples, dwell time of 1 s), 30 eV to 6 Å$^{-1}$, (0.05 Å$^{-1}$ step size, dwell time of 2 s), 6 Å$^{-1}$ to 12 Å$^{-1}$, (0.05 Å$^{-1}$ step size, dwell time of 4 s), 12 Å$^{-1}$ to 15 Å$^{-1}$, (0.05 Å$^{-1}$ step size, dwell time of 8 s). Multiple X-ray absorption spectra were collected at room temperature for each sample. Samples were ground and mixed with polyethyleneglycol (PEG) and packed in a 6-shooter sample holder to achieve adequate absorption length. Due to the similar energy between Ir L$_3$-edge (11215 eV) and Hf L$_1$-edge (11271 eV), XAS data was collected for Zr-BPY-Ir instead of Hf-BPY-Ir.

Data processing: Data were processed using the Athena and Artemis programs of the IFEFFIT package based on FEFF 6. See Ravel and Newville, 2005; and Rehr and Albers, 2000. Prior to merging, spectra were calibrated against the reference spectra and aligned to the first peak in the smoothed first derivative of the absorption spectrum, the background noise was removed, and the spectra were processed to obtain a normalized unit edge step.

EXAFS fitting: Fits of the EXAFS region were performed using the Artemis program of the IFEFFIT package. Fits were performed in R space, with a k-weight of 3 for the Ir samples and a k-weight of 2 for the Ru samples. Refinement was performed by optimizing an amplitude factor S$_0^2$ and energy shift ΔE$_0$, which are common to all paths, in addition to parameters for bond length (ΔR) and Debye-Waller factor ($\sigma^2$). The fitting models for Zr-BPY-Ir and H$_3$BPY-Ir were based on the crystal structure TEGVEI obtained from the Cambridge Crystallographic Database. The fitting models for Hf-BPY-Ru MOL and BPY-Ru Homo were based on the crystal structure ICITOD obtained from the Cambridge Crystallographic Database.

TABLE 1

Summary of EXAFS fitting parameters for Zr—BPY—Ir and H$_3$BPY—Ir.

| Sample | Zr—BPY—Ir | H$_3$BPY—Ir |
|---|---|---|
| Fitting range | k 1.8-13.9 Å$^{-1}$ | k 1.8-13.9 Å$^{-1}$ |
|  | R 1.1-5.0 Å | R 1.0-5.0 Å |
| Independent points | 30 | 30 |
| Variables | 19 | 19 |
| Reduced chi-square | 84.3 | 89.2 |
| R-factor | 0.023 | 0.012 |
| S$_0^2$ | 1.000 | 1.000 |
| ΔE$_0$(eV) | 8.92 ± 1.14 | 8.97 ± 0.91 |
| R (Ir—C30) (Å) | 1.97 ± 0.01 | 1.97 ± 0.01 |
| R (Ir—N4) (Å) | 2.05 ± 0.01 | 2.07 ± 0.06 |
| R (Ir—N1) (Å) | 2.13 ± 0.02 | 2.08 ± 0.14 |
| R (Ir—N2) (Å) | 2.25 ± 0.02 | 2.25 ± 0.02 |
| $\sigma^2$ (Ir—C(1$^{st}$ shell)) (Å$^2$) | 0.001 ± 0.002 | 0.001 ± 0.002 |
| $\sigma^2$ (Ir—N) (Å$^2$) | 0.001 ± 0.002 | 0.002 ± 0.002 |
| R (Ir—C40) (Å) | 2.94 ± 0.02 | 2.95 ± 0.03 |
| R (Ir—C5) (Å) | 3.03 ± 0.02 | 3.02 ± 0.03 |
| R (Ir—C6) (Å) | 2.87 ± 0.26 | 2.84 ± 0.07 |
| R (Ir—C31) (Å) | 3.14 ± 0.03 | 3.14 ± 0.02 |
| R (Ir—C10) (Å) | 3.31 ± 0.14 | 3.35 ± 0.06 |
| R (Ir—C11) (Å) | 3.44 ± 0.06 | 3.54 ± 0.06 |
| $\sigma^2$ (Ir—C(2$^{nd}$ shell)) (Å$^2$) | 0.003 ± 0.010 | 0.003 ± 0.005 |
| R (Ir—C16) (Å) | 4.07 ± 0.39 | 4.12 ± 0.70 |
| R (Ir—C34) (Å) | 4.08 ± 0.11 | 4.11 ± 0.11 |
| R (Ir—C32) (Å) | 4.41 ± 0.04 | 4.41 ± 0.04 |
| R (Ir—C37) (Å) | 4.83 ± 0.04 | 4.83 ± 0.06 |
| $\sigma^2$ (Ir—C(far)) (Å$^2$) | 0.008 ± 0.004 | 0.010 ± 0.004 |

TABLE 2

Summary of EXAFS fitting parameters for Hf—BPY—Ru and H$_3$BPY—Ru.

| Sample | Hf—BPY—Ru | H$_3$BPY—Ru |
|---|---|---|
| Fitting range | k 2.0-11.2 Å$^{-1}$ | k 2.0-11.3 Å$^{-1}$ |
|  | R 1.0-4.8 Å | R 1.0-4.8 Å |
| Independent points | 22 | 22 |
| Variables | 14 | 14 |
| Reduced chi-square | 355.5 | 624.1 |
| R-factor | 0.015 | 0.010 |
| S$_0^2$ | 1.000 | 1.000 |
| ΔE$_0$(eV) | 1.39 ± 1.27 | 1.25 ± 0.80 |
| R (Ru—N311) (Å) | 2.06 ± 0.01 | 2.06 ± 0.02 |
| R (Ru—N121) (Å) | 2.18 ± 0.09 | 2.12 ± 0.12 |
| $\sigma^2$ (Ru—N) (Å$^2$) | 0.004 ± 0.002 | 0.004 ± 0.002 |
| R (Ru—C222) (Å) | 3.03 ± 0.02 | 2.93 ± 0.08 |
| R (Ru—C112) (Å) | 2.68 ± 0.03 | 2.94 ± 0.14 |
| R (Ru—C226) (Å) | 2.90 ± 0.02 | 3.09 ± 0.04 |
| R (Ru—C133) (Å) | 3.13 ± 0.17 | 3.30 ± 0.10 |
| $\sigma^2$ (Ru—C(2$^{nd}$ shell)) (Å$^2$) | 0.001 ± 0.001 | 0.001 ± 0.001 |
| R (Ru—C223) (Å) | 4.52 ± 0.06 | 4.29 ± 0.06 |
| R (Ru—C225) (Å) | 4.29 ± 0.08 | 4.43 ± 0.05 |
| R (Ru—C224) (Å) | 4.84 ± 0.10 | 4.91 ± 0.04 |
| $\sigma^2$ (Ru—C(far)) (Å$^2$) | 0.007 ± 0.014 | 0.002 ± 0.005 |

1.5. Singlet Generation by 4-Nitroso-N,N-Dimethylanaline (RNO)

The MOL samples (Hf-BPY-Ir, Hf-BPY-Ru, Zr-BPY-Ir and Zr-BPY-Ru) were suspended in water in the presence of 25 μM of RNO and 10 mM of histidine. The concentration of each MOL suspension was 10 μM, based on Ir or Ru. The solutions were transferred to 1-dram vials for visible light irradiation or X-ray irradiation. For visible light irradiation, the MOLs were irradiated by a 450 W Xe lamp with a 400 nm cut-off (long pass) filter (350 mW/cm$^2$) for 1, 2, 3, 5, 7, and 10 mins. For X-ray irradiation, MOLs were given X-ray doses (225 KVp, 13 mA) of 1, 2, 4, or 8 Gy. The UV-vis absorption spectra of the solutions were taken by a spectrophotometer. The difference in the RNO peak absorbance [Δ(OD)] at 440 nm was calculated by subtracting the readout in the sample curve from that of the control curve (no irradiation).

TABLE 3

Linear fit results for PDT (Y = AX + B).

| | Slope (A) | | Intercept (B) | | Statistics |
|---|---|---|---|---|---|
| Samples | Value | Standard Error | Value | Standard Error | Adj. R$^2$ |
| Hf—BPY—Ir | 0.0109 | 0.0003 | −0.002 | 0.002 | 0.995 |
| Hf—BPY—Ru | 0.0041 | 0.0002 | 0.003 | 0.001 | 0.98 |
| Zr—BPY—Ir | 0.00878 | 0.00007 | 0.0004 | 0.0003 | 0.9996 |
| Zr—BPY—Ru | 0.00238 | 0.00007 | 0.0003 | 0.0003 | 0.995 |

TABLE 4

Linear fit results for X-PDT (Y = AX + B).

| | Slope (A) | | Intercept (B) | | Statistics |
|---|---|---|---|---|---|
| Samples | Value | Standard Error | Value | Standard Error | Adj. R$^2$ |
| Hf—BPY—Ir | 0.0122 | 0.0009 | 0.008 | 0.004 | 0.97 |
| Hf—BPY—Ru | 0.010 | 0.001 | 0.001 | 0.004 | 0.96 |
| Zr—BPY—Ir | 0.0039 | 0.0009 | 0.005 | 0.003 | 0.8 |
| Zr—BPY—Ru | 0.0019 | 0.0004 | 0.003 | 0.003 | 0.8 |

1.6. Cellular Uptake

The cellular uptakes of Hf-BPY, Hf-BPY-Ir, and Hf-BPY-Ru were evaluated in CT26 cells. CT26 cells were seeded on 6-well plates at 5×10$^5$/well and then cultured for 24 h. Hf-BPY-Ir, Hf-BPY-Ru, and Hf-BPY were added to the cells at a Hf concentration of 50 μM. After incubation of 1, 4, 8, and 24 hours, the cells were collected and counted with a hemocytometer. The cells were digested with concentrated nitric acid in a microwave reactor (CEM Corporation, Matthews, North Carolina, United States of America), and the metal concentrations were determined by ICP-MS (Agilent Technologies, Santa Clara, California, United States of America).

1.7. Cytotoxicity

The cytotoxicity of Hf-BPY-Ir, Hf-BPY-Ru, Hf-BPY, Zr-BPY-Ir, Zr-BPY-Ru and Zr-BPY upon X-ray irradiation was evaluated against two different murine colorectal adenocarcinoma cell lines, CT26 and MC38. Dark cytotoxicity was first tested without X-ray irradiation. MOLs were incubated with the cells at various concentrations, ranging from 0-100 μM based on Ir, Ru, or BPY, respectively, for 8 h. The cell culture medium was then replaced with fresh medium, and the cells were incubated another 72 h before determining the cell viability by 3-(4,5-dimethylthiazol-2-yl)-5-(3-carboxymethoxyphenyl)-2-(4-sulfophen-yl-)-2H-tetrazolium MTS assay (Promega Corporation, Madison, Wisconsin, United States of America). Cell viability was studied with a fixed X-ray irradiation dose of 2 Gy. An X-ray beam with 250 kVp and 15 mA current were used for the irradiation. Cell viability was also tested with the fixed Hf-MOLs concentration of 20 µM based on Ir, Ru or BPY and various X-ray doses.

1.8. Intracellular Singlet Oxygen ($^1O_2$) Generation $^1O_2$ generation in live cells was detected by Singlet Oxygen Sensor Green (SOSG, Life Technology, USA). CT26 cells were seeded in a 3.5-cm petri dish and cultured for 12 h. The culture medium was then replaced with fresh medium containing 1 µM SOSG to preload the cells with SOSG. After incubating for 30 min, the cells were washed by PBS three times to remove excess SOSG. The cells were incubated in PBS, with Hf-MOLs or ligands at a ligand concentration of 20 µM for 8 h, then washed with PBS three times to remove excess MOLs or ligands. X-ray irradiation was applied to cells at a dose of 2 Gy (250 kVp, 15 mA, 1-mm Cu filter). Confocal laser scanning microscopy (CLSM; FV1000 Laser Scanning Confocal Microscope, Olympus Corporation, Tokyo, Japan) was used to visualize the $^1O_2$ generated in the live cells by detecting the green fluorescence inside the cells.

1.9. In Vivo Efficacy

The in vivo anticancer efficacy of Hf-BPY-Ir and Hf-BPY-Ru were evaluated through intratumoral injections on CT26 or MC38 tumor-bearing mice. When the tumors reached 100-150 mm$^3$ in volume, MOLs with a photosensitizer concentration of 10 µM were intratumorally injected, followed by daily X-ray irradiation at a dose of 1 Gy/fraction (120 kVp, 20 mA, 2 mm-Cu filter), for a total of 5 fractions on CT26 models or 10 fractions on MC38 models on consecutive days. Tumor sizes were measured with a caliper every day, estimating tumor volume at (width$^2$×length)/2. All mice were sacrificed on day 18 and the excised tumors were photographed and weighed. Body weights of each group were monitored as an indication of systemic toxicity.

Tumors were excised from mice immediately following sacrifice and were embedded in an optimal cutting temperature (OCT) medium and stored at −80° C. Organs and tumors were then sectioned at 5-µm thickness and stained with hematoxylin and erosin (H&E) and observed with light microscopy (Pannoramic Scan Whole Slide Scanner, PerkinElmer Inc., Waltham, Massachusetts, United States of America). Tumor weight and tumor size data is summarized in Tables 5 and 6, below.

TABLE 5

Statistical analysis of the tumor weights at the end of treatment on CT26 or MC38 tumor bearing mice.

| | P values | |
|---|---|---|
| | CT26 | MC38 |
| PBS (+) vs Hf—BPY—Ir(+) | <0.0001 | <0.0001 |
| PBS (+) vs Hf—BPY—Ru (+) | <0.0001 | <0.0001 |
| PBS (+) vs Hf—BPY (+) | 0.047 | 0.048 |
| PBS (+) vs PBS (−) | 0.974 | 0.913 |

TABLE 6

Statistical analysis of the tumor sizes at the end of treatment on CT26 or MC38 tumor bearing mice.

| | P values | |
|---|---|---|
| | CT26 | MC38 |
| PBS (+) vs Hf—BPY—Ir(+) | <0.0001 | <0.0001 |
| PBS (+) vs Hf—BPY—Ru (+) | <0.0001 | <0.0001 |
| PBS (+) vs Hf—BPY (+) | 0.047 | 0.048 |
| PBS (+) vs PBS (−) | 0.974 | 0.913 |

Example 2

Discussion of Example 1

Figure 3A:
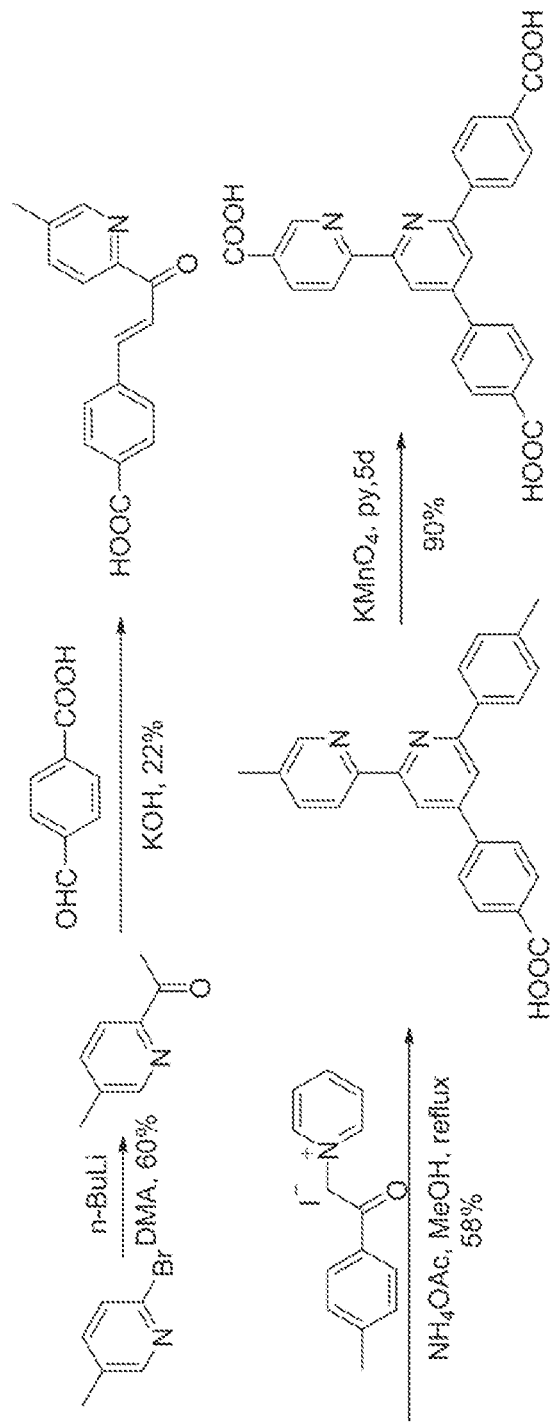
FIG. 3A is a schematic drawing showing the synthesis of 4',6'-dibenzoato-[2,2-bipyridine]-4-carboxylic acid ($H_3BPY$).

As described above in Example 1, Hf-BPY-Ir and Hf-BPY-Ru MOLs were synthesized by a postsynthetic metalation method. 4',6'-dibenzoato-[2,2'-bipyridine]-4-carboxylic acid ($H_3BPY$) was synthesized as shown in FIG. 3A and treated with $HfCl_4$ in N,N-dimethylformamide (DMF), formic acid, and water to afford Hf-BPY MOL as a white precipitate, then washed twice with DMF and once with ethanol. By optimizing the amounts of formic acid and $H_2O$, the size of Hf-BPY could be controlled to a diameter of ~500 nm, as verified by transmission electron microscopy (TEM). Hf-BPY was treated with $[Ir(ppy)_2Cl]_2$ or $Ru(bpy)_2Cl_2$ to afford Hf-BPY-Ir or Hf-BPY-Ru MOL as an orange or brown participate. Due to the 2-D structure of Hf-BPY, the bpy coordination sites are highly accessible, resulting in efficient postsynthetic metalation. The Ir and Ru loadings were determined to be 67% and 59% for Hf-BPY-Ir and Hf-BPY-Ru, respectively, as determined by Inductively Coupled Plasma-Mass Spectrometry (ICP-MS).

Figure 3B:
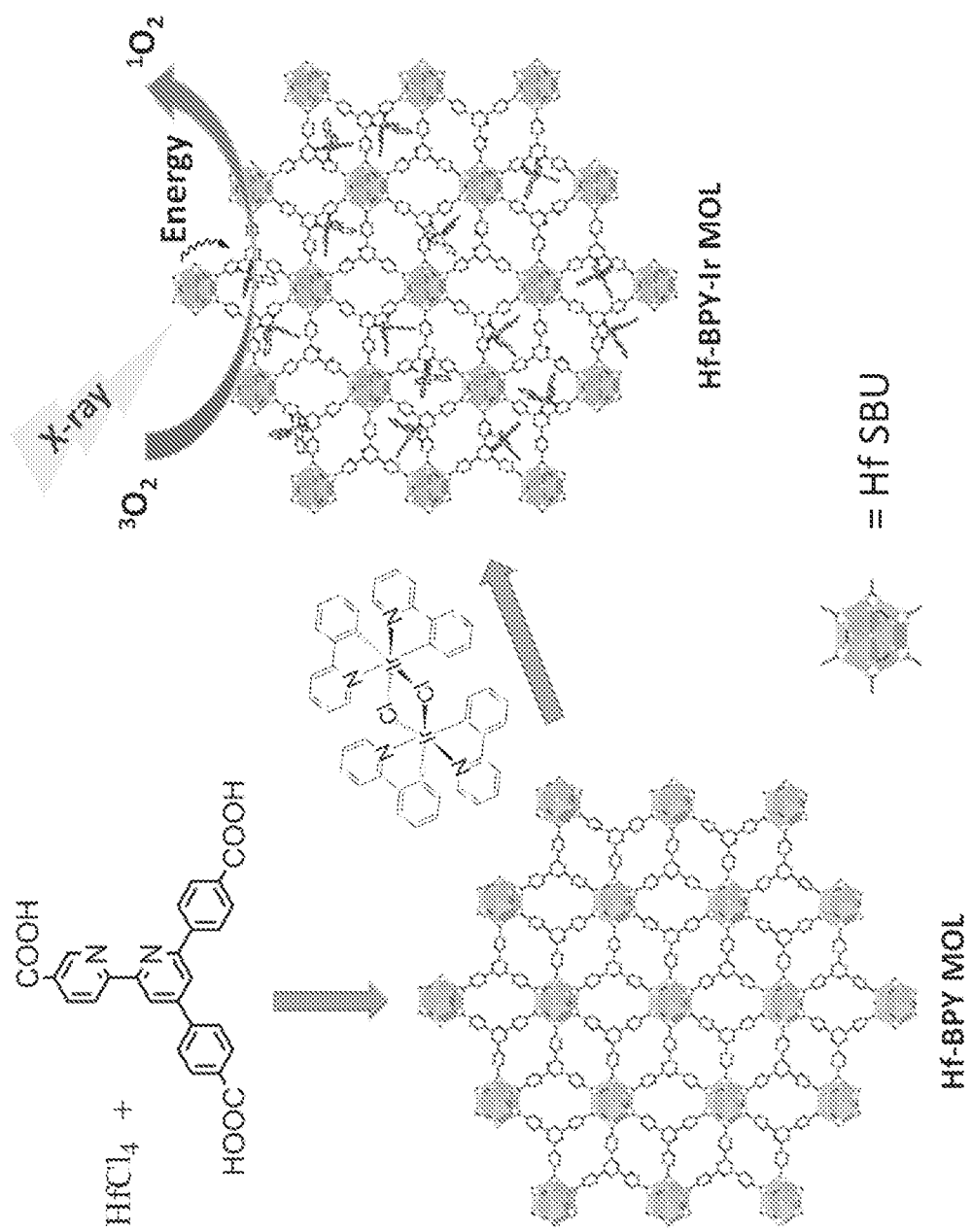
FIG. 3B is a schematic drawing showing the synthesis of a metal organic layer (MOL) comprising hafnium (Hf)-containing secondary building units (SBUs) and 4',6'-dibenzoato-[2,2-bipyridine]-4-carboxylate (BPY) bridging ligands (i.e., a Hf-BPY MOL), the complexation of the Hf-BPY MOL with an iridium (Ir) phenyl-pyridine (ppy) coordination complex to form an Ir-complexed Hf-BPY MOL (Hf-BPY-Ir MOL), and the generation of singlet oxygen ($^1O_2$) when the MOL is irradiated with x-rays in the presence of reactive oxygen species ($^3O_2$).

In Hf-BPY, each $Hf_6$ cluster of 12-connectivity was capped by 6 formate groups (three at the top and three at the bottom), leaving the remaining six sites coordinated to 3-connected BPY ligands to form a 3,6-connected 2-D network of $Hf_6(\mu_3-O)_4(\mu_3-OH)_4(HCO_2)_6(BPY)_2$ of kagome dual (kgd) topology. See FIG. 3B. High-resolution TEM (HRTEM) images of Hf-BPY, where $Hf_6$ clusters appear as dark spots, and fast Fourier transform (FFT) patterns of Hf-BPY were consistent with the kgd topology. The distance between two adjacent dark spots in the HRTEM was 2.0 nm, which matched the distance between two adjacent SBUs. The powder X-ray diffraction (PXRD) pattern of Hf-BPY was identical to the Hf-BTB MOL (see Cao et al., 2016), which further confirmed the kgd structure of Hf-BPY. Atomic force microscopy (AFM) images of Hf-BPY showed a 1.2 nm thickness, which was very close to the van der Waals size of the $Hf_6$ cluster capped by formate groups, indicating the monolayer structure of Hf-BPY. The ultrathin monolayer structure facilitates the diffusion of $^1O_2$, the diffusion length of which was estimated to be 20-220 nm in cells. See Moan and Berg, 1991.

TEM images of both Hf-BPY-Ir and Hf-BPY-Ru show that they have morphologies and sizes similar to Hf-BPY. The retention of the MOL structure after metalation was supported by the similarity among the PXRD patterns of Hf-BPY-Ir, Hf-BPY-Ru, and Hf-BPY. See FIG. 1A. In addition, the HRTEM images and FFT patterns of Hf-BPY-Ir and Hf-BPY-Ru were identical to those of Hf-BPY.

Figure 1B:
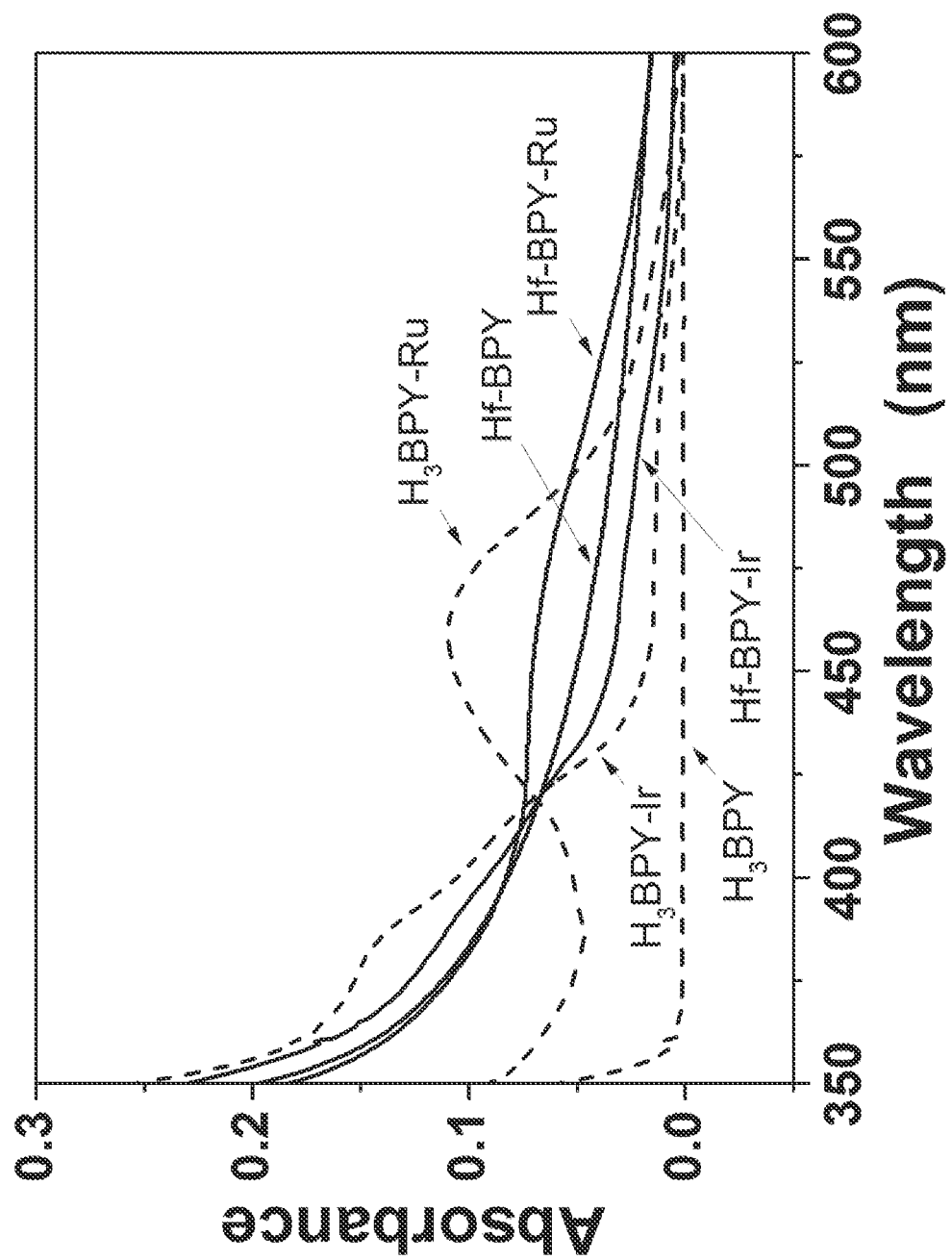
FIG. 1B is a graph showing the ultraviolet (UV)-visible absorption spectra (relative absorbance versus wavelength (from 350 nanometers (nm) to 600 nm) of metal organic layers (MOLs) including a MOL comprising a hafnium (Hf)-containing secondary building units (SBUs) and 4',6'-dibenzoato-[2,2-bipyridine]-4-carboxylate (BPY) bridging ligands (Hf-BPY); a MOL comprising Hf-containing SBUs and bridging ligands comprising a coordination complex comprising a BPY ligand, a ruthenium (Ru) ion and two bipyridine (bpy) ligands (Hf-BPY-Ru); and a MOL comprising Hf-containing SBUs and bridging ligands comprising a coordination complex comprising a BPY ligand, an iridium (Ir) ion, and two phenyl-pyridine (ppy) ligands (Hf-BPY-Ir). The spectra of the corresponding bridging ligands alone, i.e., 4',6'-dibenzoato-[2,2-bipyridine]-4-carboxylic acid ($H_3BPY$), $H_3BPY$ complexed to $Ru(bpy)_2$ ($H_3BPY$-Ru), and $H_3BPY$ complexed to $Ir(ppy)_2$ ($H_3BPY$-Ir) are also shown.

To further confirm the metalation of Hf-BPY and to better understand the coordination environments of Ir and Ru centers in Hf-MOLs, $[(H_3BPY)Ir(ppy)_2]Cl$ (i.e., $H_3BPY$-Ir) and $[(H_3BPY)Ru(bpy)_2]Cl_2$ (i.e., $H_3BPY$-Ru) were synthesized as homogeneous controls. The UV-visible absorption spectra of Hf-based MOLs exhibit similar MLCT bands as their corresponding ligands. See FIG. 1B. X-ray absorption spectroscopy indicated that Zr-BPY-Ir and Hf-BPY-Ru have the same Ir and Ru coordination environments as $H_3$BPY-Ir and $H_3$BPY-Ru, respectively. Due to similar energy between Ir $L_3$-edge (11215 eV) and Hf $L_1$-edge (11271 eV), X-ray absorption spectroscopy (XAS) data was collected for Zr-BPY-Ir instead of Hf-BPY-Ir.

Figure 1C:
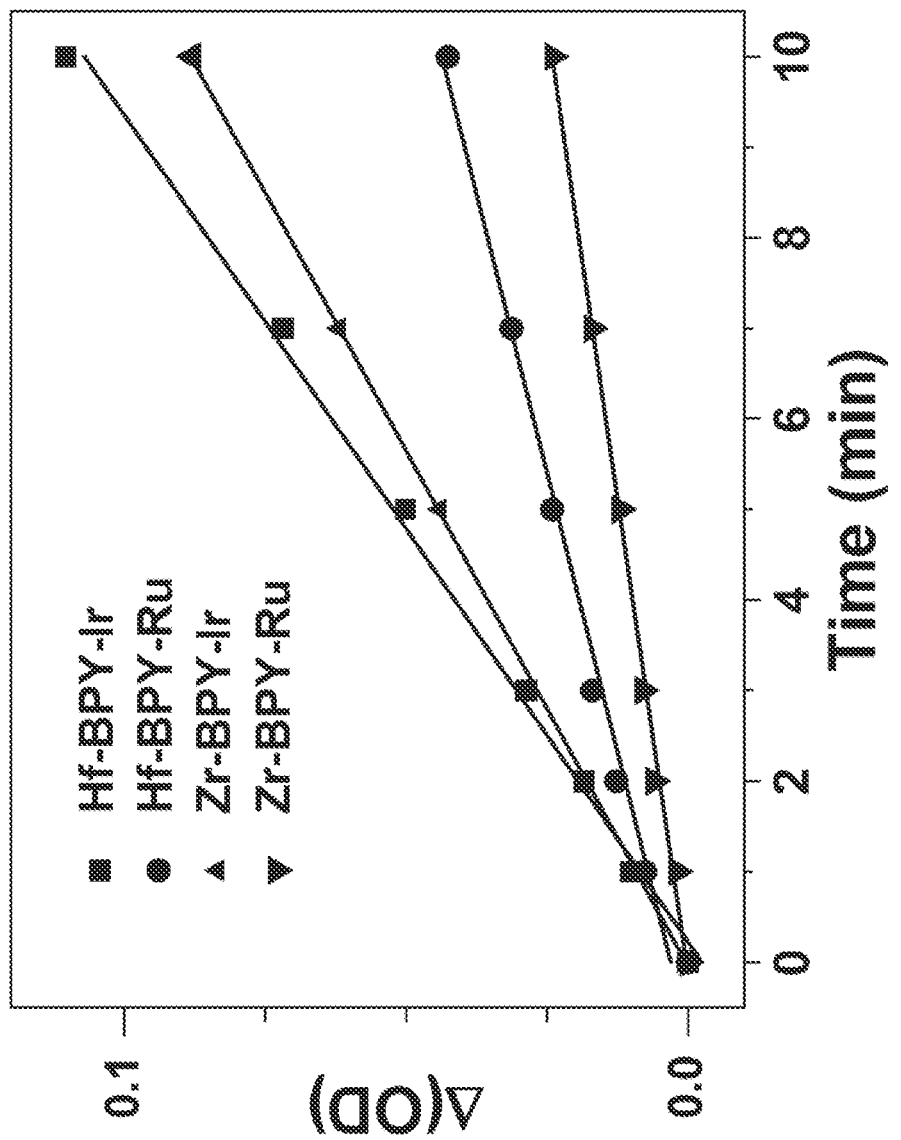
FIG. 1C is a graph showing the singlet oxygen generation of hafnium (Hf)-containing and zirconium (Zr)-containing metal-organic layers (MOLs) upon visible light irradiation. Data from MOLs comprising Hf-containing secondary building units (SBUs) and bridging ligands comprising a coordination complex containing 4',6'-dibenzoato-[2,2-bipyridine]-4-carboxylate (BPY), an iridium ion and two phenyl-pyridine (ppy) ligands (Hf-BPY-Ir, squares); a MOL comprising Hf-containing SBUs and bridging ligands comprising a coordination complex containing BPY, a ruthenium ion, and two bipyridine (bpy) ligands (Hf-BPY-Ru, circles); a MOL comprising Zr-containing SBUs and bridging ligands comprising a coordination complex comprising BPY, an iridium ion and two ppy ligands (Zr-BPY-Ir, upward pointing triangles); and a MOL comprising Zr-containing SBUs and bridging ligands comprising a coordination complex comprising BPY, a ruthenium ion and two bpy ligands (Zr-BPY-Ru, downward pointing triangles) are shown. Singlet oxygen generation efficiencies of the MOLs were determined using the 4-nitroso-N,N-dimethylanaline (RNO) assay and presented as a change in optical density ($\Delta OD$) at 440 nanometers (nm) versus time (in minutes (min)).

The singlet oxygen generation efficiencies of the MOLs was examined using a 4-nitroso-N,N-dimethylanaline (RNO) assay. Zr-MOLs (Zr-BPY-Ir and Zr-BPY-Ru) were synthesized using similar processes as the Hf MOLs and used for comparison. Upon irradiation with a Xe lamp using a 400 nm long-pass filter or X-rays (225 KVp, 13 mA), the $^1O_2$ generated by MOLs reacted with RNO in the presence of histidine, leading to a decrease of absorbance at 440 nm in the UV-visible spectra. By linearly fitting difference in RNO peak absorbance [Δ(OD)] against irradiation doses (which scale linearly with exposure times upon visible light or X-ray dose, Y=Ax+B), the RNO assay provides a quantitative measure of $^1O_2$ generation efficiencies, with a more positive slope indicating more efficient $^1O_2$ generation. Upon visible light irradiation, the linear fitting results showed that Ir-based Zr- and Hf-MOLs generated $^1O_2$ more efficiently than Ru-based Zr- and Hf-MOLs (see FIG. 1C and Table 3, above), consistent with the difference in $^1O_2$ generation quantum yields between [Ir(bpy)(ppy)$_2$]$^+$ ($\Phi_\Delta$=0.97) and [Ru(bpy)$_3$]$^{2+}$ ($\Phi_\Delta$=0.73). Furthermore, only very slight differences were observed between two Ir-based MOLs (A=1.09×10$^{-2}$ for Hf-BPY-Ir and A=0.88×10$^{-2}$ for Zr-BPY-Ir) or two Ru-based MOLs (A=4.1×10$^{-3}$ for Hf-BPY-Ru and A=2.4×10$^{-3}$ for Zr-BPY-Ru), suggesting minor effects of the SBUs in the $^1O_2$ generation efficiency through spin-orbit coupling. See Lu et al., 2014; and Scandola et al., 2006.

Figure 1D:
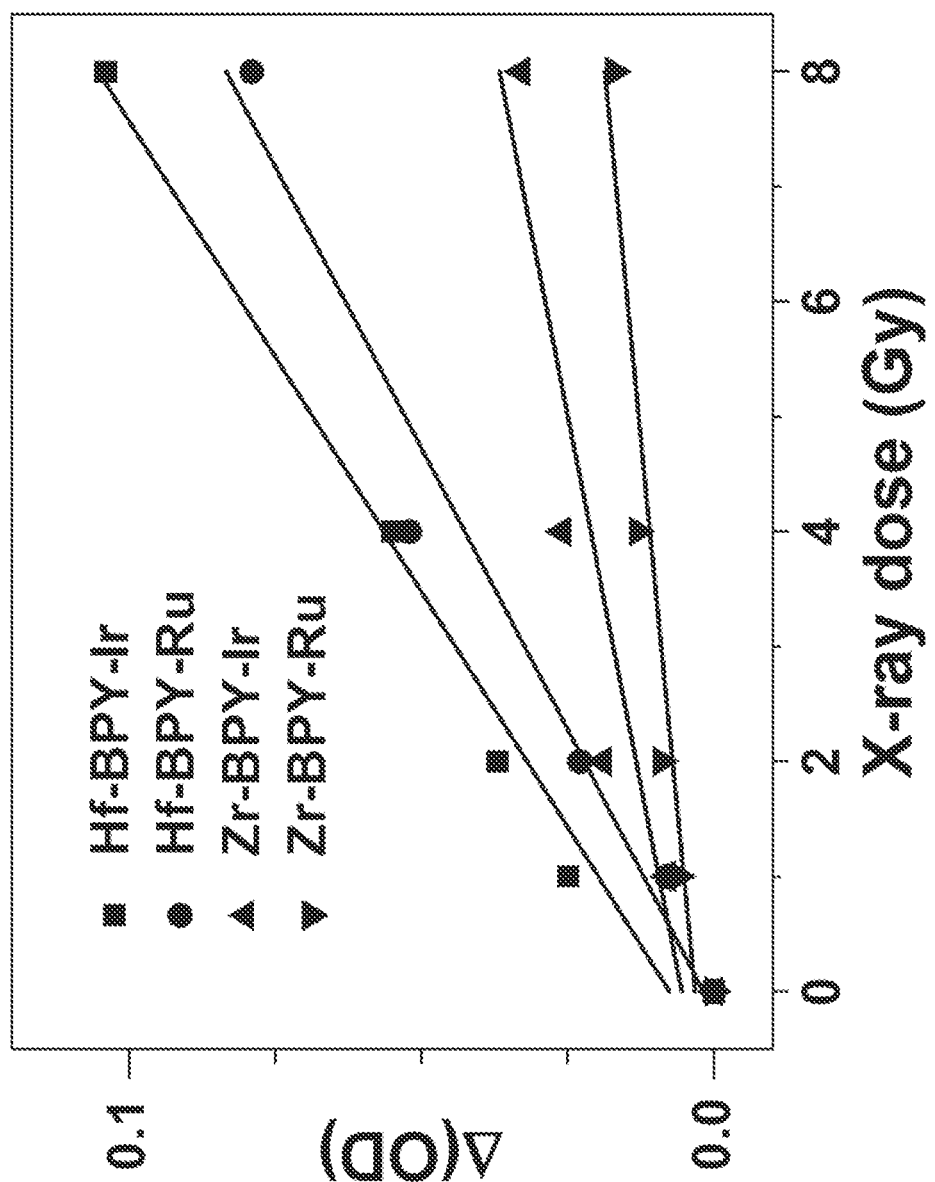
FIG. 1D is a graph showing the singlet oxygen generation of hafnium (Hf)-containing and zirconium (Zr)-containing metal-organic layers upon x-ray irradiation. Data from MOLs comprising Hf-containing secondary building units (SBUs) and bridging ligands comprising a coordination complex containing 4',6'-dibenzoato-[2,2-bipyridine]-4-carboxylate (BPY), an iridium ion and two phenyl-pyridine (ppy) ligands (Hf-BPY-Ir, squares); a MOL comprising Hf-containing SBUs and bridging ligands comprising a coordination complex containing BPY, a ruthenium ion, and two bipyridine (bpy) ligands (Hf-BPY-Ru, circles); a MOL comprising Zr-containing SBUs and bridging ligands comprising a coordination complex comprising BPY, an iridium ion and two ppy ligands (Zr-BPY-Ir, upward pointing triangles); and a MOL comprising Zr-containing SBUs and bridging ligands comprising a coordination complex comprising BPY, a ruthenium ion and two bpy ligands (Zr-BPY-Ru, downward pointing triangles) are shown. Singlet oxygen generation efficiencies of the MOLs were determined using the 4-nitroso-N,N-dimethylanaline (RNO) assay and presented as a change in optical density ($\Delta OD$) at 440 nanometers (nm) versus irradiation dose (in gray (Gy)).

However, upon X-ray irradiation, there was a drastic difference in $^1O_2$ generation efficiencies in Zr- and Hf-MOLs. See FIG. 1D and Table 4, above. Both Hf-MOLs (A=1.22×10$^{-2}$ for Hf-BPY-Ir and A=1.0×10$^{-2}$ for Hf-BPY-Ru) possessed much higher $^1O_2$ generation efficiency than their corresponding Zr-MOLs (A=0.39×10$^{-2}$ for Hf-BPY-Ir and A=0.19×10$^{-2}$ for Zr-BPY-Ir), supporting the hypothesis that the X-ray energy was first absorbed by SBUs and then transferred to the PSs in the bridging ligands to lead to the X-PDT effect. Because the heavier Hf atoms absorb X-rays more efficiently than the Zr atoms, the Hf-MOLs are expected to be more effective at X-PDT. Additionally, Ir-based MOLs showed only slightly better X-PDT efficiency than Ru-based MOLs, suggesting different energy transfer processes involved in X-PDT and PDT.

Figure 4:
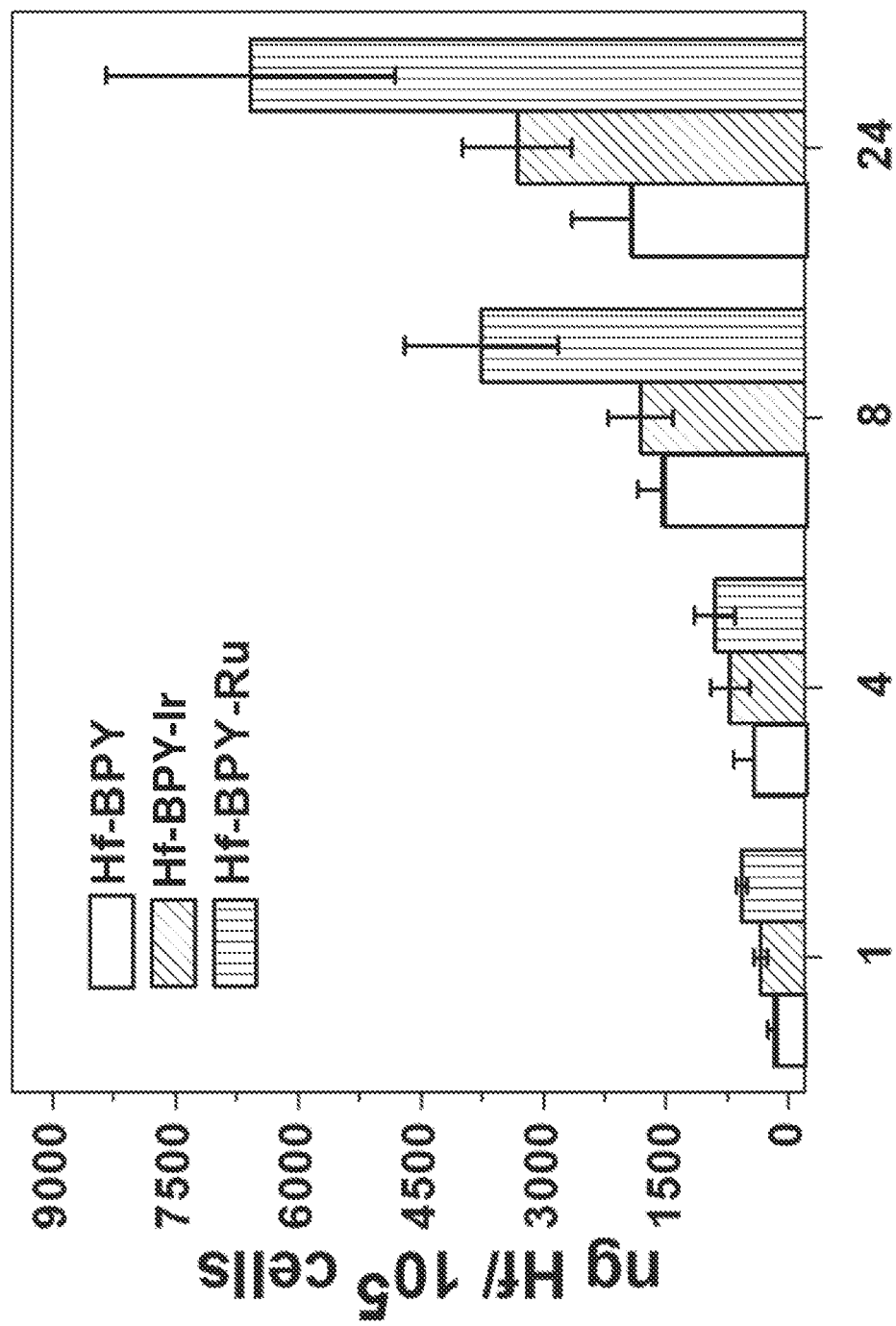
FIG. 4 is a graph showing the cellular uptake of hafnium-containing metal-organic layers (Hf-MOLs) after 1, 4, 8, or 24 hours (h) incubation with the MOLs. Uptake is based on hafnium (Hf) concentrations (nanograms (ng) Hf per 10,000 ($10^5$) cells) as determined by inductively-coupled plasma mass spectroscopy (ICP-MS). The Hf-MOLs include a metal-organic layer (MOL) comprising hafnium (Hf)-containing secondary building units (SBUs) and 4',6'-dibenzoato-[2,2-bipyridine]-4-carboxylate bridging ligands (Hf-BPY, open bars); a MOL comprising Hf-containing SBUs and bridging ligands comprising a coordination complex comprising BPY, a ruthenium (Ru) ion and two bipyridine (bpy) ligands (Hf-BPY-Ru, vertically striped bars); and a MOL comprising Hf-containing SBUs and bridging ligands comprising a coordination complex comprising BPY, an iridium (Ir) ion and two phenyl-pyridine (ppy) ligands (Hf-BPY-Ir, bars with slanted stripes). N=3.

In the clinic, PDT is typically applied to superficial malignant tumors such as skin lesions and esophageal cancer due to the shallow penetration of light (<3 mm for 800 nm photons). For deeply seated tumors, such as colon cancer, eradication of cancer cells becomes difficult even when an endoscope is used for light delivery. To examine the potential of MOL-mediated X-PDT in the treatment of deeply seated tumors, two types of murine colon adenocarcinoma cells, CT26 and MC38, were used for in vitro and in vivo studies. The cellular uptake was evaluated on CT26 cells incubated with Hf-BPY-Ir, Hf-BPY-Ru, or Hf-BPY at a Hf concentration of 50 μM for 1, 4, 8, and 24 h. At each time point, cells were digested and the Hf contents were determined by ICP-MS. Hf-BPY-Ru showed higher uptake (6580±1770 ng/10$^5$ cells) than Hf-BPY-Ir (3317±665 ng/10$^5$ cells) and Hf-BPY (1930±716 ng/10$^5$ cells), presumably because of the higher positive charge of Hf-BPY-Ru, which favors interacting with the negatively charged cell membrane to facilitate endocytosis. See FIG. 4.

Figure 2A:
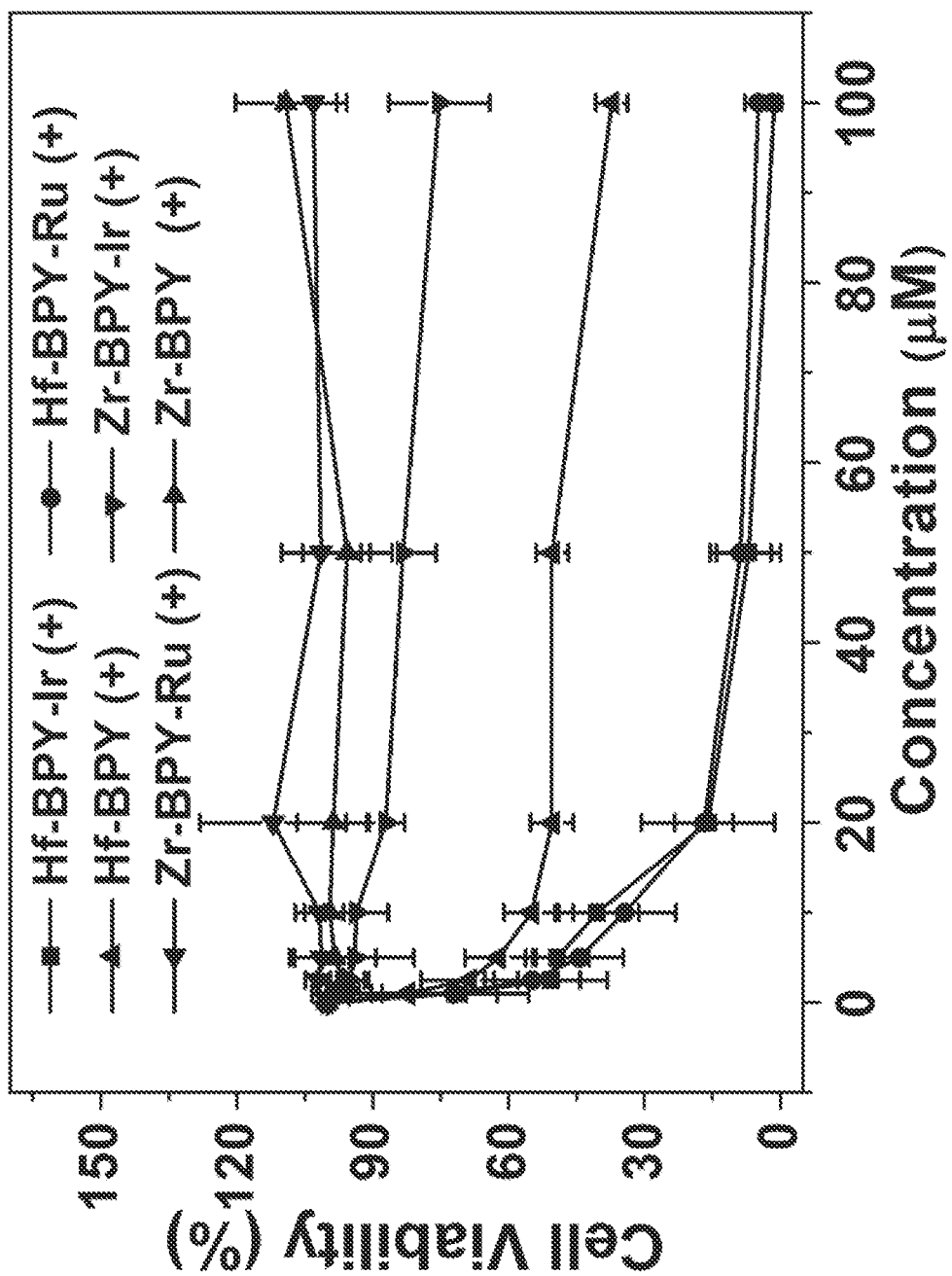
FIG. 2A is a graph showing the in vitro anticancer efficacy of hafnium-containing metal-organic layers (Hf-MOLs) in murine colon cancer cells (CT26 cells). The graphs show data for cell viability (in percent (%)) versus administered concentration (micromolar ($\mu M$)) of a metal-organic layer (MOL) comprising hafnium (Hf)-containing secondary building units (SBUs) and bridging ligands comprising a coordination complex comprising 4',6'-dibenzoato-[2,2-bipyridine]-4-carboxylate (BPY), an iridium ion and two phenyl-pyridine (ppy) ligands (Hf-BPY-Ir, squares); a MOL comprising Hf-containing SBUs and bridging ligands comprising a coordination complex comprising BPY, a ruthenium ion and two bipyridine (bpy) ligands (Hf-BPY-Ru, circles); a MOL comprising Hf-containing SBUs and BPY bridging ligands (Hf-BPY, upward pointing triangles), a MOL comprising zirconium (Zr)-containing SBUs and bridging ligands comprising a coordination complex comprising BPY, an iridium ion and two ppy ligands (Zr-BPY-Ir, downward pointing triangles); a MOL comprising Zr-containing SBUs and bridging ligands comprising a coordination complex comprising BPY, a ruthenium ion and two bpy ligands (Zr-BPY-Ru, triangles pointing left); and a MOL comprising Zr-containing SBUs and BPY bridging ligands (Zr-BPY, triangles pointing right).
Figure 2B:
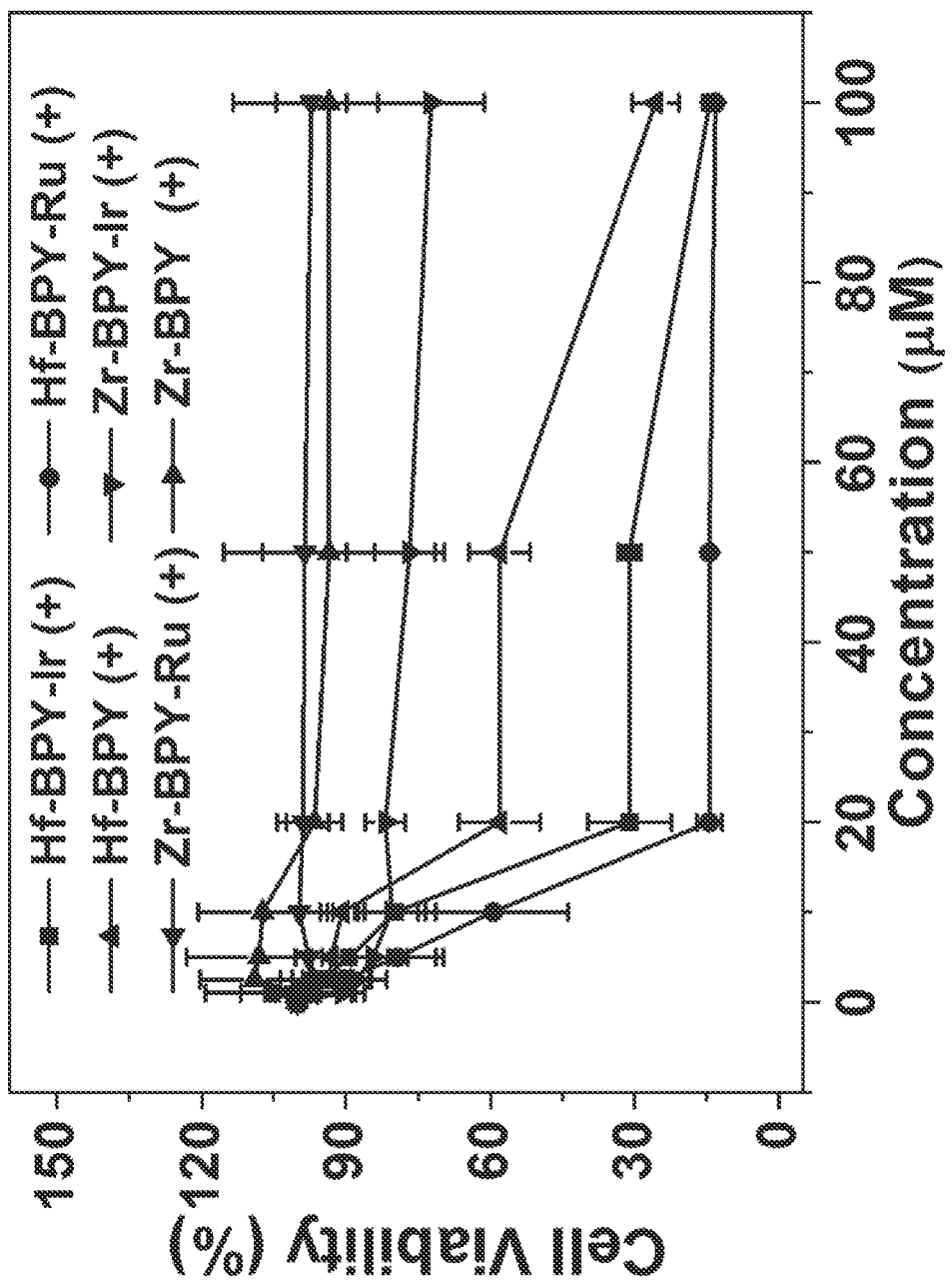
FIG. 2B is a graph showing the in vitro anticancer efficacy of hafnium-containing metal-organic layers (Hf-MOLs) in murine colon cancer cells (MC38 cells). The graphs show data for cell viability (in percent (%)) versus administered concentration (micromolar ($\mu M$)) of a metal-organic layer (MOL) comprising hafnium (Hf)-containing secondary building units (SBUs) and bridging ligands comprising a coordination complex comprising 4',6'-dibenzoato-[2,2-bipyridine]-4-carboxylate (BPY), an iridium ion and two phenyl-pyridine (ppy) ligands (Hf-BPY-Ir, squares); a MOL comprising Hf-containing SBUs and bridging ligands comprising a coordination complex comprising BPY, a ruthenium ion and two bipyridine (bpy) ligands (Hf-BPY-Ru, circles); a MOL comprising Hf-containing SBUs and BPY bridging ligands (Hf-BPY, upward pointing triangles), a MOL comprising zirconium (Zr)-containing SBUs and bridging ligands comprising a coordination complex comprising BPY, an iridium ion and two ppy ligands (Zr-BPY-Ir, downward pointing triangles); a MOL comprising Zr-containing SBUs and bridging ligands comprising a coordination complex comprising BPY, a ruthenium ion and two bpy ligands (Zr-BPY-Ru, triangles pointing left); and a MOL comprising Zr-containing SBUs and BPY bridging ligands (Zr-BPY, triangles pointing right).
Figure 5A:
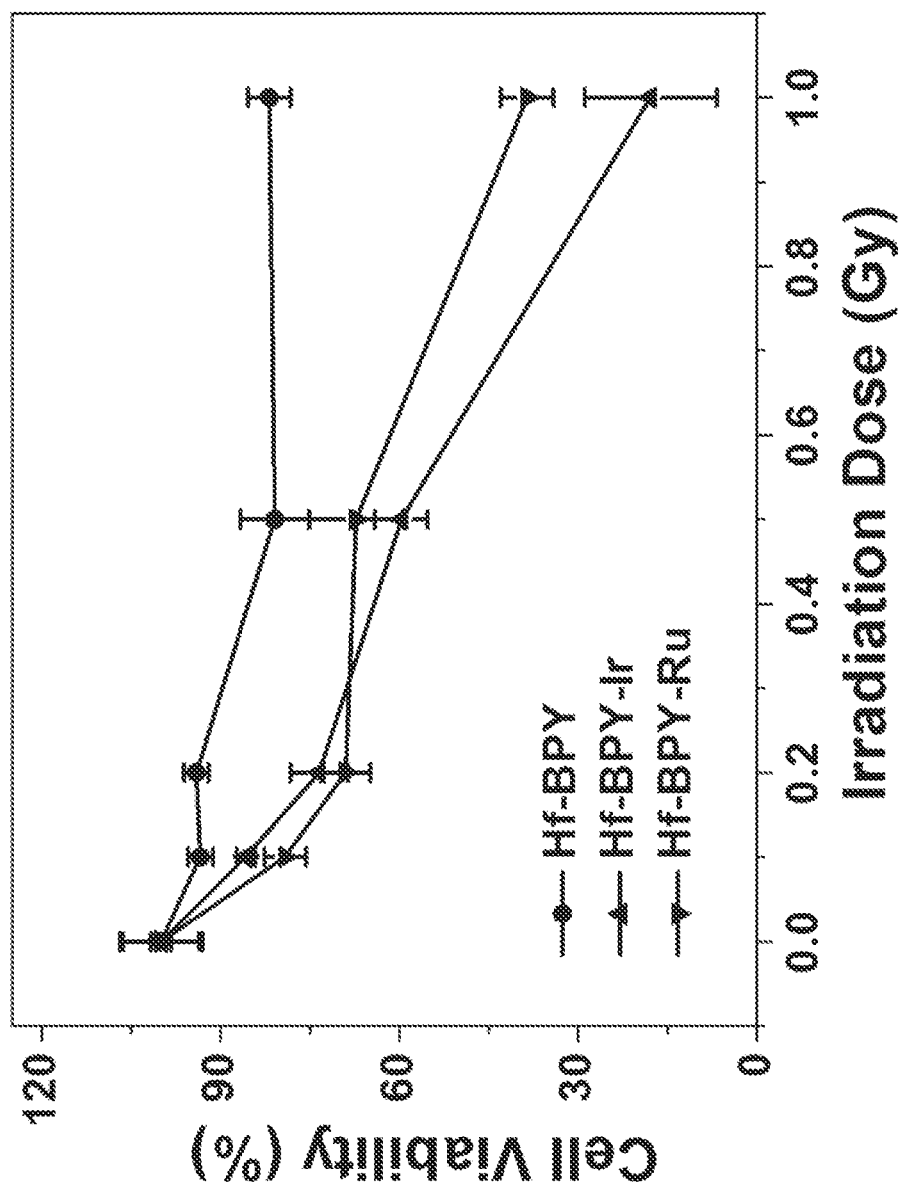
FIG. 5A is a graph showing the in vitro cytotoxicity of hafnium (Hf)-containing metal-organic layers (MOLs) in CT26 murine colon cancer cells based on X-ray dose (0.0 to 1.0 gray (Gy)) using a fixed MOL concentration (200 micromolar (μM), based on MOL organic bridging ligand or bridging ligand complexed metal (i.e., iridium (Ir) or ruthenium (Ru)) concentration). The MOLs include a MOL comprising Hf-containing secondary building units (SBUs) and 4',6'-dibenzoato-[2,2-bipyridine]-4-carboxylate (BPY) bridging ligands (Hf-BPY, circles); a MOL comprising Hf-containing SBUs and bridging ligands comprising a coordination complex comprising BPY, an Ir ion and two phenyl-pyridine (ppy) ligands (Hf-BPY-Ir, upward pointing triangles); and a MOL comprising Hf-containing SBUs and bridging ligands comprising a coordination complex comprising BPY, a Ru ion and two bipyridine (bpy) ligands (Hf-BPY-Ru, downward pointing triangles). N=6.
Figure 5B:
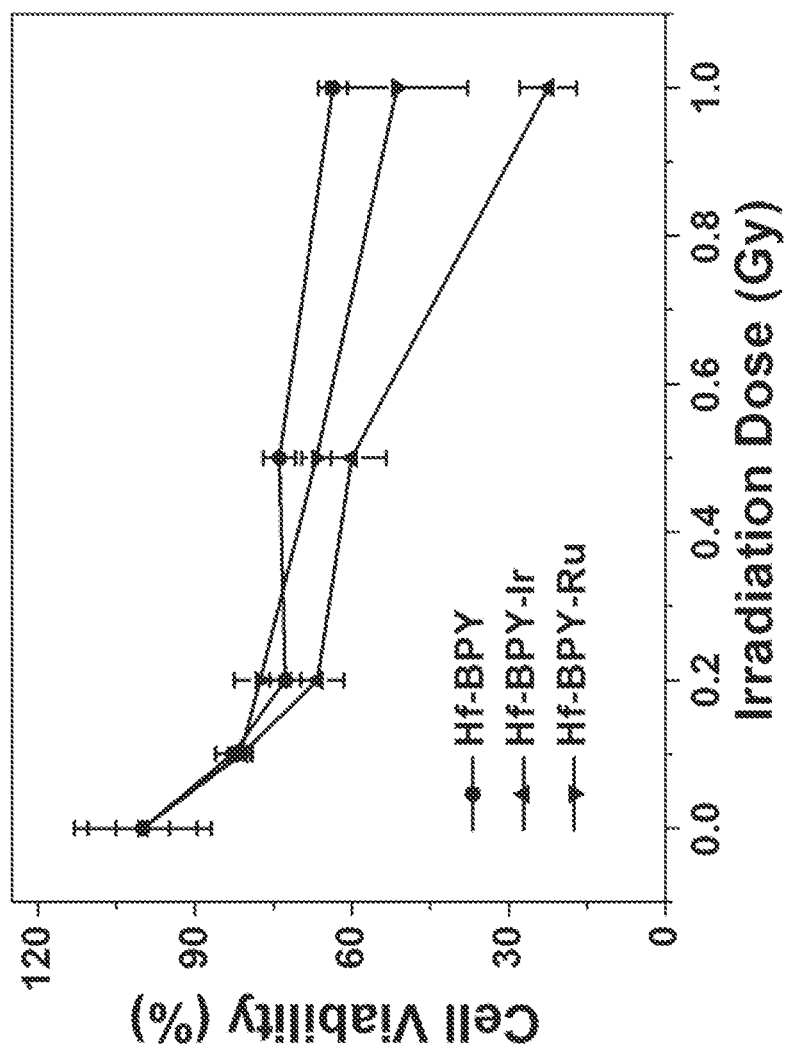
FIG. 5B is a graph showing the in vitro cytotoxicity of hafnium (Hf)-containing metal-organic layers (MOLs) against MC38 murine colon carcinoma cells based on X-ray dose (0.0 to 1.0 gray (Gy)) with a fixed MOL concentration (200 micromolar (μM), based on MOL organic ligand or ligand complexed metal (i.e., iridium (Ir) or ruthenium (Ru)) concentration). The MOLs include a MOL comprising Hf-containing secondary building units (SBUs) and 4',6'-dibenzoato-[2,2-bipyridine]-4-carboxylate (BPY) bridging ligands (Hf-BPY, circles); a MOL comprising Hf-containing SBUs and bridging ligands comprising a coordination complex comprising BPY, an Ir ion and two phenyl-pyridine (ppy) ligands (Hf-BPY-Ir, upward pointing triangles); and a MOL comprising Hf-containing SBUs and bridging ligands comprising a coordination complex comprising BPY, a Ru ion and two bipyridine (bpy) ligands (Hf-BPY-Ru, downward pointing triangles). N=6.

The in vitro anticancer efficacy of three different Hf-based MOLs against CT26 (see FIG. 2A) and MC38 (see FIG. 2B) cells was examined. To elucidate the key role of Hf in efficient absorption of X-rays, three corresponding Zr-MOLs were used as controls. MOLs were incubated with cells at various concentrations for 8 h, followed by irradiation with an X-ray irradiator at a dose of 2 Gy. Hf-BPY-Ir and Hf-BPY-Ru outperformed Hf-BPY and three Zr-MOLs. The IC$_{50}$ values for Hf-BPY-Ir, Hf-BPY-Ru, and Hf-BPY against CT26 cells were calculated to be 3.82±1.80, 3.63±2.75, and 24.90±7.87 μM, respectively. Against MC38 cells, the IC$_{50}$ values calculated were 11.66±1.84, 10.72±2.92, and 37.80±6.57 μM, respectively. IC$_{50}$ values exceeded 100 μM for Zr-BPY-Ir, Zr-BPY-Ru, and Zr-BPY both in CT26 and MC38 cell lines. No cytotoxicity was observed in dark control groups. Cell viability with fixed Hf-MOL concentrations based on Ir, Ru or BPY of 20 μM, respectively, and various X-ray doses was examined. See FIGS. 5A and 5B. All the result showed enhanced X-PDT potency of Ir[bpy(ppy)$_2$]$^+$ and [Ru(bpy)$_3$]$^{2+}$ in Hf-MOLs.

The mechanism of X-ray induced cytotoxicity on CT26 cells was explored. $^1O_2$ generation in live cells was examined by Singlet Oxygen Sensor Green (SOSG) and detected by confocal laser scanning microscopy (CLSM). After preloading cells with SOSG and incubating them with PBS, Hf-MOLs, or H$_3$BPY ligand for 8 h at a concentration of 20 μM based on Ir, Ru, or BPY, respectively, they were irradiated with X-rays at a dose of 2 Gy, immediately followed by CLSM imaging. Both Hf-BPY-Ir- and Hf-BPY-Ru-treated cells showed strong green SOSG fluorescence, indicating the efficient generation of $^1O_2$ in the MOLs upon X-ray irradiation. In contrast, PBS, Hf-BPY and H$_3$BPY ligand-treated groups showed no SOSG signal after X-ray induced $^1O_2$ generation, which supported the proposed X-PDT process using Hf-BPY-Ir and Hf-BPY-Ru MOLs.

Figure 2C:
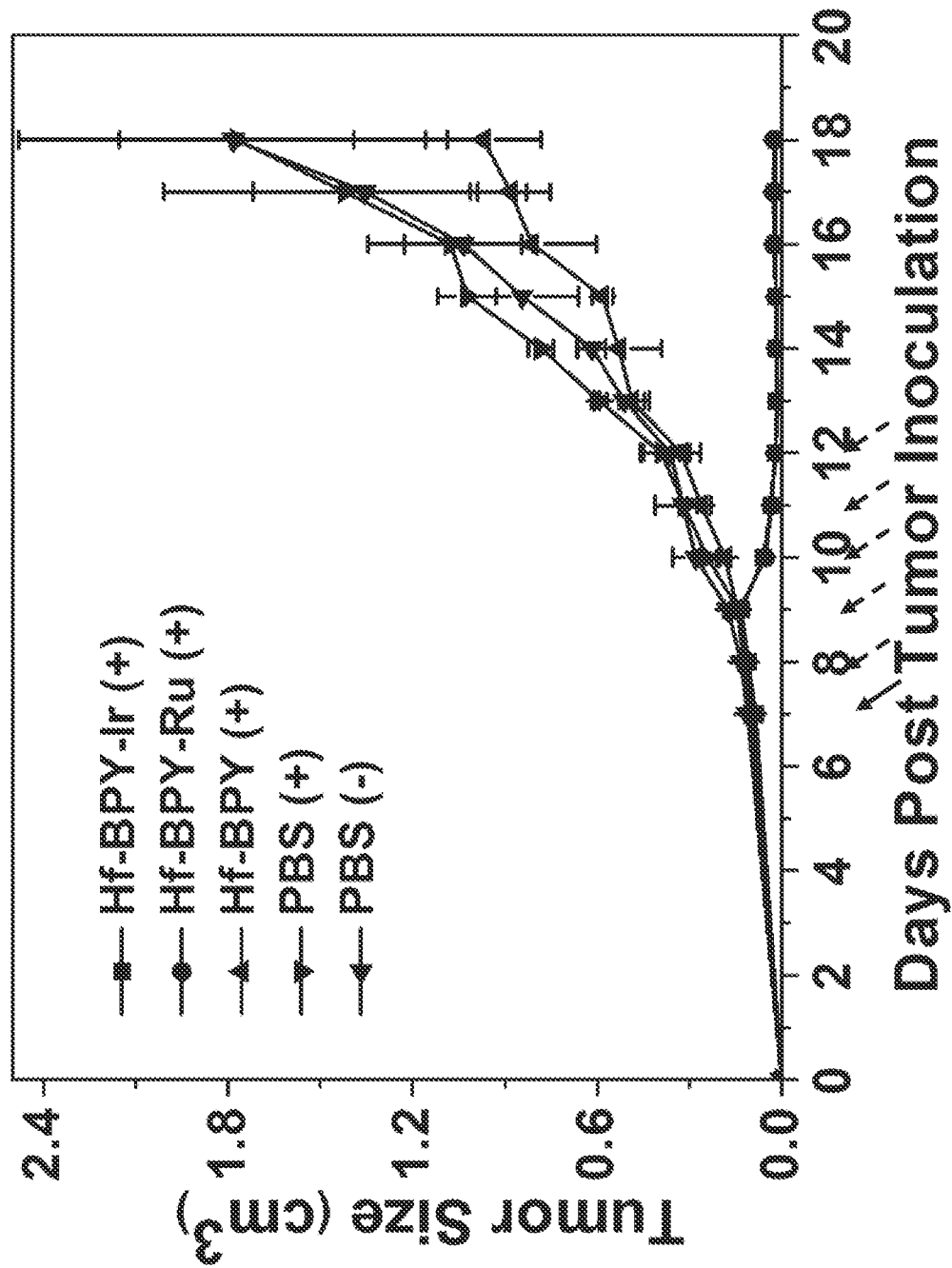
FIG. 2C is a graph showing the in vivo anticancer efficacy of hafnium (Hf)-containing metal-organic layers (Hf-MOLs) in a syngeneic model of colon cancer. Tumor growth inhibition curves are shown after x-ray photodynamic therapy (X-PDT) of mice inoculated with CT26 murine colon cancer cells. The solid arrow refers to the timing of the injection of MOLs and the dashed arrows refer to the timing of X-ray irradiation. The graphs show tumor size (in cubic millimeters ($mm^3$)) versus day post tumor inoculation for a metal-organic layer (MOL) comprising hafnium (Hf)-containing secondary building units (SBUs) and bridging ligands comprising a coordination complex comprising 4',6'-dibenzoato-[2,2-bipyridine]-4-carboxylate (BPY), an iridium ion and two phenyl-pyridine ligands (Hf-BPY-Ir (+), squares); a MOL comprising Hf-containing SBUs and bridging ligands comprising a coordination complex comprising BPY, a ruthenium ion and two bipyridine (bpy) ligands (Hf-BPY-Ru (+), circles); and a MOL comprising Hf-containing SBUs and BPY bridging ligands (Hf-BPY (+), upward pointing triangles). For comparison, data is also shown for mice treated with vehicle (phosphate buffered saline (PBS)) and irradiation (PBS (+), downward pointing triangles) and vehicle without irradiation (PBS (−), triangles pointing left).
Figure 2D:
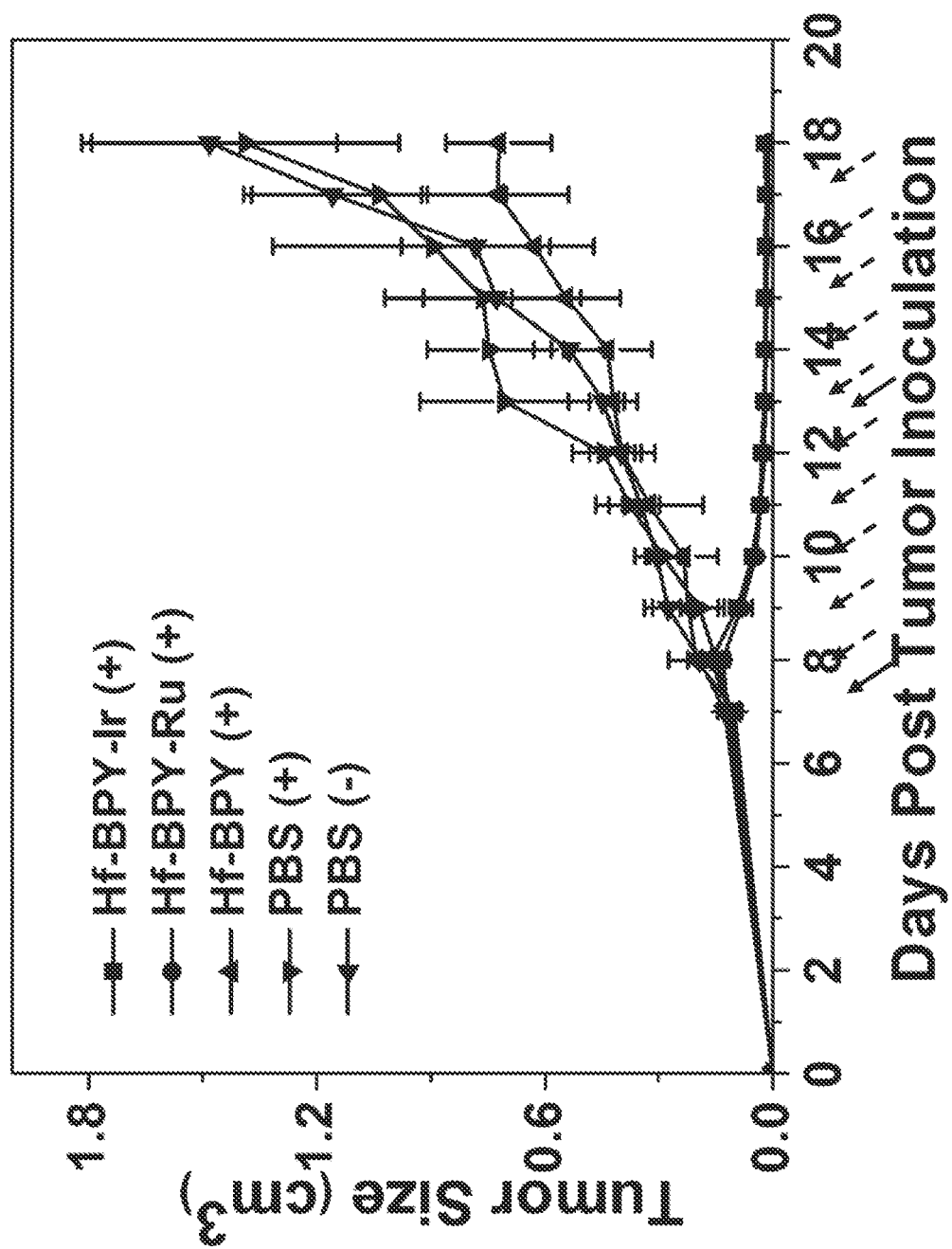
FIG. 2D is a graph showing the in vivo anticancer efficacy of hafnium-containing metal-organic layers (Hf-MOLs) in a syngeneic model of colon cancer. Tumor growth inhibition curves are shown after x-ray photodynamic therapy (X-PDT) of mice inoculated with MC38 murine colon cancer cells. Solid arrows refer to timing of the injection of MOLs and dashed arrows refer to timing of X-ray irradiation. The graphs show tumor size (in cubic millimeters ($mm^3$)) versus day post tumor inoculation for a metal-organic layer (MOL) comprising hafnium (Hf)-containing secondary building units (SBUs) and bridging ligands comprising a coordination complex comprising 4',6'-dibenzoato-[2,2-bipyridine]-4-carboxylate (BPY), an iridium ion and two phenyl-pyridine (ppy) ligands (Hf-BPY-Ir (+), squares); a MOL comprising Hf-containing SBUs and bridging ligands comprising a coordination complex comprising BPY, a ruthenium ion and two bipyridine (bpy) ligands (Hf-BPY-Ru (+), circles); and a MOL comprising Hf-containing SBUs and BPY bridging ligands (Hf-BPY (+), upward pointing triangles). For comparison, data is also shown for mice treated with vehicle (phosphate buffered saline (PBS)) and irradiation (PBS (+), downward pointing triangles) and vehicle without irradiation (PBS (−), triangles pointing left).
Figure 6A:
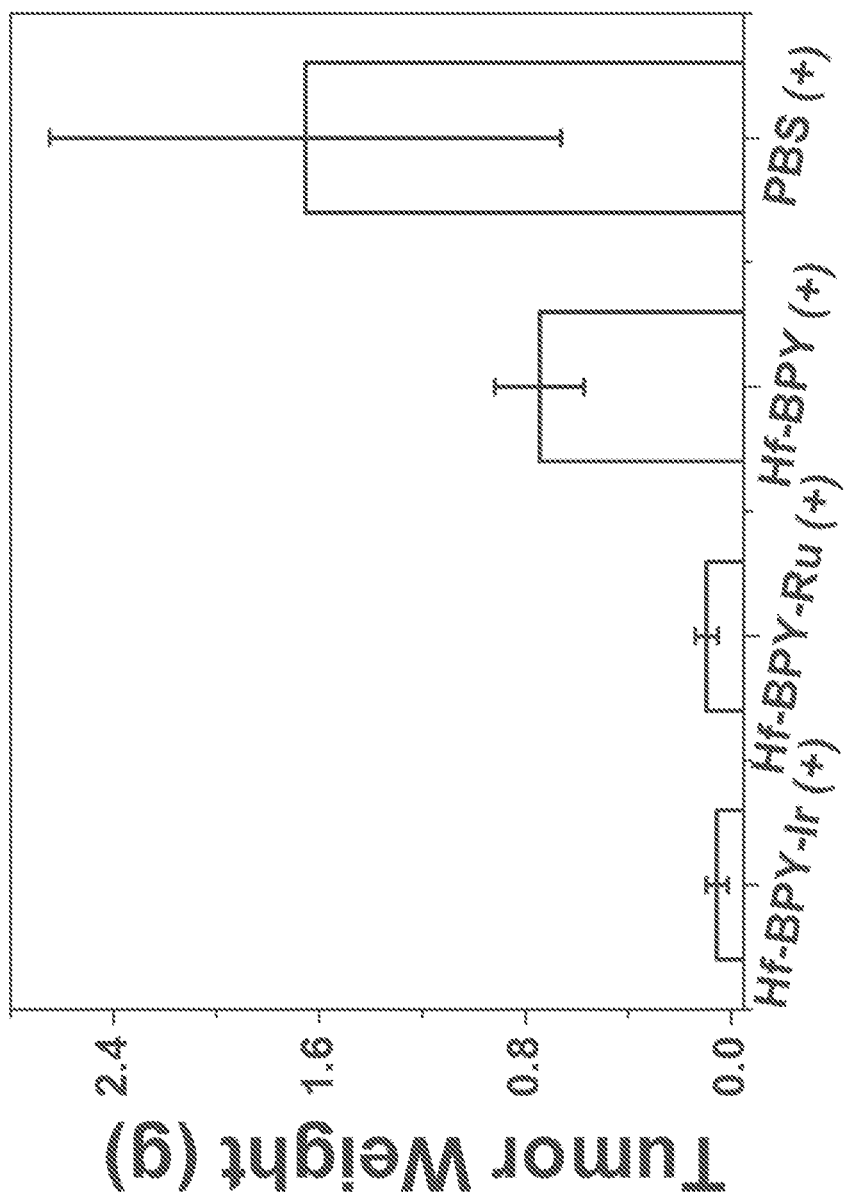
FIG. 6A is a graph showing the tumor weights (in grams (g)) of tumors in mice inoculated with CT26 murine colon cancer cells and treated with different metal-organic layers (MOLs) of the presently disclosed subject matter and X-ray irradiation (+). The tumor weights are determined from tumors excised from the mice 18 days following cancer cell inoculation. Data is shown for use of: a MOL comprising hafnium (Hf)-containing secondary building units (SBUs) and bridging ligands comprising a coordination complex comprising 4',6'-dibenzoato-[2,2-bipyridine]-4-carboxylate (BPY), an iridium ion and two phenyl-pyridine (ppy) ligands (Hf-BPY-Ir (+)); a MOL comprising Hf-containing SBUs and bridging ligands comprising a coordination complex comprising BPY, a ruthenium ion and two bipyridine (bpy) ligands (Hf-BPY-Ru (+)); and a MOL comprising Hf-containing SBUs and BPY bridging ligands (Hf-BPY (+)). For comparison, data is also shown for mice treated with vehicle (phosphate buffered saline (PBS)) and irradiation (PBS (+)).
Figure 6B:
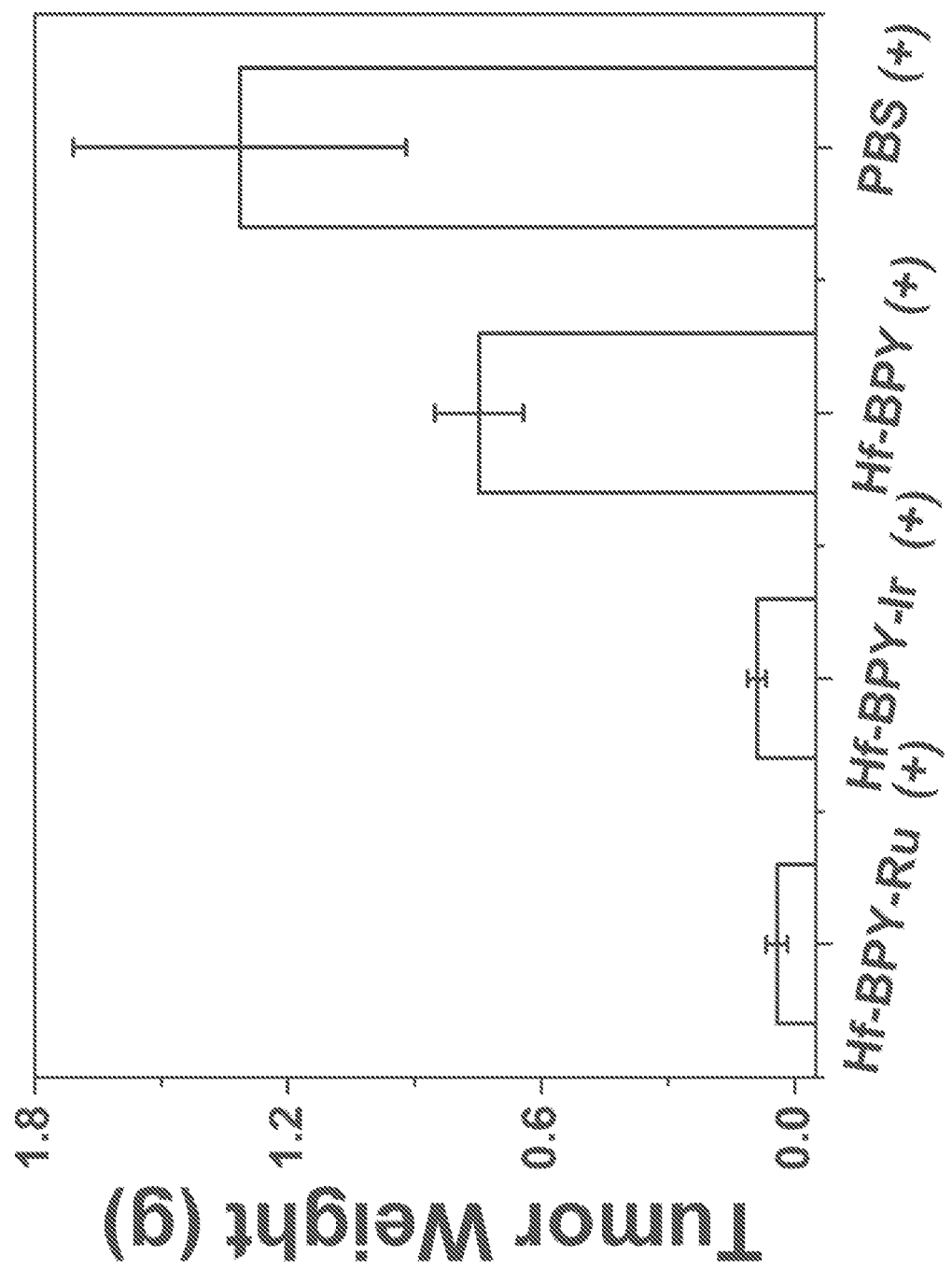
FIG. 6B is a graph showing the tumor weights (in grams (g)) of tumors in mice inoculated with MC38 murine colon cancer cells and treated with different metal-organic layers (MOLs) of the presently disclosed subject matter and X-ray irradiation (+). The tumor weights are determined from tumors excised from the mice 18 days following cancer cell inoculation. Data is shown for use of: a MOL comprising hafnium (Hf)-containing secondary building units (SBUs) and bridging ligands comprising a coordination complex comprising 4',6'-dibenzoato-[2,2-bipyridine]-4-carboxylate (BPY), an iridium ion and two phenyl-pyridine (ppy) ligands (Hf-BPY-Ir (+)); a MOL comprising Hf-containing SBUs and bridging ligands comprising a coordination complex comprising BPY, a ruthenium ion and two bipyridine (bpy) ligands (Hf-BPY-Ru (+)); and a MOL comprising Hf-containing SBUs and BPY bridging ligands (Hf-BPY (+)). For comparison, data is also shown for mice treated with vehicle (phosphate buffered saline (PBS)) and irradiation (PBS (+)).

Encouraged by the in vitro results, in vivo anticancer efficacy experiments were carried out on subcutaneous flank tumor-bearing mouse models of CT26 or MC38. When tumors reached 100-150 mm$^3$ in volume, Hf-BPY-Ir, Hf-BPY-Ru, or Hf-BPY with amount of 0.5 nmol based on Ir, Ru or BPY, respectively, or PBS was intratumorally injected followed by daily X-ray irradiation at a dose of 1 Gy/fraction (120 kVp, 20 mA, 2 mm-Cu filter) for a total of 5 fractions on the CT26 model (see FIG. 2C) or 10 fractions on the MC38 model (see FIG. 2D) on consecutive days. Tumor sizes and body weights were measured every day. All mice were sacrificed 18 days after tumor inoculation, and the excised tumors were photographed and weighed. See FIGS. 6A and 6B. To rule out any radiotherapy effects from the low dose X-ray, we used PBS-treated mice without X-ray irradiation as a dark control. The PBS groups with or without irradiation did not show any difference in tumor growth curves, indicating that low dose X-rays alone had no radiotherapeutic effects. The Hf-BPY groups appeared to show slight inhibition of tumor growth (P=0.047 or 0.048 for CT26 or MC38, respectively). In stark contrast, Hf-BPY-Ir and Hf-BPY-Ru treatments led to effective tumor regression in CT26 with 5 fractions of X-ray irradiation (5 Gy total; total volume reduction of 83.63% or 77.27%, respectively) and in MC38 with 10 fractions of X-ray irradiation (10 Gy; total volume reduction of 82.30% or 90.11%, respectively). The weights and sizes of tumors treated with Hf-BPY-Ir and Hf-BPY-Ru at the end point were significantly smaller than the other groups. See Tables 5 and 6, above. Histology of frozen tumor slices confirmed Hf-BPY-Ir- and Hf-BPY-Ru-assisted X-PDT caused apoptosis/necrosis in tumors. No abnormalities were observed on histological images of frozen organ slices, which indicated that X-PDT was not systemically toxic. The lack of systemic toxicity was further supported by steady body weights and similar weight gain patterns in all groups.

In summary, Hf-BPY-Ir and Hf-BPY-Ru MOLs were synthesized as powerful PSs for highly effective X-PDT of two colon cancer models, CT26 and MC38. Upon X-ray irradiation, Hf atoms in the SBUs absorbed X-rays and transferred energy to Ir[bpy(ppy)$_2$]$^+$ or [Ru(bpy)$_3$]$^{2+}$ in ligands to generate $^1O_2$, demonstrated by both RNO assay and in vitro $^1O_2$ detection and cytotoxicity studies. As a result of deep tissue penetration of X-rays, high $^1O_2$ quantum yields of Ir[bpy(ppy)$_2$]$^+$ or [Ru(bpy)$_3$]$^{2+}$, and efficient ROS diffusion through ultrathin MOLs, in vivo studies demonstrated a 90% reduction in tumor volumes after our X-PDT treatment.

Example 3

Synthesis and Characterization of Hf$_{12}$-QPDC-Ru MOL

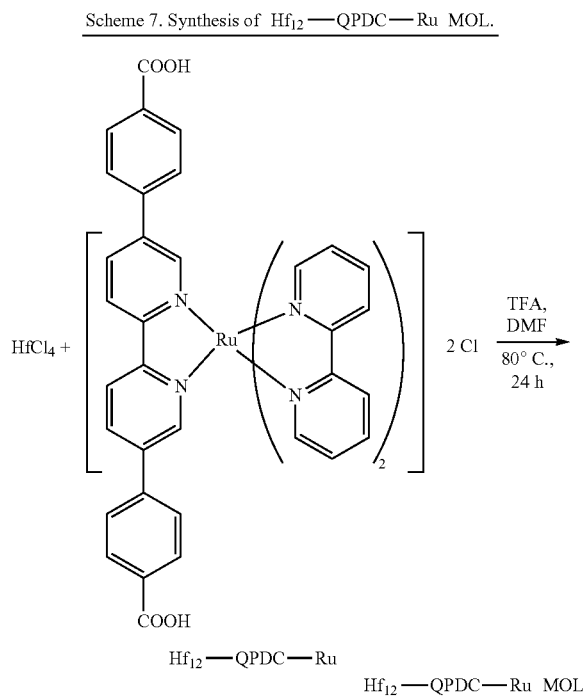

Scheme 7. Synthesis of Hf$_{12}$—QPDC—Ru MOL.

Figure 7:
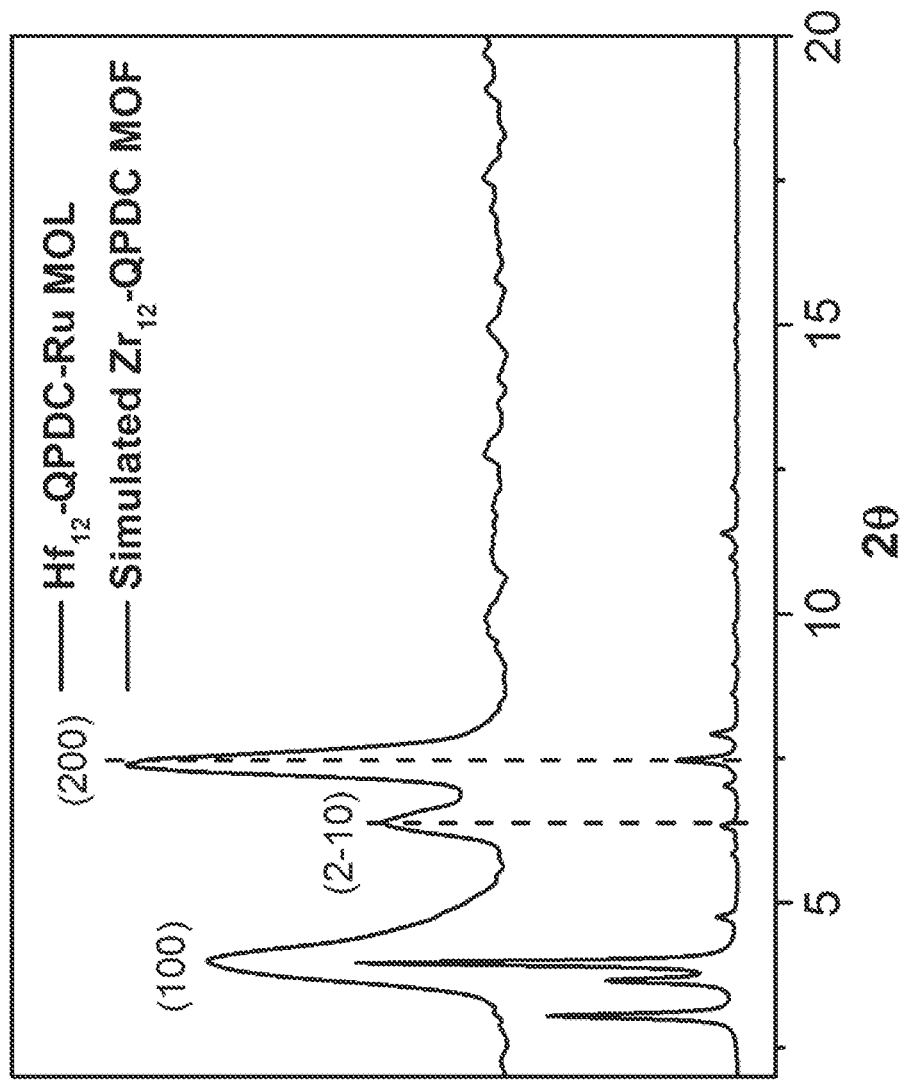
FIG. 7 is a graph showing (top) the experimental powder X-ray diffraction (PXRD) pattern of a metal-organic layer (MOL) comprising hafnium 12 ($Hf_{12}$)-oxo cluster secondary building units (SBUs) and bis(2,2'-bipyridine)(5,5'-di(4-carboxyl-phenyl)-2,2'-bipyridine) ruthenium(II) chloride bridging ligands ($Hf_{12}$-QPDC-Ru MOL); and (bottom) a simulated PXRD pattern for a metal-organic framework (MOF) prepared from zirconium 12 ($Zr_{12}$) SBUs and the same bridging ligand (i.e. 5,5'-di(4-carboxyl-phenyl)-2,2'-bipyridine), lacking the complexed ruthenium bis(bipyridine) (i.e., Simulated $Zr_{12}$-QPDC MOF).
Figure 8:
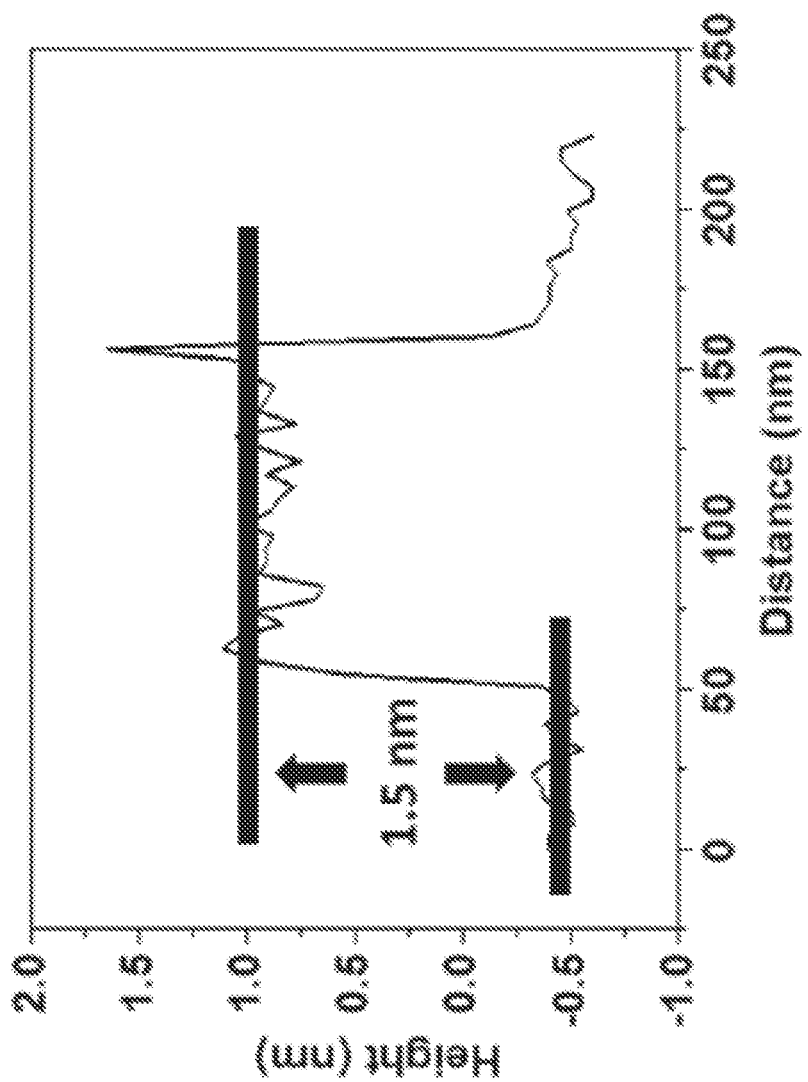
FIG. 8 is a graph showing the height profile of a tapping-mode atomic-force microscopy (AFM) topographic image of a metal-organic layer (MOL) comprising hafnium 12 ($Hf_{12}$)-oxo cluster secondary building units (SBUs) and bis(2,2'-bipyridine)(5,5'-di(4-carboxyl-phenyl)-2,2'-bipyridine) ruthenium(II) chloride bridging ligands ($Hf_{12}$-QPDC-Ru MOL). The MOL has a height of 1.5 nanometers (nm).

Bis(2,2'-bipyridine)(5,5'-di(4-carboxyl-phenyl)-2,2'-bipyridine) ruthenium(II) chloride (H$_2$QPDC-Ru) was synthesized as described previously. See Zhang et al., 2015. As shown in Scheme 7, above, to a 4 mL glass vial was added 0.5 mL of HfCl$_4$ solution (2.0 mg/mL in DMF), 0.5 mL of H$_2$QPDC-Ru solution (4.0 mg/mL in DMF), 1 µL of trifluoroacetic acid (TFA), and 5 µL of water. The reaction mixture was kept in an 80° C. oven for 24 hours (h). The orange precipitate was collected by centrifugation and washed with DMF and ethanol. TEM imaging showed that Hf$_{12}$-QPDC MOL adopted nanosheet morphology with a diameter ranging from 50 to 500 nm. FFT pattern indicated that Hf$_{12}$-QPDC MOL was crystalline. PXRD pattern showed that Hf$_{12}$-QPDC-Ru MOL, in comparison to Zr$_{12}$-QPDC MOF, only exhibited diffraction peaks corresponding to the layer structure, while all peaks perpendicular to the layer disappeared. See FIG. 7. The atomic force microscopy (AFM) images (see FIG. 8) of Hf$_{12}$-QPDC-Ru MOL showed a 1.5 nm thickness, which was very close to the Van der Waals size of the Hf$_{12}$ cluster capped by trifluoroacetate group. The combination of PXRD and AFM resulted indicated that the monolayer structure of Hf$_{12}$-QPDC-Ru MOL.

Example 4

Synthesis and Characterization of Hf$_{12}$-DBP-Pt nMOF

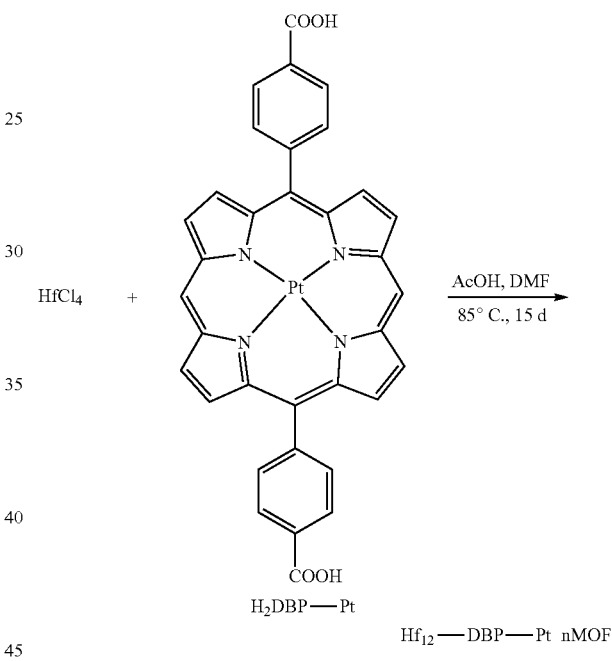

Scheme 8. Synthesis of Hf$_{12}$—DBP—Pt nMOF.

Figure 9:
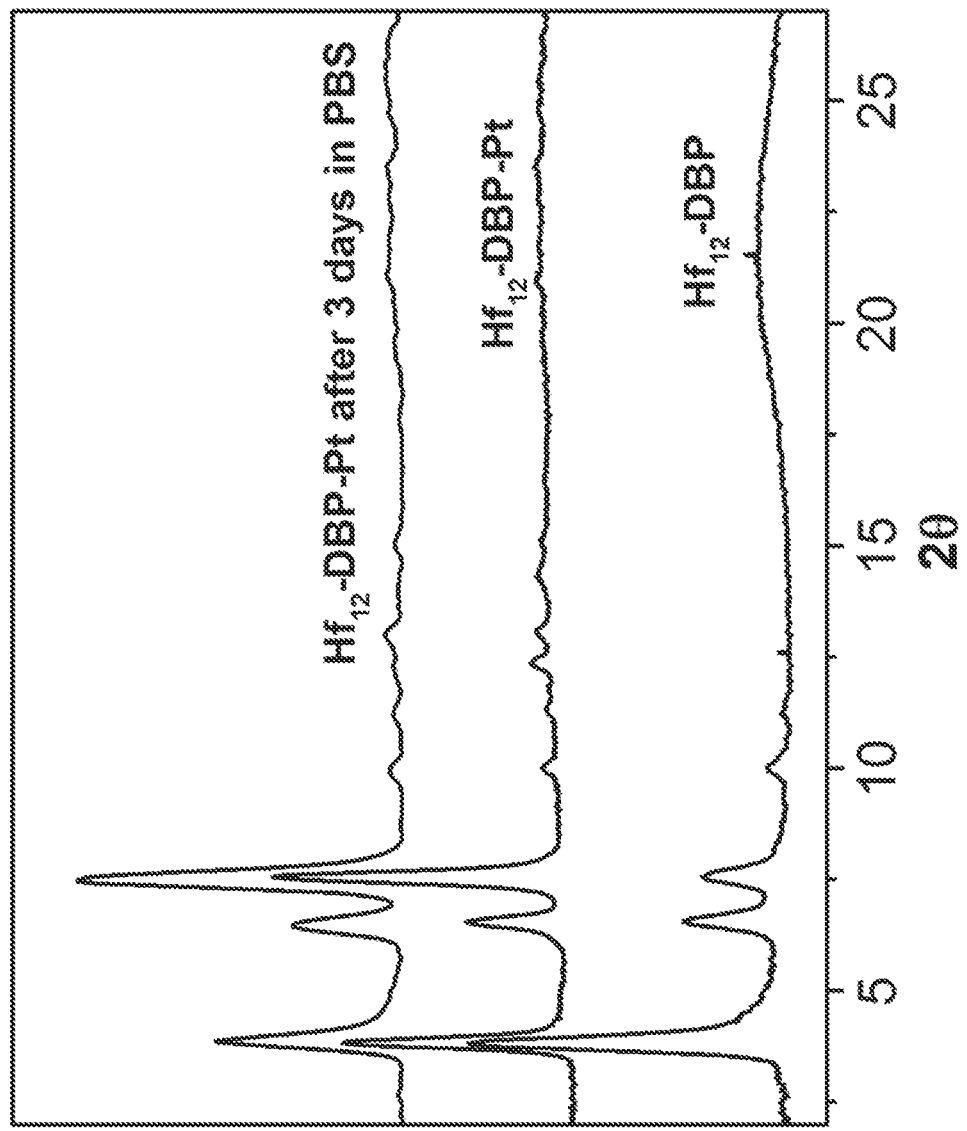
FIG. 9 is a graph showing the powder X-ray diffraction (PXRD) patterns of metal-organic layers (MOLs) including, from bottom to top, a MOL comprising hafnium 12 ($Hf_{12}$)-oxo cluster secondary building units (SBUs) and 5, 15-di(p-benzoato)porphyrin bridging ligands ($Hf_{12}$-DBP), the same MOL wherein the porphyrin bridging ligand is complexed to platinum (Pr) (i.e., $Hf_{12}$-DBP-Pt), and the Pt complexed MOL after 3 days in phosphate buffered saline (PBS) (i.e., $Hf_{12}$-DBP-Pt after 3 days in PBS).

H$_2$DBP-Pt was synthesized as described previously. See Xu et al., 2016. As shown in Scheme 8, above, to a 4 mL glass vial was added 0.5 mL of HfCl$_4$ solution (2.0 mg/mL in DMF), 0.5 mL of H$_2$DBP-Pt solution (4.8 mg/mL in DMF), 55 µL of acetic acid (AcOH), and 5 µL of water. The reaction mixture was kept in an 85° C. oven for 10-15 days. The red precipitate was collected by centrifugation and washed with DMF, 1% trimethylamine/ethanol solution and ethanol. TEM imaging showed that Hf$_{12}$-DBP-Pt nMOF adopted nanoplate morphology with a diameter of ~70 nm and a thickness of ~10 nm. PXRD studies indicated that Hf$_{12}$-DBP-Pt adopted the same crystal structure as Hf$_{12}$-DBP. See FIG. 9.

Stability test of Hf$_{12}$-DBP-Pt nMOF: Hf$_{12}$-DBP-Pt nMOF was suspended into 6 mM phosphate buffer solution to make a 1 mg/mL concentration of Hf$_{12}$-DBP-Pt. After three days, the Hf$_{12}$-DBP-Pt was collected by centrifuge and the PXRD pattern was obtained. PXRD studies indicated that Hf$_{12}$-DBP-Pt nMOF was stable in 6 mM phosphate buffer for three days. See FIG. 9.

Synthesis and Characterization of Oxa@Hf$_{12}$-DBP-Pt nMOF:

Preparation of Oxa@Hf$_{12}$-DBP-Pt: To a 4 mL glass vial was added 1 mL of oxaliplatin solution (0.4 mg/mL in water) and 3.6 mg Hf$_{12}$-DBP-Pt nMOF. The reaction mixture was stirred at room temperature for 12 h to afford oxa@Hf$_{12}$-DBP-Pt. The red precipitate was collected by centrifugation and washed with water twice. The weight ratio of oxaliplatin to Hf$_{12}$-DBP-Pt nMOF was determined to be 0.102 by ICP-MS. (0.101 mg oxaliplatin per mg nMOF). The encapsulation efficiency of oxaliplatin is 91.5%.

Figure 10:
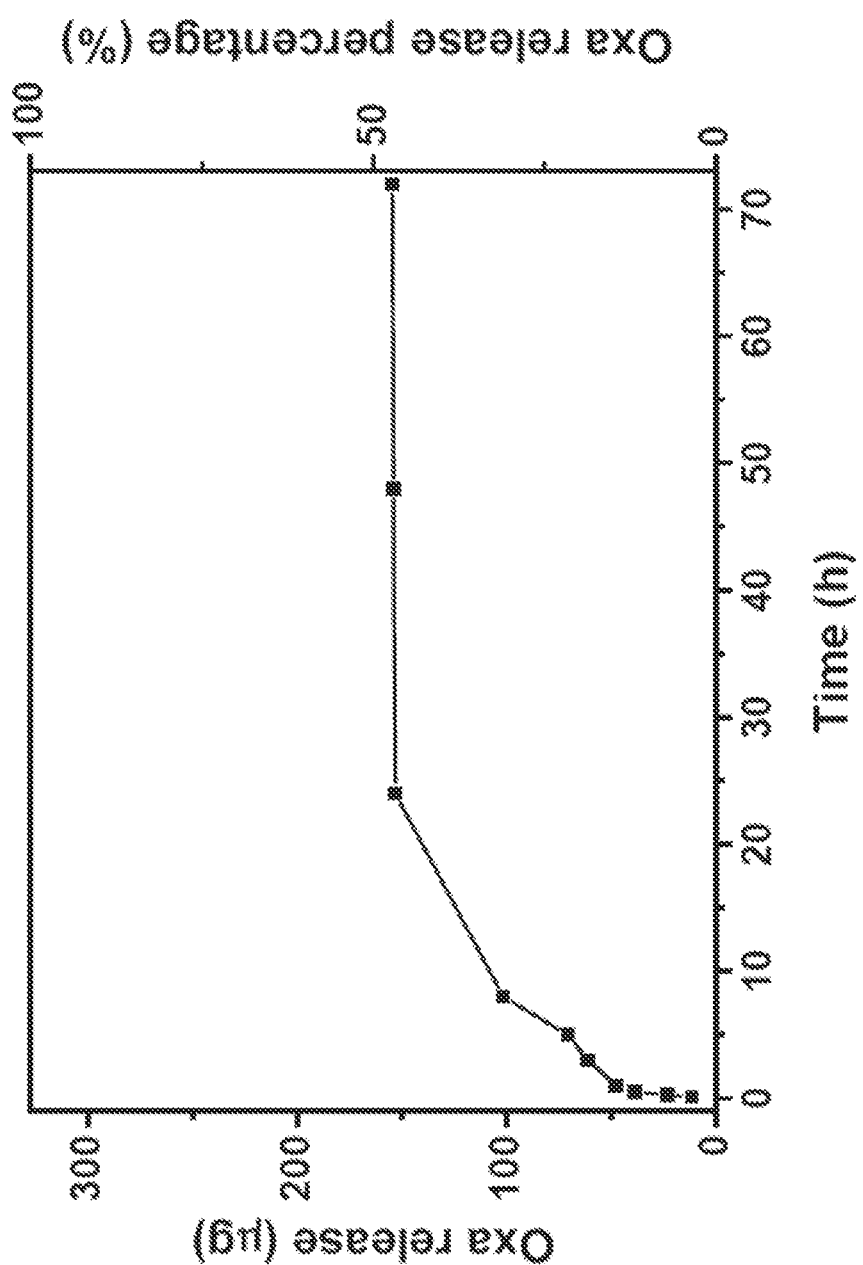
FIG. 10 is a graph showing the release profile of oxaliplatin (Oxa) in micrograms (μg) versus hours (h) or percentage (%) from a metal-organic layer (MOL) comprising hafnium 12 oxo cluster secondary building units, 5, 15-di (p-benzoato)porphyrin bridging ligands comprising complexed platinum, and encapsulated oxaliplatin (Oxa-$Hf_{12}$-DBP-Pt).

Release of Oxaliplatin from Oxa@Hf$_{12}$-DBP-Pt:

To a dialysis bag was added 1 mL of oxa@Hf$_{12}$-DBP-Pt suspension (3.96 mg oxa@Hf$_{12}$-DBP-Pt in 1 mL 6 mM PBS, containing 0.36 mg oxaliplatin+3.6 mg Hf$_{12}$-DBP-Pt). The dialysis bag was then put into a 500-mL beaker with 200 mL 6 mM PBS under stirring at 37° C. 1 mL solution was collected form the beaker at different time points (0 min, 5 min, 15 min, 30 min, 1 h, 3 h, 5 h, 8 h, 24 h, 48 h, and 72 h) and the oxaliplatin content was determined by ICP-MS. The release profile of oxaliplatin from oxa@Hf$_{12}$-DBP-Pt is shown in FIG. 10.

Material and Animals: Murine colon adenocarcinoma cell, CT26 and MC38 were purchased from the American Type Culture Collection (Rockville, Maryland, United States of America). Murine pancreatic ductal adenocarcinoma cell, Panc02 was kindly donated by Dr. Ralph. R. Weichselbaum at University of Chicago. CT26 cells were cultured in Roswell Park Memorial Institute (RPMI) 1640 medium (GE Healthcare, Chicago, Illinois, United States of America) supplemented with 10% fetal bovine serum (FBS, Hyclone Laboratories, Inc., Logan, Utah, United States of America. MC38 and Panc02 cells were cultured in Dulbecco's Modified Eagle's Medium (DMEM) medium (GE Healthcare, Chicago, Illinois, United States of America) supplemented with 10% FBS. All medium were mixed with 100 U/mL penicillin G sodium and 100 µg/mL streptomycin sulfate. Cells were cultured in a humidified atmosphere containing 5% CO$_2$ at 37° C. BALB/c and C57Bl/6 mice (6-8 weeks) were obtained from Envigo RMS, Inc. (Indianapolis, Indiana, United States of America).

Clonogenic assays were carried out to determine radioenhancements and delayed cell killing effects Hf$_{12}$-DBP-Pt and Hf$_{12}$-DBP. Cells were seeded in 6-well plates and cultured for 12 h. After incubated with particles at a Hf concentration of 20 µM for 4 h, cells were irradiated with X-ray (250 kVp, 15 mA, 1 mm Cu filter) at 0, 1, 2, 4, 8 and 16 Gy dose. Cells were trypsinized and counted immediately. 100-200 cells were seeded on 6-well plates and cultured with 2 mL medium for 10-20 days. Once cell clone formation was observed, the culture medium was discarded and plates were rinsed with PBS twice. 500 µL 0.5% crystal violet (50% methanol) were added per well for staining. Then, the wells were rinsed with water and the clones were counted. The radiation enhancement factors at 10% cell survival (REF$_{10}$ values) were determined from the clonogenic assays. See Table 7, below. Hf$_{12}$-DBP-Pt has unexpectedly larger REF$_{10}$ values than Hf$_{12}$-DBP for both CT26 and MC38 cells, indicating unexpectedly higher efficiency of Hf$_{12}$-DBP-Pt over Hf$_{12}$-DBP in killing cancer cells upon X-ray irradiation.

TABLE 7

REF$_{10}$ values by clonogenic assays in a panel of cell lines upon X-ray.

| | REF$_{10}$ | CT26 | MC38 |
|---|---|---|---|
| X-ray | Hf$_{12}$—DBP—Pt | 2.53 | 2.50 |
| | Hf$_{12}$—DBP | 2.28 | 1.88 |

The DNA double-strand break (DSB) caused by Hf$_{12}$-DBP-Pt and Hf$_{12}$-DBP upon X-ray irradiation was investigated by γ-H2AFX assay (Life Technologies, Carlsbad, California, United States of America) in CT26 cells. Cells were incubated with particles at a Hf concentration of 20 µM for 4 h followed by X-ray irradiation (250 kVp, 15 mA, 1 mm Cu filter) at 0 and 2 Gy dose. CT26 cells incubated with PBS with 2 Gy X-ray irradiation served as a control. H2AFX assays were carried out immediately after X-ray irradiation. The nuclei were stained with 4',6-diamidino-2-phenylindole (DAPI). Red fluorescence indicated the DSBs stained with antibody-labeled H2AFX. The cells were imaged with confocal laser scanning microscopy (CLSM). Upon X-ray irradiation, Hf$_{12}$-DBP-Pt showed stronger red fluorescence than Hf$_{12}$-DBP, indicating its unexpected superior ability to cause more DSBs.

The in vitro anticancer efficacy of Hf$_{12}$-DBP and Hf$_{12}$-DBP-Pt were further evaluated on CT26 and MC38 cells. Cells were cultured in a 6-well plate overnight and incubated with particles at a Hf concentration of 20 µM for 4 h followed by irradiation with 0 or 2 Gy X-ray (250 kVp, 15 mA, 1 mm Cu filter). 48 h later, the cells were stained according to the AlexaFluor 488 Annexin V/dead cell apoptosis kit (Life Technologies, Carlsbad, California United States of America) and quantified by flow cytometry. As shown in Tables 8 and 9, Hf$_{12}$-DBP-Pt has an unexpectedly larger percentage of late apoptotic and necrotic cells than Hf$_{12}$-DBP for both CT26 and MC38 cells, indicating higher acute efficacy of Hf$_{12}$-DBP-Pt over Hf$_{12}$-DBP in killing cancer cells upon low-dose X-ray irradiation.

TABLE 8

Percentage of CT26 cells treated with PBS, H$_2$DBP—Pt, Hf$_{12}$—DBP or Hf$_{12}$—DBP—Pt upon X-ray or dark after a 48-h incubation.

| X-ray | Treated agent | Healthy cells | Early apoptosis | Late apoptosis | Necrosis |
|---|---|---|---|---|---|
| 0 Gy | PBS | 96.4 | 0.61 | 1.77 | 1.18 |
| | H$_2$DBP—Pt | 88.2 | 0.66 | 4.86 | 6.26 |
| | Hf$_{12}$—DBP | 95.2 | 9.42 | 1.96 | 2.46 |
| | Hf$_{12}$—DBP—Pt | 92.2 | 0.28 | 3.90 | 3.62 |
| 2 Gy | PBS | 91.1 | 2.83 | 3.83 | 2.26 |
| | H$_2$DBP—Pt | 69.3 | 0.73 | 8.45 | 21.5 |
| | Hf$_{12}$—DBP | 54.6 | 1.09 | 25.1 | 19.2 |
| | Hf$_{12}$—DBP—Pt | 37.8 | 1.35 | 33.7 | 27.2 |

TABLE 9

Percentage of MC38 cells treated with PBS, H$_2$DBP—Pt, Hf$_{12}$—DBP or Hf$_{12}$—DBP—Pt upon X-ray or dark after a 48-h incubation.

| X-ray | Treated agent | Healthy cells | Early apoptosis | Late apoptosis | Necrosis |
|---|---|---|---|---|---|
| 0 Gy | PBS | 93.6 | 1.13 | 2.87 | 2.36 |
| | H$_2$DBP—Pt | 93.9 | 3.99 | 1.90 | 3.18 |
| | Hf$_{12}$—DBP | 93.5 | 4.54 | 1.62 | 0.29 |
| | Hfl2—DBP—Pt | 93.3 | 0.45 | 3.40 | 2.85 |

TABLE 9-continued

Percentage of MC38 cells treated with PBS, H$_2$DBP—Pt, Hf$_{12}$—DBP or Hf$_{12}$—DBP—Pt upon X-ray or dark after a 48-h incubation.

| X-ray | Treated agent | Healthy cells | Early apoptosis | Late apoptosis | Necrosis |
|---|---|---|---|---|---|
| 2 Gy | PBS | 86.9 | 7.93 | 4.84 | 0.30 |
| | H$_2$DBP—Pt | 78.2 | 15.9 | 5.31 | 0.55 |
| | Hf12—DBP | 56.6 | 18.0 | 22.3 | 3.17 |
| | Hf12—DBP—Pt | 34.1 | 26.8 | 36.1 | 2.98 |

Singlet oxygen sensor green (SOSG) reagent (Life Technologies, Carlsbad, California, United States of America) was employed for the in vitro detection of singlet oxygen under dark and X-ray irradiation. CT26 cells were seeded on cover slides in 6-well plate at 2×10$^5$/well and further cultured for 12 hours. Hf$_{12}$-DBP, Hf$_{12}$-DBP-Pt, H$_2$DBP-Pt or H$_2$DBP were added to the cells at an equivalent ligand dose of 10 µM. Cells incubated with PBS served as a control. After incubation of 4 hours, cells were irradiated by X-ray (250 kVp, 15 mA, 1 mm Cu filter) at a dose of 2 Gy. The slides were then washed with PBS and observed under CLSM. Stronger green fluorescence was observed from Hf$_{12}$-DBP-Pt treated group compared with Hf$_{12}$-DBP, indicating a better $^1O_2$ generation capability.

COX-2, a cyclooxygenase responsible for membrane damage repair, is often up-regulated after $^1O_2$-induced cell membrane damage. Thus, the cell membrane damage caused by RDT upon X-ray irradiation was investigated by COX-2 assay (BD Bioscience, Franklin Lakes, New Jersey, United States of America) in CT26 cells. Cells were seeded on cover slides in 6-well plates and cultured for 12 h then incubated with Hf$_{12}$-DBP, Hf$_{12}$-DBP-Pt, H$_2$DBP-Pt or PBS at a Hf concentration of 10 µM or ligand with concentration of 10 µM for 4 h followed by X-ray irradiation (250 kVp, 15 mA, mm Cu filter) at 0 and 2 Gy dose. Cells were fixed with 4% paraformaldehyde immediately after X-ray or light irradiation. Biotin-conjugated anti-COX-2 antibody with concentration of 10 µg/mL were incubated with cells at 4° C. overnight then followed by incubation with Cy3-conjugated streptavidin. The nuclei were stained with DAPI. Red fluorescence indicated the up-regulated expression of COX-2 stained with Cy3-labeled antibody. The cells were imaged with CLSM and quantified by flow cytometry.

The upregulation of COX-2 was directly observed by CLSM after Hf$_{12}$-DBP-Pt or Hf$_{12}$-DBP incubation and X-ray irradiation. No fluorescence signal was observed in cells treated with Hf$_{12}$-DBP-Pt or Hf$_{12}$-DBP without X-ray irradiation group and PBS or H$_2$DBP-Pt with or without X-ray irradiation groups. To further study the stronger RDT effect from the Hf$_{12}$-DBP-Pt treated group, flow cytometry was performed to quantify the difference of COX-2 upregulation of cells treated with Hf$_{12}$-DBP-Pt, Hf$_{12}$-DBP, H$_2$DBP-Pt or H$_2$DBP. The mean fluorescence intensities were 7441, 1804, 821, and 225 for the t cells treated with Hf$_{12}$-DBP-Pt, Hf$_{12}$-DBP, H$_2$DBP-Pt and H$_2$DBP with X-ray irradiation, respectively. Both confocal imaging and flow cytometry showed that Pt metalation increase the RDT effect.

The immunogenic cell death (ICD) induced by RT-RDT treatment was investigated by detecting cell-surface expression of calreticulin (CRT) in vitro. CT26 cells were seeded in 6-well plates on cover slides overnight and incubated with H$_2$DBP-Pt, Hf$_{12}$-DBP or Hf$_{12}$-DBP-Pt at 20 µM based on ligand concentration for 4 hours followed by treatment of X-ray irradiation (250 kVp, 15 mA, 1 mm Cu filter) at a dose of 2 Gy. Then cells were cultured in the incubator for another 4 hours to have enough CRT exposure. Cells were stained with AlexaFluor 488-CRT and DAPI, and observed under CLSM. Stronger green fluorescence was observed in group treated with Hf$_{12}$-DBP-Pt compared to either H$_2$DBP-Pt or Hf$_{12}$-DBP treated groups under CLSM.

Figure 11A:
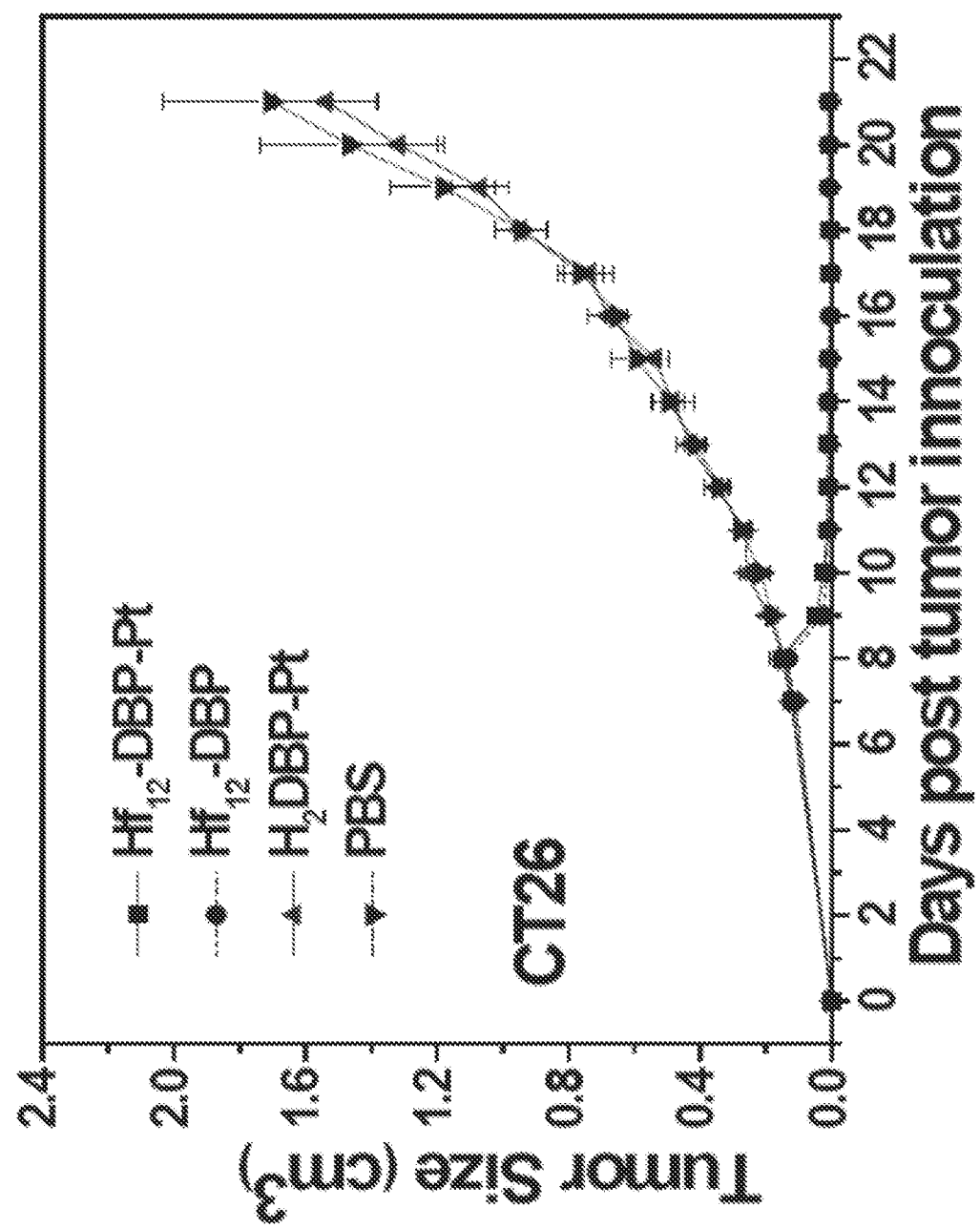
FIG. 11A is a graph showing tumor growth curves in mice inoculated with CT26 mouse colon cells and treated with radiotherapy-radiodynamic therapy (RT-RDT). Nanoscale metal-organic frameworks (nMOFs) comprising hafnium 12 ($Hf_{12}$)-oxo cluster secondary building units (SBUs) and 5, 15-di(p-benzoato)porphyrin bridging ligands ($Hf_{12}$-DBP, circles), the same nMOF wherein the porphyrin bridging ligand is complexed to platinum (Pt) (i.e., $Hf_{12}$-DBP-Pt, squares), and the bridging ligand complexed to Pt alone ($H_2$DBP-Pt, upward pointing triangles) were injected intratumorally to the mice at a nMOF or ligand concentration of 10 micromoles per kilogram (μmol/kg) followed by daily X-ray irradiation at a dose of 1 Gray per fraction (Gy/fraction, 120 peak kilovoltage (kVp), 20 milliampere (mA), 2 millimeter (mm)-copper (Cu) filter) for a total of 5 fractions on consecutive days. Tumor size (in cubic centimeters ($cm^3$)) is shown versus day post cancer cell inoculation. For comparison, data for mice injected with vehicle (phosphate buffered saline (PBS, downward pointing triangles) is also shown.
Figure 11B:
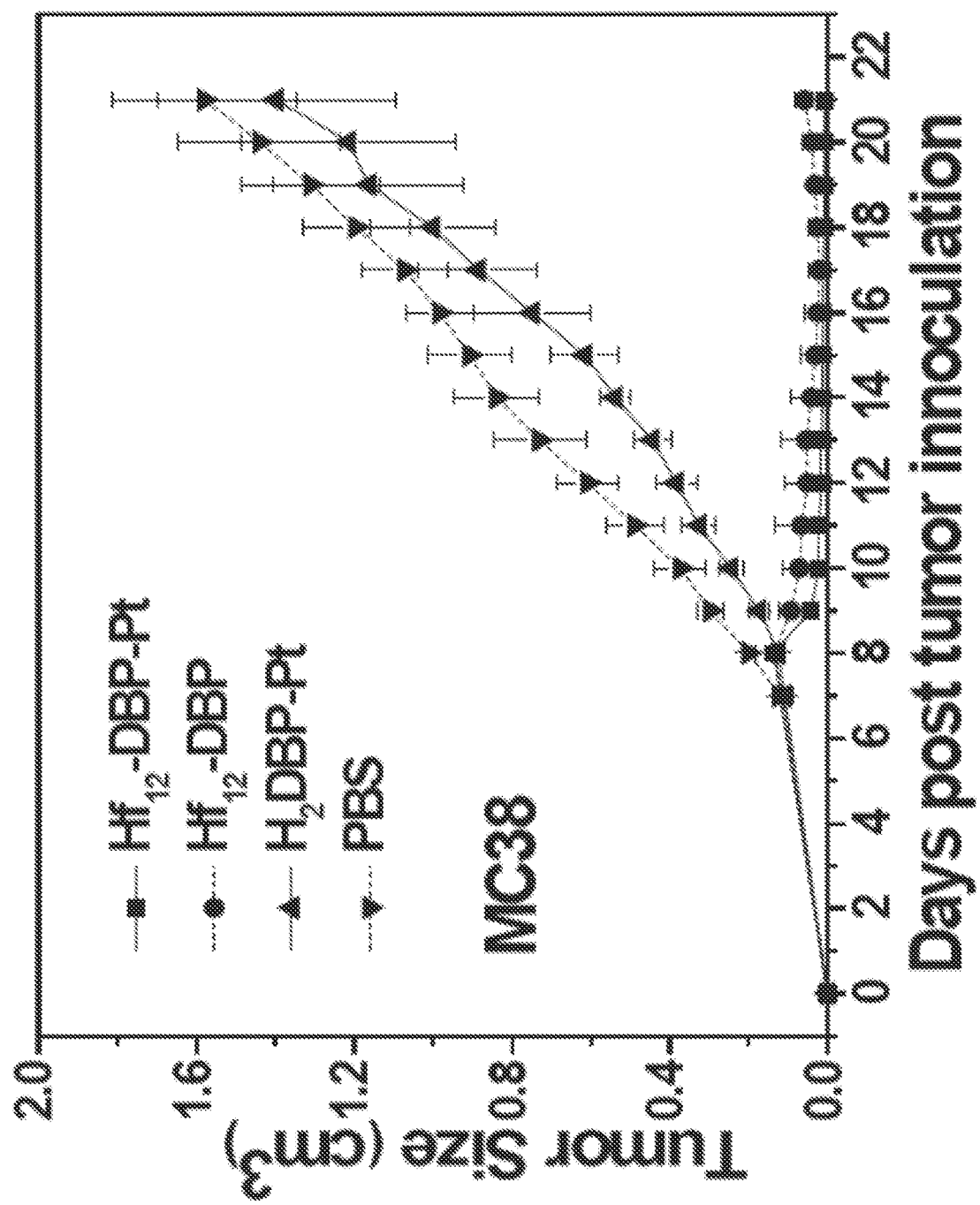
FIG. 11B is a graph showing tumor growth curves in mice inoculated with MC38 mouse colon cancer cells and treated with radiotherapy-radiodynamic therapy (RT-RDT). Nanoscale metal-organic frameworks (nMOFs) comprising hafnium 12 ($Hf_{12}$)-oxo cluster secondary building units (SBUs) and 5, 15-di(p-benzoato)porphyrin bridging ligands ($Hf_{12}$-DBP, circles), the same nMOF wherein the porphyrin bridging ligand is complexed to platinum (Pt) (i.e., $Hf_{12}$-DBP-Pt, squares), and the bridging ligand complexed to Pt alone ($H_2$DBP-Pt, upward pointing triangles) were injected intratumorally to the mice at a nMOF or ligand concentration of 10 micromoles per kilogram (μmmol/kg) followed by daily X-ray irradiation at a dose of 1 Gray per fraction (Gy/fraction, 120 peak kilovoltage (kVp), 20 milliampere (mA), 2 millimeter (mm)-copper (Cu) filter) for a total of 5 fractions on consecutive days. Tumor size (in cubic centimeters ($cm^3$)) is shown versus day post cancer cell inoculation. For comparison, data for mice injected with vehicle (phosphate buffered saline (PBS, downward pointing triangles) is also shown.

Two syngeneic subcutaneous flank tumor-bearing mouse models, CT26 and MC38, were selected for the evaluation of in vivo RT-RDT efficacy of Hf$_{12}$-DBP, Hf$_{12}$-DBP-Pt and H$_2$DBP-Pt. 2×10$^6$ CT26 or MC38 cells were injected into the right flank subcutaneous tissues of BALB/c or C57Bl/6 mice on day 0. When the tumors reached 100-150 mm$^3$ in volume, nMOFs or ligand with ligand concentration of 10 µmol 10 µmol/kg were intratumorally injected followed by daily X-ray irradiation at a dose of 1 Gy/fraction (120 kVp, 20 mA, 2 mm-Cu filter) for a total of 5 fractions on consecutive days. The tumor size was measured with a caliper every day and the tumor volume equals (width$^2$× length)/2. All mice were sacrificed on Day 21 and the excised tumors were photographed and weighed. Body weight of each group was monitored for the analysis of systemic toxicity. As shown in FIGS. 11A and 11B, Hf$_{12}$-DBP-Pt outperformed Hf$_{12}$-DBP in tumor regression on both CT26 and MC38 mouse models.

The cytotoxicity of oxa@Hf$_{12}$-DBP and oxa@Hf$_{12}$-DBP-Pt against Panc02 cells was evaluated with X-ray irradiation at a dose of 2 Gy, respectively. Panc02 cells were seeded on 96-well plates at 2×10$^4$/well and further cultured for 12 hours. Oxa@Hf$_{12}$-DBP and oxa@Hf$_{12}$-DBP-Pt were prepared freshly and added to the cells at an equivalent ligand dose of 0, 0.2, 0.5, 1, 2, 5, 10, 20 and 50 µM. The cells were further incubated for 72 hours before determining the cell viability by 3-(4,5-dimethylthiazol-2-yl)-5-(3-carboxymethoxyphenyl)-2-(4-sulfophen-yl+2H-tetrazolium (MTS) assay (Promega, Madison, Wisconsin, United States of America). The IC$_{50}$ values for oxa@Hf$_{12}$-DBP-Pt and oxa@Hf$_{12}$-DBP against Panc02 cells were calculated to be 30.02±3.89 and 49.91±5.47 µM, respectively, indicating oxa@Hf$_{12}$-DBP-Pt outperformed oxa@Hf$_{12}$-DBP on pancreatic cancer cell line in vitro.

Figure 12:
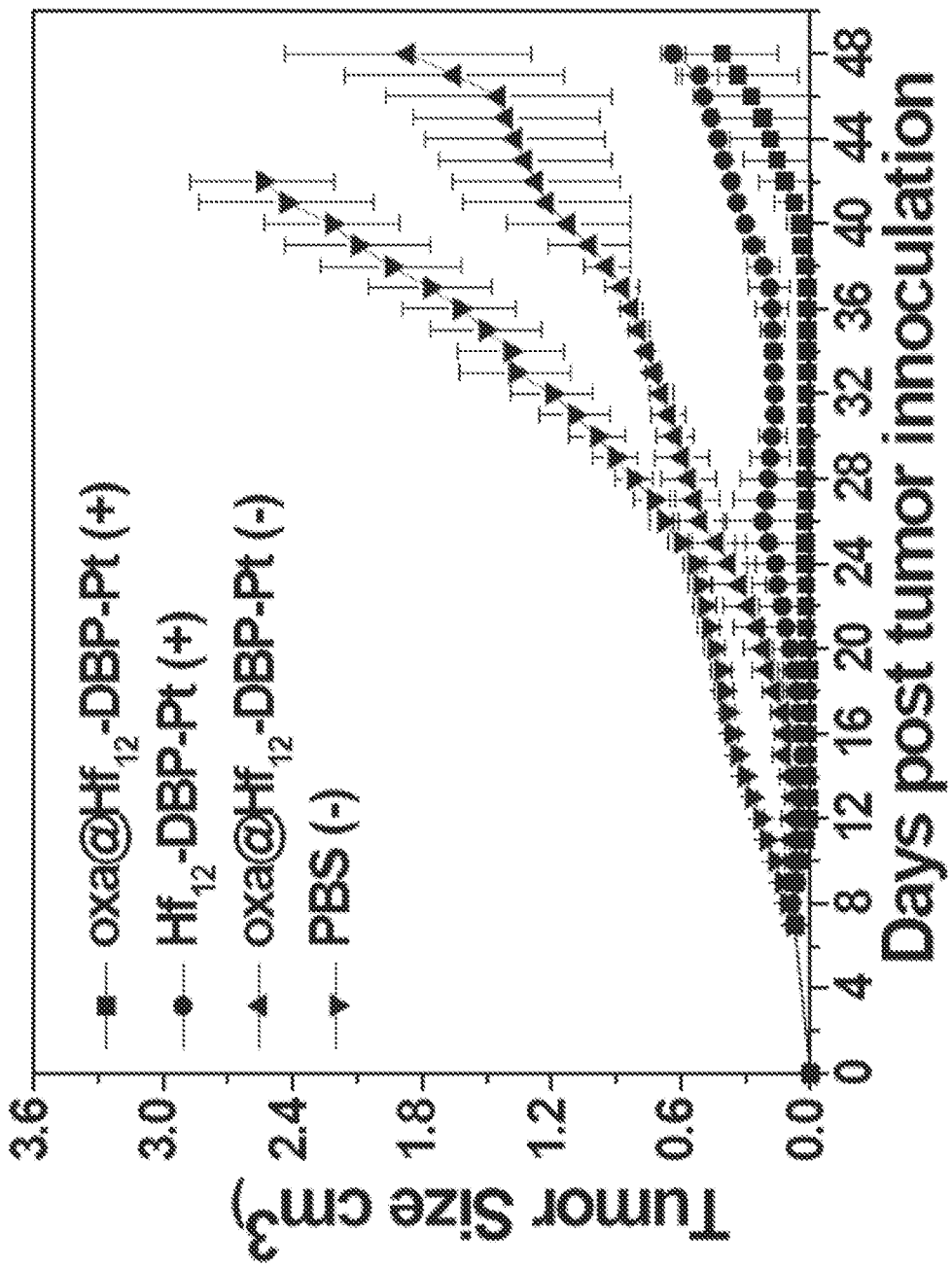
FIG. 12 is a graph showing tumor growth curves in mice inoculated with Panc02 mouse pancreatic cancer cells and treated with radiotherapy-radiodynamic therapy (RT-RDT) and/or oxaliplatin-based chemotherapy. Nanoscale metal-organic frameworks (nMOFs) comprising hafnium 12 ($Hf_{12}$)-oxo cluster secondary building units (SBUs) and 5, 15-di(p-benzoato)porphyrin bridging ligands complexed with platinum (Pt) ($Hf_{12}$-DBP-PT (+), circles) or the same nMOF further including encapsulated oxaliplatin (i.e., oxa@$Hf_{12}$-DBP-Pt (+), squares) were injected intratumorally to the mice followed by daily X-ray irradiation. Tumor size (in cubic centimeters ($cm^3$)) is shown versus day post cancer cell inoculation. For comparison, data for mice injected with vehicle (phosphate buffered saline (PBS) and not irradiated (PBS (−), downward pointing triangles) or the oxaliplatin-containing nMOF without X-ray irradiation (oxa@$Hf_{12}$-DBP-Pt (−), upward pointing triangles) is also shown.

The synergistic effect of oxaliplatin and RT-RDT against pancreatic ductal adenocarcinoma cancer was evaluated on syngeneic subcutaneous flank Panc02 tumor-bearing mouse model. 5×10$^6$ Panc02 cells were injected into the right flank subcutaneous tissues of C57Bl/6 mice on day 0. When the tumors reached 100-150 mm$^3$ in volume, nMOFs or ligand with ligand concentration of 10 µmol/kg were intratumorally injected followed by daily X-ray irradiation at a dose of 1 Gy/fraction (120 kVp, 20 mA, 2 mm-Cu filter) for a total of 6 fractions on consecutive days. The tumor size was measured with a caliper every day and the tumor volume equals (width$^2$×length)/2. Control mice were sacrificed on Day 42 and the treated groups were sacrificed on Day 48. The synergy between oxaliplatin-based chemotherapy and RT-RDT is clearly shown in the tumor growth curves shown in FIG. 12.

Example 5

Figure 13:
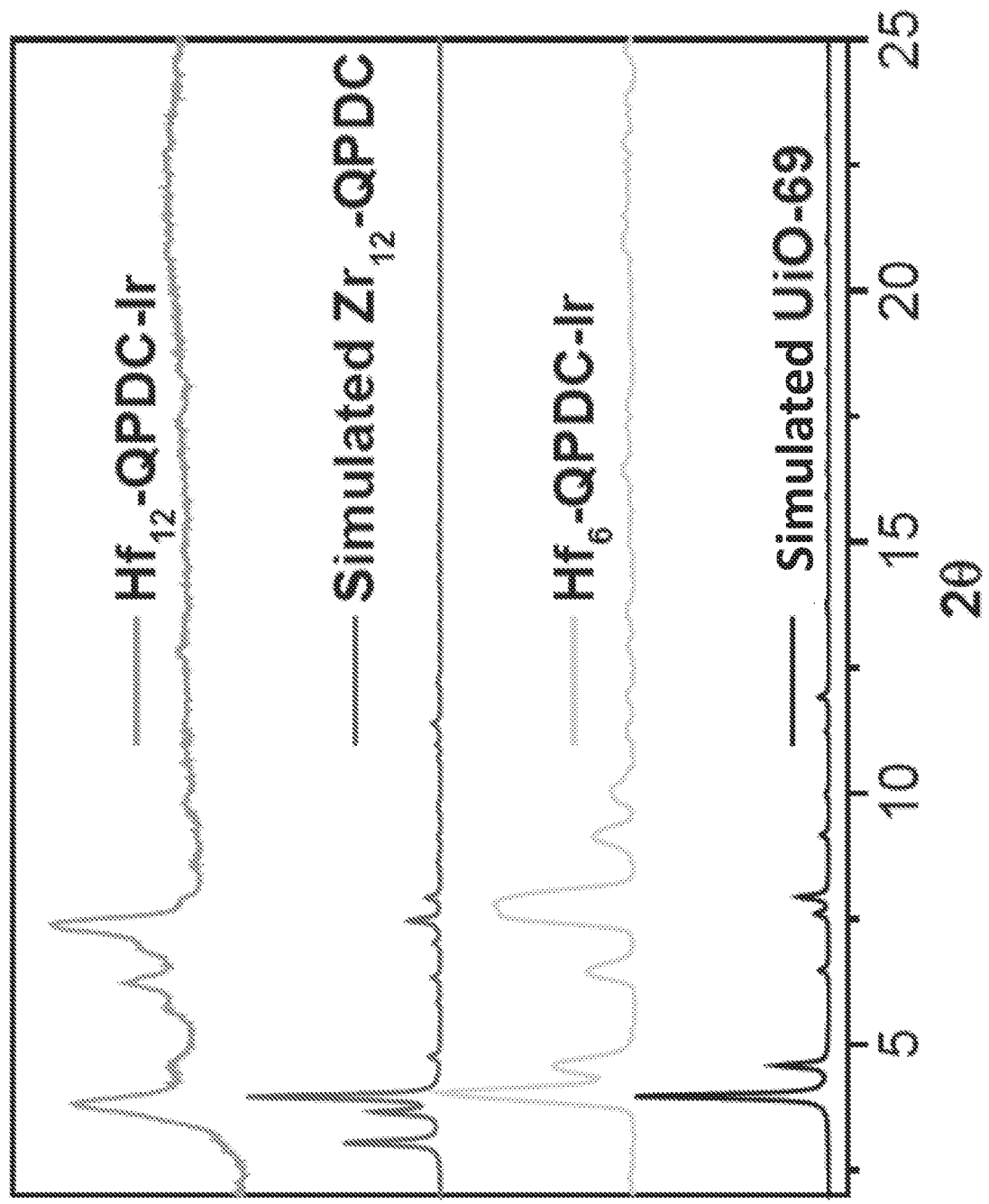
FIG. 13 is a graph showing powder X-ray diffraction (PXRD) patterns of nanoscale metal-organic frameworks (nMOFs) including, from top to bottom, an experimental PXRD pattern of a nMOF comprising hafnium 12 ($Hf_{12}$)-oxo cluster secondary building units (SBUs) and bis(4-phenyl-2-pyridine)(5,5'-di(4-carboxyl-phenyl)-2,2'-bipyridine)iridium(III) chloride bridging ligands (i.e., $Hf_{12}$-QPDC-Ir); a simulated PXRD pattern for a nMOF comprising zirconium 12 ($Zr_{12}$) SBUs and 5,5'-di(4-carboxyl-phenyl)-2,2'-bipyridine bridging ligands (Simulated $Zr_{12}$-QPDC); an experimental PXRD pattern for a nMOF comprising $Hf_6$ SBUs and bis(4-phenyl-2-pyridine)(5,5'-di (4-carboxyl-phenyl)-2,2'-bipyridine)iridium(III) chloride bridging ligands ($Hf_6$-QPDC-Ir); and a simulated PXRD pattern of a UiO-69 nMOF.

Synthesis and Characterization of Hf$_6$-QPDC-Ir, Hf$_{12}$-QPDC-Ir, and POM@Hf$_{12}$-QPDC-Ir Hf$_6$-QPDC-Ir nMOF: Bis(4-phenyl-2-pyridine)(5,5'-di(4-carboxyl-phenyl)-2,2'-bipyridine)iridium(III) chloride (H$_2$QPDC-Ir) was synthesized as described previously. See Wang et al., 2012. To a 4 mL glass vial was added 0.5 mL of HfCl$_4$ solution (2.0 mg/mL in DMF), 0.5 mL of the H$_2$QPDC-Ir solution (5.8 mg/mL in DMF), 40 µL of acetic acid. The reaction mixture was kept in a 70° C. oven for 3 days. The orange precipitate was collected by centrifugation and washed with DMF, 1% trimethylamine/ethanol solution and ethanol. TEM imaging showed that $Hf_{12}$-QPDC-Ir had a spherical morphology with a diameter of ~70 nm. PXRD pattern indicated that $Hf_6$-QPDC-Ir had a same structure as a Universitetet I Oslo (Norwegian for University of Oslo) MOF structure (UiO-69). See FIG. 13. See also, Dai et al., 2017.

$Hf_{12}$-QPDC-Ir nMOF: To a 4 mL glass vial was added 0.5 mL of $HfCl_4$ solution (2.7 mg/mL in DMF), 0.5 mL of the $H_2$QPDC-Ir solution (5.2 mg/mL in DMF), 16 μL of trifluoroacetic acid and 5 μL of water. See Scheme X, below. The mixture was kept in a 100° C. oven for 3 days. The orange precipitate of $Hf_{12}$-QPDC-Ir was collected by centrifugation and washed with DMF, 1% TEA/EtOH solution and EtOH. TEM imaging showed that $Hf_{12}$-QPDC-Ir had a plate morphology with a diameter of ~100 nm. PXRD pattern indicated that $Hf_{12}$-QPDC-Ir had same structure as $Zr_{12}$-QPDC. See FIG. 13. See also, Graham et al., 2008.

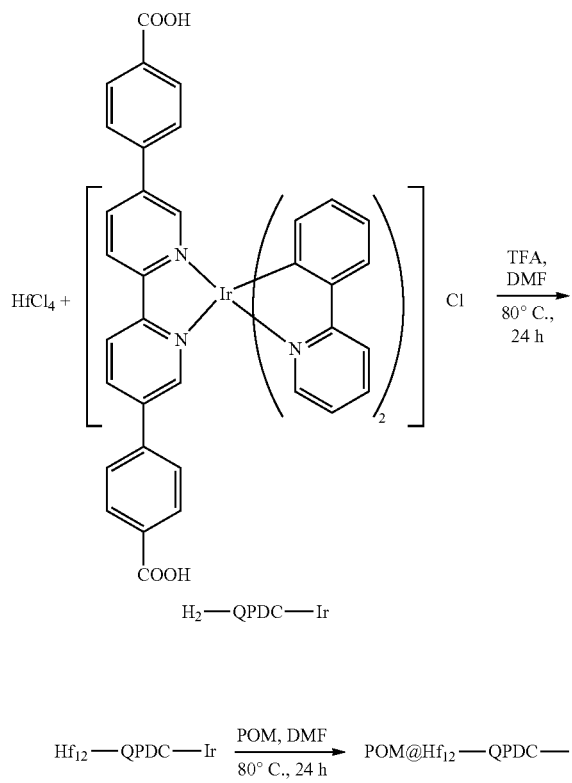

Scheme 9. Synthesis route of POM@$Hf_{12}$—QPDC—Ir.

The polyoxometalate (POM) $K_6[P_2W_{18}O_{62}]\cdot 14H_2O$ was synthesized as described previously (see Zhang et al., 2015) and characterized by IR spectroscopy. Organic-soluble $[(n\text{-}C_4H_9)_4N]_6[P_2W_{18}O_{62}]$ was further synthesized based on $K_6[P_2W_{18}O_{62}]\cdot 14H_2O$ as described previously (see Navath et al., 2008) and characterized by IR spectroscopy. As shown in Scheme 9, to a 4 mL glass vial was added 1 mL $Hf_{12}$-QPDC-Ir suspension (1 mM based on Hf in DMF) and 1 mg $[(n\text{-}C_4H_9)_4N]_6[P_2W_{18}O_{62}]$. The reaction mixture was kept in an 80° C. oven for 24 h to afford POM@$Hf_{12}$-QPDC-Ir (POM=$[P_2W_{18}O_{62}]^{6-}$). The orange precipitate was collected by centrifugation and washed with DMF and ethanol. TEM imaging showed that POM@$Hf_{12}$-QPDC-Ir remained similar size and morphology to $Hf_{12}$-QPDC-Ir. The ratio of W:Hf was determined to be 1.11±0.1 by ICP-MS.

Example 6

Synthesis and Characterization of POM@$Hf_{12}$-QPDC-Ir@PEG

Figure 14:
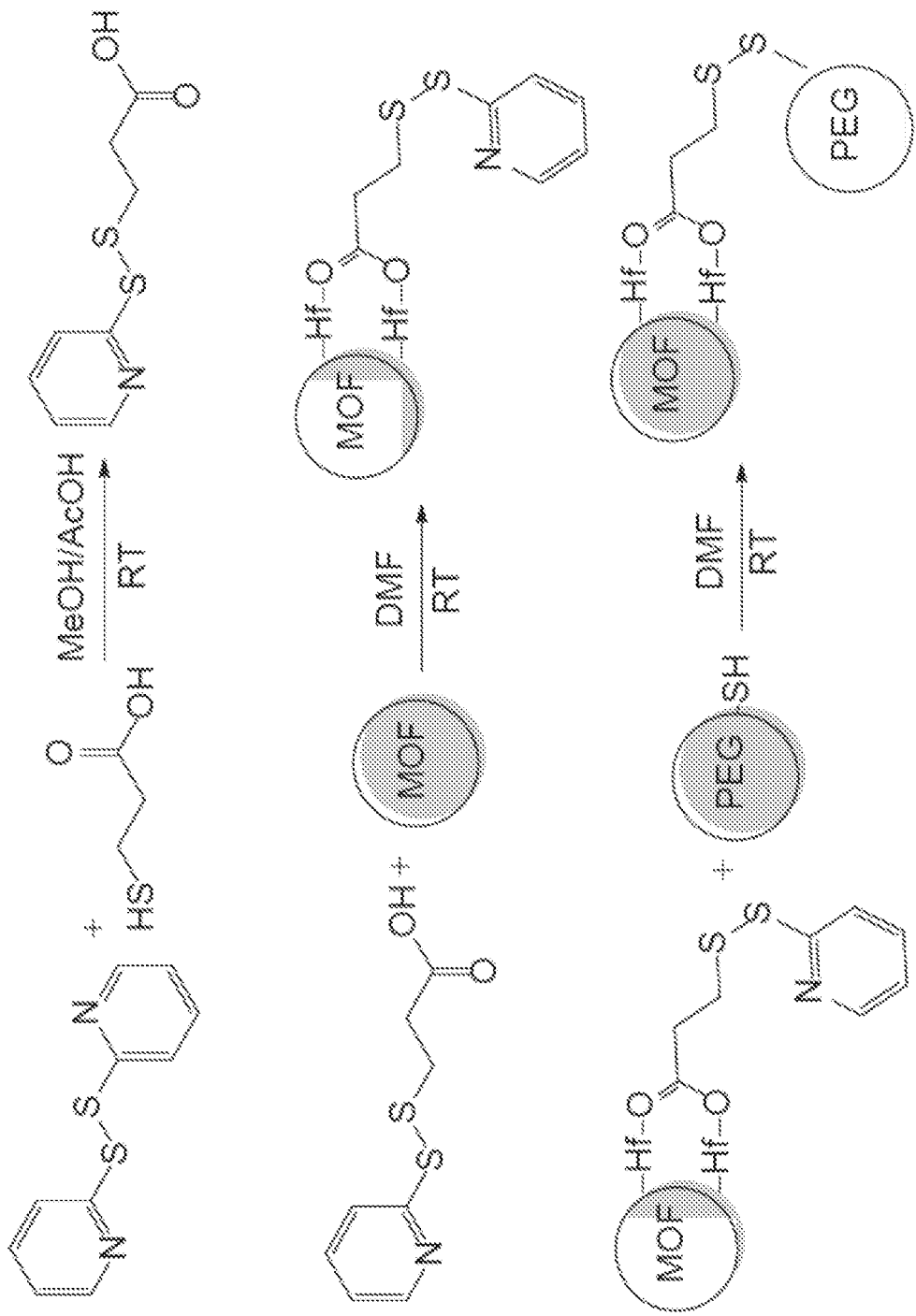
FIG. 14 is a schematic drawing showing the synthesis of polyoxometalate (POM)-hafnium 12-bis(4-phenyl-2-pyridine)(5,5'-di(4-carboxyl-phenyl)-2,2'-bipyridine)iridium (III) chloride nanoscale metal-organic framework (POM@$Hf_{12}$-QPDC-IR) polyethylene glycol (PEG) conjugate (POM@—$Hf_{12}$-QPDC-IR@PEG). The top step shows the synthesis of 2-carboxyethyl 2-pyridyl disulfide from 3-mercaptopropionic acid and 2,2'-dipyridyl disulfide; the middle step shows the grafting of the 2-carboxyethyl 2-pyridyl disulfide to Hf atoms on the surface of the metal-organic framework (MOF); and the bottom step shows the conjugation of a thiolated PEG (i.e., PEG-SH) to the MOF via a disulfide bond.

Step a: 2-carboxyethyl 2-pyridyl disulfide was synthesized as described previously. See FIG. 14, top and Horikawa et al., 2016. 2,2'-dipyridyl disulfide (700 mg, 3.1 mmol), 3-mercaptopropionic acid (165 mg, 1.5 mmol) and 180 μL AcOH were suspended in 5 mL EtOH. The reaction mixture was stirred at room temperature for 2 h. The crude product was purified by basic $Al_2O_3$ column chromatography [DCM/EtOH (3/2 v/v) and DCM/EtOH/AcOH (15/10/1 v/v/v)] to afford a colorless product (2-carboxyethyl 2-pyridyl disulfide). $^1$H-NMR (500 HZ, DMSO-d6): δ=2.59 (t, 2H), 2.98 (t, 2H,), 7.23 (m, 1H), 7.75 (d, 1H), 7.8 (m, 1H), 8.4 (d, 1H).

Step b: To a 4 mL glass vial was added 1 mL POM@$Hf_{12}$-QPDC-Ir suspension (1 mM based on Hf in DMF) and 1 mg 2-carboxyethyl 2-pyridyl disulfide. See FIG. 14, middle. The reaction mixture was stirred at room temperature for 2 h. 2-carboxyethyl 2-pyridyl disulfide was grafted on the surface of POM@$Hf_{12}$-QPDC-Ir by replacing trifluoroacetate coordinating to the Hf SBUs. The yellow precipitate was collected by centrifugation and washed with DMF.

Step c: To a 4 mL glass vial was added 1 mL 2-carboxyethyl 2-pyridyl disulfide modified POM@$Hf_{12}$-QPDC-Ir suspension (1 mM based on Hf in DMF) and 2 mg poly (ethylene glycol) methyl ether thiol (PEG-SH). See FIG. 14, bottom. The reaction mixture was stirred at room temperature for 24 h to afford POM@$Hf_{12}$-QPDC-Ir@PEG. The yellow precipitate was collected by centrifugation and washed with DMF and EtOH. The pegylated nanoparticles POM@$Hf_{12}$-QPDC-Ir@PEG will have the surface property to circulate for a long period of time upon intravenous injection.

The in vitro anticancer efficacy of POM, $Hf_6$-QPDC-Ir, $Hf_{12}$-QPDC-Ir and POM@$Hf_{12}$-QPDC-Ir were evaluated on CT26 and MC38 cells. Cells were cultured in a 6-well plate overnight and incubated with particles at a Hf concentration of 20 μM or equivalent W concentration for 4 h followed by irradiation with 0 or 2 Gy X-ray (250 kVp, 15 mA, 1 mm Cu filter). 48 h later, the cells were stained according to the AlexaFluor 488 Annexin V/dead cell apoptosis kit (Life Technologies, Carlsbad, California, United States of America) and quantified by flow cytometry. As shown in Tables 10 and 11, POM@$Hf_{12}$-QPDC-Ir has larger percentage of late apoptotic and necrotic cells than POM, $Hf_6$-QPDC-Ir and $Hf_{12}$-QPDC-Ir for both CT26 and MC38 cells, indicating higher acute efficacy of POM@$Hf_{12}$-QPDC-Ir over POM, $Hf_6$-QPDC-Ir, and $Hf_{12}$-QPDC-Ir in killing cancer cells upon low-dose X-ray irradiation.

TABLE 10

Percentage of CT26 cells treated with PBS, POM, Hf$_6$—QPDC—Ir, Hf$_{12}$—QPDC—Ir and POM@Hf$_{12}$—QPDC—Ir upon X-ray or dark after a 48-h incubation.

| X-ray | Treated agent | Healthy cells | Early apoptosis | Late apoptosis | Necrosis |
|---|---|---|---|---|---|
| 0 Gy | PBS | 99.0 | 0.16 | 0.55 | 0.28 |
| | POM | 99.7 | 0.051 | 0.0057 | 0.21 |
| | Hf$_6$—QPDC—Ir | 94.7 | 3.17 | 1.73 | 0.36 |
| | Hf$_{12}$—QPDC—Ir | 94.8 | 3.02 | 1.78 | 0.42 |
| | POM@Hf$_{12}$—QPDC—Ir | 96.3 | 2.81 | 0.69 | 0.21 |
| 2 Gy | PBS | 90.9 | 5.87 | 2.94 | 0.32 |
| | POM | 83.1 | 5.71 | 8.14 | 3.05 |
| | Hf$_6$—QPDC—Ir | 76.2 | 1.25 | 18.3 | 4.18 |
| | Hf$_{12}$—QPDC—Ir | 54.3 | 20.7 | 20.6 | 4.37 |
| | POM@Hf$_{12}$—QPDC—Ir | 45.9 | 14.9 | 28.3 | 11.0 |

TABLE 11

Percentage of MC38 cells treated with PBS, POM, Hf$_6$—QPDC—Ir, Hf$_{12}$—QPDC—Ir and POM@Hf$_{12}$—QPDC—Ir upon X-ray or dark after a 48-h incubation.

| X-ray | Treated agent | Healthy cells | Early apoptosis | Late apoptosis | Necrosis |
|---|---|---|---|---|---|
| 0 Gy | PBS | 99.0 | 0.69 | 0.34 | 0.016 |
| | POM | 97.3 | 0.44 | 0.86 | 1.53 |
| | Hf$_6$—QPDC—Ir | 95.7 | 3.25 | 0.71 | 0.32 |
| | Hf$_{12}$—QPDC—Ir | 97.8 | 0.81 | 0.76 | 0.58 |
| | POM@Hf$_{12}$—QPDC—Ir | 97.2 | 0.30 | 0.97 | 1.57 |
| 2 Gy | PBS | 93.0 | 5.60 | 1.19 | 0.17 |
| | POM | 70.9 | 2.35 | 14.0 | 12.7 |
| | Hf$_6$—QPDC—Ir | 76.2 | 1.25 | 18.3 | 4.18 |
| | Hf$_{12}$—QPDC—Ir | 55.5 | 7.37 | 23.1 | 3.03 |
| | POM@Hf$_{12}$—QPDC—Ir | 48.8 | 6.66 | 30.5 | 14.0 |

Figure 15A:
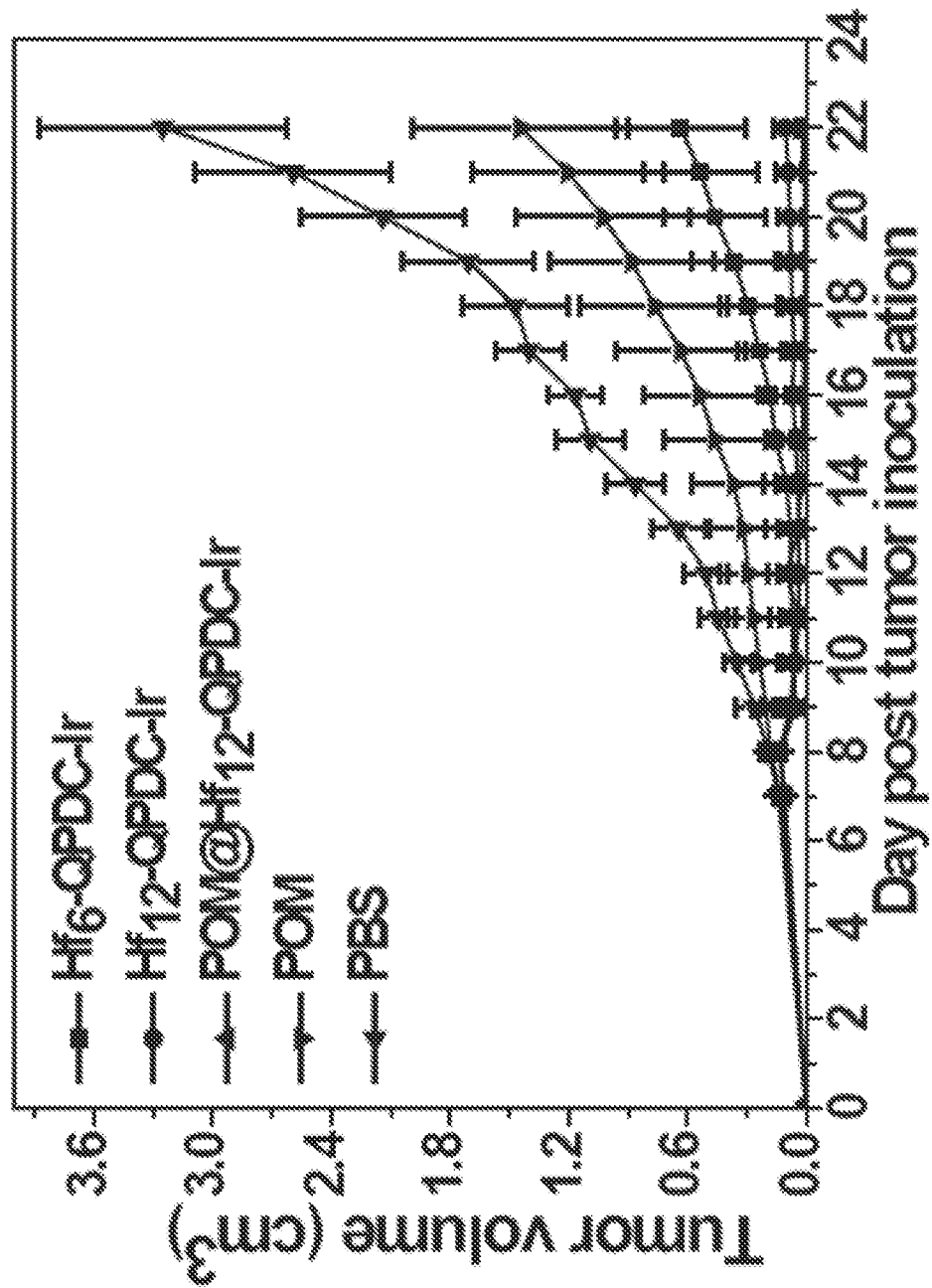
FIG. 15A is a graph showing the tumor growth curves of mice inoculated with CT26 mouse colon cancer cells and treated with different nanoscale metal-organic frameworks (nMOFs), including a nMOF comprising hafnium 6 ($Hf_6$)-oxo cluster secondary building units (SBUs) and bis(4-phenyl-2-pyridine)(5,5'-di(4-carboxyl-phenyl)-2,2'-bipyridine)iridium(III) chloride bridging ligands ($Hf_6$-QPDC-Ir, squares); $Hf_{12}$-oxo cluster SBUs and bis(4-phenyl-2-pyridine)(5,5'-di(4-carboxyl-phenyl)-2,2'-bipyridine)iridium (III) chloride ($Hf_{12}$-QPDC-Ir, circles); and $Hf_{12}$-QPDC-Ir with polyoxometalate (POM@$Hf_{12}$-QPDC-Ir, upward pointing triangles). Data is also provided for tumor-bearing mice treated with polyoxometalate alone (POM, downward pointing triangles) or with vehicle (phosphate buffered saline (PBS), triangles pointing left). N=6.
Figure 15B:
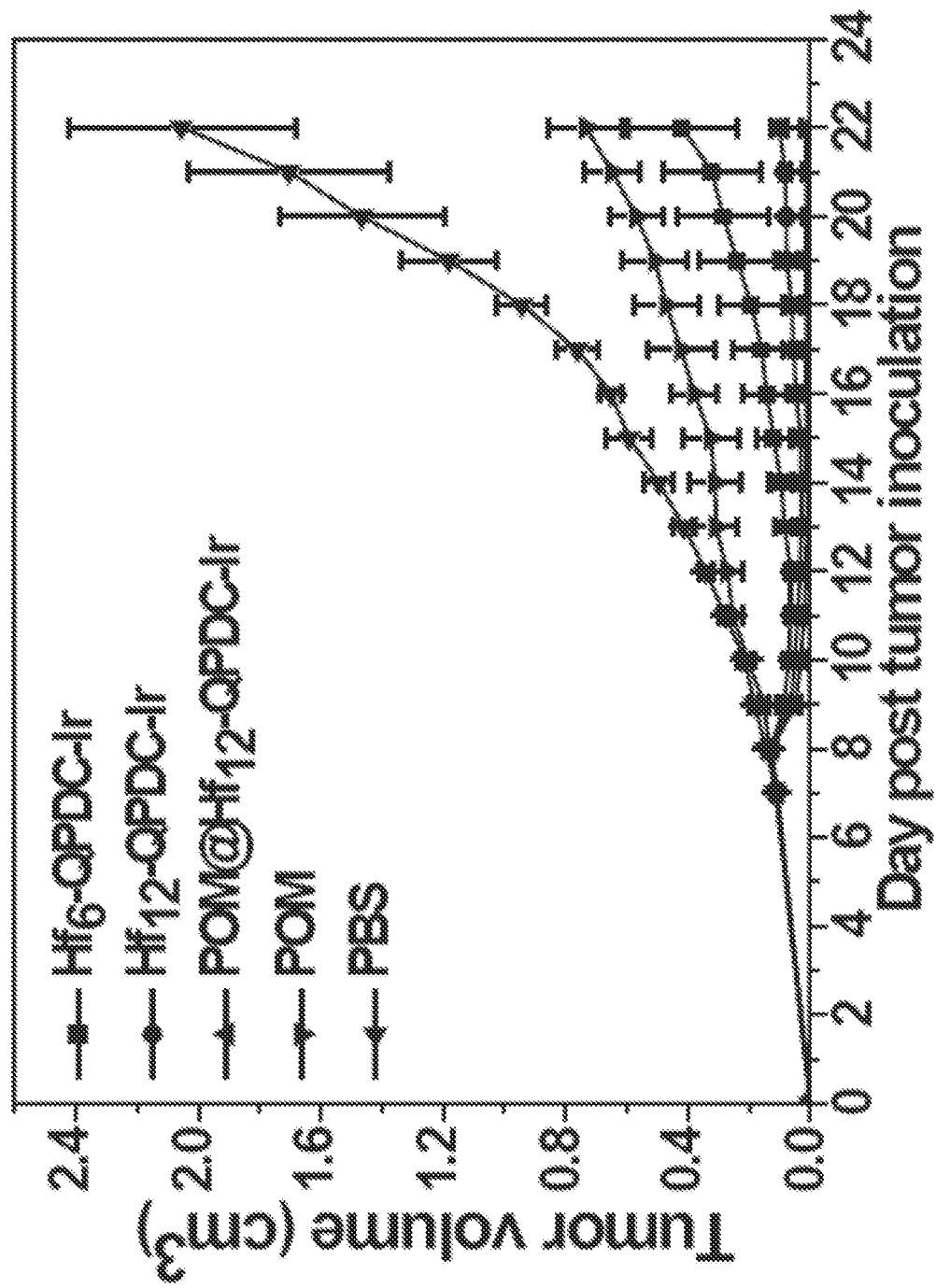
FIG. 15B is a graph showing the tumor growth curves from mice inoculated with MC38 mouse colon cancer cells and treated with different nanoscale metal-organic frameworks (nMOFs), including a nMOF comprising hafnium 6 ($Hf_6$)-oxo cluster secondary building units (SBUs) and bis(4-phenyl-2-pyridine)(5,5'-di(4-carboxyl-phenyl)-2,2'-bipyridine)iridium(III) chloride bridging ligands ($Hf_6$-QPDC-Ir, squares); $Hf_{12}$-oxo cluster SBUs and bis(4-phenyl-2-pyridine)(5,5'-di(4-carboxyl-phenyl)-2,2'-bipyridine)iridium(III) chloride ($Hf_{12}$-QPDC-Ir, circles); and $Hf_{12}$-QPDC-Ir with polyoxometalate (POM@$Hf_{12}$-QPDC-Ir, upward pointing triangles). Data is also provided for tumor-bearing mice treated with polyoxometalate alone (POM, downward pointing triangles) or with vehicle (phosphate buffered saline (PBS), triangles pointing left). N=6.

Two syngeneic subcutaneous flank tumor-bearing mouse models, CT26 and MC38, were selected for the evaluation of in vivo anti-cancer efficacy of POM, Hf$_6$-QPDC-Ir, Hf$_{12}$-QPDC-Ir and POM@Hf$_{12}$-QPDC-Ir. 2×10$^6$ CT26 or MC38 cells were injected into the right flank subcutaneous tissues of BALB/c or C57Bl/6 mice on day 0. When the tumors reached 100-150 mm$^3$ in volume, nMOFs or ligand with ligand concentration of 10 μmol/kg were intratumorally injected followed by daily X-ray irradiation at a dose of 1 Gy/fraction (225 kVp, 13 mA, 0.3 mm-Cu filter) for a total of 5 fractions on consecutive days. The tumor size was measured with a caliper every day and the tumor volume equals (width$^2$×length)/2. All mice were sacrificed on Day 22 and the excised tumors were photographed and weighed. As shown in FIGS. 15A and 15B, POM@Hf$_{12}$-QPDC-Ir outperformed Hf$_{12}$-QPDC-Ir, Hf$_6$-QPDC-Ir or POM in tumor regression on both CT26 and MC38 mouse models.

Example 7

HF$_{12}$-QPDC-Ir—F and Hf$_6$-BPY-Ir—F

Synthesis and Characterization of Hf$_{12}$-QPDC-Ir—F and Hf$_6$-BPY-Ir—F

Me$_2$QPDC-Ir—F: Ir[dF(CF$_3$)ppy]$_2$Cl dimer [dF(CF$_3$)ppy=2-(2',4'-difluorophenyl)-5-(trifluoromethyl)pyridine] and 4,4'-([2,2'-bipyridine]-5,5'-diyl)dibenzoic acid (H$_2$QPDC) were synthesized as described previously. See Lowry et al., 2005; and Zhang et al., 2016. As shown in Scheme 10, below, Ir[dF(CF$_3$)ppy]$_2$Cl dimer (595 mg, 0.4 mmol), H$_2$QPDC (318 mg, 0.75 mmol), methanol (20 mL) and chloroform (20 mL) were added to a 200 mL thick-walled sealed tube. The tube was sealed and heated at 120° C. for 2 days. The solution gradually became clear under heating. After cooling to ambient temperature, the solvent was removed under reduced pressure and the crude product was purified by column chromatography (SiO$_2$, CHCl$_3$/MeOH, 10:1 to 5:1) to yield the product as a light yellow solid (570 mg, 65%). $^1$H NMR (500 MHz, CDCl$_3$): δ 10.34 (d, J=9.0 Hz, 2H), 8.67 (d d, J$_1$=8.5 Hz, J$_2$=2.5 Hz, 2H), 8.53 (d d, J$_1$=9.0 Hz, J$_2$=2.5 Hz, 2H), 8.14 (d, J=8.0 Hz, 4H), 8.10-8.08 (m, 4H), 7.66 (s, 2H), 7.42 (d, J=8.0 Hz, 4H), 6.70 (d d d, J$_1$=10.0 Hz, J$_2$=9.0 Hz, J$_3$=2.5 Hz, 2H), 5.70 (d d, J$_1$=8.0 Hz, J$_2$=2.5 Hz, 2H), 3.95 (s, 6H). $^{19}$F NMR (470 MHz, CDCl$_3$): δ −62.72 (s, 6H), −100.42 (d t, J$_1$=12.2 Hz, J$_2$=8.5 Hz, 2H), −105.44 (t, J=12.2 Hz, 2H). HRMS (ESI-FT) m/z Calcd. for C$_{50}$H$_{30}$F$_{10}$IrN$_4$O$_4$$^+$ ([M−Cl$^-$]) 1133.1731. Found: 1133.1744.

Scheme 10. Synthesis of Me₂QPDC—Ir—F ligand.

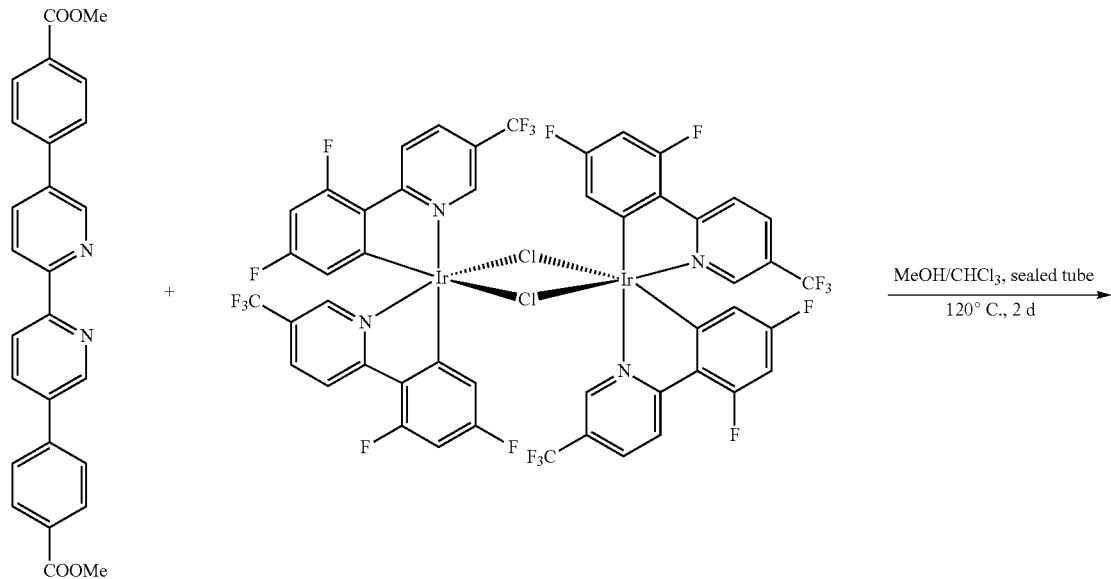

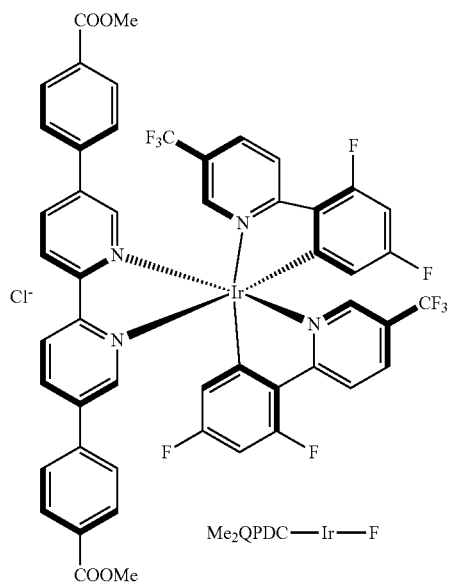

H₂QPDC-Ir—F: As shown in Scheme 11, below, Me₂QPDC-Ir—F (116 mg, 0.1 mmol) and THF (10 mL) were added to a 100 mL flask. After the solid was fully dissolved, an aqueous solution of lithium hydroxide (25 mg LiOH·H₂O in 10 mL deionized water) was added dropwise to the solution while stirring. The solution was stirred at ambient temperature for 5 h and the progress of the reaction was tracked by LC-MS. After the starting material and partially hydrolyzed product were completely consumed the solution was acidified by adding concentrated HCl until reaching pH=1. Next, the THF was removed under reduced pressure and a light-yellow precipitate formed. The solid was filtered under reduced pressure, washed by deionized water, and ether, and finally dried under vacuum to afford H₂QPDC-Ir—F as a fine light-yellow powder (105 mg, 92%). $^1$H NMR (500 MHz, CDCl₃): δ 9.10 (d, J=8.5 Hz, 2H), 8.77 (d d, J₁=8.5 Hz, J₂=2.0 Hz, 2H), 8.48 (d, J=9.0 Hz, 2H), 8.44 (d, J=9.0 Hz, 2H), 8.15 (d, J=2.0 Hz, 2H), 8.04 (d, J=8.5 Hz, 4H), 7.81 (s, 2H), 7.67 (d, J=8.5 Hz, 4H), 7.10 (d d d, J₁=10.0 Hz, J₂=9.0 Hz, J₃=2.5 Hz, 2H), 5.89 (d d, J₁=8.0 Hz, J₂=2.5 Hz, 2H). $^{19}$F NMR (470 MHz, DMSO-d₆): δ −61.33 (s, 6H), −103.44 (m, 2H), −106.88 (t, J=12.2 Hz, 2H). HRMS (ESI-FT) m/z Calcd. for C₄₈H₂₆F₁₀IrN₄O₄⁺ ([M−Cl⁻]) 1105.1418. Found: 1105.1443.

Scheme 11. Synthesis of H₂QPDC—Ir—F ligand.

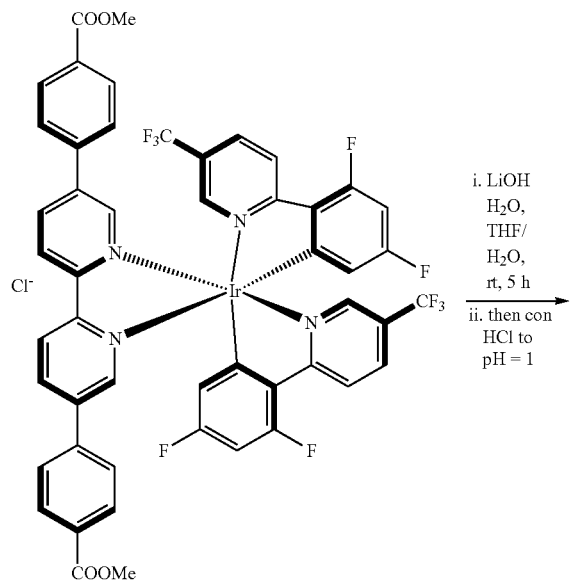

nMOL structure in the (001) direction. The distance between two adjacent lattice points in the HRTEM imaging was measured to be 2.7 nm, matching the distance between two adjacent $Hf_{12}$ SBUs. PXRD pattern showed that $Hf_{12}$-QPDC-Ir—F nMOL, in comparison to $Zr_{12}$-QPDC MOF, only exhibited diffraction peaks corresponding to the layer structure, while all peaks perpendicular to the layer disappeared, which is similar to the case of $Hf_{12}$-QPDC-Ru MOL. The atomic force microscopy (AFM) images of $Hf_{12}$-QPDC-Ir—F nMOL showed a 1.7 nm thickness, which was very close to the Van der Waals size of the $Hf_{12}$ cluster capped by trifluoroacetate group. The combination of PXRD and AFM results indicated that the monolayer structure of $Hf_{12}$-QPDC-Ir—F nMOL.

Scheme 12. Synthesis of $Hf_{12}$—QPDC—Ir—F nMOL.

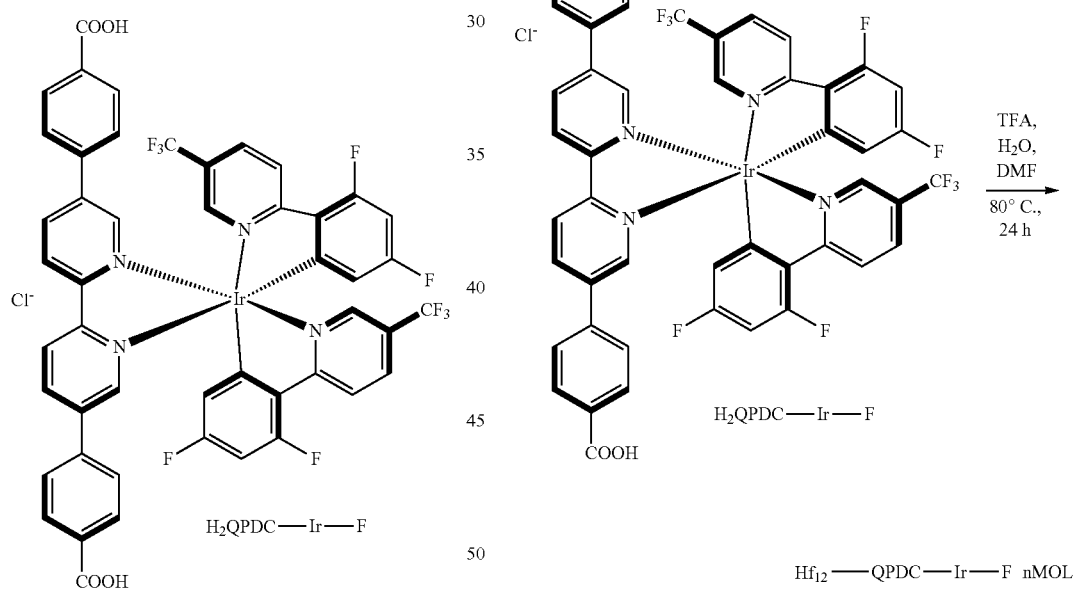

$Hf_{12}$-QPDC-Ir—F nMOL: As shown in Scheme 12, below, to a 4 mL glass vial was added 0.5 mL of $HfCl_4$ solution (2.0 mg/mL in DMF), 0.5 mL of $H_2QPDC$-Ir—F solution (4 mg/mL in DMF), 2 μL of trifluoroacetic acid (TFA), and 5 μL of water. The reaction mixture was kept in an 80° C. oven for 24 hours. The yellow precipitate was collected by centrifugation and washed with DMF and ethanol. TEM imaging showed that $Hf_{12}$-QPDC-Ir—F nMOL adopted nanosheet morphology with a diameter ranging from 100 to 300 nm. HRTEM imaging showed lattice points corresponding to $Hf_{12}$ SBUs with the fast Fourier transform (FFT) revealing a six-fold symmetry, which is consistent with the projection of $Hf_{12}$-QPDC-Ir—F $Hf_6$-BPY-Ir—F MOL: $Hf_6$-BPY MOL was first synthesized as previously described in Example 1, above. As shown in Scheme 13, below, to a 20 mL glass vial was added 5 mL of $Hf_6$-BPY MOL solution (2 mM based on Hf in MeOH), 5 mL of $Ir[dF(CF_3)ppy]_2Cl$ dimer solution (2.0 mg/mL in MeOH). The reaction mixture was kept in an 80° C. oven for 2 days. The yellow precipitate was collected by centrifugation and washed with ethanol for three times. TEM imaging showed that $Hf_6$-BPY-Ir—F MOL adopted monolayer morphology with a diameter of ~500 nm. HRTEM imaging showed lattice points corresponding to $Hf_6$ SBUs with the fast Fourier transform (FFT) revealing a six-fold symmetry, which is consistent with the projection of Hf$_6$-BPY-Ir—F MOL structure in the (001) direction. The distance between two adjacent lattice points in the HRTEM imaging was measured to be 2.0 nm, matching the distance between two adjacent Hf$_6$ SBUs. PXRD pattern indicated that Hf$_6$-BPY-Ir—F MOL adopted the same crystal structure as Hf$_6$-BPY MOL. The atomic force microscopy (AFM) images of Hf$_6$-BPY-Ir—F MOL showed a 1.2 nm thickness, which was very close to the Van der Waals size of the Hf$_6$ cluster capped by formic group. The AFM results confirmed the monolayer structure of Hf$_6$-BPY-Ir—F MOL.

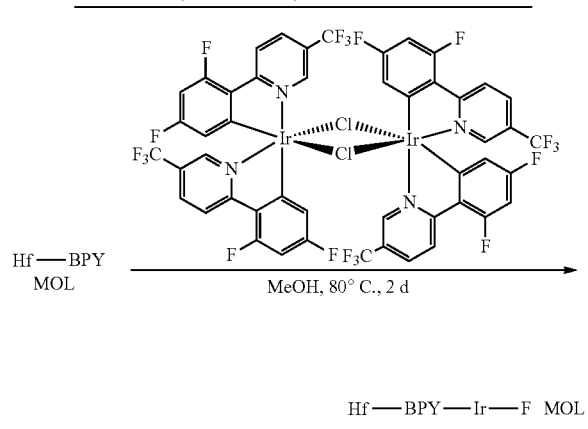

Scheme 13. Synthesis of Hf$_6$—BPY—Ir—F nMOL.

Figure 16:
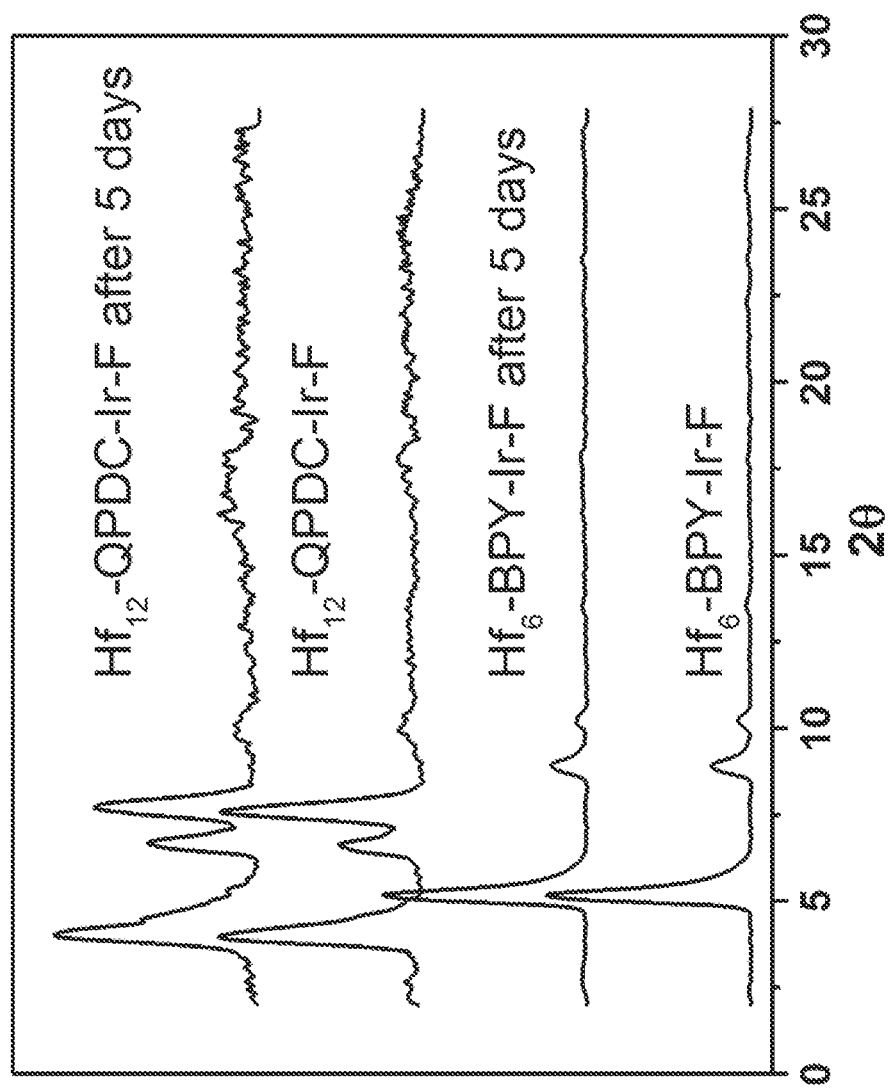
FIG. 16 is graph showing powder X-ray diffraction (PXRD) patterns of metal-organic layers including, from bottom to top, a MOL comprising hafnium 6 ($Hf_6$)-oxo cluster secondary building units (SBUs) and bridging ligands comprising a coordination complex comprising 4',6'-dibenzoato-[2,2-bipyridine]-4-carboxylate (BPY), an iridium (Ir) ion, and two 2-(2',4'-difluorophenyl)-5-(trifluorophenyl)pyridine ligands ($Hf_6$-BPY-Ir—F); the same MOL after suspension in 6 millimolar (mM) phosphate buffer for 5 days ($Hf_6$-BPY-Ir—F after 5 days); a MOL comprising hafnium 12 ($Hf_{12}$)-oxo cluster SBUs and bis(2-(2',4'-difluorophenyl)-5-(trifluoromethyl)pyridine)(5,5'-di(4-carboxyl-phenyl)-2,2'-bipyridine)iridium(III) bridging ligands ($Hf_{12}$-QPDC-Ir—F); and the same MOL after suspension in 6 mM phosphate buffer for 5 days ($Hf_{12}$-QDPC-Ir—F after 5 days).

Stability test of Hf$_{12}$-QPDC-Ir—F and Hf$_6$-BPY-Ir—F MOL: Hf$_{12}$-QPDC-Ir—F and Hf$_6$-BPY-Ir—F MOL were suspended into 6 mM phosphate buffer solution for three days. Then, the Hf$_{12}$-QPDC-Ir—F and Hf$_6$-BPY-Ir—F MOL were collected by centrifuge and tested the PXRD pattern. PXRD studies indicated that Hf$_{12}$-QPDC-Ir—F and Hf$_6$-BPY-Ir—F MOL were stable in 6 mM phosphate buffer for five days. See FIG. 16.

Murine colon adenocarcinoma cells (MC38) were purchased and cultured as described above. Clonogenic assays was carried out to determine radioenhancements and delayed cell killing effects of Hf$_{12}$-QPDC-Ir—F and Hf$_6$-BPY-Ir—F MOL. Cells were seeded in 6-well plates and cultured for 12 h. After incubated with particles at a Hf concentration of 20 µM for 4 h, cells were irradiated with X-ray (250 kVp, 15 mA, 1 mm Cu filter) at 0, 1, 2, 4, 8 and 16 Gy dose. Cells were trypsinized and counted immediately. 100-200 cells were seeded on 6-well plates and cultured with 2 mL medium for 10-20 days. Once observing cell clone formation, the culture medium was discarded and plates were rinsed with PBS twice. 500 µL 0.5% crystal violet (50% methanol) were added per well for staining. Then rinse all the wells with water and count the clones. The radiation enhancement factors at 10% cell survival (REF$_{10}$ values) were determined from clonogenic assays. Hf$_{12}$-QPDC-Ir—F MOL and Hf$_6$-BPY-Ir—F MOL have similar REF$_{10}$ of 2.04 and 2.24, respectively.

The in vitro anticancer efficacy of Hf$_{12}$-QPDC-Ir—F MOL and Hf$_6$-BPY-Ir—F MOL were further evaluated on MC38 cells. Cells were cultured in a 6-well plate overnight and incubated with particles at a Hf concentration of 20 µM for 4 h followed by irradiation with 0 or 2 Gy X-ray (250 kVp, 15 mA, 1 mm Cu filter). 48 h later, the cells were stained according to the AlexaFluor 488 Annexin V/dead cell apoptosis kit (Life Technologies, Carlsbad, California, United States of America) and quantified by flow cytometry. As shown in Table 12, Hf$_{12}$-QPDC-Ir—F MOL has larger percentage of late apoptotic and necrotic cells than Hf$_6$-BPY-Ir—F MOL, indicating higher acute efficacy of Hf$_{12}$-QPDC-Ir—F MOL over Hf$_6$-BPY-Ir—F MOL in killing cancer cells upon low-dose X-ray irradiation.

TABLE 12

Percentage of MC38 cells treated with PBS, H$_2$QPDC—Ir—F, Hf$_6$—BPY—Ir—F MOL or Hf$_{12}$—QPDC—Ir—F MOL upon X-ray or dark after a 48-h incubation.

| X-ray | Treated agent | Healthy cells | Early apoptosis | Late apoptosis | Necrosis |
|---|---|---|---|---|---|
| 0 Gy | PBS | 96.4 | 2.49 | 0.41 | 2.36 |
| | H$_2$QPDC—Ir—F | 93.7 | 4.33 | 1.57 | 0.43 |
| | Hf$_6$—BPY—Ir—F | 87.4 | 1.81 | 2.43 | 8.41 |
| | Hf$_{12}$—QPDC—Ir—F | 94.7 | 3.45 | 1.04 | 0.84 |
| 2 Gy | PBS | 91.3 | 3.37 | 3.63 | 1.67 |
| | H$_2$QPDC—Ir—F | 69.7 | 14.3 | 6.23 | 9.77 |
| | Hf$_6$—BPY—Ir—F | 57.8 | 18.1 | 19.6 | 4.46 |
| | Hf$_{12}$—QPDC—Ir—F | 46.3 | 15.1 | 27.8 | 10.8 |

Figure 17:
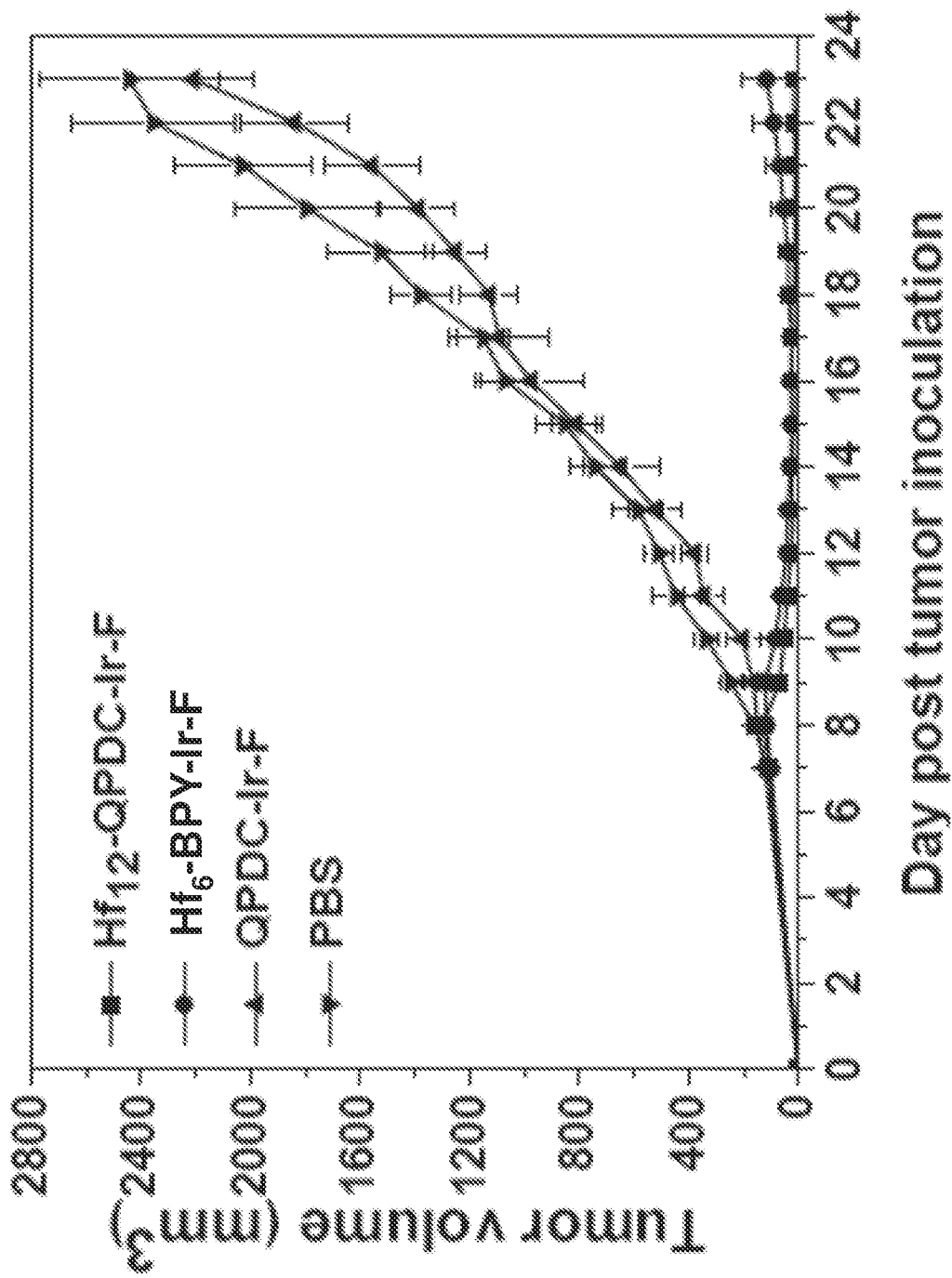
FIG. 17 is a graph showing tumor growth curves from mice inoculated with MC38 mouse colon cancer cells and treated with different nanoscale metal-organic layers (MOLs), including a MOL comprising hafnium 12 ($Hf_{12}$)-oxo cluster secondary building units (SBUs) and bis(2-(2',4'-difluorophenyl)-5-(trifluoromethyl)pyridine)(5,5'-di(4-carboxyl-phenyl)-2,2'-bipyridine)-iridium(III) bridging ligands ($Hf_{12}$-QPDC-Ir—F, squares) and a MOL comprising hafnium 6 ($Hf_6$)-oxo cluster SBUs and bridging ligands comprising a coordination complex comprising 4',6'-dibenzoato-[2,2-bipyridine]-4-carboxylate (BPY), an iridium (Ir) ion, and two 2-(2',4'-difluorophenyl)-5-(trifluorophenyl)pyridine ligands ($Hf_6$-BPY-Ir—F, circles). Data is also provided for tumor-bearing mice treated with bis(2-(2',4'-difluorophenyl)-5-(trifluoromethyl)pyridine)(5,5'-di(4-carboxyl-phenyl)-2,2'-bipyridine)-iridium(III) ($H_2$QPDC-Ir—F, upward pointing triangles) or with vehicle (phosphate buffered saline (PBS), downward pointing triangles. Data is shown as tumor volume measured in cubic millimeters ($mm^3$) versus day after cancer cell inoculation. N=6.

Syngeneic subcutaneous flank tumor-bearing mouse model, MC38, was selected for the evaluation of in vivo RT-RDT efficacy of Hf$_{12}$-QPDC-Ir—F MOL, Hf$_6$-BPY-Ir—F MOL, and H$_2$QPDC-Ir—F. 2×10$^6$ MC38 cells were injected into the right flank subcutaneous tissues of BALB/c or C57Bl/6 mice on day 0. When the tumors reached 100-150 mm$^3$ in volume, MOLs or ligand with ligand concentration of 10 µmol/kg were intratumorally injected followed by daily X-ray irradiation at a dose of 0.5 Gy/fraction (120 kVp, 20 mA, 2 mm-Cu filter) for a total of 5 fractions on consecutive days. The tumor size was measured with a caliper every day and the tumor volume equals (width$^2$×length)/2. All mice were sacrificed on Day 23 and the excised tumors were photographed and weighed. Body weight of each group was monitored for the analysis of systemic toxicity. As shown in FIG. 17, both Hf$_{12}$-QPDC-Ir—F MOL and Hf$_6$-BPY-Ir—F MOL showed efficient tumor regression and Hf$_{12}$-QPDC-Ir—F MOL outperformed Hf$_6$-BPY-Ir—F MOL. Besides, the consistent body weight proved no dark toxicity of Hf$_{12}$-QPDC-Ir—F MOL and Hf$_6$-BPY-Ir—F MOL.

Example 8

Hf$_{12}$-DBP-Pt nMOL

Synthesis and Characterization of Hf$_{12}$-DBP-Pt nMOL:

Scheme 14. Synthesis of Hf$_{12}$—DBP nMOL.

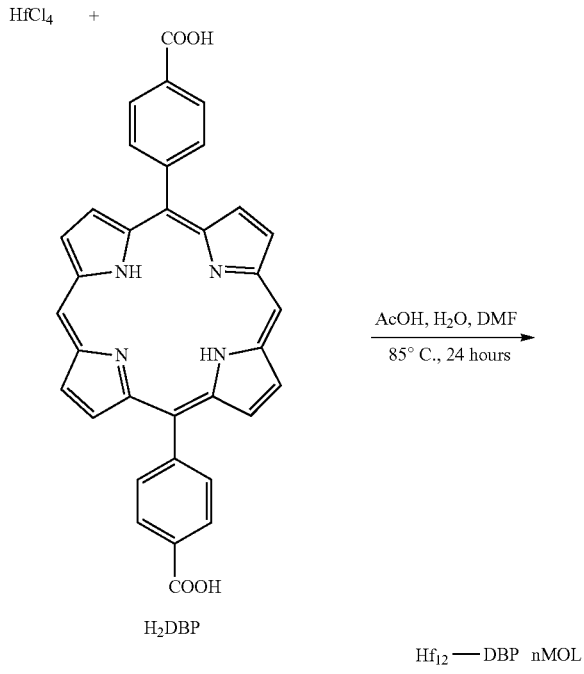

As shown in Scheme 14, above, to a 4 mL glass vial was added 0.5 mL of HfCl$_4$ solution (2.0 mg/mL in DMF), 0.5 mL of H$_2$DBP solution (3.5 mg/mL in DMF), 55 μL of acetic acid, and 5 μL of water. The reaction mixture was kept in an 85° C. oven for 24 hours. The purple precipitate was collected by centrifugation and washed with DMF, 1% trimethylamine/ethanol solution and ethanol. TEM imaging showed that Hf$_{12}$-DBP-Pt nMOL adopted nanoplate morphology with a diameter of ~70 nm. The atomic force microscopy (AFM) images of Hf$_{12}$-DBP-Pt showed a 1.7 nm thickness, which was very close to the Van der Waals size of the Hf$_{12}$ cluster capped by acetic group. The AFM results indicated the monolayer structure of Hf$_{12}$-DBP nMOL.

Figure 18:
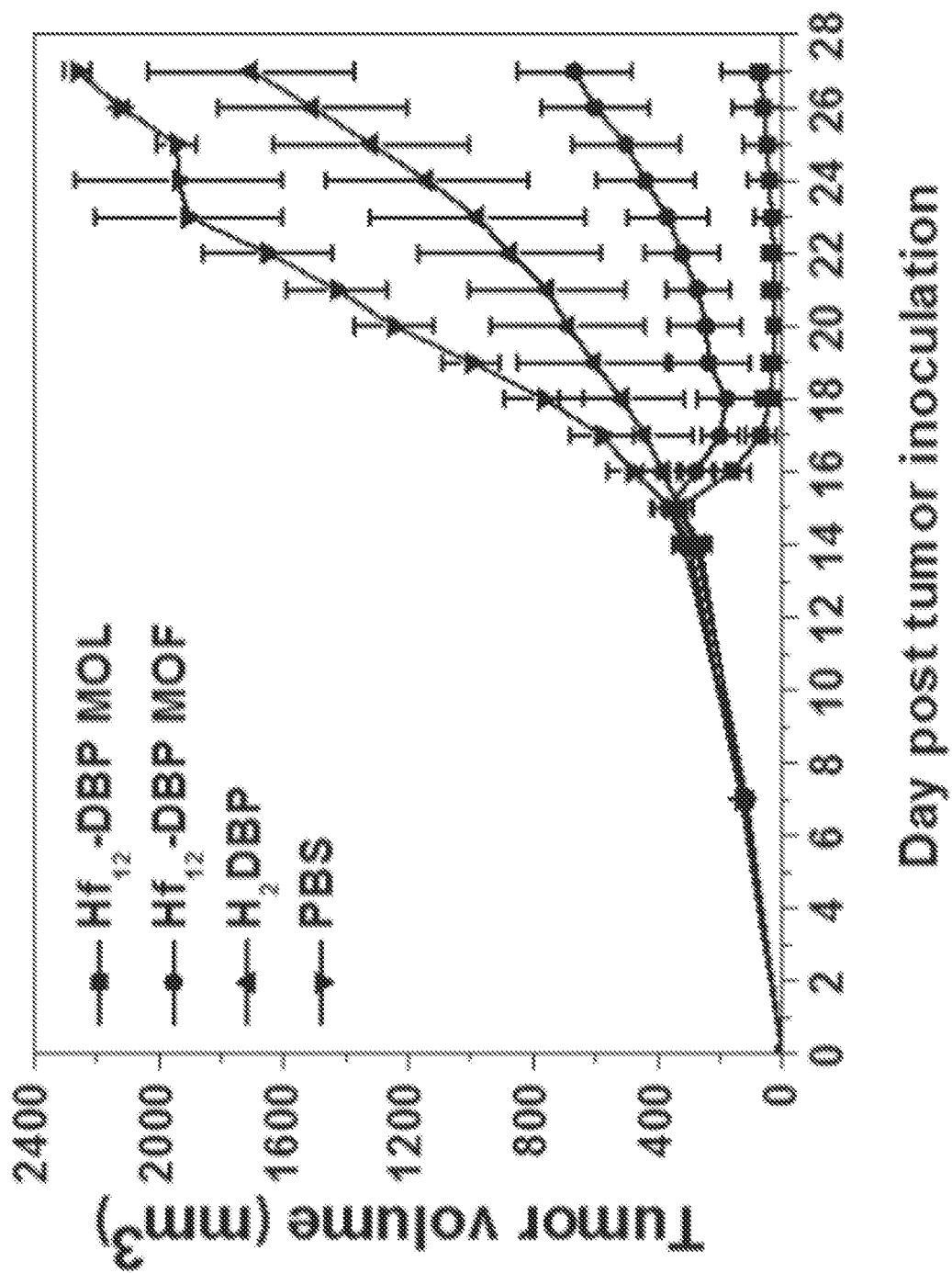
FIG. 18 is a graph showing tumor growth curves from mice inoculated with CT26 mouse colon cancer cells and treated with a metal-organic layer (MOL) comprising hafnium 12 ($Hf_{12}$)-oxo cluster secondary building units (SBUs) and di(benzoate)porphyrin (DBP) bridging ligands ($Hf_{12}$-DBP MOL, squares); a metal-organic framework (MOF) comprising hafnium 12 ($Hf_{12}$)-oxo cluster SBUs and DBP bridging ligands ($Hf_{12}$-DBP MOF, circles); the DBP bridging ligand ($H_2$DBP, upward pointing triangles); and vehicle (phosphate buffered saline (PBS), downward pointing triangles). Data is shown as tumor volume measured in cubic millimeters ($mm^3$) versus day after cancer cell inoculation. N=6.

Syngeneic subcutaneous flank tumor-bearing mouse model CT26 was selected for the evaluation of in vivo RT-RDT efficacy of Hf$_{12}$-DBP MOL, Hf$_{12}$-DBP MOF and H$_2$DBP. 2×10$^6$ CT26 cells were injected into the right flank subcutaneous tissues of BALB/c mice on day 0. When the tumors reached 100-150 mm$^3$ in volume, nMOFs/nMOLs or ligand with ligand concentration of 10 μmol/kg were intratumorally injected followed by irradiation once with LED lamp at a dose of 100 mW/cm$^2$ for 7.5 minutes. The tumor size was measured with a caliper every day and the tumor volume equals (width$^2$×length)/2. All mice were sacrificed on Day 27. Body weight of each group was monitored for the analysis of systemic toxicity. As shown in FIG. 18, Hf$_{12}$-DBP MOL showed efficient tumor regression and outperformed Hf$_{12}$-DBP MOF. In addition, the consistent body weight proved no dark toxicity of Hf$_{12}$-DBP MOL and Hf$_{12}$-DBP MOF.

REFERENCES

All references listed herein including but not limited to all patents, patent applications and publications thereof, scientific journal articles, and database entries are incorporated herein by reference in their entireties to the extent that they supplement, explain, provide a background for, or teach methodology, techniques, and/or compositions employed herein.

Bechet, D.; Couleaud, P.; Frochot, C.; Viriot, M.-L.; Guillemin, F.; Barberi-Heyob, M., Nanoparticles as vehicles for delivery of photodynamic therapy agents. *Trends Biotechnol.* 2008, 26 (11), 612-621.

Cao, L.; Lin, Z.; Peng, F.; Wang, W; Huang, R.; Wang, C.; Yan, J.; Liang, J.; Zhang, Z.; Zhang, T., Self-Supporting Metal—Organic Layers as Single-Site Solid Catalysts. *Angewandte Chemie International Edition* 2016, 55 (16), 4962-4966.

Carter, K. A.; Shao, S.; Hoopes, M. I.; Luo, D.; Ahsan, B.; Grigoryants, V. M.; Song, W.; Huang, H.; Zhang, G.; Pandey, R. K., Porphyrin-phospholipid liposomes permeabilized by near-infrared light. *Nature communications* 2014, 5.

Celli, J. P.; Spring, B. Q.; Rizvi, I.; Evans, C. L.; Samkoe, K. S.; Verma, S.; Pogue, B. W.; Hasan, T., Imaging and photodynamic therapy: mechanisms, monitoring, and optimization. *Chem. Rev.* 2010, 110 (5), 2795-2838.

Chatterjee, D. K.; Fong, L. S.; Zhang, Y, Nanoparticles in photodynamic therapy: an emerging paradigm. *Advanced drug delivery reviews* 2008, 60 (15), 1627-1637.

Cheng, Y.; C. Samia, A.; Meyers, J. D.; Panagopoulos, I.; Fei, B.; Burda, C., Highly efficient drug delivery with gold nanoparticle vectors for in vivo photodynamic therapy of cancer. *J. Am. Chem. Soc.* 2008, 130 (32), 10643-10647.

Dai, R.; Peng, F.; Ji, P.; Lu, K.; Wang, C.; Sun, J.; Lin, W., Electron Crystallography Reveals Atomic Structures of Metal-Organic Nanoplates with M12 (μ3-O) 8 (μ3-OH) 8 (μ2-OH) 6 (M=Zr, Hf) Secondary Building Units. *Inorganic chemistry* 2017, 56 (14), 8128-8134.

Dolmans, D. E.; Fukumura, D.; Jain, R. K., Photodynamic therapy for cancer. *Nature reviews cancer* 2003, 3 (5), 380-387.

Ethirajan, M.; Chen, Y.; Joshi, P.; Pandey, R. K., The role of porphyrin chemistry in tumor imaging and photodynamic therapy. *Chem Soc Rev* 2011, 40 (1), 340-362.

Graham, C. R.; Finke, R. G., The classic Wells-Dawson polyoxometalate, K6 [α-P2W18O62]. 14H2O. Answering an 88 year-old question: what is its preferred, optimum synthesis? *Inorganic chemistry* 2008, 47 (9), 3679-3686.

Hamblin, M. R.; Hasan, T., Photodynamic therapy: a new antimicrobial approach to infectious disease? *Photoch Photobio Sci* 2004, 3 (5), 436-450.

He, C.; Liu, D.; Lin, W., Self-assembled core-shell nanoparticles for combined chemotherapy and photodynamic therapy of resistant head and neck cancers. *ACS nano* 2015, 9 (1), 991-1003.

He, C.; Duan, X.; Guo, N.; Chan, C.; Poon, C.; Weichselbaum, R. R.; Lin, W., Core-shell nanoscale coordination polymers combine chemotherapy and photodynamic therapy to potentiate checkpoint blockade cancer immunotherapy. *Nature Communications* 2016, 7.

Horikawa, R., Sunayama, H., Kitayama, Y., Takano, E., Takeuchi, T., Angew. Chem. 2016, 128, 13217.

Huynh, E.; Leung, B. Y.; Helfield, B. L.; Shakiba, M.; Gandier, J.-A.; Jin, C. S.; Master, E. R.; Wilson, B. C.;

Goertz, D. E.; Zheng, G., In situ conversion of porphyrin microbubbles to nanoparticles for multimodality imaging. *Nat Nanotechnol* 2015, 10 (4), 325-332.

Idris, N. M.; Gnanasammandhan, M. K.; Zhang, J.; Ho, P. C.; Mahendran, R.; Zhang, Y., In vivo photodynamic therapy using upconversion nanoparticles as remote-controlled nanotransducers. *Nat. Med.* 2012, 18 (10), 1580-1585.

Lovell, J. F.; Jin, C. S.; Huynh, E.; Jin, H.; Kim, C.; Rubinstein, J. L.; Chan, W. C.; Cao, W.; Wang, L. V.; Zheng, G., Porphysome nanovesicles generated by porphyrin bilayers for use as multimodal biophotonic contrast agents. *Nature materials* 2011, 10 (4), 324-332.

Lowry, M. S., Goldsmith, J. I., Slinker, J. D., Rohl, R., Pascal, R. A., Malliaras, G. G., Bernhard, S., *Chem. Mater.* 2005, 17, 5712-5719.

Lu, K.; He, C.; Lin, W., Nanoscale Metal-Organic Framework for Highly Effective Photodynamic Therapy of Resistant Head and Neck Cancer. *J. Am. Chem. Soc.* 2014, 136 (48), 16712-16715.

Lu, K.; He, C.; Lin, W., A Chlorin-Based Nanoscale Metal-Organic Framework for Photodynamic Therapy of Colon Cancers. *J. Am. Chem. Soc.* 2015, 137 (24), 7600-7603.

Lu, K.; He, C.; Guo, N.; Chan, C.; Ni, K.; Weichselbaum, R. R.; Lin, W., A Chlorin-based Nanoscale Metal-Organic Framework Systemically Rejects Colorectal Cancers via Synergistic Photodynamic Therapy and Checkpoint Blockade Immunotherapy. *Journal of the American Chemical Society* 2016.

Moan, J.; Berg, K., The photodegradation of porphyrins in cells can be used to estimate the lifetime of singlet oxygen. *Photochemistry and photobiology* 1991, 53 (4), 549-553.

Navath, R. S.; Kurtoglu, Y. E.; Wang, B.; Kannan, S.; Romero, R.; Kannan, R. M., Dendrimer-drug conjugates for tailored intracellular drug release based on glutathione levels. *Bioconjugate chemistry* 2008, 19 (12), 2446-2455.

Ng, K. K.; Zheng, G., Molecular interactions in organic nanoparticles for phototheranostic applications. *Chem. Rev.* 2015, 115 (19), 11012-11042.

Pass, H. I., Photodynamic therapy in oncology: mechanisms and clinical use. *J. Natl. Cancer Inst.* 1993, 85 (6), 443-456.

Ravel, B.; Newville, M. *J. Synchrotron Rad.* 2005, 12 (4), 537-541.

Rehr, J. J.; Albers, R. *Rev. Mod. Phys.* 2000, 72 (3), 621.

Roy, I.; Ohulchanskyy, T. Y.; Pudavar, H. E.; Bergey, E. J.; Oseroff, A. R.; Morgan, J.; Dougherty, T. J.; Prasad, P. N., Ceramic-based nanoparticles entrapping water-insoluble photosensitizing anticancer drugs: a novel drug-carrier system for photodynamic therapy. *Journal of the American Chemical Society* 2003, 125 (26), 7860-7865.

Scandola, F.; Chiorboli, C.; Prodi, A.; Iengo, E.; Alessio, E., Photophysical properties of metal-mediated assemblies of porphyrins. *Coordination chemistry reviews* 2006, 250 (11), 1471-1496.

Wang, C.; Tao, H.; Cheng, L.; Liu, Z., Near-infrared light induced in vivo photodynamic therapy of cancer based on upconversion nanoparticles. *Biomaterials* 2011, 32 (26), 6145-6154.

Wang, C.; deKrafft, K. E.; Lin, W., Pt nanoparticles@photoactive metal-organic frameworks: efficient hydrogen evolution via synergistic photoexcitation and electron injection. *Journal of the American Chemical Society* 2012, 134 (17), 7211-7214.

Xu, R.; Wang, Y.; Duan, X.; Lu, K.; Micheroni, D.; Hu, A.; Lin, W., Nanoscale Metal-Organic Frameworks for Ratiometric Oxygen Sensing in Live Cells. *Journal of the American Chemical Society* 2016, 138 (7), 2158.

Zhang, Z.-M.; Zhang, T.; Wang, C.; Lin, Z.; Long, L.-S.; Lin, W., Photosensitizing metal-organic framework enabling visible-light-driven proton reduction by a Wells-Dawson-type polyoxometalate. *Journal of the American Chemical Society* 2015, 137 (9), 3197-3200).

Zhang, T., Manna, K., Lin, W., *J. Am. Chem. Soc.* 2016, 138, 3241-3249.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A metal-organic layer (MOL), wherein the MOL has a thickness of about 1.2 nanometers (nm) to about 1.7 nm and comprises periodic repeats of metal-based secondary building units (SBUs) and organic bridging ligands, wherein one or more of the SBUs comprise a metal ion capable of absorbing x-rays, wherein the metal ion capable of absorbing x-rays is a Hf ion, and wherein each SBU is bonded to at least one other SBU via coordinative bonding to the same bridging ligand, and wherein at least one of the organic bridging ligands comprises a photosensitizer, wherein said at least one organic bridging ligand comprises a moiety selected from the group consisting of a porphyrin, a chlorin, a chlorophyll, a phthalocyanine, a ruthenium (Ru) coordination complex, and an iridium (Ir) coordination complex.

2. The MOL of claim 1, wherein one or more of the SBUs comprise a $Hf_{12}$ oxo cluster or a $Hf_6$ oxo cluster.

3. The MOL of claim 1, wherein each of the organic bridging ligands is a dicarboxylate or a tricarboxylate.

4. The MOL of claim 1, wherein at least one bridging ligand comprises a Ru coordination complex or an Ir coordination complex, wherein said Ru or Ir coordination complex comprises:

(a) a di- or tricarboxylate ligand further comprising a nitrogen-donor group;

(b) a Ru or Ir ion complexed to the nitrogen-donor group in the di- or tricarboxylate ligand, and (c) one or more additional ligands complexed to the Ru or Ir ion, optionally wherein each of the one or more additional ligands is independently selected from the group consisting of substituted or unsubstituted 2,2'-bipyridine (bpy) and substituted or unsubstituted 2-phenyl-pyridine (ppy), wherein substituted bpy and substituted ppy comprise bpy or ppy substituted with one or more aryl group substituents, optionally wherein the one or more aryl group substituents are selected from halo and halo-substituted alkyl, further optionally wherein the one or more aryl group substituents are selected from fluoro and trifluoromethyl.

5. The MOL of claim 4, wherein the Ru or Ir coordination complex comprises a complex comprising a carboxylate of one of the formulas:

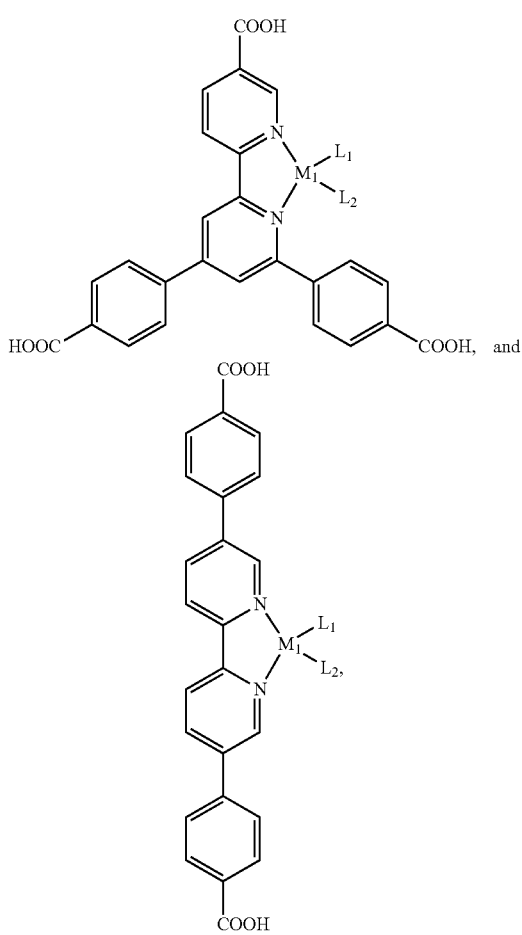

wherein:
M₁ is Ru or Ir; and
L₁ and L₂ are each have a structure of the formula:

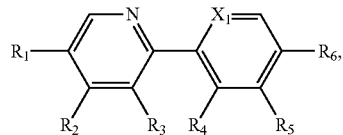

wherein X₁ is CH or N; and
each of R₁, R₂, R₃, R₄, R₅, and R₆ is independently selected from the group consisting of H, halo, alkyl, and substituted alkyl, optionally wherein the substituted alkyl is perhaloalkyl.

6. The MOL of claim 5, wherein X₁ is N.

7. The MOL of claim 5, wherein X₁ is CH.

8. The MOL of claim 5, wherein R₂, R₃, and R₅ are each H.

9. The MOL of claim 5, wherein R₁ is perfluoromethyl and/or wherein R₄ and R₆ are each fluoro.

10. The MOL of claim 1, wherein at least one of the organic bridging ligands is 5, 15-di(p-benzoato)porphyrin (DBP).

11. The MOL of claim 1, comprising Hf₁₂ oxo cluster SBUs and at least one organic bridging ligand selected from the group consisting of bis(2,2'-bipyridine)(5,5'-di(4-carboxyl-phenyl)-2,2'-bipyridine)ruthenium(II) chloride (QDPC-Ru); bis(4-phenyl-2-pyridine)(5,5'-di(4-carboxyl-phenyl)-2,2'-bipyridine)iridium(III) chloride (QDPC-Ir); 5,15-di(p-benzoato)porphyrin (DBP); platinum-complexed 5, 15-di(p-benzoato)porphyrin (DBP-Pt); and bis[2-(2',4'-diflurophenyl)-5-(trifluoromethyl)pyridine](5, 5'-di(4-carboxyl-phenyl)-2,2'-bipyridine iridium (QDPC-Ir—F).

12. The MOL of claim 1, comprising Hf₆ oxo cluster SBUs and at least one organic bridging ligand selected from the group consisting of bis(2,2-bipyridine)-4',6'-dibenzoato-[2,2'-dipyridine]-4-carboxylate ruthenium (II) chloride (BPY-Ru); bis(4-phenyl-2-pyridine)-4',6'-dibenzoato-[2,2'-dipyridine]-4-carboxylate iridium (III) chloride (BPY-Ir); and bis[2-(2',4'-diflurophenyl)-5-(trifluoromethyl)pyridine]-4',6'-dibenzoato-[2,2'-bipyridine]-4-carboxylate iridium bridging ligands (BPY-Ir—F).

13. The MOL of claim 1, further comprising a poly(ethylene glycol) (PEG) moiety, optionally wherein the PEG moiety is attached to the MOL via a disulfide group-containing linker moiety coordinated to metal ions in the SBUs.

14. The MOL of claim 1, further comprising oxaliplatin or a prodrug thereof coordinated to a MOL metal ion or encapsulated in said MOL.

15. The MOL of claim 1, further comprising a polyoxometalate (POM) encapsulated in the MOL.

16. The MOL of claim 1, further comprising an immunotherapy agent, optionally wherein the immunotherapy agent is selected from the group consisting of an agonist of DNA or RNA sensors, a TLR3 agonist, a TLR7 agonist, a TLR9 agonist, a stimulator of interferon genes (STING) agonist, and an indoleamine 2,3-dioxygenate (IDO) inhibitor (IDOi), further optionally wherein the immunotherapy agent is a CpG ODN or STING agonist that is electrostatically bonded to a positively charged moiety in the MOL.

17. A pharmaceutical composition comprising a MOL of claim 1 and a pharmaceutically acceptable carrier.

18. A method for treating a disease in a subject in need thereof, the method comprising:
administering to the subject a MOL of claim 1; and
exposing at least a portion of the subject to ionizing irradiation energy,
optionally X-rays.

19. The method of claim 18, wherein the subject is a mammal, optionally a human.

20. The method of claim 18, wherein the disease is selected from the group consisting of a head tumor, a neck tumor, breast cancer, a gynecological tumor, a brain tumor, colorectal cancer, lung cancer, mesothelioma, a soft tissue sarcoma, skin cancer, connective tissue cancer, adipose cancer, stomach cancer, anogenital cancer, kidney cancer, bladder cancer, colon cancer, prostate cancer, central nervous system cancer, retinal cancer, blood cancer, a neuroblastoma, multiple myeloma, lymphoid cancer, and pancreatic cancer, optionally wherein the disease is colon cancer or pancreatic cancer.

21. The method of claim 18, wherein the disease is a metastatic cancer.

22. The method of claim 18, wherein the method further comprises administering to the subject an additional therapeutic agent or treatment, optionally wherein the additional therapeutic agent or treatment is an immunotherapy agent and/or a cancer treatment selected from the group consisting of surgery, chemotherapy, toxin therapy, cryotherapy and gene therapy.

23. The method of claim 22, wherein the method further comprises administering an immunotherapy agent, optionally wherein the immunotherapy agent is an immune checkpoint inhibitor.

24. The MOL of claim 10, wherein nitrogen atoms of the DBP are complexed to a metal ion.

25. The MOL of claim 24, wherein the metal ion is a platinum (Pt) ion.

* * * * *